(12) United States Patent
Passini et al.

(10) Patent No.: US 10,905,709 B2
(45) Date of Patent: Feb. 2, 2021

(54) MODIFIED ANTISENSE OLIGOMERS FOR EXON INCLUSION IN SPINAL MUSCULAR ATROPHY

(71) Applicant: Sarepta Therapeutics, Inc., Cambridge, MA (US)

(72) Inventors: Marco A. Passini, Cambridge, MA (US); Gunnar J. Hanson, Cambridge, MA (US)

(73) Assignee: SAREPTA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/754,782

(22) PCT Filed: Aug. 26, 2016

(86) PCT No.: PCT/US2016/048965
§ 371 (c)(1),
(2) Date: Feb. 23, 2018

(87) PCT Pub. No.: WO2017/040271
PCT Pub. Date: Mar. 9, 2017

(65) Prior Publication Data
US 2019/0015440 A1    Jan. 17, 2019

Related U.S. Application Data

(60) Provisional application No. 62/211,678, filed on Aug. 28, 2015, provisional application No. 62/379,696, filed on Aug. 25, 2016.

(51) Int. Cl.
| | |
|---|---|
| *A61K 31/712* | (2006.01) |
| *C12N 15/11* | (2006.01) |
| *A61K 31/7125* | (2006.01) |
| *A61P 25/14* | (2006.01) |
| *A61P 21/00* | (2006.01) |

(52) U.S. Cl.
CPC ........ *A61K 31/712* (2013.01); *A61K 31/7125* (2013.01); *A61P 21/00* (2018.01); *A61P 25/14* (2018.01); *C12N 15/11* (2013.01); *C12N 2310/3145* (2013.01); *C12N 2310/3233* (2013.01); *C12N 2310/33* (2013.01)

(58) Field of Classification Search
None
See application file for complete search history.

(56) References Cited

U.S. PATENT DOCUMENTS

| | | | | |
|---|---|---|---|---|
| 8,980,853 | B2 * | 3/2015 | Bennett | A61K 31/7088 514/44 A |
| 9,161,948 | B2 | 10/2015 | Hanson | |
| 9,845,469 | B2 * | 12/2017 | Burghes | C12N 15/111 |
| 9,944,926 | B2 | 4/2018 | Linsley et al. | |
| 9,988,626 | B2 * | 6/2018 | Wirth | C12N 15/113 |
| 10,066,228 | B2 | 10/2018 | Linsley et al. | |
| 2004/0006089 | A1 | 1/2004 | Thurieau et al. | |
| 2006/0287268 | A1 | 12/2006 | Iversen et al. | |
| 2008/0194463 | A1 | 8/2008 | Weller et al. | |
| 2010/0016215 | A1 | 1/2010 | Moulton et al. | |
| 2011/0269820 | A1 | 11/2011 | Singh et al. | |
| 2014/0329772 | A1 * | 11/2014 | Linsley | C12N 15/113 514/85 |

FOREIGN PATENT DOCUMENTS

| | | |
|---|---|---|
| JP | 2003-516965 A | 5/2003 |
| JP | 2010-505741 A | 2/2010 |
| JP | 2011-236157 A | 11/2011 |
| WO | WO 2007/002390 A2 | 1/2007 |
| WO | WO 2008/018795 A1 | 2/2008 |
| WO | WO 2008/036127 A2 | 3/2008 |
| WO | WO 2010/120820 A1 | 10/2010 |
| WO | WO 2010/148249 A1 | 12/2010 |
| WO | WO 2011/150408 A2 | 12/2011 |
| WO | WO 2011/159836 A2 | 12/2011 |
| WO | WO 2012/150960 A1 | 11/2012 |
| WO | WO 2012/178122 A2 | 12/2012 |
| WO | WO 2013/082551 A1 | 6/2013 |
| WO | WO 2013/086207 A1 | 6/2013 |
| WO | WO 2013/142087 A1 | 9/2013 |
| WO | WO 2013/173638 A1 | 11/2013 |
| WO | WO 2013/173789 A2 | 11/2013 |
| WO | WO 2014/110291 A1 | 7/2014 |
| WO | WO 2014/113540 A1 | 7/2014 |
| WO | WO 2014/169243 A2 | 10/2014 |
| WO | WO 2015/035460 A1 | 3/2015 |
| WO | WO-2015035460 A1 * | 3/2015 ........... A61K 31/712 |
| WO | WO 2015/120450 A1 | 8/2015 |

OTHER PUBLICATIONS

Burghes, A.H.M. et al. (Aug. 1, 2010) "Antisense oligonucleotides and spinal muscular atrophy: skipping along" *Genes & Development*, 24(15):1574-1579.

Cartegni, L. et al. (Feb. 1, 2003) "Correction of disease-associated exon skipping by synthetic exon-specific activators" *Nature Structural Biology*, 10(2):120-125.

European Patent Application No. 12812432.8, by Sarepta Therapeutics, Inc.: Examination Report, dated Apr. 1, 2016 (5 pages).

Hua, Y. et al. (Apr. 1, 2007) "Enhancement of SMN2 exon 7 inclusion by antisense oligonucleotides targeting the exon" *PLOS Biology*, 5(4):E73, pp. 0729-0744.

International Patent Application No. PCT/US2012/067470: International Preliminary Report on Patentability, dated Jun. 3, 2014 (7 pages).

(Continued)

*Primary Examiner* — Tracy Vivlemore
(74) *Attorney, Agent, or Firm* — Finnegan, Henderson, Farabow, Garrett & Dunner LLP

(57) ABSTRACT

The present disclosure relates to modified antisense oligomers and related compositions and methods for increasing the expression of functional SMN protein and methods for treating spinal muscular atrophy and relates to inducing inclusion of exon 7 in SMN2 mRNA.

11 Claims, 17 Drawing Sheets
Specification includes a Sequence Listing.

(56) References Cited

OTHER PUBLICATIONS

International Patent Application No. PCT/US2012/067470: International Search Report and Written Opinion, dated Mar. 26, 2013 (11 pages).

International Patent Application No. PCT/US2012/067475: International Preliminary Report on Patentability, dated Jun. 30, 2014 (7 pages).

International Patent Application No. PCT/US2012/067475: International Search Report, dated Mar. 26, 2013 (6 pages).

International Patent Application No. PCT/US2016/048965: International Search Report and Written Opinion, dated Feb. 15, 2017 (25 pages).

Japanese Patent Application No. 2014-544962: Notice of Reasons for Rejection, dated Sep. 6, 2017 (8 pages).

Kaya, I. et al. (2003) "The synthesis and characterization of oligo-N-4-aminopryridine, oligo-2-[(pyridine-4-yl-imino) methyl] phenol and its some oligomer-metal complexes" *Polymer*, 44:7299-7309.

Lim, S.R. et al. (Nov. 30, 2001) "Modulation of Survival Motor Neuron Pre-MRNA Splicing by Inhibition of Alternative 3'Splice Site Pairing" *Journal of Biological Chemistry*, 276(48):45476-45483; DOI: 10.1074/JBC.M107632200 [online]. Retrieved on Oct. 2, 2001.

Prabahar, K.J. et al. (1994) "Effect of Phosphate Activating Group on Oligonucleotide Formation on Montmorillonite: The Regioselective Formation of 3',5'-Linked Oligoadenylates" *J Am Chem Soc*, 116:10914-10920.

Sazani, P. et al. (Oct. 1, 2001) "Nuclear antisense effects of neutral, anionic and cationic oligonucleotide analogs" *Nucleic Acids Research*, 29(19):3965-3974.

Singh, N.N. et al. (2009) "A short antisense oligonucleotide masking a unique intronic motif prevents skipping of a critical exon in spinal muscular atrophy" *RNA Biology*, 6(3):341-350.

Singh, N.N. et al. (Jun. 1, 2010) "An antisense microwalk reveals critical role of an intronic position linked to a unique long-distance interaction in pre-mRNA splicing" *RNA*, 16(6):1167-1181; ISSN: 1355-8382, DOI: 10.1261/rna.2154310.

Swenson, D.L. et al. (May 1, 2009) "Chemical Modifications of Antisense Morpholino Oligomers Enhance Their Efficacy against Ebola Virus Infection" *Antimicrobial Agents and Chemotherapy*, 53(5):2089-2099; ISSN: 0066-4804, DOI: 10.1128/AAC.00936-08.

U.S. Appl. No. 14/360,890: Office Action, dated Mar. 9, 2017.

* cited by examiner

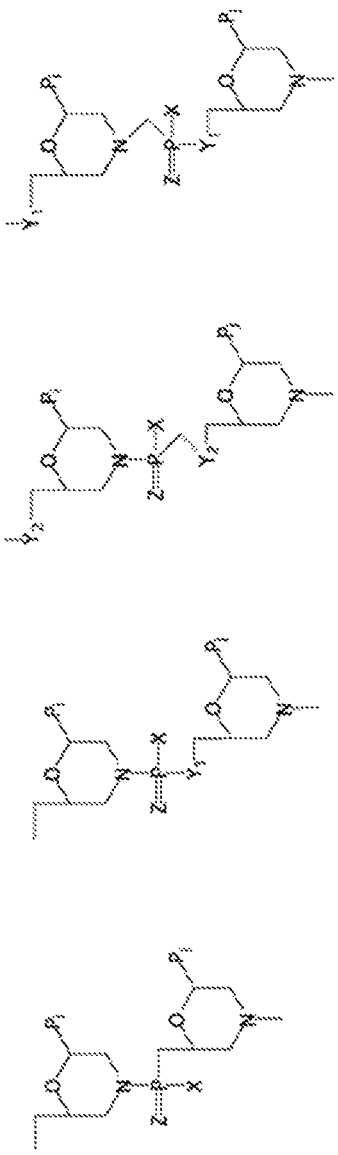

SEQUENCE LISTING

<160> NUMBER OF SEQ ID NOS: 54

<210> SEQ ID NO 1
<211> LENGTH: 444
<212> TYPE: DNA
<213> ORGANISM: Homo sapiens

<400> SEQUENCE: 1

```
gtaagtctgc cagcattatg aaagtgaatc ttacttttgt aaaactttat ggtttgtgga      60
aaacaaatgt ttttgaacat ttaaaaagtt cagatgttag aaagttgaaa ggttaatgta     120
aaacaatcaa tattaaagaa ttttgatgcc aaaactatta gataaaaggt taatctacat     180
ccctactaga attctcatac ttaactggtt ggttgtgtgg aagaaacata ctttcacaat     240
aaagagcttt aggatatgat gccattttat atcactagta ggcagaccag cagactttt      300
tttattgtga tatgggataa cctaggcata ctgcactgta cactctgaca tatgaagtgc     360
tctagtcaag tttaactggt gtccacagag gacatggttt aactggaatt cgtcaagcct     420
ctggttctaa tttctcattt gcag                                            444
```

<210> SEQ ID NO 2
<211> LENGTH: 111
<212> TYPE: DNA
<213> ORGANISM: Homo sapiens

<400> SEQUENCE: 2

```
ataattcccc caccacctcc catatgtcca gattctcttg atgatgctga tgctttggga      60
agtatgttaa tttcatggta catgagtggc tatcatactg gctattatat g              111
```

<210> SEQ ID NO 3
<211> LENGTH: 807
<212> TYPE: DNA
<213> ORGANISM: Homo sapiens

<400> SEQUENCE: 3

| | | | | | |
|---|---|---|---|---|---|
| ctcaggctgg | agtgcaaggg | cacattcaca | gctcactgca | gccttgacct | ccagggctca | 60 |
| agcagtcctc | tcacctcagt | ttcccgagta | gctgggacta | cagtgataat | gccactgcac | 120 |
| ctggctaatt | tttattttta | tttatttatt | ttttttgag | acagagtctt | gctctgtcac | 180 |
| ccaggctgga | gtgcagtggt | gtaaatctca | gctcactgca | gcctccgcct | cctgggttca | 240 |
| agtgattctc | ctgcctcaac | ctcccaagta | gctgggatta | gaggtcccca | ccaccatgcc | 300 |
| tggctaattt | tttgtacttt | cagtagaaac | ggggttttgc | catgttggcc | aggctgttct | 360 |
| cgaactcctg | agctcaggtg | atccaactgt | ctcggcctcc | caaagtgctg | ggattacagg | 420 |
| cgtgagccac | tgtgcctagc | ctgagccacc | acgccggcct | aattttttaaa | tttttttgtag | 480 |
| agacagggtc | tcattatgtt | gcccagggtg | gtgtcaagct | ccaggtctca | agtgatcccc | 540 |
| ctacctccgc | ctcccaaagt | tgtgggattg | taggcatgag | ccactgcaag | aaaaccttaa | 600 |
| ctgcagccta | ataattgttt | tctttgggat | aactttttaaa | gtacattaaa | agactatcaa | 660 |
| cttaatttct | gatcatattt | tgttgaataa | aataagtaaa | atgtcttgtg | aaacaaaatg | 720 |
| cttttttaaca | tccatataaa | gctatctata | tatagctatc | tatatctata | tagctatttt | 780 |
| ttttaacttc | ctttattttc | cttacag | | | | 807 |

<210> SEQ ID NO 4
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: u or t

<400> SEQUENCE: 4 gcnggcag                                                                8

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: u or t
<220> FEATURE:
<221> NAME/KEY: modified_base
<222> LOCATION: (5)..(5)
<223> OTHER INFORMATION: u or t

<400> SEQUENCE: 5 angcnggcag                                                              10

```
<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: u or t
<220> FEATURE:
<221> NAME/KEY: modified_base
<222> LOCATION: (7)..(8)
<223> OTHER INFORMATION: u or t
<220> FEATURE:
<221> NAME/KEY: modified_base
<222> LOCATION: (12)..(14)
<223> OTHER INFORMATION: u or t
<220> FEATURE:
<221> NAME/KEY: modified_base
<222> LOCATION: (17)..(17)
<223> OTHER INFORMATION: u or t
<220> FEATURE:
<221> NAME/KEY: modified_base
<222> LOCATION: (20)..(20)
<223> OTHER INFORMATION: u or t
<220> FEATURE:
<221> NAME/KEY: modified_base
<222> LOCATION: (23)..(23)
<223> OTHER INFORMATION: u or t

<400> SEQUENCE: 6
gnaaganncg cnnncanaan gcngg                                             25

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: u or t
<220> FEATURE:
<221> NAME/KEY: modified_base
<222> LOCATION: (5)..(7)
<223> OTHER INFORMATION: u or t
<220> FEATURE:
<221> NAME/KEY: modified_base
<222> LOCATION: (10)..(10)
<223> OTHER INFORMATION: u or t
<220> FEATURE:
<221> NAME/KEY: modified_base
<222> LOCATION: (13)..(13)
<223> OTHER INFORMATION: u or t
<220> FEATURE:
<221> NAME/KEY: modified_base
<222> LOCATION: (16)..(16)
<223> OTHER INFORMATION: u or t

<400> SEQUENCE: 7
ncacnnncan aangcngg                                                     18

<210> SEQ ID NO 8
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(3)
<223> OTHER INFORMATION: u or t
<220> FEATURE:
<221> NAME/KEY: modified_base
<222> LOCATION: (7)..(9)
<223> OTHER INFORMATION: u or t
<220> FEATURE:
<221> NAME/KEY: modified_base
<222> LOCATION: (12)..(12)
<223> OTHER INFORMATION: u or t
<220> FEATURE:
<221> NAME/KEY: modified_base
<222> LOCATION: (15)..(15)
<223> OTHER INFORMATION: u or t
<220> FEATURE:
<221> NAME/KEY: modified_base
<222> LOCATION: (18)..(18)
<223> OTHER INFORMATION: u or t

<400> SEQUENCE: 8
anncacnnnc anaangcngg                                              20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: u or t
<220> FEATURE:
<221> NAME/KEY: modified_base
<222> LOCATION: (8)..(8)
<223> OTHER INFORMATION: u or t
<220> FEATURE:
<221> NAME/KEY: modified_base
<222> LOCATION: (11)..(11)
<223> OTHER INFORMATION: u or t
<220> FEATURE:
<221> NAME/KEY: modified_base
<222> LOCATION: (14)..(14)
<223> OTHER INFORMATION: u or t
<220> FEATURE:
<221> NAME/KEY: modified_base
<222> LOCATION: (16)..(16)
<223> OTHER INFORMATION: u or t

<400> SEQUENCE: 9
aaaagncngc nggncngcc                                               19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: u or t
<220> FEATURE:
<221> NAME/KEY: modified_base
<222> LOCATION: (6)..(6)
<223> OTHER INFORMATION: u or t
<220> FEATURE:
<221> NAME/KEY: modified_base
<222> LOCATION: (8)..(8)
<223> OTHER INFORMATION: u or t
<220> FEATURE:
<221> NAME/KEY: modified_base
<222> LOCATION: (12)..(12)
<223> OTHER INFORMATION: u or t
<220> FEATURE:
<221> NAME/KEY: modified_base
<222> LOCATION: (16)..(16)
<223> OTHER INFORMATION: u or t
<220> FEATURE:
<221> NAME/KEY: modified_base
<222> LOCATION: (18)..(18)
<223> OTHER INFORMATION: u or t
<220> FEATURE:
<221> NAME/KEY: modified_base
<222> LOCATION: (20)..(20)
<223> OTHER INFORMATION: u or t

<400> SEQUENCE: 10
anagananag anagcnanan                                                  20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: u or t
<220> FEATURE:
<221> NAME/KEY: modified_base
<222> LOCATION: (6)..(9)
<223> OTHER INFORMATION: u or t
<220> FEATURE:
<221> NAME/KEY: modified_base
<222> LOCATION: (14)..(14)
<223> OTHER INFORMATION: u or t
<220> FEATURE:
<221> NAME/KEY: modified_base
<222> LOCATION: (20)..(21)
<223> OTHER INFORMATION: u or t
<220> FEATURE:
<221> NAME/KEY: modified_base
<222> LOCATION: (23)..(23)
<223> OTHER INFORMATION: u or t

<400> SEQUENCE: 11
aanagnnnng gcancaaaan ncn                                              23

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: u or t
<220> FEATURE:
<221> NAME/KEY: modified_base
<222> LOCATION: (5)..(5)
<223> OTHER INFORMATION: u or t
<220> FEATURE:
<221> NAME/KEY: modified_base
<222> LOCATION: (10)..(10)
<223> OTHER INFORMATION: u or t
<220> FEATURE:
<221> NAME/KEY: modified_base
<222> LOCATION: (15)..(15)
<223> OTHER INFORMATION: u or t
<220> FEATURE:
<221> NAME/KEY: modified_base
<222> LOCATION: (18)..(18)
<223> OTHER INFORMATION: u or t
<220> FEATURE:
<221> NAME/KEY: modified_base
<222> LOCATION: (20)..(20)
<223> OTHER INFORMATION: u or t
<220> FEATURE:
<221> NAME/KEY: modified_base
<222> LOCATION: (23)..(23)
<223> OTHER INFORMATION: u or t

<400> SEQUENCE: 12
gananaaaan ggcancanan ccnaa                                           25

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(3)
<223> OTHER INFORMATION: u or t
<220> FEATURE:
<221> NAME/KEY: modified_base
<222> LOCATION: (8)..(11)
<223> OTHER INFORMATION: u or t
<220> FEATURE:
<221> NAME/KEY: modified_base
<222> LOCATION: (13)..(13)
<223> OTHER INFORMATION: u or t
<220> FEATURE:
<221> NAME/KEY: modified_base
<222> LOCATION: (15)..(15)
<223> OTHER INFORMATION: u or t
<220> FEATURE:
<221> NAME/KEY: modified_base
<222> LOCATION: (18)..(18)
<223> OTHER INFORMATION: u or t
<220> FEATURE:
<221> NAME/KEY: modified_base
<222> LOCATION: (21)..(24)
<223> OTHER INFORMATION: u or t

<400> SEQUENCE: 13
annaaccnnn nancnaanag nnnngg                                          26

<210> SEQ ID NO 14
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(8)
<223> OTHER INFORMATION: u or t

<400> SEQUENCE: 14
acaacnnngg gaggcggagg                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: u or t
<220> FEATURE:
<221> NAME/KEY: modified_base
<222> LOCATION: (8)..(8)
<223> OTHER INFORMATION: u or t
<220> FEATURE:
<221> NAME/KEY: modified_base
<222> LOCATION: (10)..(10)
<223> OTHER INFORMATION: u or t
<220> FEATURE:
<221> NAME/KEY: modified_base
<222> LOCATION: (14)..(15)
<223> OTHER INFORMATION: u or t
<220> FEATURE:
<221> NAME/KEY: modified_base
<222> LOCATION: (20)..(20)
<223> OTHER INFORMATION: u or t

<400> SEQUENCE: 15
gnagggangn agannaaccn                                                   20

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: u or t
<220> FEATURE:
<221> NAME/KEY: modified_base
<222> LOCATION: (4)..(4)
<223> OTHER INFORMATION: u or t
<220> FEATURE:
<221> NAME/KEY: modified_base
<222> LOCATION: (6)..(6)
<223> OTHER INFORMATION: u or t
<220> FEATURE:
<221> NAME/KEY: modified_base
<222> LOCATION: (8)..(8)
```

```
<223> OTHER INFORMATION: u or t
<220> FEATURE:
<221> NAME/KEY: modified_base
<222> LOCATION: (12)..(12)
<223> OTHER INFORMATION: u or t
<220> FEATURE:
<221> NAME/KEY: modified_base
<222> LOCATION: (15)..(16)
<223> OTHER INFORMATION: u or t
<220> FEATURE:
<221> NAME/KEY: modified_base
<222> LOCATION: (18)..(19)
<223> OTHER INFORMATION: u or t

<400> SEQUENCE: 16
cnanananag anagnnannc aacaaa                                            26

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide transporter

<400> SEQUENCE: 17

Arg Arg Arg Gln Arg Arg Lys Lys Arg
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide transporter

<400> SEQUENCE: 18

Arg Lys Lys Arg Arg Gln Arg Arg Arg
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide transporter

<400> SEQUENCE: 19

Arg Arg Arg Arg Arg Arg Arg Arg Arg Phe Phe
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide transporter

<400> SEQUENCE: 20

Arg Arg Arg Arg Arg Phe Phe Arg Arg Arg Arg
1               5                   10

<210> SEQ ID NO 21
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide transporter

<400> SEQUENCE: 21

Arg Arg Arg Arg
1

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide transporter

<400> SEQUENCE: 22

Arg Arg Arg Arg Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide transporter

<400> SEQUENCE: 23

Arg Arg Arg Arg Arg Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide transporter

<400> SEQUENCE: 24

Arg Arg Arg Arg Arg Arg Arg
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide transporter

<400> SEQUENCE: 25

Arg Arg Arg Arg Arg Arg Arg Arg
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide transporter

<400> SEQUENCE: 26

Arg Arg Arg Arg Arg Arg Arg Arg Arg
1               5
```

```
<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide transporter
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (6)..(6)
<223> OTHER INFORMATION: 6-aminohexanoic acid
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (10)..(10)
<223> OTHER INFORMATION: 6-aminohexanoic acid
<220> FEATURE:
<221> NAME/KEY: MOD_RES
<222> LOCATION: (12)..(12)
<223> OTHER INFORMATION: 6-aminohexanoic acid
<220> FEATURE:
<221> NAME/KEY: MOD_RES
<222> LOCATION: (14)..(14)
<223> OTHER INFORMATION: 6-aminohexanoic acid
<220> FEATURE:
<221> NAME/KEY: MOD_RES
<222> LOCATION: (16)..(16)
<223> OTHER INFORMATION: 6-aminohexanoic acid

<400> SEQUENCE: 27

Arg Xaa Arg Xaa Arg Xaa Arg Xaa Arg Xaa Arg Xaa Arg Xaa Arg Xaa
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide transporter
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (11)..(11)
<223> OTHER INFORMATION: 6-aminohexanoic acid

<400> SEQUENCE: 28

Arg Xaa Arg Arg Xaa Arg Arg Xaa Arg Arg Xaa Arg
1               5                   10

<210> SEQ ID NO 29
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide transporter
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (11)..(11)
<223> OTHER INFORMATION: 6-aminohexanoic acid
<220> FEATURE:
<221> NAME/KEY: MOD_RES
<222> LOCATION: (14)..(14)
<223> OTHER INFORMATION: 6-aminohexanoic acid

<400> SEQUENCE: 29

Arg Xaa Arg Arg Xaa Arg Arg Xaa Arg Arg Xaa Arg Arg Xaa Arg
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide transporter
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (5)..(5)
<223> OTHER INFORMATION: beta-alanine
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (11)..(11)
<223> OTHER INFORMATION: beta-alanine

<400> SEQUENCE: 30

Arg Xaa Arg Arg Xaa Arg Arg Xaa Arg Arg Xaa Arg
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide transporter

<400> SEQUENCE: 31

Arg Ala Arg Arg Ala Arg Arg Ala Arg Arg Ala Arg Phe Phe
1               5                   10

<210> SEQ ID NO 32
<211> LENGTH: 14
<212> TYPE: PRT
```

<213> ORGANISM: Artificial Sequence
<220> FEATURE:
<223> OTHER INFORMATION: Description of Artificial Sequence: Synthetic
      peptide transporter

<400> SEQUENCE: 32

Arg Gly Arg Arg Gly Arg Arg Gly Arg Arg Gly Arg Phe Phe
1               5                   10

<210> SEQ ID NO 33
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 gctggcag                                                              8

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atgctggcag                                                           10

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tcactttcat aatgctgg                                                  18

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
attcactttc ataatgctgg                                                20

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gtaagattca ctttcataat gctgg                                          25

<210> SEQ ID NO 38
<211> LENGTH: 19
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 38
aaaagtctgc tggtctgcc                                                  19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
atagatatag atagctatat                                                 20

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aatagttttg gcatcaaaat tct                                             23

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gatataaaat ggcatcatat cctaa                                           25

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
attaaccttt tatctaatag ttttgg                                          26

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
acaactttgg gaggcggagg                                                 20

<210> SEQ ID NO 44
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 44
gtagggatgt agattaacct                                                    20

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctatatatag atagttattc aacaaa                                             26

<210> SEQ ID NO 46
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
augcuggcag                                                               10

<210> SEQ ID NO 47
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ucacuuucau aaugcugg                                                      18

<210> SEQ ID NO 48
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
auucacuuuc auaaugcugg                                                    20

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
aaaagucugc uggucugcc                                                     19

<210> SEQ ID NO 50
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 50
aauaguuuug gcaucaaaau ucu                                              23

<210> SEQ ID NO 51
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cuauauauag auaguuauuc aacaaa                                           26

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
actttcccca atctgtgaag t                                                21

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Arg Arg Arg Arg Arg Gly
1               5

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
catttagtgc tgctctatgc c                                                21
```

MODIFIED ANTISENSE OLIGOMERS FOR EXON INCLUSION IN SPINAL MUSCULAR ATROPHY

This is a national stage application under 35 U.S.C. § 371 of international application number PCT/US2016/048965, filed Aug. 26, 2016, which designated the U.S. and claims priority to U.S. Provisional Application No. 62/211,678, filed Aug. 28, 2015, and U.S. Provisional Application No. 62/379,696, filed Aug. 25, 2016, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 5, 2018, is named SL.txt and is 21,039 bytes in size.

Modified antisense oligomers and related compositions and methods are disclosed, including methods for increasing expression levels of functional Survival Motor Neuron (SMN) protein, methods for treating Spinal Muscular Atrophy (SMA), and methods for inducing exon inclusion as a treatment for SMA. Furthermore, methods for inducing inclusion of exon 7 to restore levels of SMN protein encoded by the SMN gene are disclosed.

Antisense technology, recently has been adapted to alter the splicing process of a precursor messenger RNA (pre-mRNA). Pre-mRNA is an immature single strand of messenger RNA synthesized from a DNA transcript through a process known as transcription. The pre-mRNA transcript comprises two different segment types, introns and exons. Introns are removed in a process called splicing, which is generally performed by a spliceosome complex. The remaining exons are joined together and become part of the final, mature mRNA molecule.

The precise process of intron/exon splicing involves various structural elements within the intron region. These include an intron splice donor site, located at the 5' end of the intron, a branch site, located near the 3' end of the intron, and a splice acceptor site, located at the 3' end of the intron. The splice donor site generally includes a conserved GU sequence at the 5' end of the exon/intron junction. The splice acceptor site generally includes an AG sequence at the 3' end of the intron/exon junction.

Variations in the splicing process can create variations in the resultant mRNA by varying the exon composition within the mRNA, a process often referred to as alternative splicing. Alternative splicing can occur in many ways. Exons may be extended or skipped. Portions of introns may be retained. Alternative splicing increases the coding potential of the human genome by producing multiple proteins from a single gene. Inappropriate alternative splicing is also associated with a growing number of human diseases.

SMA is an often-fatal genetic disorder resulting from the loss of the SMN protein encoded by the Survival Motor Neuron SMN gene. The SMN genes, SMN1 and SMN2, are located on chromosome 5 and SMA is caused by the loss of SMN1 from both chromosomes. SMN2, while being almost identical to SMN1, is less effective at making the SMN protein. The severity of SMA is affected by the efficiency at which SMN2, of which there are several copies, produces the SMN protein.

SMN1 encodes a ubiquitously expressed 38 kDa SMN protein that is necessary for snRNP assembly, an essential process for cell survival. A nearly identical copy of the gene, SMN2, fails to compensate for the loss of SMN1 because of exon 7 skipping, producing an unstable truncated protein, SMNΔ7. SMN1 and SMN2 differ by a critical C to T substitution at position 6 of exon 7 (C6U in transcript of SMN2). C6U does not change the coding sequence, but is sufficient to cause exon 7 skipping in SMN2.

Current treatment for SMA consists of prevention and management of the secondary effect of chronic motor unit loss. Currently, there are no drug therapies available for the treatment or prevention of SMA.

Antisense technology, used mostly for RNA downregulation, recently has been adapted to alter the splicing process. Effective agents that can alter splicing of SMN2 pre-mRNAs are likely to be useful therapeutically.

Accordingly, novel antisense oligomers and methods of increasing the expression of functional SMN protein as described herein are believed to be advantageous.

In certain aspects, the present disclosure provides compositions and methods for increasing the expression of functional SMN protein. In further aspects, the present disclosure provides variously described modified antisense oligomers for enhancing levels of exon 7-containing SMN2 mRNA in a subject. In further aspects, the present disclosure provides methods of enhancing levels of exon 7-containing SMN2 mRNA in a subject, comprising administering a modified antisense oligomer of sufficient length and complementarity to specifically hybridize a region within the SMN2 pre-mRNA. In certain aspects, the subject has SMA.

Various aspects include a modified antisense oligomer of 8 to 40 subunits, optionally comprising at least one subunit that is a nucleotide analog having (i) a modified internucleoside linkage, (ii) a modified sugar moiety, or (iii) a combination of the foregoing; and a targeting sequence which is complementary to a target region of 8 or more contiguous nucleotides within SMN2 pre-mRNA, such as a region within intron 6, exon 7, intron 7 or exon 8 (or a region which spans a splice junction) of the SMN2 gene. In further aspects, the modified antisense oligomers further comprise a peptide moiety which enhances cellular uptake.

Additional aspects include modified antisense oligomers of 8 to 40 subunits, comprising at least one subunit that is a nucleotide analog having (i) a modified internucleoside linkage, (ii) a modified sugar moiety, and (iii) a targeting sequence which is complementary to intron 6 or intron 7 of SMN2 pre-mRNA. In further aspects, the antisense oligomer comprises a sequence which is complimentary to the −7/−14, −7/−16, −10/−27, −10/−29, −10/−34, −137/−159, −149/−174, −167/−186, −249/−273, or −281/−299 region of intron 7 or the −58/−39, −112/−67, or −264/−245 region of intron 6 of SMN2 pre-mRNA. In some aspects, the modified antisense oligomer comprises a sequence which is complimentary to the −10/−27, −10/−29, or −10/−34 region of intron 7 of SMN2 pre-mRNA.

Additional aspects include modified antisense oligomers of 8 to 40 subunits, comprising at least one subunit that is a nucleotide analog having (i) a modified internucleoside linkage, (ii) a modified sugar moiety, and (iii) a targeting sequence comprising a sequence selected from SEQ ID NOS: 4 to 16. In some aspects, the antisense oligomer comprises a sequence selected from SEQ ID NOS: 6, 7, and 8.

Additional aspects include modified antisense oligomers having a nucleotide analog subunit comprising a modified sugar moiety. In various embodiments, at least one modified sugar moiety includes a peptide nucleic acid (PNA) subunit, a locked nucleic acid (LNA) subunit, a 2'O,4'C-ethylene-bridged nucleic acid (ENA) subunit, a tricyclo-DNA (tc- DNA) subunit, a 2' O-methyl subunit, a 2' O-methoxyethyl subunit, a 2'-fluoro subunit, a 2'-O-[2-(N-methylcarbamoyl)ethyl] subunit, and a morpholino subunit. In some embodiments, the modified antisense oligomer has at least one modified sugar moiety, wherein the at least one modified sugar moiety is a morpholino subunit.

Additional aspects include modified antisense oligomers having a nucleotide analog subunit comprising a modified internucleoside linkage. In various embodiments, the modified internucleoside is selected from a phosphorothioate internucleoside linkage, a phosphoramidate internucleoside linkage, a phosphorodiamidate internucleoside linkage, and a phosphorotriamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

Additional aspects include modified antisense oligomers having a nucleotide analog subunit comprising at least one combination of a modified sugar moiety and a modified internucleoside linkage, wherein one or more subunits are selected from:

a morpholino subunit optionally substituted with a phosphoramidate internucleoside linkage, a phosphorodiamidate internucleoside linkage, phosphorotriamidate internucleoside linkage, or a phosphorothioate internucleoside linkage, a 2' O-methyl subunit optionally substituted with a phosphoramidate internucleoside linkage, a phosphorodiamidate internucleoside linkage, or a phosphorothioate internucleoside linkage, a 2'O-methoxyethyl subunit optionally substituted with a phosphoramidate internucleoside linkage, a phosphorodiamidate internucleoside linkage, or a phosphorothioate internucleoside linkage, a 2'-fluoro subunit optionally substituted with a phosphoramidate internucleoside linkage, a phosphorodiamidate internucleoside linkage, or a phosphorothioate internucleoside linkages, a 2'O,4'C-ethylene-bridged nucleic acid subunit optionally substituted with a phosphoramidate internucleoside linkage, a phosphorodiamidate internucleoside linkage, or a phosphorothioate internucleoside linkage, a 2'-O-[2-(N-methylcarbamoyl)ethyl] subunit optionally substituted with a phosphoramidate internucleoside linkage, a phosphorodiamidate internucleoside linkage, or a phosphorothioate internucleoside linkage, a tricyclo-DNA subunit optionally substituted with a phosphoramidate internucleoside linkage, a phosphorodiamidate internucleoside linkage, or a phosphorothioate internucleoside linkage, a locked nucleic acid subunit optionally substituted with a phosphoramidate internucleoside linkage, a phosphorodiamidate internucleoside linkage, or a phosphorothioate internucleoside linkage, a morpholino subunit further comprising a phosphorodiamidate internucleoside linkage where a phosphorous atom of the phosphorodiamidate is covalently bonded to the nitrogen atom of the morpholino ring, and is covalently bonded to a (1,4-piperazin)-1-yl moiety or to a substituted (1,4-piperazin)-1-yl moiety, a morpholino subunit further comprising a phosphorodiamidate internucleoside linkage where a phosphorus atom of the phosphorodiamidate is covalently bonded to the nitrogen atom of the morpholino ring, and is covalently bonded to a 4-aminopiperdin-1-yl moiety or a substituted 4-aminopiperdin-1-yl moiety, a morpholino subunit further comprising a phosphorodiamidate internucleoside linkage where a phosphorus atom of the phosphorodiamidate is covalently bonded to the nitrogen atom of the morpholino ring, and is covalently bonded to a dimethylamino moiety, a ribose sugar subunit substituted with a phosphorothioate internucleoside or a phosphoramidate internucleoside linkage, a deoxyribose sugar subunit substituted with a phosphorothioate internucleoside linkage or a phosphoramidate internucleoside linkage, a peptide nucleic acid subunit optionally substituted, or any combination of the foregoing.

In various aspects and embodiments, antisense oligomers further comprise a peptide covalently bonded to the antisense oligomer. In various embodiments, an arginine-rich cell-penetrating peptide is conjugated to the 3' or the 5' end of the antisense oligomer.

In various embodiments, the antisense oligomer comprises any of the following: a targeting sequence set forth in Table 1, a fragment of at least 8 contiguous nucleotides of a targeting sequence in Table 1, or a variant having at least 90% sequence identity to a targeting sequence in Table 1. In further embodiments, the antisense oligomer consists or consists essentially of a targeting sequence set forth in Table 1.

In various aspects and embodiments, a nucleobase of a nucleotide subunit is independently selected from adenine, guanine, thymine, uracil, cytosine, inosine, hypoxanthine, 2,6-diaminopurine, 5-methyl cytosine, C5-propynyl-modified pyrimidines, and 10-(9-(aminoethoxy)phenoxazinyl).

In various aspects, the antisense oligomer of the disclosure is a compound of formula (I):

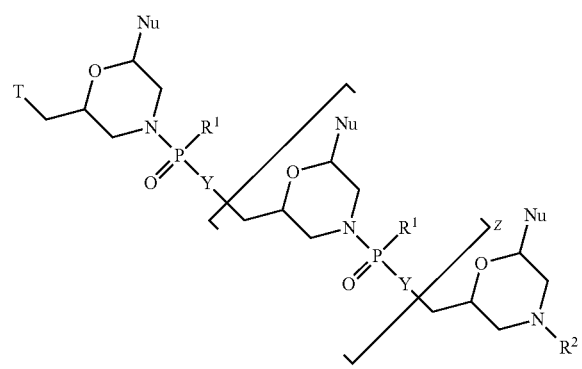

or a pharmaceutically acceptable salt thereof, where:

each Nu is a nucleobase which taken together forms a targeting sequence;

Z is an integer from 6 to 38;

each Y is independently selected from O and —NR$^4$ where each R$^4$ is independently selected from H, $C_1$-$C_6$ alkyl, aralkyl, —C(=NH)NH$_2$, —C(O)(CH$_2$)$_n$NR$^5$C(=NH)NH$_2$, —C(O)(CH$_2$)$_2$NHC(O)(CH$_2$)$_5$NR$^5$C(=NH)NH$_2$, and G, where R$^5$ is selected from H and $C_1$-$C_6$ alkyl and n is an integer from 1 to 5;

T is selected from OH and a moiety of the formula:

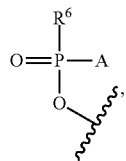

where:
A is selected from —OH and —N(R⁷)₂R⁸ where:
each $R^7$ is independently selected from H and $C_1$-$C_6$ alkyl, and
$R^8$ is selected from an electron pair and H, and
$R^6$ is selected from OH, —N(R⁹)CH₂C(O)NH₂, and a moiety of the formula:

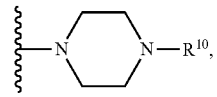

where:
$R^9$ is selected from H and $C_1$-$C_6$ alkyl; and
$R^{10}$ is selected from G, —C(O)—R¹¹OH, acyl, trityl, 4-methoxytrityl, —C(=NH)NH₂, —C(O)(CH₂)ₘNR¹²C(=NH)NH₂, and —C(O)(CH₂)₂NHC(O)(CH₂)₅NR¹²C(=NH)NH₂, where:
m is an integer from 1 to 5,
$R^{11}$ is of the formula —(O-alkyl)ᵧ- where y is an integer from 3 to 10 and
each of the y alkyl groups is independently selected from $C_2$-$C_6$ alkyl; and
$R^{12}$ is selected from H and $C_1$-$C_6$ alkyl;
each instance of $R^1$ is independently selected from:
—N(R¹³)₂R¹⁴ where each $R^{13}$ is independently selected from H and $C_1$-$C_6$ alkyl, and $R^H$ is selected from an electron pair and H;
a moiety of formula (II):

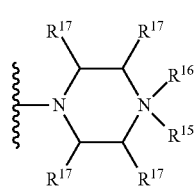

where:
$R^{15}$ is selected from H, G, $C_1$-$C_6$ alkyl, —C(=NH)NH₂, —C(O)(CH₂)_qNR¹⁸C(=NH)NH₂, and —C(O)(CH₂)₂NHC(O)(CH₂)₅NR¹⁸C(=NH)NH₂, where:
$R^{18}$ is selected from H and $C_1$-$C_6$ alkyl; and
q is an integer from 1 to 5,
$R^{16}$ is selected from an electron pair and H; and
each $R^{17}$ is independently selected from H and methyl; and a moiety of formula (III):

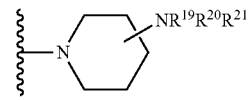

where:
$R^{19}$ is selected from H, $C_1$-$C_6$ alkyl, —C(=NH)NH₂,
—C(O)(CH₂)ᵣNR²²C(=NH)NH₂,
—C(O)CH(NH₂)(CH₂)₃NHC(=NH)NH₂,
—C(O)(CH₂)₂NHC(O)(CH₂)₅NR²²C(=NH)NH₂,
—C(O)CH(NH₂)(CH₂)₄NH₂ and G, where:
$R^{22}$ is selected from H and $C_1$-$C_6$ alkyl; and
r is an integer from 1 to 5,
$R^{20}$ is selected from H and $C_1$-$C_6$ alkyl; and
$R^{21}$ is selected from an electron pair and H; and
$R^2$ is selected from H, G, acyl, trityl, 4-methoxytrityl, $C_1$-$C_6$ alkyl, —C(=NH)NH₂, —C(O)—R²³, —C(O)(CH₂)ₛNR²⁴C(=NH)NH₂, —C(O)(CH₂)₂NHC(O)(CH₂)₅NR²⁴C(=NH)NH₂, —C(O)CH(NH₂)(CH₂)₃NHC(=NH)NH₂, and a moiety of the formula:

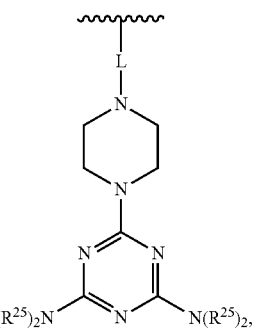

where,
$R^{23}$ is of the formula —(O-alkyl) OH where v is an integer from 3 to 10 and each of the v alkyl groups is independently selected from $C_2$-$C_6$ alkyl; and
$R^{24}$ is selected from H and $C_1$-$C_6$ alkyl;
s is an integer from 1 to 5;
L is selected from —C(O)(CH₂)₆C(O)— and —C(O)(CH₂)₂S₂(CH₂)₂C(O)—; and
each $R^{25}$ is of the formula —(CH₂)₂OC(O)N(R²⁶)₂ where each $R^{26}$ is of the formula —(CH₂)₆NHC(=NH)NH₂,
where G is a cell penetrating peptide ("CPP") and linker moiety selected from —C(O)(CH₂)₅NH—CPP, —C(O)(CH₂)₂NH—CPP, —C(O)(CH₂)₂NHC(O)(CH₂)₅NH—CPP, and —C(O)CH₂NH—CPP, or G is of the formula:

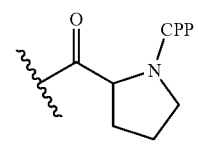

where the CPP is attached to the linker moiety by an amide bond at the CPP carboxy terminus, with the proviso that up to one instance of G is present, and
where the targeting sequence is complementary to 8 or more contiguous nucleotides in a target region of within the SMN2 pre-mRNA. In some embodiments, the contiguous nucleotides include a target region of 8 or more continuous nucleotides within intron 6 or intron 7 of the SMN2 pre-mRNA.

In various embodiments, Nu is independently adenine, guanine, thymine, uracil, cytosine, inosine, hypoxanthine, 2,6-diaminopurine, 5-methyl cytosine, C5-propynyl-modified pyrimidines, or 10-(9-(aminoethoxy)phenoxazinyl).

In various embodiments, the targeting sequence (a) comprises a sequence selected from SEQ ID NOS: 4 to 16, (b) is selected from SEQ ID NOS: 4 to 16, (c) is a fragment of at least 8 contiguous nucleotides of a targeting sequence selected from SEQ ID NOS: 4 to 16, or (d) is a variant having at least 90% sequence identity to a targeting sequence selected from SEQ ID NOS: 4 to 16, wherein each X is independently selected from uracil (U) or thymine (T), and wherein each Y is independently selected from cytosine (C) or 5-Methylcytosine (5mC). In some embodiments, each X of SEQ ID NOS: 4 to 16 is thymine (T), and each Y of SEQ ID NOS: 4 to 16 is cytosine (C).

In some embodiments, the targeting sequence of formula (I) is selected from:
a) SEQ ID NO: 7 (XYAYXXXYAXAAXGYXGG) wherein Z is 16;
b) SEQ ID NO: 8 (AXXYAYXXXYAXAAXGYXGG) wherein Z is 18; and
c) SEQ ID NO: 6 (GXAAGAXXYAYXXXYAXAAXGYXGG) wherein Z is 23;
wherein each X is independently selected from uracil (U) or thymine (T), and wherein each Y is independently selected from cytosine (C) or 5-Methylcytosine (5mC). In some embodiments, each X of SEQ ID NOS: 6 to 8 is thymine (T), and each Y of SEQ ID NOS: 6 to 8 is cytosine (C).

In various embodiments, at least one X of the targeting sequence is T. In various embodiments, each X of the targeting sequence is T.

In various embodiments, at least one X of the targeting sequence is U. In various embodiments, each X of the targeting sequence is U.

In various embodiments, at least one Y of the targeting sequence is 5mC. In various embodiments, each Y of the targeting sequence is 5mC.

In various embodiments, at least one Y of the targeting sequence is C. In various embodiments, each Y of the targeting sequence is C.

In various embodiments, at least one X of SEQ ID NOS: 4 to 16 is T. In various embodiments, each X of SEQ ID NOS: 4 to 16 is T.

In various embodiments, at least one X of SEQ ID NOS: 4 to 16 is U. In various embodiments, each X of SEQ ID NOS: 4 to 16 is U.

In various embodiments, at least one Y of SEQ ID NOS: 4 to 16 is 5mC. In various embodiments, each Y of SEQ ID NOS: 4 to 16 is 5mC.

In various embodiments, at least one Y of SEQ ID NOS: 4 to 16 is C. In various embodiments, each Y of SEQ ID NOS: 4 to 16 is C.

In various embodiments, $R^1$ of formula (I) is —$N(CH_3)_2$. In some embodiments, about 50% to about 95% of the $R^1$ groups are —$N(CH_3)_2$. In some embodiments, at least one $R^1$ is selected from:

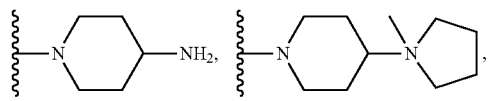

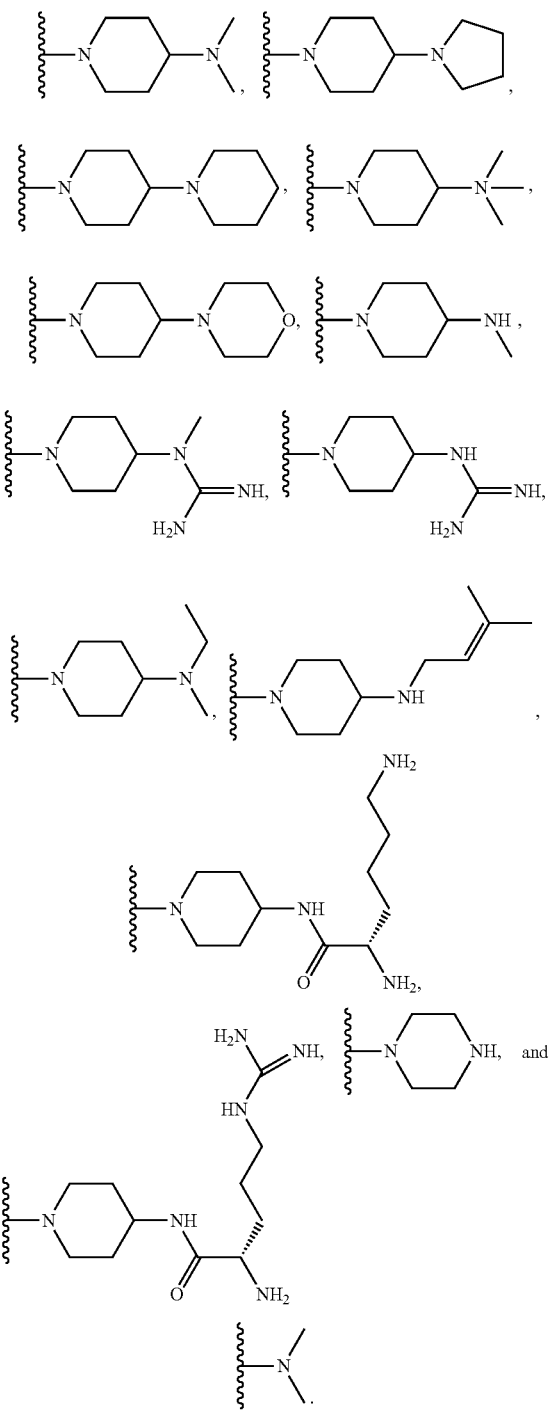

In various embodiments, T is of the formula:

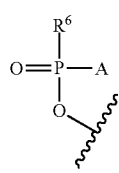

where A is —N(CH$_3$)$_2$, and R$^6$ is of the formula:

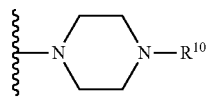

where R$^{10}$ is —C(O)R$^{11}$OH.

In various embodiments, the antisense oligomer is a compound of formula (V):

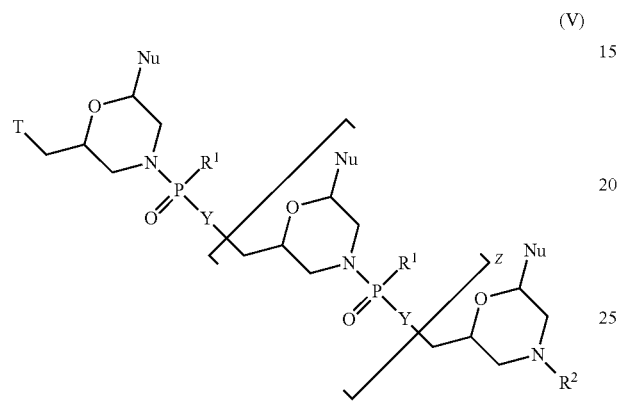

(V)

or a pharmaceutically acceptable salt thereof, wherein:
each Nu is a nucleobase which taken together forms a targeting sequence;
Z is an integer from 6 to 38;
each Y is independently selected from O and —NR$^4$, wherein each R$^4$ is independently selected from H, C$_1$-C$_6$ alkyl, aralkyl, —C(=NH)NH$_2$, —C(O)(CH$_2$)$_{11}$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and C$_1$-C$_6$ alkyl and n is an integer from 1 to 5;
T is selected from OH and a moiety of the formula:

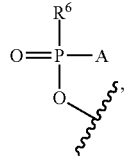

wherein:
A is selected from —OH, —N(R$^7$)$_2$R$^8$, and R$^1$ wherein:
each R$^7$ is independently selected from H and C$_1$-C$_6$ alkyl, and
R$^8$ is selected from an electron pair and H, and
R$^6$ is selected from OH, —N(R$^9$)CH$_2$C(O)NH$_2$, and a moiety of the formula:

wherein:
R$^9$ is selected from H and C$_1$-C$_6$ alkyl; and
R$^{10}$ is selected from G, —C(O)—R$^{11}$OH, acyl, trityl, 4-methoxytrityl, —C(=NH)NH$_2$, —C(O)(CH$_2$)$_m$NR$^{12}$C(=NH)NH$_2$, and —C(O)(CH$_2$)$_2$NHC(O)(CH$_2$)$_5$NR$^{12}$C(=NH)NH$_2$, wherein:
m is an integer from 1 to 5,
R$^{11}$ is of the formula —(O-alkyl)$_y$- wherein y is an integer from 3 to 10 and
each of the y alkyl groups is independently selected from C$_2$-C$_6$ alkyl; and
R$^{12}$ is selected from H and C$_1$-C$_6$ alkyl;
each instance of R$^1$ is independently selected from:
—N(R$^{13}$)$_2$R$^{14}$ wherein each R$^{13}$ is independently selected from H and C$_1$-C$_6$ alkyl, and R$^{14}$ is selected from an electron pair and H;
a moiety of formula (II):

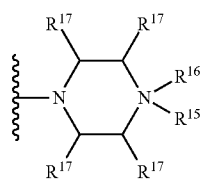

(II)

wherein:
R$^{15}$ is selected from H, G, C$_1$-C$_6$ alkyl, —C(=NH)NH$_2$, —C(O)(CH$_2$)$_q$NR$^{18}$C(=NH)NH$_2$, and —C(O)(CH$_2$)$_2$NHC(O)(CH$_2$)$_5$NR$^{18}$C(=NH)NH$_2$, wherein:
R$^{18}$ is selected from H and C$_1$-C$_6$ alkyl; and
q is an integer from 1 to 5,
R$^{16}$ is selected from an electron pair and H; and
each R$^{17}$ is independently selected from H and methyl; and
a moiety of formula (III):

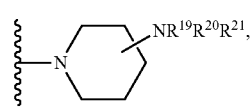

(III)

wherein:
R$^{19}$ is selected from H, C$_1$-C$_6$ alkyl, —C(=NH)NH$_2$, —C(O)(CH$_2$)$_r$NR$^{22}$C(=NH)NH$_2$, —C(O)CH(NH$_2$)(CH$_2$)$_3$NHC(=NH)NH$_2$, —C(O)(CH$_2$)$_2$NHC(O)(CH$_2$)$_5$NR$^{22}$C(=NH)NH$_2$, —C(O)CH(NH$_2$)(CH$_2$)$_4$NH$_2$, and G, wherein:
R$^{22}$ is selected from H and C$_1$-C$_6$ alkyl; and
r is an integer from 1 to 5,
R$^{20}$ is selected from H and C$_1$-C$_6$ alkyl; and
R$^{21}$ is selected from an electron pair and H; and
R$^2$ is selected from G, H, acyl, trityl, 4-methoxytrityl, and C$_1$-C$_6$ alkyl,
wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

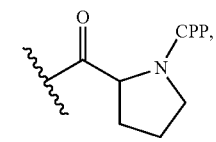

wherein the CPP is attached to the linker moiety by an amide bond at the CPP carboxy terminus, with the proviso that up to one instance of G is present, and wherein at least one of the following conditions is present:

a) at least one are $R^1$ is of formula (II) or of formula (III), or b) $R^2$ is G or T is:

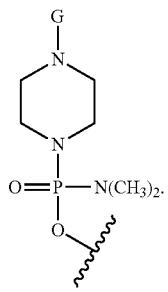

In various embodiments, the targeting sequence of compound (V) (a) comprises a sequence selected from SEQ ID NOS: 4 to 16, (b) is selected from SEQ ID NOS: 4 to 16, (c) is a fragment of at least 8 contiguous nucleotides of a sequence selected from SEQ ID NOS: 4 to 16, or (d) is a variant having at least 90% sequence identity to a sequence selected from SEQ ID NOS: 4 to 16, wherein each X is independently selected from uracil (U) or thymine (T), and wherein each Y is independently selected from cytosine (C) or 5-Methylcytosine (5mC). In some embodiments, each X of SEQ ID NOS: 4 to 16 is thymine (T), and each Y of SEQ ID NOS: 4 to 16 is cytosine (C).

In some embodiments, the targeting sequence of formula (V) is selected from:

a) SEQ ID NO: 7 (XYAYXXXYAXAAXGYXGG) wherein Z is 16;

b) SEQ ID NO: 8 (AXXYAYXXXYAXAAXGYXGG) wherein Z is 18; and c) SEQ ID NO: 6 (GXAAGAXXYAYXXXYAX-AAXGYXGG) wherein Z is 23;

wherein each X is independently selected from uracil (U) or thymine (T), and wherein each Y is independently selected from cytosine (C) or 5-Methylcytosine (5mC). In some embodiments, each X of SEQ ID NOS: 6 to 8 is thymine (T), and each Y of SEQ ID NOS: 6 to 8 is cytosine (C)

In various embodiments, at least one X of the targeting sequence is T. In various embodiments, each X of the targeting sequence is T.

In various embodiments, at least one X of the targeting sequence is U. In various embodiments, each X of the targeting sequence is U.

In various embodiments, at least one Y of the targeting sequence is 5mC. In various embodiments, each Y of the targeting sequence is 5mC.

In various embodiments, at least one Y of the targeting sequence is C. In various embodiments, each Y of the targeting sequence is C.

In various embodiments, at least one X of SEQ ID NOS: 4 to 16 is T. In various embodiments, each X of SEQ ID NOS: 4 to 16 is T.

In various embodiments, at least one X of the targeting sequence is U. In various embodiments, each X of SEQ ID NOS: 4 to 16 is U.

In various embodiments, at least one Y of SEQ ID NOS: 4 to 16 is 5mC. In various embodiments, each Y of SEQ ID NOS: 4 to 16 is 5mC.

In various embodiments, at least one Y of SEQ ID NOS: 4 to 16 is C. In various embodiments, each Y of SEQ ID NOS: 4 to 16 is C.

In some embodiments, the targeting sequence is selected from SEQ ID NOS: 4 to 16.

In various embodiments, the antisense oligomer further comprises a peptide moiety which enhances cellular uptake.

In various aspects, modified antisense oligomers comprising a targeting sequence complementary to 8 or more contiguous nucleotides in a target region within SMN2 pre-mRNA are provided. In some embodiments, the contiguous nucleotides include a target region of 8 or more continuous nucleotides within intron 6 or intron 7 of the SMN2 pre-mRNA. In some embodiments, the targeting sequence (a) comprises one of SEQ ID NOS: 4 to 16, (b) is selected from SEQ ID NOS: 4 to 16, (c) is a fragment of at least 8 contiguous nucleotides of a sequence selected from SEQ ID NOS: 4 to 16, or (d) is a variant having at least 90% sequence identity to a sequence selected from SEQ ID NOS: 4 to 16, wherein each X is independently selected from uracil (U) or thymine (T), and wherein each Y is independently selected from cytosine (C) or 5-Methylcytosine (5mC). In various embodiments, the targeting sequence comprises SEQ ID NOS: 4 to 16.

Also included are pharmaceutical compositions, comprising a physiologically-acceptable carrier and a modified antisense oligomer described herein.

Various aspects relate to methods of treating spinal muscular atrophy (SMA) in a subject in need thereof including, administering to the subject in need thereof an effective amount of a modified antisense oligomer described herein. Such methods include administering to the patient a modified antisense oligonucleotide comprising a nucleotide sequence of sufficient length and complementarity to specifically hybridize to a region within the SMN2 gene, such that the level of exon 7-containing SMN2 mRNA relative to exon-deleted SMN2 mRNA is enhanced, thereby treating the patient. In various embodiments, the antisense oligomer comprises a modified antisense oligomer as described herein. In further embodiments, the antisense oligomer comprises a morpholino moiety.

Methods for increasing the expression of functional Survival of Motor Neuron (SMN) protein include administering a modified antisense oligomer to a subject in need thereof, where the modified antisense oligomer binds to a target region of a SMN2 pre-mRNA, where expression of functional SMN protein is increased. Expression of SMN2 mRNA containing exon 7 is increased. In various embodiments, the target is a region within intron 6 or intron 7 of SMN2 pre-mRNA. In further embodiments, the target region is a region within intron 7 of SMN2 pre-mRNA. In further embodiments, the modified antisense oligomer comprises a morpholino moiety.

In various embodiments, administering a modified antisense oligomer of the disclosure results in an increase of at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% in the amount of SMN2 mRNA having exon 7.

In various embodiments, administering a modified antisense oligomer of the disclosure results in an increase of at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% in the amount of functional SMN protein expressed.

Medicaments for the treatment of spinal muscular atrophy (SMA) are provided comprising a modified antisense oligomer compound of 8 to 40 subunits, comprising at least one subunit that is a nucleotide analog having (i) a modified internucleoside linkage, (ii) a modified sugar moiety, or (iii) a combination of the foregoing; and a targeting sequence complementary to 8 or more contiguous nucleotides in a target region within SMN2 pre-mRNA, where the contiguous nucleotides include a target region of 8 or more continuous nucleotides within intron 6 or intron 7 of the SMN2 pre-mRNA. In some embodiments, the modified antisense oligomer comprises a morpholino moiety.

Methods of inhibiting the progression of spinal muscular atrophy (SMA) include administering a modified antisense oligomer as described herein that binds to a target region of SMN2 pre-mRNA and increases translation of functional SMN protein. In some embodiments, the modified antisense oligomer comprises a morpholino moiety.

Methods of treating spinal muscular atrophy in a subject in need thereof, include, in various embodiments, administering to the subject an effective amount of a modified antisense oligomer of the disclosure, where the modified antisense oligomer binds to a target region of SMN2 pre-mRNA, and where expression of functional SMN protein is increased. Further aspects include modified antisense oligomers for use in the preparation of a medicament for the treatment of spinal muscular atrophy. In some embodiments, the modified antisense oligomer comprises a morpholino moiety.

In certain embodiments, the methods described herein comprises increasing the expression levels of functional SMN protein in a subject by at least about 10% relative to a control, by administering to the subject an effective amount of a modified antisense oligomer of the disclosure. In some embodiments, the levels of functional SMN protein in a subject are increased by at least about 5, 10, 20, 30, 40, 50, 60, 70, 80, 90, and 100%.

These and other aspects of the present disclosure will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1D, 1E, 1F and 1G illustrate a repeating subunit segment of exemplary phosphorodiamidate morpholino-based oligomers, designated D through G.

DETAILED DESCRIPTION

I. Definitions

Figure 1A:
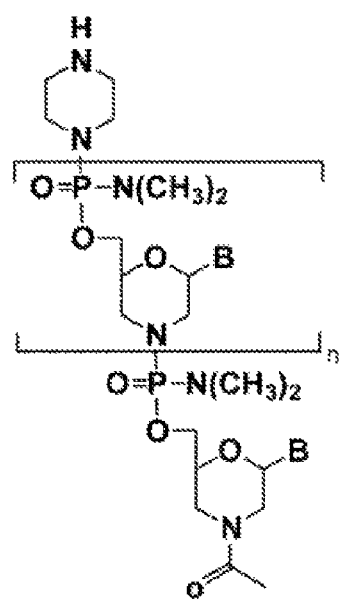
FIG. 1A illustrates an embodiment of a modified oligomer.
Figure 1B:
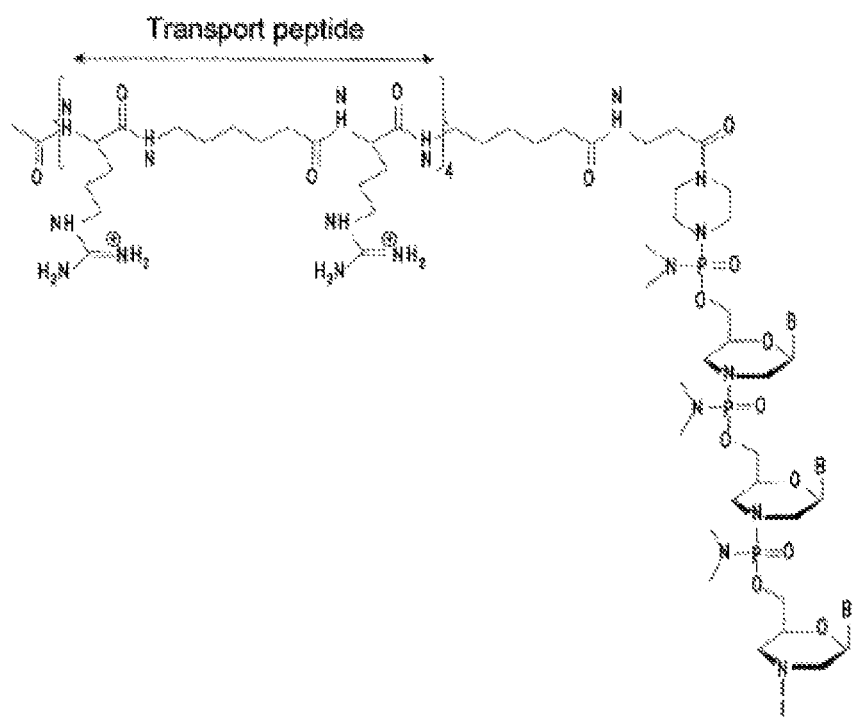
FIGS. 1B and 1C illustrates an antisense oligomer conjugated to a cell penetrating peptide (CPP).
Figure 1C:
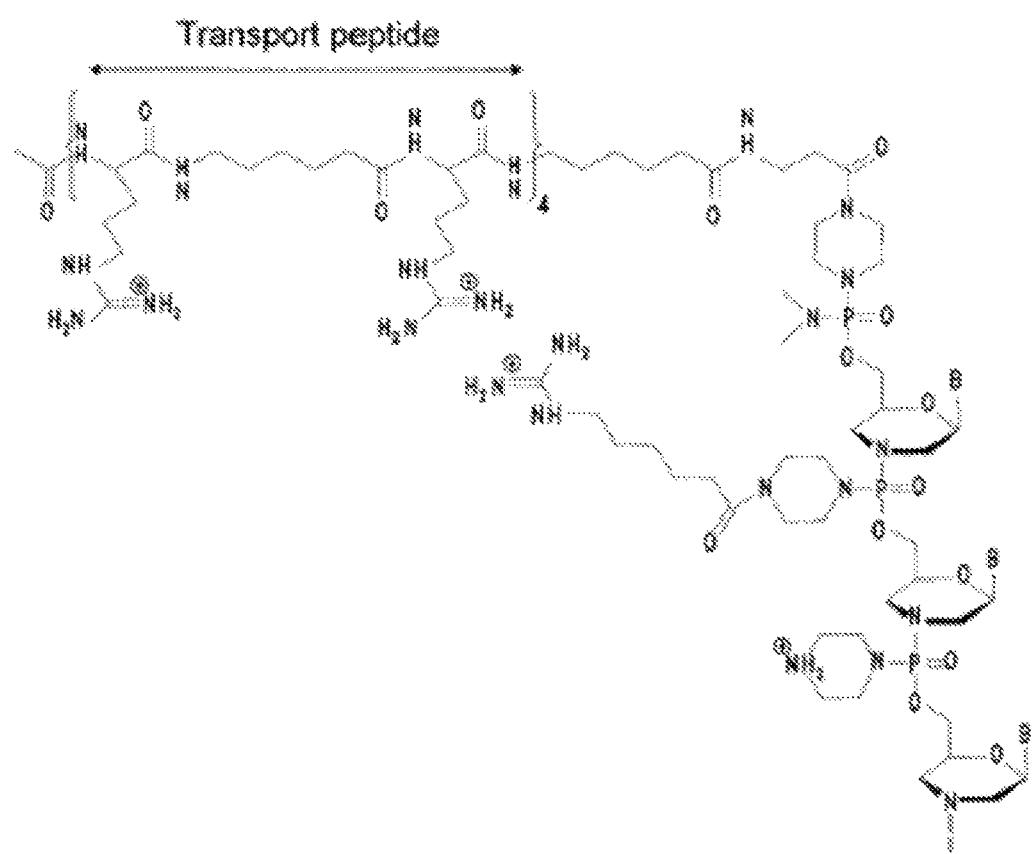
Figure 2A:
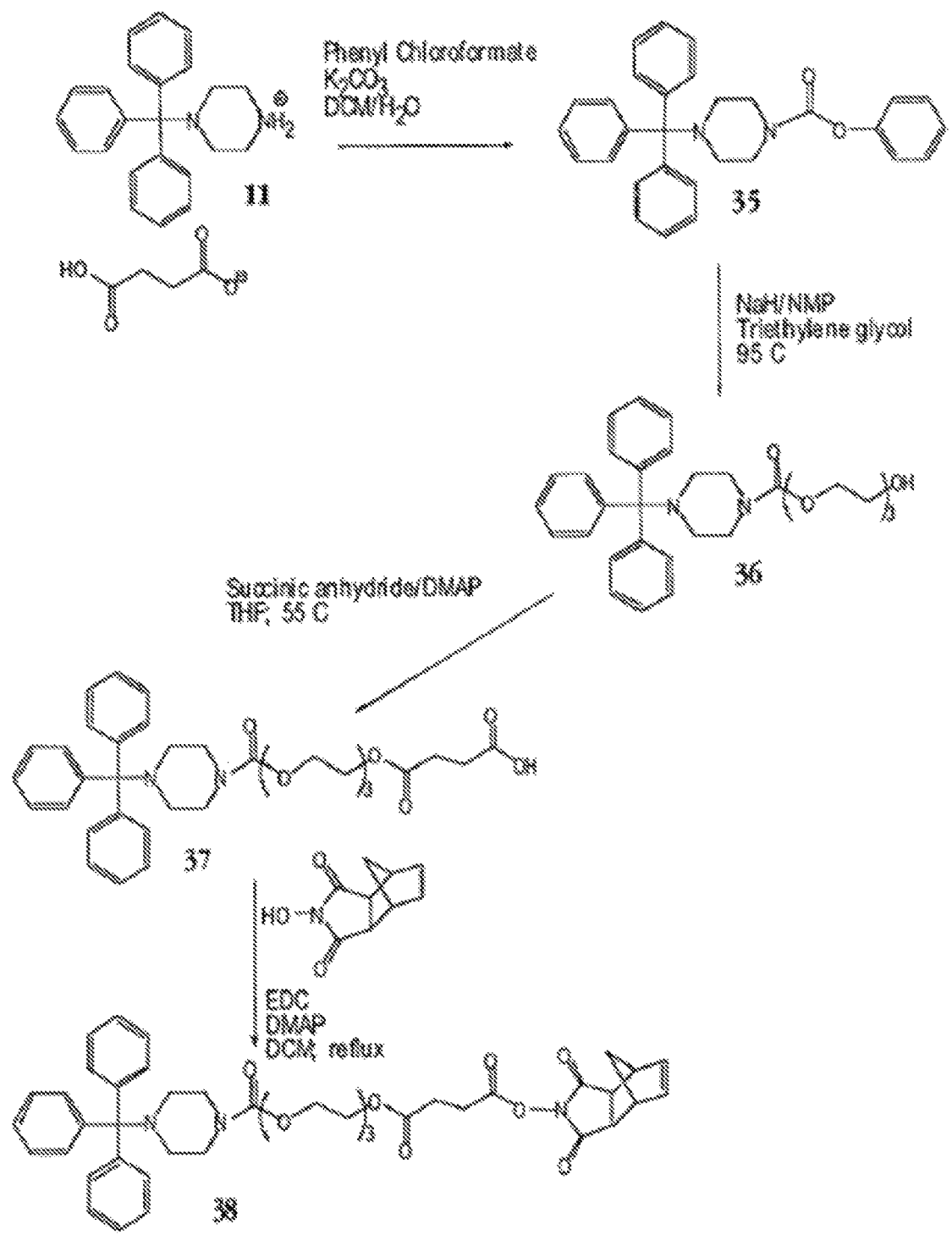
FIG. 2A illustrates preparation of trityl piperazine phenyl carbamate.
Figure 2B:
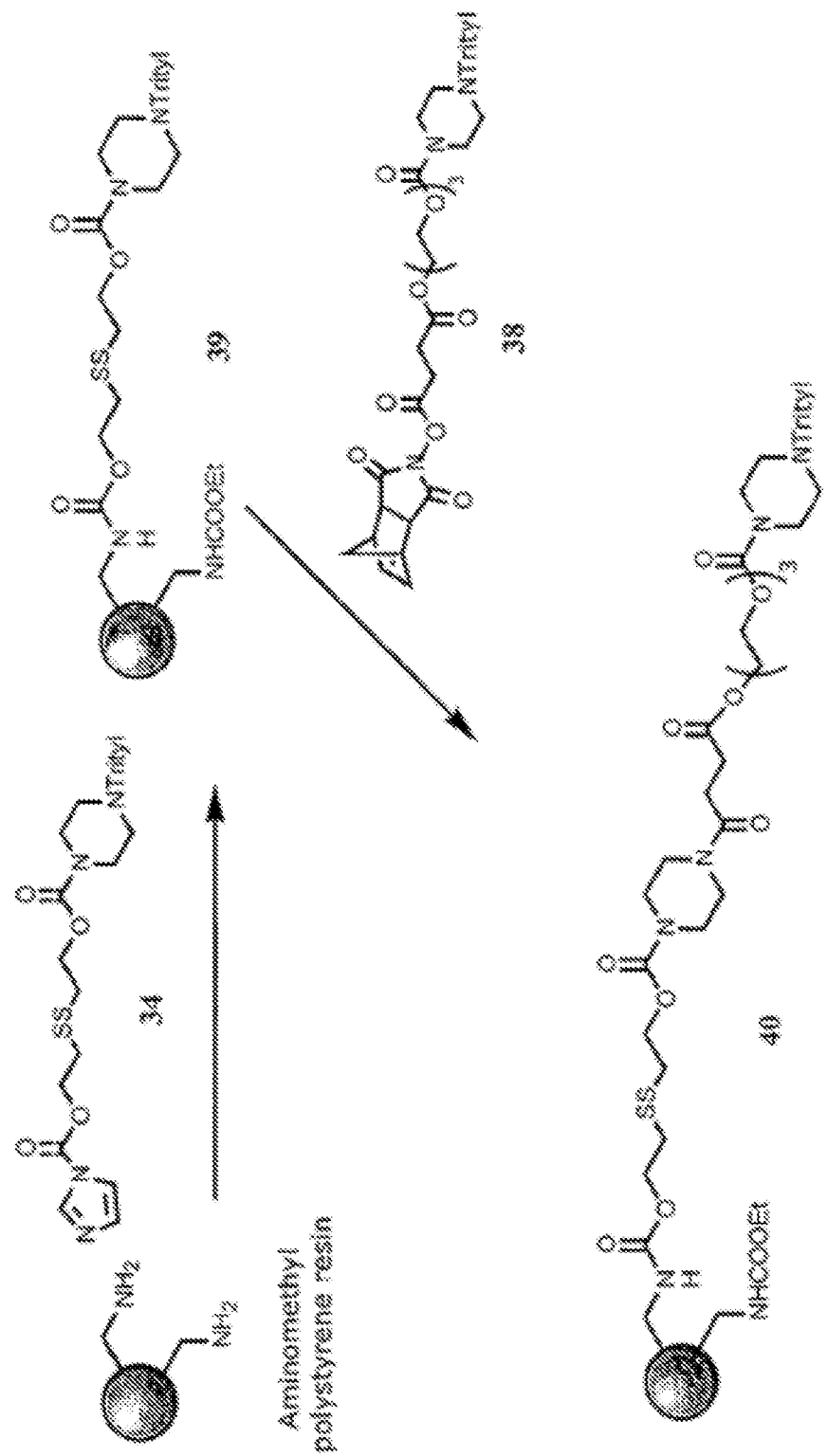
FIG. 2B illustrates preparation of a resin/reagent mixture.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the subject matter of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

The term "about" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. When the term "about" is used in conjunction with a numerical range, it modifies that range by extending the boundaries above and below the numerical values set forth. In general, the term "about" is intended to modify a numerical value above and below the stated value by a variance of 10%.

The terms "sequence" and "coding sequence" mean any nucleic acid sequence that contributes to the code for the polypeptide product of a gene. By contrast, the term "non-coding sequence" refers to any nucleic acid sequence that does not directly contribute to the code for the polypeptide product of a gene.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

The term "consisting of" means including, and limited to, whatever follows the phrase "consisting of" Thus, the phrase "consisting of" indicates that the listed elements are required or mandatory, and that no other elements may be present. The term "consisting essentially of" means including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "administering," or "administer" include delivery of the modified antisense oligomers of the disclosure to a subject either by local or systemic administration. Administration may be topical (including ophthalmic and to mucous membranes including vaginal and rectal delivery), pulmonary, e.g., by inhalation or insufflation of powders or aerosols, including by nebulizer, intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

The terms "contacting a cell," "introducing" or "delivering" include delivery of the oligomers of the disclosure into a cell by methods routine in the art, e.g., transfection (e.g., liposome, calcium-phosphate, polyethyleneimine), electroporation (e.g., nucleofection), microinjection).

The term "alkyl" refers to a linear (i.e., unbranched or acyclic), branched, cyclic, or polycyclic non aromatic hydrocarbon groups, which are optionally substituted with one or more functional groups. Unless otherwise specified, "alkyl" groups contain one to eight, and preferably one to six carbon atoms. $C_1$-$C_6$ alkyl, is intended to include $C_1$, $C_2$, $C_3$, $C_4$, $C_5$, and $C_6$ alkyl groups. Lower alkyl refers to alkyl groups containing 1 to 6 carbon atoms. Examples of alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

The term "alkoxy" refers to a subset of alkyl in which an alkyl group as defined above with the indicated number of carbons attached through an oxygen bridge. For example, "alkoxy" refers to groups —O-alkyl, where the alkyl group contains 1 to 8 carbons atoms of a linear, branched, cyclic configuration. Examples of "alkoxy" include, but are not limited to, methoxy, ethoxy, n-propoxy, i-propoxy, t-butoxy, n-butoxy, s-pentoxy and the like.

The term "aryl" used alone or as part of a larger moiety as in "aralkyl,", "aralkoxy," or "aryloxy-alkyl," refers to aromatic ring groups having six to fourteen ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring." "Aryl" also includes fused polycyclic aromatic ring systems in which an aromatic ring is fused to one or more rings. Non-limiting examples of useful aryl ring groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl," as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "acyl" refers to a C(O)R group (in which R signifies H, alkyl or aryl as defined above). Examples of acyl groups include formyl, acetyl, benzoyl, phenylacetyl and similar groups.

The term "homolog" refers to compounds differing regularly by the successive addition of the same chemical group. For example, a homolog of a compound may differ by the addition of one or more —$CH_2$— groups, amino acid residues, nucleotides, or nucleotide analogs.

The terms "cell penetrating peptide" (CPP) or "a peptide moiety which enhances cellular uptake" are used interchangeably and refer to cationic cell penetrating peptides, also called "transport peptides," "carrier peptides," or "peptide transduction domains." For example, a peptide-conjugated phosphoramidate or phosphorodiamidate morpholino (PPMO) may include a cell penetrating peptide or peptide moiety which enhances cellular uptake as described herein. In various embodiments, a peptide may be covalently bonded to the modified antisense oligomer. In further embodiments, a peptide may be conjugated to the 3' end or the 5' end of the modified antisense oligomer. In further embodiments, a peptide may be linked to a piperazinyl moiety or to a nitrogen atom of the 3' terminal morpholino ring. In some embodiments, a cell penetrating peptide or peptide moiety which enhances cellular uptake may include an arginine-rich peptide as described herein. In a non-limiting example, modified antisense oligomers as disclosed herein can be coupled to an arginine-rich peptide such as (Arg)6Gly (6 arginine and 1 glycine linked to an oligonucleotide).

The peptides, as shown herein, have the capability of inducing cell penetration within about or at least about 30%, 40%, 50%, 60%, 70%, 80%, 90%, or 100% of cells of a given cell culture population and allow macromolecular translocation within multiple tissues in vivo upon systemic administration. In some embodiments, the CPPs are of the formula —$[(C(O)CHR'NH)_m]R''$ where R' is a side chain of a naturally occurring amino acid or a one- or two-carbon homolog thereof, R" is selected from Hydrogen or acyl, and m is an integer up to 50. Additional CPPs are well-known in the art and are disclosed, for example, in U.S. Published Application No. 20100016215, which is hereby incorporated by reference in its entirety. In other embodiments, m is an integer selected from 1 to 50 where, when m is 1, the moiety is a single amino acid or derivative thereof.

The term "amino acid" refers to a compound comprising a carbon atom to which are attached a primary amino group, a carboxylic acid group, a side chain, and a hydrogen atom. For example, the term "amino acid" includes, but is not limited to, Glycine, Alanine, Valine, Leucine, Isoleucine, Asparagine, Glutamine, Lysine, Aspartic Acid, Histidine, Methionine, Proline, Phenylalanine, Threonine, Tryptophan, Cysteine, Glutamic Acid, Serine, Tyrosine, Pyrolysine, Selenocystenine and Arginine. Additionally, as used herein, "amino acid" also includes derivatives of amino acids such as esters, and amides, and salts, as well as other derivatives, including derivatives having pharmaco properties upon metabolism to an active form. Accordingly, the term "amino acid" is understood to include naturally occurring and non-naturally occurring amino acids.

The term "an electron pair" refers to a valence pair of electrons that are not bonded or shared with other atoms.

The term "homology" refers to the percentage number of amino acids that are identical or constitute conservative substitutions. Homology may be determined using sequence comparison programs such as GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

The term "isolated" refers to a material that is substantially or essentially free from components that normally accompany it in its native state. For example, an "isolated oligonucleotide," or "isolated oligomer" as used herein, may refer to an oligomer that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with an oligonucleotide repeat disease). In the context of mRNA or protein, "isolating" refers to the recovery of mRNA or protein from a source, e.g., cells.

The term "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or more modified antisense oligomer compounds or compositions to produce or cause a greater physiological response (e.g., downstream effects) in a cell or a subject relative to the response caused by either no antisense oligomer compound or a control compound. Relevant physiological or cellular responses (in vivo or in vitro) will be apparent to persons skilled in the art, and may include increases in the inclusion of exon 7 in SMN2 mRNA, and/or an increase in the expression of functional SMN protein in a cell, or tissue, such as in a subject in need thereof. A "decreased" or "reduced" amount is typically a "statistically significant" amount, and may include a decrease that is 1, 2, 3, 4, 5, 6, 7, 8, 9, 10, 15, 20, 30, 40, 50 or more times less (e.g., 100, 500, 1000 times), including all integers and decimal points in between and above 1 (e.g., 1.1, 1.2, 1.3, 1.4, 1.5, 1.6, 1.7, 1.8, 1.9), the amount produced by a subject in need thereof in the absence of administration of a modified antisense oligomer compound (e.g. the "native" or "natural" rate of expression of a specific subject or cohort) or a control compound. The terms "reduce" or "inhibit" may relate generally to the ability of one or more antisense oligomer compounds or compositions to "decrease" a relevant physiological or cellular response, such as a symptom of a disease or condition described herein, as measured according to routine techniques in the diagnostic art. An "increased" or "enhanced" amount is typically a "statistically significant" amount, and may include an increase that is 1, 2, 3, 4, 5, 6, 7, 8, 9, 10, 15, 20, 30, 40, 50 or more times greater than (e.g., 100, 500, 1000 times), including all integers and decimal points in between and above 1 (e.g., 1.1, 1.2, 1.3, 1.4, 1.5, 1.6, 1.7, 1.8, 1.9), the amount produced by a subject in need thereof in the absence of administration of a modified antisense oligomer compound (e.g. the "native" or "natural" rate of expression of a specific subject or cohort) or a control compound. The term "enhance" may relate generally to the ability of one or more modified antisense oligomer compounds or compositions to "increase" a relevant physiological or cellular response, such as a symptom of a disease or condition described herein, as measured according to routine techniques in the diagnostic art.

Relevant physiological or cellular responses (in vivo or in vitro) will be apparent to persons skilled in the art, and may include reductions in the symptoms or pathology of spinal muscular atrophy (SMA), such as SMA Type I, SMA Type II, SMA Type III, and SMA Type IV. In other embodiments, methods of treating spinal muscular atrophy are provided, for example, where a reduction in symptoms or pathology may accompany or relate to an increase in the expression of functional SMN protein. An "increase" in a response may be "statistically significant" as compared to the response produced by a subject in need thereof in the absence of administration of a modified antisense oligomer compound (e.g. the "native" or "natural" rate of expression of a specific subject or cohort) or a control compound, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase, including all integers in between.

The term "functional" in reference to a SMN protein includes those SMN proteins derived from an mRNA transcription where exon 7 is included and/or possessing the functionality of wild-type or normal SMN protein.

A non-functional, dysfunctional or inactive protein includes a protein derived from a mRNA transcript excluding exon 7 and/or having little to no functionality of wild-type SMN protein.

Thus, in various embodiments, the presence of, expression of, or increased expression of functional SMN protein may be determined, for example, by western blot analysis and SMN2 gene expression of, for example, SMA patient derived fibroblasts treated with a modified antisense oligomer of the present disclosure. In various embodiments, treatment of SMA fibroblasts or a subject in need of treatment of SMA with a modified antisense oligomer of the disclosure may result in expression of exon 7-included SMN protein in an amount that is, for example, about 5%, 10%, 15%, 20%, 25%, 30%, 35%, 40%, 45%, 50%, 55%, 60%, 65%, 70%, 75%, 80%, 85%, 90%, 95%, or 100%, or any of the percentile ranges disclosed above, of the normal amount of SMN protein expressed in normal cells or a normal subject.

In various embodiments, functionality of exon 7-included SMN protein expressed by a tissue or a subject in need of treatment of SMA may be determined by immunohistochemical analysis of, for example, the architecture of neuromuscular junctions in muscles, the quantity and quality of motor neurons in spinal cord, the amount of exon 7-containing SMN protein as compared to untreated equivalents. The functionality of exon 7-included SMN protein of a subject in need of treatment of SMA may be further analyzed by physical and physiological tests such as motor function tests including measurements of muscle size, muscle tone, tenderness, strength, reflex, involuntary muscle movements, electromyography, nerve conduction velocity test, and cardiovascular function tests including electrocardiogram (EKG or EGG).

In the present case, modified antisense oligomers are used to induce exon-7 inclusion, resulting in an amelioration of Spinal Muscular Atrophy symptoms (i.e. restoration of SMN protein function or stability) in the range of about 30% to about 100% or the percentages disclosed above with regard to functionality, as compared to non-treatment. Such amelioration of symptoms may be observed on a micro level (i.e. restoration of SMN1/2 protein expression measured by, for example, immunohistochemistry, immunofluorescence, western-blot analyses; increase of motor neurons; restoration of neuromuscular junction in muscles) and physiological level (i.e. improvement of motor function assessed by physical examination).

The term "nucleotide" refers to a naturally occurring nucleotide comprising a nucleobase, a sugar and at least one phosphate group (e.g., a phosphodiester linking group).

The term "nucleotide analog" refers to a derivative of, or modification to, a naturally occurring nucleotide, for example, a nucleotide comprising at least one modification. Such modifications may include at least one of (i) a modified internucleoside linkage, (ii) a modified sugar moiety, or (iii) a combination of the foregoing. The skilled practitioner will appreciate that where a modification is specified with respect to any one component of a nucleotide subunit (e.g., a modified sugar), the unspecified portion(s) of the nucleotide subunit may remain unmodified (e.g., an unmodified internucleoside linkage, an unmodified nucleobase).

The terms "oligonucleotide," "oligomer," "oligo," "antisense oligonucleotide," "antisense oligomer," "modified antisense oligomer" and "antisense oligo," and other appropriate combinations and derivations thereof, refer to linear sequences of nucleotides, or nucleotide analogs, where one or more nucleobases may hybridize to a portion of a target RNA against which the oligomer is directed, referred to as a target sequence, by Watson-Crick base pairing, to form an oligomer:RNA heteroduplex within the target sequence. Specifically, the terms "antisense," "oligonucleotide," "oligomer," "oligo" and "compound" may be used in various combinations and interchangeably to refer to such an oligomer. Cyclic subunits comprising portions of the nucleotides may be based on ribose or another pentose sugar, sugar analog or, in certain embodiments may be a modified sugar, for example, a morpholino group (see description of morpholino-based oligomers below).

The term "modified," "non-naturally-occurring," or "analogs," and other appropriate combinations and derivatives thereof, when referring to oligomers, refer to oligomers having one or more nucleotide subunits having at least one modification selected from (i) a modified internucleoside linkage, e.g., an internucleoside linkage other than the standard phosphodiester linkage found in naturally-occurring oligonucleotides, (ii) modified sugar moieties, e.g., moieties other rather than ribose or deoxyribose moieties found in naturally occurring oligonucleotides, or (iii) a combination of the foregoing. In various embodiments, a modified internucleoside linkage is selected from a phosphorothioate internucleoside linkage, a phosphoramidate internucleoside linkage, a phosphorodiamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety. In various embodiments, the modified sugar moiety is selected from a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' O-methoxyethyl subunit, a 2'-fluoro subunit, a 2'-O-[2-(N-methylcarbamoyl)ethyl] subunit, and a morpholino subunit.

A modification to the internucleoside linkage may be between at least two sugar and/or modified sugar moieties of an oligomer. Nucleotide analogs support bases capable of hydrogen bonding by Watson-Crick base pairing to naturally occurring oligonucleotide bases, where the analog presents the bases in a manner to permit such hydrogen bonding in a sequence-specific fashion between the oligomer analog molecule and bases in the naturally occurring oligonucleotide (e.g., single-stranded RNA or single-stranded DNA). Exemplary analogs are those having a substantially uncharged, phosphorus containing internucleoside linkages.

A "nuclease-resistant" oligomer refers to one whose internucleoside linkage is substantially resistant to nuclease cleavage, in non-hybridized or hybridized form; by common extracellular and intracellular nucleases in the body (for example, by exonucleases such as 3'-exonucleases, endonucleases, RNase H); that is, the oligomer shows little or no nuclease cleavage under normal nuclease conditions in the body to which the oligomer is exposed. A "nuclease-resistant heteroduplex" refers to a heteroduplex formed by the binding of a modified antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between a modified antisense oligomer and the complementary portion of a target RNA. For example, a nuclease-resistant oligomer may be a modified antisense oligomer as described herein.

The terms "nucleobase" (Nu), "base pairing moiety" or "base" are used interchangeably to refer to a purine or pyrimidine base found in naturally occurring, or "native." DNA or RNA (e.g., uracil, thymine, adenine, cytosine, and guanine), as well as analogs of these naturally occurring purines and pyrimidines, that may confer improved properties, such as binding affinity to the oligomer. Exemplary analogs include hypoxanthine (the base component of the nucleoside inosine); 2, 6-diaminopurine; 5-methyl cytosine; C5-propynyl-modified pyrimidines; 10-(9-(aminoethoxy) phenoxazinyl) (G-clamp) and the like.

Further examples of base pairing moieties include, but are not limited to, uracil, thymine, adenine, cytosine, guanine and hypoxanthine (inosine) having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated, the contents of which are incorporated herein by reference.

Further examples of base pairing moieties include, but are not limited to, expanded-size nucleobases in which one or more benzene rings has been added. Nucleic base replacements described in the Glen Research catalog (www.glen-research.com); Krueger A T et al., Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, the contents of which are incorporated herein by reference, are contemplated as useful for the synthesis of the oligomers described herein. Examples of expanded-size nucleobases are shown below:

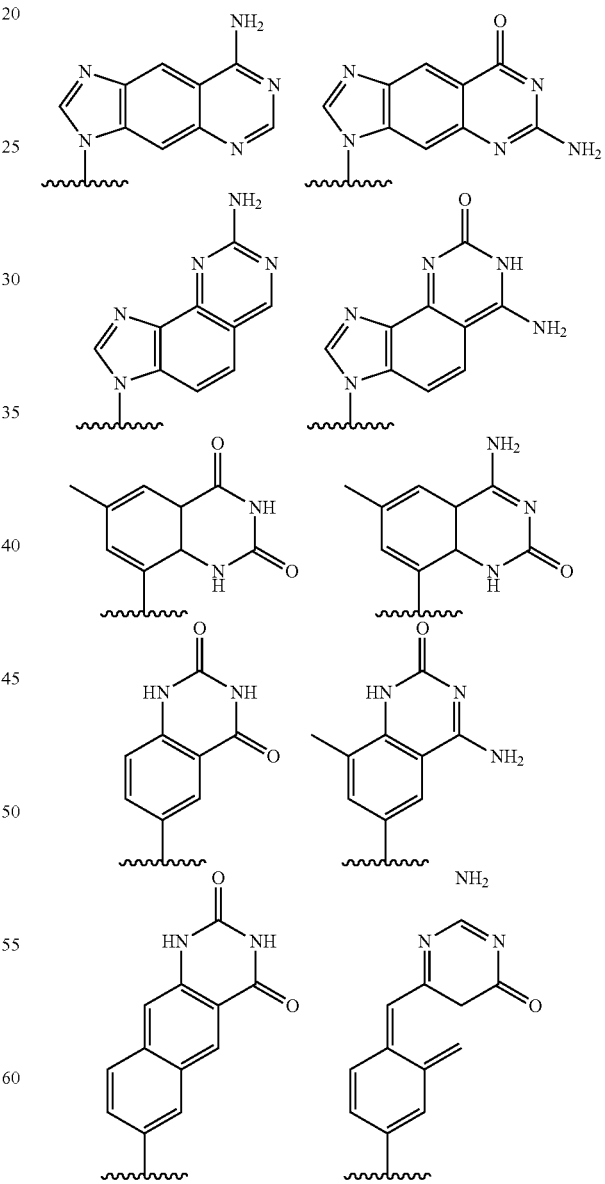

A nucleobase covalently linked to a ribose, sugar analog, modified sugar or morpholino comprises a nucleoside.

"Nucleotides" comprise a nucleoside together with at least one linking phosphate group. The phosphate groups comprise covalent linkages to adjacent nucleosides form an oligomer. Thus, the phosphate group of the nucleotide is commonly referred to as forming an "internucleoside linkage." Accordingly, a nucleotide comprises a nucleoside as further described herein and an internucleoside linkage. In some embodiments, a modified antisense oligomer of the disclosure comprises subunits wherein a "subunit" includes naturally occurring nucleotides, nucleotide analogs as described herein, and combinations thereof. In certain embodiments, a modified antisense oligomer of the disclosure comprises subunits wherein at least one subunit is a nucleotide analog.

The term "PMO-APN" refers to a phosphorodiamidate morpholino oligomer comprising intersubunit linkages each independently selected from dimethylamino phosphorodiamidate linkages and 2-(4-aminopiperadinyl) phosphorodiamidate linakges (also referred to as "APN" linkages) wherein at least one intersubunit linkage is an APN linkage. For example, in some embodiments of the disclosure, "PMO-APN" includes wherein each $R^1$ of the compound of, for example, formulas (I), (V), (Va), (Vb), (VI), (VIa), (VII), and (VIIa), is independently selected from

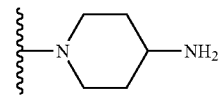

(for an APN linkage) and —$N(CH_3)_2$ (for a dimethylamino phosphorodiamidate linkage), wherein at least one $R^1$ is

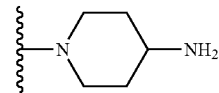

(for an APN linkage).

The term "PMO-Plus" refers to a phosphorodiamitate morpholino oligomer comprising intersubunit linkages each independently selected from dimethylamino phosphorodiamidate linkages and 1-piperazinyl phosphorodiamidate linakges (also referred to as "Plus" linkages) wherein at least one intersubunit linkage is a Plus linkage. For example, in some embodiments of the disclosure, "PMO-Plus" includes wherein each $R^1$ of the compound of, for example, formulas (I), (V), (Va), (Vb), (VI), (VIa), (VIII), and (VIIIa) is independently selected from

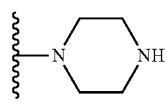

(for a Plus linkage) and —$N(CH_3)_2$ (for a dimethylamino phosphorodiamidate linkage), wherein at least one $R^1$ is

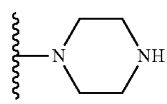

(for a Plus linkage).

The term "PMO-$R_6$Gly" refers to a phosphorodiamitate morpholino oligomer comprising dimethylamino phosphorodiamidate linkages and cell-penetrating peptide ("CPP" discussed in further detail below) consisting of six arginine residues linked to either the 3' or 5' end of the oligomer by a glycine linker. For a 3' linked CPP, for example, the glycine may be attached to the 3' most morpholino subunit ring nitrogen by an amide bond. For a 5' linked CPP, the glycine may be linked to a PIP group ring nitrogen by an amide bond. "PIP" refers to a chemical moiety of the formula:

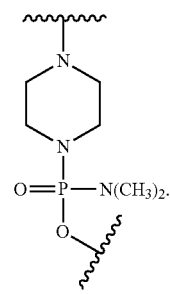 [SMILES: *OP(=O)(N(C)C)N1CCN(*)CC1]

The term "2'-OMe" refers to a 2'-Omethyl phosphorothioate oligomer further described below.

The term "PMO-ETpipT" refers to a phosphorodiamitate morpholino oligomer comprising intersubunit linkages each independently selected from dimethylamino phosphorodiamidate linkages and 1-(2-ethyl-piperazinyl) phosphorodiamidate linakges (also referred to as ETpipT linkages) wherein at least one intersubunit linkage is a ETpipT linkage. For example, in some embodiments of the disclosure, "PMO-ETpipT" includes wherein each $R^1$ of the compound of, for example, formulas (I), (V), (Va), (Vb), (VI), (VIa), (VIII), and (VIIIa) is independently selected from

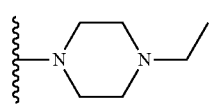

(for a ETpipT linkage) and —$N(CH_3)_2$ (for a dimethylamino phosphorodiamidate linkage), wherein at least one $R^1$ is

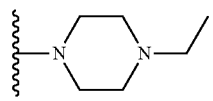

(for a ETpipT linkage).

The terms "sequence identity" and "sequence homology" (e.g. a "sequence 50% identical to) refer to the extent that a sequence is identical on a nucleotide-by-nucleotide basis over a window of comparison. A "percentage identity" may be calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997. In various embodiments, a modified antisense oligomer of the disclosure may have at least 70%, 75%, 80%, 85%, 90%, 95%, 99% or 100% sequence identity with a targeting sequence in Table 1 (SEQ ID NOS: 4 to 16).

As used herein, an oligomer "specifically hybridizes" to a target oligonucleotide if the oligomer hybridizes to the target under physiological conditions, with a melting point (Tm) substantially greater than 40° C., 45° C., 50° C., and in various embodiments, 60° C.–80° C. or higher. Such hybridization preferably corresponds to stringent hybridization conditions. At a given ionic strength and pH, the Tm is the temperature at which 50% of a target sequence hybridizes to a complementary sequence. Such hybridization may occur with "near" or "substantial" complementarity of the modified antisense oligomer to the target sequence, as well as with exact complementarity. In some embodiments, an oligomer may hybridize to a target sequence at about 50%, 55%, 60%, 65%, 70%, 75%, 80%, 85%, 90%, 95%, 99% or 100%.

As used herein, the term "subunit" refers to a naturally occurring nucleotide or a naturally occurring nucleotide comprising at least one modification. A modification may comprise at least one of (i) a modified internucleoside linkage, (ii) a modified sugar moiety, or (iii) a combination of the foregoing. In further embodiments, a modification may include a modified nucleobase.

As used herein, the term "sufficient length" refers to a modified antisense oligomer that is complementary to at least 8, more typically 8-40, contiguous nucleobases in a region within SMN2 pre-mRNA, such as intron 6 or intron 7 of SMN2 pre-mRNA. In various embodiments, the modified antisense oligomer comprises at least a number of nucleotides to be capable of specifically hybridizing to a target region of a SMN2 pre-mRNA sequence. Preferably an oligomer of sufficient length is from 8 to 30 nucleotides, 8 to 25 nucleotides, 8 to 20 nucleotides, 8 to 18 nucleotides, 10 to 30 nucleotides, 10 to 25 nucleotides, 10 to 20 nucleotides, 10 to 18 nucleotides, 15 to 30 nucleotides, 15 to 25 nucleotides, 15 to 20 nucleotides, 15 to 18 nucleotides, 18 to 30 nucleotides, 18 to 25 nucleotides, or 18 to 20 nucleotides in length, including all integers in between these ranges. Preferably, a modified antisense oligomer is of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length. Preferably, an oligomer of sufficient length is from 18 to 25 nucleotides in length.

As used herein, the term a "subject" or a "subject in need thereof" includes a mammalian subject such as a human subject. Exemplary mammalian subjects have spinal muscular atrophy.

As used herein, the term "target" or "target region" refers to a region within a pre-mRNA transcript as relating to the modified antisense oligomers contemplated herein. In various aspects, the target is a region of a SMN2 pre-mRNA. In various embodiments, the target region is a region comprising intron 6 or intron 7 of the SMN2 pre-mRNA. In various embodiments, the target region comprises the −7/−14, −7/−16, −10/−27, −10/−29, −10/−34, −137/−159, −149/−174, −167/−186, −249/−273, or −281/−299 region of intron 7 or the −58/−39, −112/−67, or −264/−245 region of intron 6. Preferably, in some aspects, the target region comprises the −10/−27, −10/−29, or −10/−34 region of intron 7 of SMN2 pre-mRNA.

In various embodiments, the term "targeting sequence" refers to the sequence in the modified antisense oligomer or oligomer analog that is complementary to the target sequence in the pre-mRNA transcript. The entire sequence, or only a portion, of the modified antisense oligomer may be complementary to the target sequence. For example, in an oligomer having 15-30 bases, about 7, 8, 9, 10, 11, 12, 13, 14, 15, 16, 17, 18, 19, 20, 21, 22, 23, 24, 25, 26, 27, 28, 29, or 30 may contain sequences (e.g. "targeting sequences") that are complementary to the target region within the pre-mRNA transcript. Typically, the targeting sequence is formed of contiguous bases in the oligomer, but may alternatively be formed of non-contiguous sequences that when placed together, e.g., from opposite ends of the oligomer, constitute a sequence that spans the target sequence.

A "targeting sequence" may have "near" or "substantial" complementarity to the target sequence and still function for its intended purpose, for example, to enhance the level of exon-7 containing SMN2 mRNA, or increase expression of functional SMN protein. Preferably, modified antisense oligomer compounds employed in the present disclosure have at most one mismatch with the target sequence out of 12 nucleotides, and preferably at most one mismatch out of 20. Alternatively, the modified antisense oligomers employed have at least 90% sequence homology, and preferably at least 95% sequence homology, with the exemplary targeting sequences as designated herein. A targeting sequence may comprise a sequence selected from SEQ ID NOS: 4 to 16, is selected from SEQ ID NOS: 4 to 16, is a fragment of at least 8 contiguous nucleotides of a sequence selected from SEQ ID NOS: 4 to 16, or is a variant having at least 90% sequence identity to a sequence selected from SEQ ID NOS: 4 to 16, wherein each X is independently selected from uracil (U) or thymine (T), and wherein each Y is independently selected from cytosine (C) or 5-Methylcytosine (5mC). In some embodiments, each X of SEQ ID NOS: 4 to 16 is thymine (T), and each Y of SEQ ID NOS: 4 to 16 is cytosine (C).

In some embodiments, the targeting sequence is selected from:

a) SEQ ID NO: 7 (XYAYXXXYAXAAXGYXGG) wherein Z is 16;

b) SEQ ID NO: 8 (AXXYAYXXXYAXAAXGYXGG) wherein Z is 18; and c) SEQ ID NO: 6 (GXAAGAXXYAYXXXYAX-AAXGYXGG) wherein Z is 23;

wherein each X is independently selected from uracil (U) or thymine (T), and wherein each Y is independently selected from cytosine (C) or 5-Methylcytosine (5mC). In some embodiments, each X of SEQ ID NOS: 6 to 8 is thymine (T), and each Y of SEQ ID NOS: 6 to 8 is cytosine (C)

In various embodiments, at least one X of the targeting sequence is T. In various embodiments, each X of the targeting sequence is T.

In various embodiments, at least one X of the targeting sequence is U. In various embodiments, each X of the targeting sequence is U.

In various embodiments, at least one Y of the targeting sequence is 5mC. In various embodiments, each Y of the targeting sequence is 5mC.

In various embodiments, at least one Y of the targeting sequence is C. In various embodiments, each Y of the targeting sequence is C.

In various embodiments, at least one X of SEQ ID NOS: 4 to 16 is T. In various embodiments, each X of SEQ ID NOS: 4 to 16 is T.

In various embodiments, at least one X of the targeting sequence is U. In various embodiments, each X of SEQ ID NOS: 4 to 16 is U.

In various embodiments, at least one Y of SEQ ID NOS: 4 to 16 is 5mC. In various embodiments, each Y of SEQ ID NOS: 4 to 16 is 5mC.

In various embodiments, at least one Y of SEQ ID NOS: 4 to 16 is C. In various embodiments, each Y of SEQ ID NOS: 4 to 16 is C.

As used herein, the term "TEG," "triethylene glycol tail," or "EG3" refers to triethylene glycol moieties conjugated to the oligomer, e.g., at its 3'- or 5'-end. For example, in some embodiments, "TEG" includes wherein T of the compound of, for example, formulas (I), (IV), (V), (Va), (Vb), (VI), (VII), (VIII), (IX), (IXa), and (X) is of the formula:

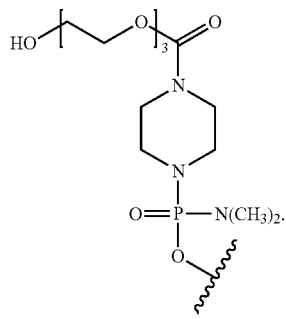

As used herein, the term a "therapeutically effective amount" or "effective amount" of a composition refers to an amount effective in the prevention or treatment of a disorder for the treatment of which the composition is effective. A "disorder" refers to any spinal muscular atrophy, such as SMA Type I, SMA Type II, SMA Type III, and SMA Type IV.

As used herein, the terms "quantifying," "quantification" or other related words refer to determining the quantity, mass, or concentration in a unit volume, of a nucleic acid, oligonucleotide, oligomer, peptide, polypeptide, or protein.

In various embodiments, as used herein, the term "treatment" includes treatment of a subject (e.g. a mammal, such as a human) or a cell to alter the current course of the subject or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

II. Modulation of the Splicing of SMN2 Pre-mRNA

Various aspects relate to methods for modulating the splicing of intron and exons of SMN2 pre-mRNA, such that the level of exon 7-containing SMN2 mRNA relative to the level of exon 7-deleted SMN2 mRNA is enhanced, in a given sample (e.g., serum, plasma, tissue, cellular etc.). Various methods include administering a modified antisense oligomer described herein that is complementary to a target region within the SMN2 pre-mRNA, where expression of exon 7-containing SMN2 mRNA is increased relative to the expression of exon 7-deleted SMN2 mRNA.

For illustration purposes, and without being bound by theory, modified antisense oligomers as described herein are believed to facilitate blocking, inhibiting or modulating the processing of a pre-mRNA, such as by inhibiting the action of a spliceosome and production of a mature mRNA transcript, and may also induce degradation of targeted mRNAs. In some instances, a spliceosome may be inhibited from binding to an exon/intron splice junction such that an exon/intron splice junction is skipped and one or more exons are removed from a mRNA transcript. A mature mRNA transcript having one or more exons less than a wild-type mRNA transcript may result in a mRNA transcript that maintains the open reading frame such that the mRNA transcript may be translated to functional protein rather than degraded. A protein translated from a mRNA transcript having fewer exons than the wild-type mRNA may result in a transcribed protein comprising fewer amino acid residues than a protein transcribed from a wild-type mRNA transcript. A functional protein composed of fewer amino acid residues than a wild-type protein may have the same or similar activity/functionality as the wildtype protein. The modified antisense oligomer may be said to be "directed to" or "targeted against" a target sequence or target region with which it hybridizes. In certain embodiments, the target sequence includes a region including a 3' or 5' splice junction site of a pre-mRNA, a branch point, Exonic Splicing Enhancers (ESE) or Intronic Splicing Enhancers (ISE), or other sequence involved in the regulation of splicing. Within an intron, a donor site (5' end of the intron) and an acceptor site (3' end of the intron) are required for splicing. The splice donor site includes an almost invariant sequence GU at the 5' end of the intron, within a larger, less highly conserved region. The splice acceptor site at the 3' end of the intron terminates the intron with an almost invariant AG sequence. The target sequence may include sequences within an exon/intron splice junction site, or spanning an exon/intron splice junction. The target sequence may include an exon/intron donor splice site.

A modified antisense oligomer having a sufficient sequence complementarity to a target pre-mRNA sequence to modulate splicing of the target RNA includes where the modified antisense oligomer has a sequence sufficient to trigger the masking or hindrance of a binding site for a spliceosome complex that would otherwise affect such splicing and/or otherwise includes alterations in the three-dimensional structure of the targeted pre-mRNA.

In various embodiments, the modified antisense oligomer has sufficient length and complementarity to a sequence within SMN2 pre-mRNA. In various embodiments, targeting sequences within a modified antisense oligomer hybridize to a region of the target sequences within SMN2 pre-mRNA, such as, for example, the −7/−14, −7/−16, −10/−27, −10/−29, −10/−34, −137/−159, −149/−174, −167/−186, −249/−273, or −281/−299 region of intron 7 or the −58/−39, −112/−67, or −264/−245 region of intron 6 of SMN2 pre-mRNA. In some embodiments, the modified antisense oligomers may about 8 bases to about 40 bases, and include a small number of mismatches, as long as the sequence is sufficiently complementary to effect splice modulation upon hybridization to the target sequence, and optionally forms with the RNA a heteroduplex having a Tm of 45° C. or greater.

In various embodiments, the degree of complementarity between the antisense targeting sequence and the target sequence is sufficient to form a stable duplex. The region of complementarity of the modified antisense oligomers with the target sequence may be as short as 8-15 bases but can be 8-18 bases or more, e.g., 8-40 bases, 8-30 bases, 8-25 bases, 8-22 bases, 8-20 bases, 15-25 bases, 15-22 bases, or 15-20 bases, including all integers in between these ranges. In certain embodiments, a minimum length of complementary bases may be required to achieve the requisite binding Tm, as discussed herein.

In various aspects, the oligomers are configured for additional functionality, including but not limited to bio-availability, stability, cellular update, and resistance to nuclease degradation. Generally, oligomers comprising 40 bases may be suitable, where at least a minimum number of bases, e.g., 8 bases, are complementary to the target sequence. In various aspects, the oligomers are configured to enhance facilitated or active cellular uptake. In various aspects, the modified antisense oligomers comprise one or more phosphoramidate morpholino monomer or phosphorodiamidate morpholino monomer subunits. In various embodiments, the modified antisense oligomers, comprise about 8-40 phosphoramidate morpholino monomer or phosphorodiamidate morpholino monomer subunits. In various embodiments, the modified antisense oligomers, comprise about 8-26 phosphoramidate morpholino monomer or phosphorodiamidate morpholino monomer subunits. In various embodiments, the modified antisense oligomers, comprise about 15-25 phosphoramidate morpholino monomer or phosphorodiamidate morpholino monomer subunits. In various embodiments, the modified antisense oligomers, comprise about 18-25 phosphoramidate morpholino monomer or phosphorodiamidate morpholino monomer subunits. In various embodiments, the modified antisense oligomers, comprise about 18-26 phosphoramidate morpholino monomer or phosphorodiamidate morpholino monomer subunits.

In various aspects, the modified antisense oligomers comprise, consist of, or consist essentially of 8 to 40 subunits, optionally comprising at least one subunit that is a nucleotide analog having (i) a modified internucleoside linkage, (ii) a modified sugar moiety, or (iii) a combination of the foregoing; and a targeting sequence complementary to a target region of 8 or more contiguous nucleotides within SMN2 pre-mRNA. In various embodiments, the target region comprises 8 or more contiguous nucleotides within a region of intron 6, exon 7, intron 7 or exon 8 (or a region which spans a splice junction) of the SMN2 gene. In various embodiments, the target region comprises a region within intron 6 or intron 7 of SMN2 pre-mRNA. In further embodiments, the target region comprises the −7/−14, −7/−16, −10/−27, −10/−29, −10/−34, −137/−159, −149/−174, −167/−186, −249/−273, or −281/−299 region of intron 7 or the −58/−39, −112/−67, or −264/−245 region of intron 6 of SMN2 pre-mRNA. In further embodiments, the target region comprises the −10/−27, −10/−29, or −10/−34 region of intron 7 of SMN2 pre-mRNA.

In various aspects, the modified antisense oligomers comprise, consist of, or consist essentially of 8 to 40 subunits, optionally comprising at least one subunit that is a nucleotide analog having (i) a modified internucleoside linkage, (ii) a modified sugar moiety, or (iii) a combination of the foregoing; and a targeting sequence comprising, consisting of, or consisting essentially of, a sequence selected from SEQ IDS 4 to 16. Preferably, in some aspects, the modified antisense oligomer comprises a sequence selected from SEQ IDS 6, 7, and 8.

Additional aspects include modified antisense oligomers of 8 to 40 subunits that specifically hybridize to a target region within SMN2 pre-mRNA. In various embodiments, the target region comprises a region within intron 6, exon 7, intron 7 or exon 8 (or a region which spans a splice junction) of the SMN2 gene. In various embodiments, the target region comprises a region within intron 6 or intron 7 of SMN2 pre-mRNA. In further embodiments, the target region comprises the −7/−14, −7/−16, −10/−27, −10/−29, −10/−34, −137/−159, −149/−174, −167/−186, −249/−273, or −281/−299 region of intron 7 or the −58/−39, −112/−67, or −264/−245 region of intron 6 of SMN2 pre-mRNA. In further embodiments, the target region comprises the −10/−27, −10/−29, or −10/−34 region of intron 7 of SMN2 pre-mRNA.

Additional aspects include modified antisense oligomers having a nucleotide analog subunit comprising a modified sugar moiety. In various embodiments, the modified sugar moiety is selected from a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' O-methoxyethyl subunit, a 2'-fluoro subunit, a 2'-O-[2-(N-methylcarbamoyl)ethyl] subunit, and a morpholino subunit.

Additional aspects include modified antisense oligomers having a nucleotide analog subunit comprising a modified internucleoside linkage. In various embodiments, the modified internucleoside linkage is selected from a phosphorothioate internucleoside linkage, a phosphoramidate internucleoside linkage, a phosphorodiamidate internucleoside linkage, and a phosphorotriamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

Additional aspects include modified antisense oligomers having a nucleotide analog subunit comprising at least one combination of a modified sugar moiety and a modified internucleoside linkage, wherein various embodiments, one or more subunits are selected from:

a morpholino subunit optionally substituted with a phosphoramidate internucleoside linkage, a phosphorodiamidate internucleoside linkage, phosphorotriamidate internucleoside linkage, or a phosphorothioate internucleoside linkage, a 2' O-methyl subunit optionally substituted with a phosphoramidate internucleoside linkage, a phosphorodiamidate internucleoside linkage, or a phosphorothioate internucleoside linkage, a 2'O-methoxyethyl subunit optionally substituted with a phosphoramidate internucleoside linkage, a phosphorodiamidate internucleoside linkage, or a phosphorothioate internucleoside linkage, a 2'-fluoro subunit optionally substituted with a phosphoramidate internucleoside linkage, a phosphorodiamidate internucleoside linkage, or a phosphorothioate internucleoside linkages, a 2'O,4'C-ethylene-bridged nucleic acid subunit optionally substituted with a phosphoramidate internucleoside linkage, a phosphorodiamidate internucleoside linkage, or a phosphorothioate internucleoside linkage, a 2'-O-[2-(N-methylcarbamoyl)ethyl] subunit optionally substituted with a phosphoramidate internucleoside linkage, a phosphorodiamidate internucleoside linkage, or a phosphorothioate internucleoside linkage, a tricyclo-DNA subunit optionally substituted with a phosphoramidate internucleoside linkage, a phosphorodiamidate internucleoside linkage, or a phosphorothioate internucleoside linkage, a locked nucleic acid subunit optionally substituted with a phosphoramidate internucleoside linkage, a phosphorodiamidate internucleoside linkage, or a phosphorothioate internucleoside linkage, a morpholino subunit further comprising a phosphorodiamidate internucleoside linkage where a phosphorous atom of the phosphorodiamidate is covalently bonded to the nitrogen atom of the morpholino ring, and is covalently bonded to a (1,4-piperazin)-1-yl moiety or to a substituted (1,4-piperazin)-1-yl moiety, a morpholino subunit further comprising a phosphorodiamidate internucleoside linkage where a phosphorus atom of the phosphorodiamidate is covalently bonded to a 4-aminopiperdin-1-yl moiety or a substituted 4-aminopiperdin-1-yl moiety, a morpholino subunit further comprising a phosphorodiamidate internucleoside linkage where a phosphorus atom of the phosphorodiamidate is covalently bonded to the nitrogen atom of the morpholino ring, and is covalently bonded to a dimethylamino moiety, a ribose sugar subunit substituted with a phosphorothioate internucleoside or a phosphoramidate internucleoside linkage, a deoxyribose sugar subunit substituted with a phosphorothioate internucleoside linkage or a phosphoramidate internucleoside linkage, a peptide nucleic acid subunit optionally substituted, or any combination of the foregoing.

In various aspects and embodiments, modified antisense oligomers of the disclosure further comprise a peptide covalently bonded to the modified antisense oligomer. In various embodiments, an arginine-rich cell-penetrating peptide is conjugated to the 3' or the 5' end of the modified antisense oligomer.

In various embodiments, a modified antisense oligomer may consist of about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, or range from 8 to 40, 8 to 30, 8 to 30, 8 to 25, 8 to 20, 8 to 18, 10 to 30, 10 to 25, 10 to 20, 10 to 18, 15 to 30, 15 to 25, 15 to 20, 15 to 18, 18 to 30, 18 to 25, or 18 to 20 bases, including all integers in between these ranges. In some embodiments, the modified antisense oligomer is about 8 to about 40 or about 8 to about 30 bases in length. In some embodiments, the modified antisense oligomer is about 18 to about 25 bases in length. In some embodiments, a modified antisense oligomer sequence comprises at least about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases that are complementary to a target sequences within SMN2 pre-mRNA, such as, intron 6 or intron 7 of SMN2 pre-mRNA, or sequences that span at least a portion of SMN2 pre-mRNA.

The modified antisense oligomers typically comprise a base sequence which is sufficiently complementary to a sequence or region within intron 6, exon 7, or intron 7 of the SMN2 pre-mRNA sequence of the SMN protein. Table 1 below recites sequences or regions within intron 6, exon 7, and intron 7.

TABLE 1

Exemplary Sequences of Intron 7, Exon 7, and Partial Intron 6 of SMN2 Gene

| Region within SMN2 Gene (SEQ ID NO) | Sequence |
| --- | --- |
| Intron 7 (SEQ ID NO: 1) | GTAAGTCTGCCAGCATTATGAAAGTGAATCTTACTTTTGTAAAACTTTA TGGTTTGTGGAAAACAAATGTTTTTGAACATTTAAAAAGTTCAGATGTT AGAAAGTTGAAAGGTTAATGTAAAACAATCAATATTAAAGAATTTTGA TGCCAAAACTATTAGATAAAAGGTTAATCTACATCCCTACTAGAATTCT CATACTTAACTGGTTGGTTGTGTGGAAGAAACATACTTTCACAATAAA GAGCTTTAGGATATGATGCCATTTTATATCACTAGTAGGCAGACCAGC AGACTTTTTTTTATTGTGATATGGGATAACCTAGGCATACTGCACTGTA CACTCTGACATATGAAGTGCTCTAGTCAAGTTTAACTGGTGTCCACAGA GGACATGGTTTAACTGGAATTCGTCAAGCCTCTGGTTCTAATTTCTCAT TTGCAG |
| Exon 7 (SEQ ID NO: 2) | ATAATTCCCCCACCACCTCCCATATGTCCAGATTCTCTTGATGATGCTG ATGCTTTGGGAAGTATGTTAATTTCATGGTACATGAGTGGCTATCATAC TGGCTATTATATG |
| Intron 6 (SEQ ID NO: 3) | CTCAGGCTGGAGTGCAAGGGCACATTCACAGCTCACTGCAGCCTTGAC CTCCAGGGCTCAAGCAGTCCTCTCACCTCAGTTTCCCGAGTAGCTGGGA CTACAGTGATAATGCCACTGCACCTGGCTAATTTTTATTTTTATTTATTT ATTTTTTTTTGAGACAGAGTCTTGCTCTGTCACCCAGGCTGGAGTGCAG TGGTGTAAATCTCAGCTCACTGCAGCCTCCGCCTCCTGGGTTCAAGTGA TTCTCCTGCCTCAACCTCCCAAGTAGCTGGGATTAGAGGTCCCCACCAC CATGCCTGGCTAATTTTTTGTACTTTCAGTAGAAACGGGGTTTTGCCAT GTTGGCCAGGCTGTTCTCGAACTCCTGAGCTCAGGTGATCCAACTGTCT CGGCCTCCCAAAGTGCTGGGATTACAGGCGTGAGCCACTGTGCCTAGC CTGAGCCACCACGCCGGCCTAATTTTTAAATTTTTTGTAGAGACAGGGT CTCATTATGTTGCCCAGGGTGGTGTCAAGCTCCAGGTCTCAAGTGATCC CCCTACCTCCGCCTCCCAAAGTTGTGGGATTGTAGGCATGAGCCACTGC AAGAAAACCTTAACTGCAGCCTAATAATTGTTTTCTTTGGGATAACTTT TAAAGTACATTAAAAGACTATCAACTTAATTTCTGATCATATTTTGTTG AATAAAATAAGTAAAATGTCTTGTGAAACAAAATGCTTTTTAACATCC |

TABLE 1-continued

Exemplary Sequences of Intron 7, Exon 7, and
Partial Intron 6 of SMN2 Gene

| Region within SMN2 Gene (SEQ ID NO) | Sequence |
|---|---|
| | ATATAAAGCTATCTATATATAGCTATCTATATCTATATAGCTATTTTTTT TAACTTCCTTTATTTTCCTTACAG |

Ideally, a modified antisense oligomer is able to effectively modulate aberrant splicing of the SMN2 pre-mRNA, and thereby increase expression of functional SMN protein. This requirement is optionally met when the oligomer compound has the ability to be actively taken up by mammalian cells, and once taken up, form a stable duplex (or heteroduplex) with the target mRNA, optionally with a Tm greater than about 40° C. or 45° C.

"Complementary" or "complementary" as used herein, refers to a modified antisense oligomer having about 90% to about 100% of the nucleotide sequence complementary to a target sequence. In embodiments, a complementary nucleotide sequence specifically hybridizes to a target sequence to induce a desired effect, for example, a therapeutic effect as described herein. In certain embodiments, modified antisense oligomers may be 100% complementary to the target sequence, or may include mismatches, e.g., to accommodate variants, as long as a heteroduplex formed between the oligomer and target sequence is sufficiently stable to withstand the action of cellular nucleases and other modes of degradation which may occur in vivo. Hence, certain oligomers may have substantial complementarity, meaning, about or at least about 90% sequence complementarity, e.g., 90%, 91%, 92%, 93%, 94%, 95%, 96%, 97%, 98%, 99% or 100% sequence complementarity, between the oligomer and the target sequence. Oligomer internucleoside linkages that are less susceptible to cleavage by nucleases are provided herein. Mismatches, if present, are typically less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such a modified antisense oligomer need not necessarily comprise 100% complementary to the target sequence, it should have sufficient complementarity to effectively, stably and specifically bind to the target sequence, such that splicing of the target pre-mRNA is sufficiently modulated, for example, to achieve a therapeutic effect, as described herein.

Without being bound by theory, the stability of the duplex formed between an oligomer and a target sequence is believed to be a function of the binding Tm and the susceptibility of the duplex to cellular enzymatic cleavage. The Tm of an oligomer with respect to a complementary-sequence RNA duplex may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107, the contents of which are incorporated herein by reference. In various embodiments, the modified antisense oligomers have a binding Tm, with respect to a complementary-sequence RNA duplex, of greater than body temperature, such as, for example, greater than about 45° C. or 50° C. Tm's in the range 60-80° C. or greater are also included. According to well-known principles, the Tm of an oligomer, with respect to a complementary-based RNA hybrid duplex, can be increased by increasing the ratio of C:G paired bases in the duplex, and/or by increasing the length (in base pairs) of the heteroduplex.

Table 2 below shows exemplary targeting sequences (in a 5'-to-3' orientation) that are complementary to the target regions within intron 6 or intron 7 of SMN2 pre-mRNA.

TABLE 2

Targeting Sequences for Human SMN2-targeted Oligomers

| Targeting SEQ ID NO | Targeting Sequences | Target Length | Target Coordinates | Target Intron |
|---|---|---|---|---|
| 4 | GYX GGY AG | 8 | -7-14 | 7 |
| 5 | AXG YXG GYA G | 10 | -7-16 | 7 |
| 6 | GXA AGA XXY AYX XXY AXA AXG YXG G | 25 | -10-34 | 7 |
| 7 | XYA YXX XYA XAA XGY XGG | 18 | -10-27 | 7 |
| 8 | AXX YAY XXX YAX AAX GYX GG | 20 | -10-29 | 7 |
| 9 | AAA AGX YXG YXG GXY XGY Y | 19 | -281-299 | 7 |
| 10 | AXA GAX AXA GAX AGY XAX AX | 20 | -58-39 | 6 |
| 11 | AAX AGX XXX GGY AXY AAA AXX YX | 23 | -137-159 | 7 |
| 12 | GAX AXA AAA XGG YAX YAX AXY YXA A | 25 | -249-273 | 7 |
| 13 | AXX AAY YXX XXA XYX AAX AGX XXX GG | 26 | -149-174 | 7 |

TABLE 2-continued

Targeting Sequences for Human SMN2-targeted Oligomers

| Targeting SEQ ID NO | Targeting Sequences | Target Length | Target Coordinates | Target Intron |
|---|---|---|---|---|
| 14 | AYA AYX XXG GGA GGY GGA GG | 20 | -264-245 | 6 |
| 15 | GXA GGG AXG XAG AXX AAY YX | 20 | -167-186 | 7 |
| 16 | YXA XAX AXA GAX AGX XAX XYA AYA AA | 26 | -112-67 | 6 |
| 33 | GCT GGC AG | 8 | -7-14 | 7 |
| 34 | ATG CTG GCA G | 10 | -7-16 | 7 |
| 35 | TCA CTT TCA TAA TGC TGG | 18 | -10-27 | 7 |
| 36 | ATT CAC TTT CAT AAT GCT GG | 20 | -10-29 | 7 |
| 37 | GTA AGA TTC ACT TTC ATA ATG CTG G | 25 | -10-34 | 7 |
| 38 | AAA AGT CTG CTG GTC TGC C | 19 | -281-299 | 7 |
| 39 | ATA GAT ATA GAT AGC TAT AT | 20 | -58-39 | 6 |
| 40 | AAT AGT TTT GGC ATC AAA ATT CT | 23 | -137-159 | 7 |
| 41 | GAT ATA AAA TGG CAT CAT ATC CTA A | 25 | -249-273 | 7 |
| 42 | ATT AAC CTT TTA TCT AAT AGT TTT GG | 26 | -149-174 | 7 |
| 43 | ACA ACT TTG GGA GGC GGA GG | 20 | -264-245 | 6 |
| 44 | GTA GGG ATG TAG ATT AAC CT | 20 | -167-186 | 7 |
| 45 | CTA TAT ATA GAT AGT TAT TCA ACA AA | 26 | -112-67 | 6 | wherein each "X" is independently selected from either uracil (U) or thymine (T)
wherein each "Y" is independently selected from either cytosine (C) or 5-methylcytosine (5mC)

Certain modified antisense oligomers thus comprise, consist, or consist essentially of a sequence in Table 1 (e.g., SEQ ID NOS: 4 to 16), is selected from SEQ ID NOS: 4 to 16, is a fragment of at least 8 contiguous nucleotides of a sequence selected from SEQ ID NOS: 4 to 16, or is a variant having at least 90% sequence identity to a sequence selected from SEQ ID NOS: 4 to 16, wherein each X is independently selected from uracil (U) or thymine (T), and wherein each Y is independently selected from cytosine (C) or 5-Methylcytosine (5mC). For instance, certain modified antisense oligomers comprise about or at least about 8, 9, 10, 11, 12, 13, 14, 15, 16, 17, 18, 19, 20, 21, 22, 23, 24, 25, 26, 27, 28, 29 or 30 contiguous or non-contiguous nucleotides of any of SEQ ID NOS: 4 to 16. For non-contiguous portions, intervening nucleotides can be deleted or substituted with a different nucleotide, or intervening nucleotides can be added. Additional examples of variants include oligomers having about or at least about 90% sequence identity or homology, e.g., 90%, 91%, 92%, 93%, 94%, 95%, 96%, 97%, 98%, 99% or 100% sequence identity or homology, over the entire length of any of SEQ ID NOS: 4 to 16. In certain embodiments, the targeting sequence is selected from SEQ ID NOS: 4 to 16.

The activity/functionality of modified antisense oligomers and variants thereof can be assayed according to routine techniques in the art. For example, splice forms and expression levels of surveyed RNAs may be assessed by any of a wide variety of well-known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e., a transcribed oligonucleotide) from a cell, tissue or organism, and by hybridizing the mRNA/cDNA with a reference oligonucleotide that is a complement of the assayed nucleic acid, or a fragment thereof cDNA can, optionally, be amplified using any of a variety of polymerase chain reaction or in vitro transcription methods prior to hybridization with the complementary oligonucleotide; preferably, it is not amplified. Expression of one or more transcripts can also be detected using quantitative PCR to assess the level of expression of the transcript(s).

III. Modified Antisense Oligomer Chemistries

A. General Characteristics

In various aspects and embodiments, the modified antisense oligomers specifically hybridize to target region within SMN2 pre-mRNA. Exemplary modified antisense oligomers comprise a targeting sequence set forth in Table 1, a fragment of at least 8 contiguous nucleotides of a targeting sequence in Table 1, or a variant having at least 90% sequence identity to a targeting sequence in Table 1. Other exemplary modified antisense oligomers consist or consist essentially of a targeting sequence set forth in Table 1.

Nuclease-resistant modified antisense oligomers are provided in a further aspect. In various embodiments, a modified antisense oligomer is provided comprising one or more internucleoside linkage modification(s). In other embodiments, a modified antisense oligomer is provided comprising one or more modified sugar moieties. In other embodiments, a modified antisense oligomer is provided comprising a combination of one or more modified internucleoside linkages and one or more modified sugar moieties. In other embodiments, a modified antisense oligomer is provided comprising a modified nucleobase, alone or in combination with any of a modified internucleoside linkage or a modified sugar moiety.

In various embodiments, a modified antisense oligomer may comprise an oligomer having completely modified internucleoside linkages, for example, 100% of the internucleoside linkages are modified (for example, a 25-mer modified antisense oligomer comprises 24 internucleoside linkages modified with one or any combination of the modifications as described herein). In various embodiments, a modified antisense oligomer may comprise about 100% to 2.5% of its internucleoside linkages modified. In various embodiments, a modified antisense oligomer may comprise about 99%, 95%, 90%, 85%, 80%, 75%, 70%, 65%, 60%, 55%, 50%, 45%, 40%, 35%, 30%, 25%, 20%, 15%, 10%, 5%, or 2.5% of its internucleoside linkages modified, and iterations in between. In other embodiments, a modified antisense oligomer may comprise any combination of modifications as described herein.

In various embodiments, including embodiments in combination with embodiments of percent of modified internucleoside linkages, a modified antisense oligomer may comprise an oligomer having completely modified sugar moieties, for example, 100% of the sugar moieties are modified (for example, a 25 mer modified antisense oligomer comprises 25 sugar moieties modified with one or any combination of the modifications as described herein). In various embodiments, a modified antisense oligomer may comprise about 100% to 2.5% of its sugar moieties modified. In various embodiments, a modified antisense oligomer may comprise about 99%, 95%, 90%, 85%, 80%, 75%, 70%, 65%, 60%, 55%, 50%, 45%, 40%, 35%, 30%, 25%, 20%, 15%, 10%, 5%, or 2.5% of its sugar moieties modified, and iterations in between. In other embodiments, a modified antisense oligomer may comprise any combination of modifications as described herein.

In various embodiments, the modified antisense oligomer is substantially uncharged, and is optionally suitable as a substrate for active or facilitated transport across the cell membrane. In some embodiments, all of the internucleoside linkages are uncharged. The ability of the oligomer to form a stable duplex with the target pre-mRNA may also relate to other features of the oligomer, including the length and degree of complementarity of the modified antisense oligomer with respect to the target, the ratio of G:C to A:T base matches, and the positions of any mismatched bases. The ability of the modified antisense oligomer to resist cellular nucleases may promote survival and ultimate delivery of the agent to the cell cytoplasm.

In various embodiments, the modified antisense oligomer has at least one internucleoside linkage that is positively charged or cationic at physiological pH. In further embodiments, the modified antisense oligomer has at least one internucleoside linkage that exhibits a pKa between about 5.5 and about 12. In further embodiments, the modified antisense oligomer contains about, at least about, or no more than about 1, 2, 3, 4, 5, 6, 7, 8, 9, or 10 internucleoside linkages that exhibits a pKa between about 4.5 and about 12. In some embodiments, the modified antisense oligomer contains about or at least about 10%, 15%, 20%, 25%, 30%, 35%, 40%, 45%, 50%, 55%, 60%, 65%, 70%, 75%, 80%, 85%, 90%, 95%, or 100% internucleoside linkages that exhibit a pKa between about 4.5 and about 12. Optionally, the modified antisense oligomer has at least one internucleoside linkage with both a basic nitrogen and an alkyl, aryl, or aralkyl group. In particular embodiments, the cationic internucleoside linkage or linkages comprise a 4-aminopiperdin-1-yl (APN) group, or a derivative thereof. In some embodiments, the modified antisense oligomer comprises a morpholino ring. While not being bound by theory, it is believed that the presence of a cationic linkage or linkages (e.g., APN group or APN derivative) in the oligomer facilitates binding to the negatively charged phosphates in the target nucleotide. Thus, the formation of a heteroduplex between mutant RNA and the cationic linkage-containing oligomer may be held together by both an ionic attractive force and Watson-Crick base pairing.

In various embodiments, the number of cationic linkages is at least 2 and no more than about half the total internucleoside linkages, e.g., about or no more than about 1, 2, 3, 4, 5, 6, 7, 8, 9, 10, 11, 12, 13, 14, 15, 16, 17, 18, 19, 20 cationic linkages. In some embodiments, however, up to all of the internucleoside linkages are cationic linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are cationic linkages. In further embodiments, an oligomer of about 19-20 monomer subunits may have 2-10, e.g., 4-8, cationic linkages, and the remainder uncharged linkages. In other specific embodiments, an oligomer of 14-15 subunits may have 2-7, e.g., 2, 3, 4, 5, 6, or 7 cationic linkages and the remainder uncharged linkages. The total number of cationic linkages in the oligomer can thus vary from about 1 to 10 to 18 to 20 to 30 or more (including all integers in between), and can be interspersed throughout the oligomer.

In some embodiments, a modified antisense oligomer may have about or up to about 1 cationic linkage per every 2-5 or 2, 3, 4, or 5 uncharged linkages, such as about 4-5 or 4 or 5 per every 10 uncharged linkages.

Certain embodiments include modified antisense oligomers that contain about 10%, 15%, 20%, 25%, 30%, 35%, 40%, 45%, 50%, 55%, 60%, 65%, 70%, 75%, 80%, 85%, 90%, 95%, or 100% cationic linkages. In certain embodiments, optimal improvement in antisense activity may be seen if about 25% of the internucleoside linkages are cationic. In certain embodiments, enhancement may be seen with a small number e.g., 10-20% cationic linkages, or where the number of cationic linkages are in the range 50-80%, such as about 60%.

In further embodiments, the cationic linkages are interspersed along the internucleoside linkage. Such oligomers optionally contain at least two consecutive uncharged linkages; that is, the oligomer optionally does not have a strictly alternating pattern along its entire length. In specific instances, each one or two cationic linkage(s) is/are separated along the internucleoside linkage by at least 1, 2, 3, 4, or 5 uncharged linkages.

Also included are oligomers having blocks of cationic linkages and blocks of uncharged linkages. For example, a central block of uncharged linkages may be flanked by blocks of cationic linkages, or vice versa. In some embodiments, the oligomer has approximately equal-length 5', 3' and center regions, and the percentage of cationic linkages in the center region is greater than about 50%, 60%, 70%, or 80% of the total number of cationic linkages.

In certain modified antisense oligomers, the bulk of the cationic linkages (e.g., 70, 75%, 80%, 90% of the cationic linkages) are distributed close to the "center-region" of the internucleoside linkages, e.g., the 6, 7, 8, 9, 10, 11, 12, 13, 14, or 15 centermost linkages. For example, a 16, 17, 18, 19, 20, 21, 22, 23, or 24-mer oligomer may have at least 50%, 60%, 70%, or 80% of the total cationic linkages localized to the 8, 9, 10, 11, or 12 centermost linkages.

B. Chemistry Features

The modified antisense oligomers may contain a variety of nucleotide analog subunits. Further examples include:

phosphoramidate containing oligomers, phosphorodiamidate containing oligomers, phosphorotriamidate containing oligomers, phosphorothioate containing oligomers, morpholino containing oligomers optionally substituted with a phosphoramidate internucleoside linkage or a phosphorodiamidate internucleoside linkage, 2'O-methyl containing oligomers optionally substituted with a phosphorothioate internucleoside linkage, locked nucleic acid (LNA) containing oligomers optionally substituted with a phosphorothioate internucleoside linkage, 2' O-methoxyethyl (MOE) containing oligomers optionally substituted with a phosphorothioate internucleoside linkage, 2'-fluoro-containing oligomers optionally substituted with a phosphorothioate internucleoside linkage, 2'O,4'C-ethylene-bridged nucleic acids (ENAs) containing oligomers optionally substituted with a phosphorothioate internucleoside linkage, tricyclo-DNA (tc-DNA) containing oligomers optionally substituted with a phosphorothioate internucleoside linkage, 2'-O-[2-(N-methylcarbamoyl)ethyl] containing oligomers optionally substituted with a phosphorothioate internucleoside linkage, morpholino containing oligomers further comprising a phosphorodiamidate internucleoside linkage wherein the phosphorous atom of the phosphorodiamidate is covalently bonded to the nitrogen atom of a morpholino ring, and is covalently bonded to a (1,4-piperazin)-1-yl moiety or to a substituted (1,4-piperazin)-1-yl (PMOplus) moiety, morpholino containing oligomers further comprising a phosphorodiamidate internucleoside linkage wherein the phosphorus atom of the phosphorodiamidate is covalently bonded to the nitrogen atom of a morpholino ring and is covalently bonded to a 4-aminopiperdin-1-yl moiety (i.e., APN) or a substituted 4-aminopiperdin-1-yl (PMO-X) moiety, a morpholino subunit further comprising a phosphorodiamidate internucleoside linkage where a phosphorus atom of the phosphorodiamidate is covalently bonded to the nitrogen atom of the morpholino ring, and is covalently bonded to a dimethylamino moiety, ribose sugar containing oligomers further comprising a phosphorothioate internucleoside linkage or a phosphoramidate internucleoside linkage, deoxyribose sugar containing oligomers further comprising a phosphorothioate internucleoside linkage oligomer or a phosphoramidate internucleoside linkage, peptide-conjugated phosphorodiamidate morpholino containing oligomers (PPMO) which are further optionally substituted, peptide nucleic acid (PNA) oligomers which are further optionally substituted including further substitutions, and combinations of any of the foregoing.

In certain embodiments, the phosphorous atom of a phosphorodiamidate linkage is further substituted with a (1,4-piperazin)-1-yl moiety, a substituted (1,4-piperazin)-1-yl moiety, a 4-aminopiperidin-1-yl moiety, or a substituted 4-aminopiperidin-1-yl moiety.

In general, PNA and LNA chemistries can utilize shorter targeting sequences because of their relatively high target binding strength relative to PMO and 2'O-Me oligomers. Phosphorothioate and 2'O-Me chemistries can be combined to generate a 2'O-Me-phosphorothioate analog. See, e.g., PCT Publication Nos. WO/2013/112053 and WO/2009/008725, which are hereby incorporated by reference in their entireties.

In some instances, modified antisense oligomers, such as phosphorodiamidate morpholino oligomers (PMO), can be conjugated to cell penetrating peptides (CPPs) to facilitate intracellular delivery. Peptide-conjugated PMOs are called PPMOs and certain embodiments include those described in PCT Publication No. WO/2012/150960, which is hereby incorporated by reference in its entirety. In some embodiments, an arginine-rich peptide sequence conjugated or linked to, for example, the 3' terminal end of a modified antisense oligomer as described herein may be used.

1. Peptide Nucleic Acids (PNAs)

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligomers obeying Watson-Crick base-pairing rules, and mimic DNA in terms of base pair recognition (Egholm, Buchardt et al. 1993). The internucleoside linkages of PNAs are formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases. A non-limiting example of a PNA oligomer comprising PNA subunits is depicted below:

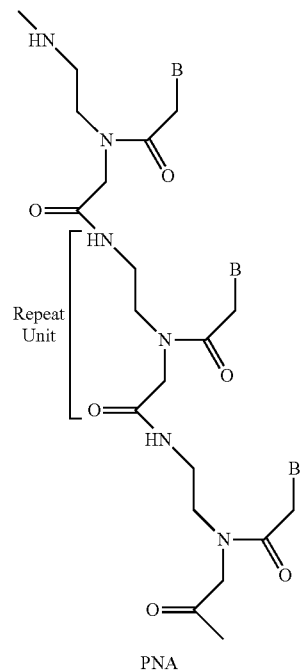

PNA

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE (Daejeon, Korea) has developed Bts PNA monomers (Bts; benzothiazole-2-sulfonyl group) and oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766, 7,211,668, 7,022,851, 7,125,994, 7,145,006 and 7,179,896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is hereby incorporated by reference in its entirety.

2. Locked Nucleic Acids (LNAs)

Modified antisense oligomer compounds may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230, which are hereby incorporated by reference in their entirety. A non-limiting example of an LNA oligomer comprising LNA subunits and phosphodiester internucleoside linkages is depicted below:

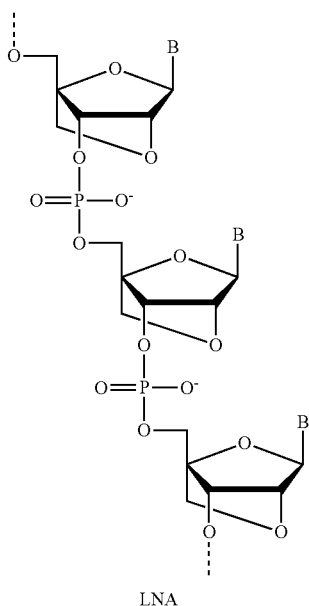

LNA

Compounds of the disclosure may incorporate one or more LNAs; in some cases, the compounds may be entirely composed of LNAs. Methods for the synthesis of individual LNA nucleoside subunits and their incorporation into oligomers are described, for example, in U.S. Pat. Nos. 7,572, 582, 7,569,575, 7,084,125, 7,060,809, 7,053,207, 7,034,133, 6,794,499, and 6,670,461, which are hereby incorporated by reference in their entirety. Typical internucleoside linkers include phosphodiester and phosphorothioate moieties; alternatively, non-phosphorous containing linkers may be employed. Further embodiments include an LNA containing compound where each LNA subunit is separated by a DNA subunit. Certain compounds are composed of alternating LNA and DNA subunits where the internucleoside linker is phosphorothioate.

2'O,4'C-ethylene-bridged nucleic acids (ENAs) are another member of the class of BNAs. A non-limiting example of an ENA subunit and phosphodiester internucleoside linkage is depicted below:

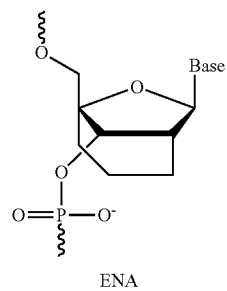

ENA

ENA oligomers and their preparation are described in Obika et al., *Tetrahedron Ltt* 38(50): 8735, which is hereby incorporated by reference in its entirety. Compounds of the disclosure may incorporate one or more ENA subunits.

3. Phosphorothioates

"Phosphorothioates" (or S-oligos) are a variant of native DNA or RNA in which one of the nonbridging oxygens of the phosphodiester internucleoside linkages is replaced by sulfur. A non-limiting example of a phosphorothioate DNA (left), comprising deoxyribose subunits and phosphorothioate internucleoside linkages, and phosphorothioate RNA (right), comprising ribose subunits and phosphorothioate internucleoside linkages, are depicted below:

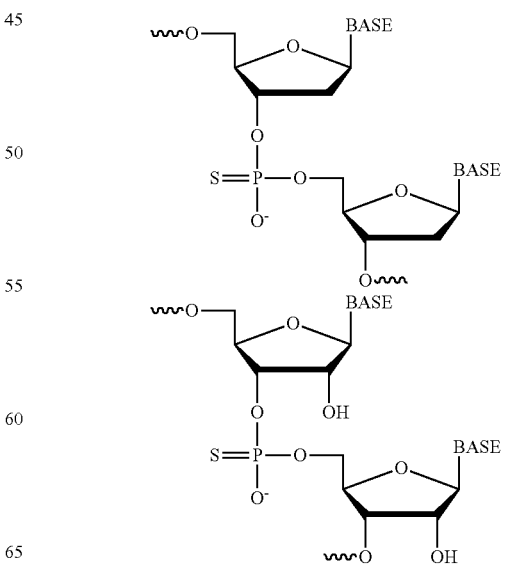

The sulfurization of the internucleoside bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates may be made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990, which are hereby incorporated by reference in their entirety). The latter methods avoid the problem of elemental sulfur's insolubility in most organic solvents and the toxicity of carbon disulfide. The TETD and BDTD methods also yield higher purity phosphorothioates.

4. Tricyclo-DNAs and Tricyclo-Phosphorothioate Nucleotides

Tricyclo-DNAs (tc-DNA) are a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Tricyclo-DNAs and their synthesis are described in PCT Publication No. WO 2010/115993, which is hereby incorporated by reference in its entirety. Compounds of the disclosure may incorporate one or more tricyclo-DNA subunits; in some cases, the compounds may be entirely composed of tricyclo-DNA subunits.

Tricyclo-phosphorothioate nucleotides are tricyclo-DNA subunits with phosphorothioate internucleoside linkages. Tricyclo-phosphorothioate nucleotides and their synthesis are described in PCT Publication No. WO 2013/053928, which is hereby incorporated by reference in its entirety. Compounds of the disclosure may incorporate one or more tricyclo-DNA subunits; in some cases, the compounds may be entirely composed of tricyclo-DNA nucleotides. A non-limiting example of a tricyclo-DNA/tricycle subunit and phosphodiester internucleoside linkage is depicted below:

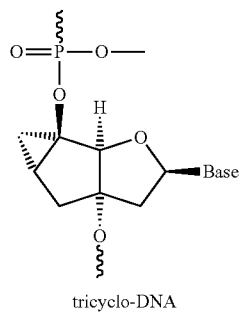

tricyclo-DNA 5. 2' O-Methyl, 2' O-MOE, and 2'-F Oligomers

"2'O-Me oligomer" molecules comprise subunits that carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphorothioate oligomers (PTOs) for further stabilization. 2'O-Me oligomers (wherein the 2'-OMe subunits are connected by phosphodiester or phosphorothioate internucleoside linkages) can be synthesized according to routine techniques in the art (see, e.g., Yoo et al., Nucleic Acids Res. 32:2008-16, 2004, which is hereby incorporated by reference in its entirety). A non-limiting example of a 2' O-Me oligomer comprising 2'-OMe subunits and phosphodiester intersubunit linkages is depicted below:

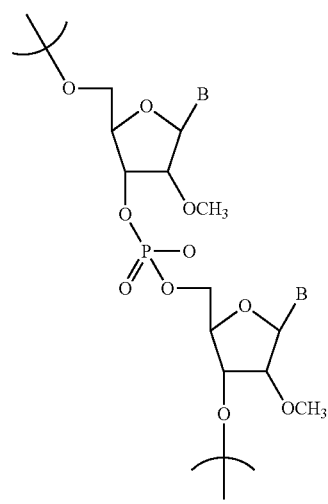

2' O-Me oligomers may also comprise a phosphorothioate linkage (2' O-Me phosphorothioate oligomers). 2' O-Methoxyethyl Oligomers (2'-O MOE), like 2' O-Me oligomers, comprise subunits that carry a methoxyethyl group at the 2'-OH residue of the ribose molecule and are discussed in Martin et al., Helv. Chim. Acta, 78, 486-504, 1995, which is hereby incorporated by reference in its entirety. A non-limiting example of a 2' 0-MOE subunit is depicted below:

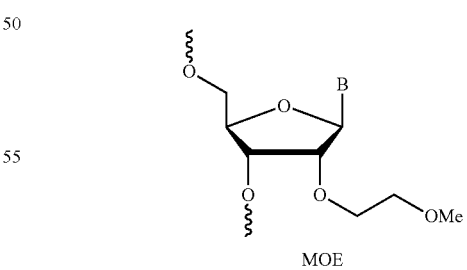

MOE

In contrast to the preceding alkylated 2'OH ribose derivatives, 2'-fluoro oligomers comprise subunits that have a fluoro radical in at the 2' position in place of the 2'OH. A non-limiting example of a 2'-F oligomer comprising 2'-F subunits and phosphodiester internucleoside linkages is depicted below:

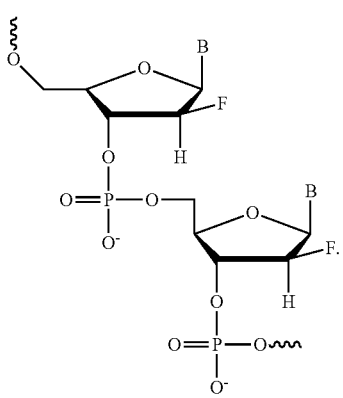

2'-fluoro oligomers are further described in WO 2004/043977, which is hereby incorporated by reference in its entirety. Compounds of the disclosure may incorporate one or more 2'O-Methyl, 2' O-MOE, and 2'-F subunits and may utilize any of the internucleoside linkages described here. In some instances, a compound of the disclosure could be composed of entirely 2'O-Methyl, 2' O-MOE, or 2'-F subunits. One embodiment of a compound of the disclosure is composed entirely of 2'O-methyl subunits.

6. 2'-O-[2-(N-Methylcarbamoyl)Ethyl] Oligomers (MCEs)

MCEs are another example of 2'O modified ribonucleotides useful in the compounds of the disclosure. Here, the 2'OH is derivatized to a 2-(N-methylcarbamoyl)ethyl moiety to increase nuclease resistance. A non-limiting example of an MCE oligomer comprising MCE subunits and phosphodiester internucleoside linkages is depicted below:

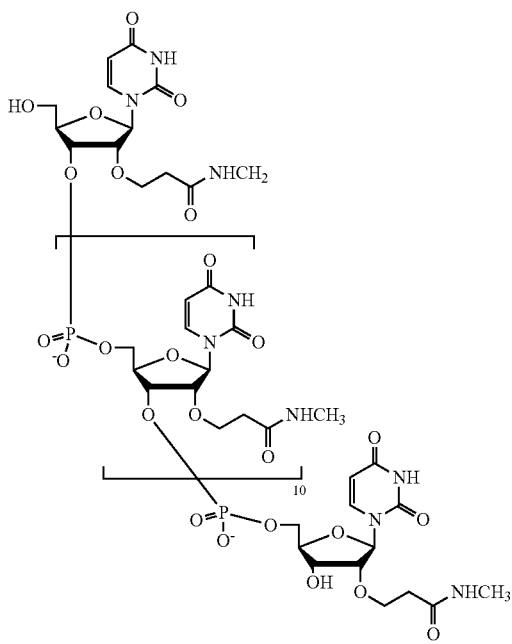

MCEs and their synthesis are described in Yamada et al., J. Org. Chem., 76(9):3042-53, which is hereby incorporated by reference in its entirety. Compounds of the disclosure may incorporate one or more MCE subunits.

7. Morpholino-Based Oligomers

Morpholino-based oligomers refer to an oligomer comprising morpholino subunits supporting a nucleobase and, instead of a ribose, contains a morpholinyl ring. Exemplary internucleoside linkages include, for example, phosphoramidate or phosphorodiamidate internucleoside linkages joining the morpholinyl ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligonucleotide.

Morpholino-based oligomers (including modified antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety. The term "morpholino subunit", is used herein as described in Summerton et al.

Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. A "phosphorotriamidate" group (or a phosphoric acid triamide group) comprises phosphorus having one attached oxygen atom and three attached nitrogen atoms. In the uncharged or the cationic internucleoside linkages of the morpholino-based oligomers described herein, one nitrogen is always pendant to the linkage chain. The second nitrogen, in a phosphorodiamidate linkage, is typically the ring nitrogen in a morpholino ring structure.

"PMO" refers to phosphorodiamidate morpholino-based oligomers having a phosphorus atom with (i) a covalent bond to the nitrogen atom of a morpholino ring and (ii) a second covalent bond to the nitrogen of a dimethylamino. "PMO-X" refers to phosphorodiamidate morpholino-based oligomers having a phosphorus atom with (i) a covalent bond to the nitrogen atom of a morpholino ring and (ii) a second covalent bond to the ring nitrogen of, for example, a 4-aminopiperdin-1-yl (i.e., APN) or a derivative of 4-aminopiperdin-1-yl. Exemplary PMO-X oligomers are disclosed in PCT Application No. PCT/US2011/38459 and PCT Publication No. WO 2013/074834, which are hereby incorporated by reference in their entirety. PMO-X includes "PMO-apn", "PMO-APN" or "APN," which refers to a PMO-X oligomer which comprises at least one internucleoside linkage where a phosphorus atom is linked to a morpholino group and to the ring nitrogen of a 4-aminopiperdin-1-yl (i.e., APN). In specific embodiments, a modified antisense oligomer comprising a targeting sequence as set forth in Table 2 comprises at least one APN-containing linkage or APN derivative-containing linkage. Various embodiments include morpholino-based oligomers that have about 10%, 15%, 20%, 25%, 30%, 35%, 40%, 45%, 50%, 55%, 60%, 65%, 70%, 75%, 80%, 85%, 90%, 95%, or 100% APN/APN derivative-containing linkages, where the remaining linkages (if less than 100%) are uncharged linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are APN/APN derivative-containing linkages.

In various embodiments, the modified antisense oligomer is a compound of formula (I):

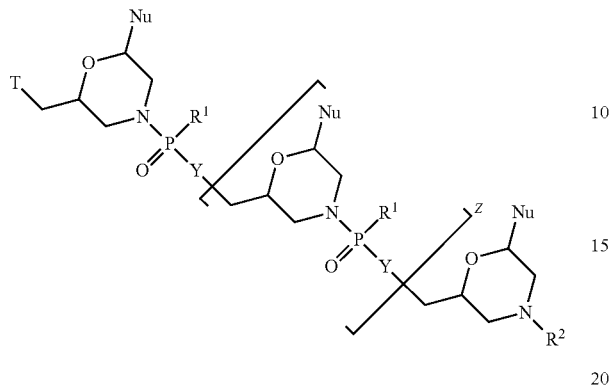

(I)

or a pharmaceutically acceptable salt thereof, wherein:
each Nu is a nucleobase which taken together forms a targeting sequence;
Z is an integer from 6 to 38;
each Y is independently selected from O and —NR$^4$, wherein each R$^4$ is independently selected from H, C$_1$-C$_6$ alkyl, aralkyl, —C(=NH)NH$_2$, —C(O)(CH$_2$)$_n$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and C$_1$-C$_6$ alkyl and n is an integer from 1 to 5;
T is selected from OH and a moiety of the formula:

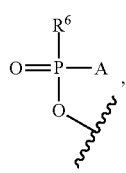

wherein:
A is selected from —OH, —N(R$^7$)$_2$R$^8$, and R$^1$ wherein:
each R$^7$ is independently selected from H and C$_1$-C$_6$ alkyl, and
R$^8$ is selected from an electron pair and H, and
R$^6$ is selected from OH, —N(R$^9$)CH$_2$C(O)NH$_2$, and a moiety of the formula:

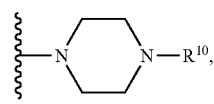

wherein:
R$^9$ is selected from H and C$_1$-C$_6$ alkyl; and
R$^{10}$ is selected from G, —C(O)—R$^{11}$OH, acyl, trityl, 4-methoxytrityl, —C(=NH)NH$_2$, —C(O)(CH$_2$)$_m$NR$^{12}$C(=NH)NH$_2$, and —C(O)(CH$_2$)$_2$NHC(O)(CH$_2$)$_5$NR$^{12}$C(=NH)NH$_2$, wherein:
m is an integer from 1 to 5,
R$^{11}$ is of the formula —(O-alkyl)$_y$- wherein y is an integer from 3 to 10 and
each of the y alkyl groups is independently selected from C$_2$-C$_6$ alkyl; and
R$^{12}$ is selected from H and C$_1$-C$_6$ alkyl;

each instance of R$^1$ is independently selected from:
—N(R$^{13}$)$_2$R$^{14}$ wherein each R$^{13}$ is independently selected from H and C$_1$-C$_6$ alkyl, and R$^{14}$ is selected from an electron pair and H;
a moiety of formula (II):

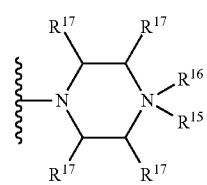

(II)

wherein:
R$^{15}$ is selected from H, G, C$_1$-C$_6$ alkyl, —C(=NH)NH$_2$, —C(O)(CH$_2$)$_q$NR$^{18}$C(=NH)NH$_2$, and —C(O)(CH$_2$)$_2$NHC(O)(CH$_2$)$_5$NR$^{18}$C(=NH)NH$_2$, wherein:
R$^{18}$ is selected from H and C$_1$-C$_6$ alkyl; and
q is an integer from 1 to 5,
R$^{16}$ is selected from an electron pair and H; and
each R$^{17}$ is independently selected from H and methyl; and
a moiety of formula (III):

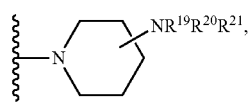

(III)

wherein:
R$^{19}$ is selected from H, C$_1$-C$_6$ alkyl, —C(=NH)NH$_2$,
—C(O)(CH$_2$)$_r$NR$^{22}$C(=NH)NH$_2$,
—C(O)CH(NH$_2$)(CH$_2$)$_3$NHC(=NH)NH$_2$,
—C(O)(CH$_2$)$_2$NHC(O)(CH$_2$)$_5$NR$^{22}$C(=NH)NH$_2$,
—C(O)CH(NH$_2$)(CH$_2$)$_4$NH$_2$, and G wherein:
R$^{22}$ is selected from H and C$_1$-C$_6$ alkyl; and
r is an integer from 1 to 5,
R$^{20}$ is selected from H and C$_1$-C$_6$ alkyl; and
R$^{21}$ is selected from an electron pair and H; and
R$^2$ is selected from H, G, acyl, trityl, 4-methoxytrityl, C$_1$-C$_6$ alkyl, —C(=NH)NH$_2$, —C(O)—R$^{23}$, —C(O)(CH$_2$)$_s$NR$^{24}$C(=NH)NH$_2$, —C(O)(CH$_2$)$_2$NHC(O)(CH$_2$)$_5$NR$^{24}$C(=NH)NH$_2$, —C(O)CH(NH$_2$)(CH$_2$)$_3$NHC(=NH)NH$_2$, and a moiety of the formula:

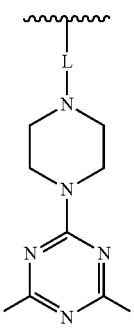

wherein,
R²³ is of the formula —(O-alkyl)$_v$-OH, wherein v is an integer from 3 to 10 and each of the v alkyl groups is independently selected from $C_2$-$C_6$ alkyl; and
R²⁴ is selected from H and $C_1$-$C_6$ alkyl;
s is an integer from 1 to 5;
L is selected from —C(O)(CH$_2$)$_6$C(O)— and —C(O)(CH$_2$)$_2$S$_2$(CH$_2$)$_2$C(O)—; and
each R²⁵ is of the formula —(CH$_2$)$_2$OC(O)N(R²⁶)$_2$ wherein each R²⁶ is of the formula —(CH$_2$)$_6$NHC(=NH)NH$_2$,
wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

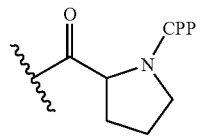

wherein the CPP is attached to the linker moiety by an amide bond at the CPP carboxy terminus, with the proviso that up to one instance of G is present.

In some embodiments, R² is a moiety of the formula:

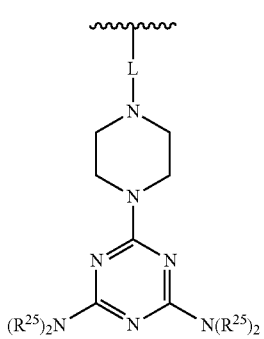

where L is selected from —C(O)(CH$_2$)$_6$C(O)— or —C(O)(CH$_2$)$_2$S$_2$(CH$_2$)$_2$C(O)—, and and each R²⁵ is of the formula —(CH$_2$)$_2$OC(O)N(R²⁶)$_2$ wherein each R²⁶ is of the formula —(CH$_2$)$_6$NHC(=NH)NH$_2$. Such moieties are further described in U.S. Pat. No. 7,935,816, which is hereby incorporated by reference in its entirety.

In certain embodiments, R² may comprise either moiety depicted below:

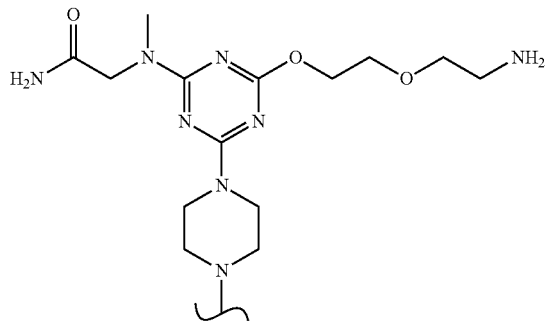

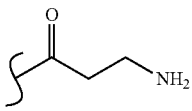

In various embodiments, each Y is O, and R² is selected from H or G. In some embodiments, R² is G wherein the CPP is of a sequence selected from SEQ ID NOS: 17 to 32. In certain embodiments, R² is H.

In certain embodiments, each R¹ is —N(CH$_3$)$_2$. In some embodiments, about 50-95% of the R¹ groups are dimethylamino (i.e. —N(CH$_3$)$_2$). In certain embodiments, about 70% to about 80% of the R¹ groups are diemethylamino. In certain embodiments about 75% of the R¹ groups are dimethylamino. In certain embodiments, about 66% of the R¹ groups are dimethylamino.

In some embodiments of the disclosure. R¹ may be selected from:

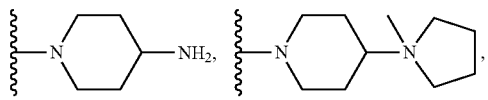

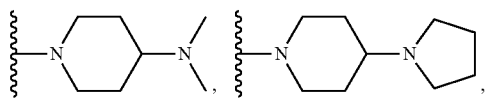

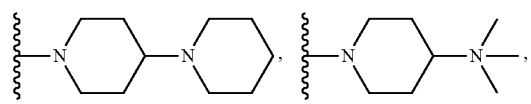

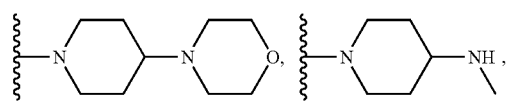

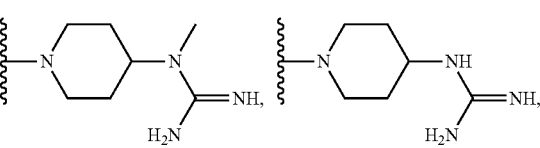

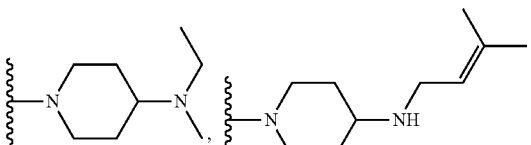

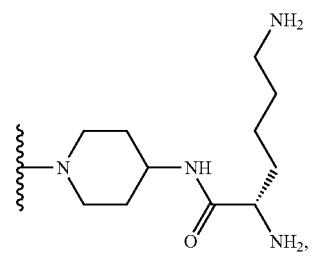

-continued

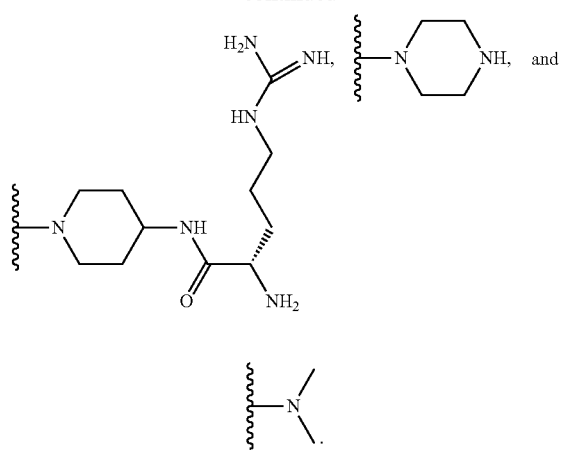

In certain embodiments, at least one R¹ is selected from:

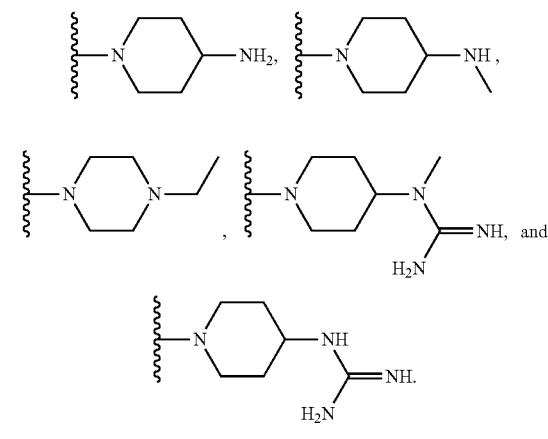

In some embodiments, at least one R¹ is:

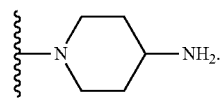

In various embodiments, at least one R¹ is:

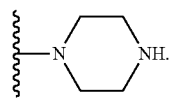

In some embodiments, at least one R¹ is:

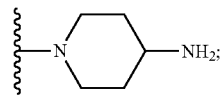

and at least one other R¹ is:

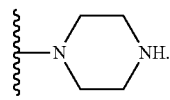

In certain embodiments, T is of the formula:

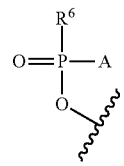

wherein A is —N(CH₃)₂, and R⁶ is of the formula:

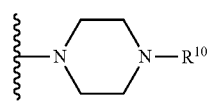

wherein $R^{10}$ is —C(O)$R^{11}$OH.

In some embodiments, each Y is O, R² is H, G, or acyl, and T is selected from:

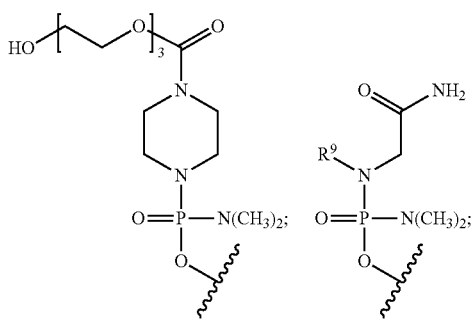

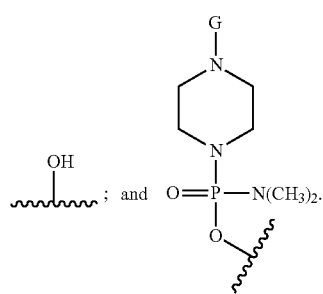

In some embodiments, T is selected from:

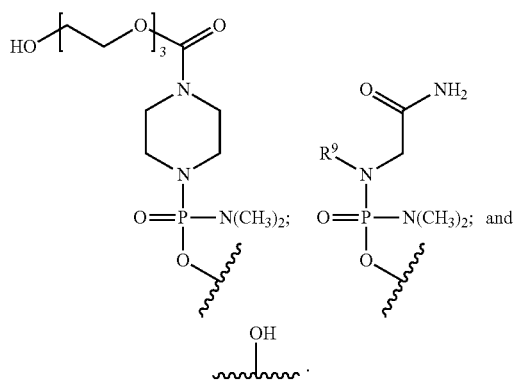

In certain embodiments, T is of the formula:

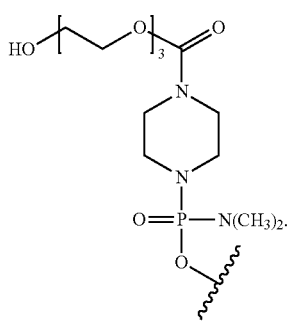

In various embodiments, T is of the formula:

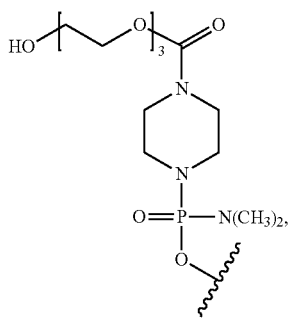

each Y is O and $R^2$ is G.

In some embodiments, T is of the formula:

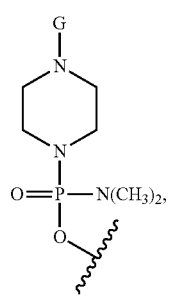

each Y is O, and $R^2$ is H or acyl.

In various embodiments, $R^2$ is selected from H or acyl, T is of the formula:

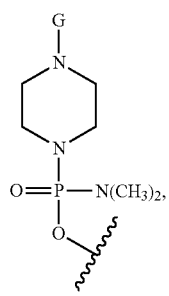

each Y is O and each $R^1$ is —$N(CH_3)_2$.

In certain embodiments, T is of the formula:

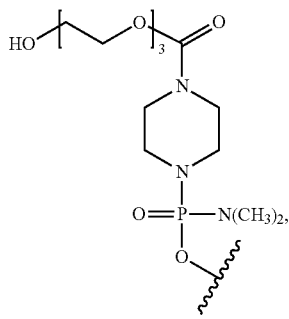

each Y is O, each $R^1$ is —$N(CH_3)_2$, and $R^2$ is G.

In various embodiments, T is of the formula:

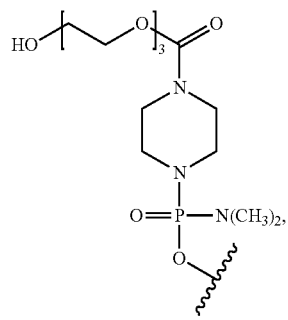

each Y is O, and $R^2$ is H.

In some embodiments, each Y is O, each $R^1$ is independently selected from

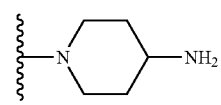 [SMILES: *N1CCC(N)CC1]

and —N(CH₃)₂; T is:

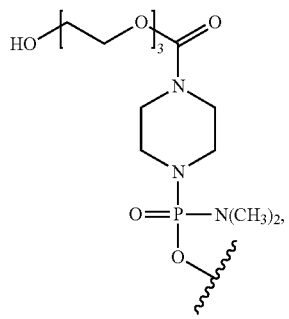

and R² is H, wherein at least one R¹ is

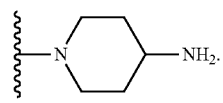 [SMILES: *N1CCC(N)CC1]

In certain embodiments, each Y is O, each R¹ is independently selected from

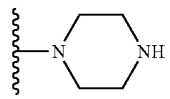

and —N(CH₃)₂; T is:

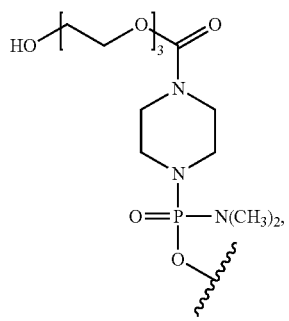

and R² is H, wherein at least one R¹ is

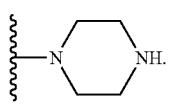

In some embodiments, at least one R¹ is:

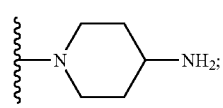 [SMILES: *N1CCC(N)CC1]

T is:

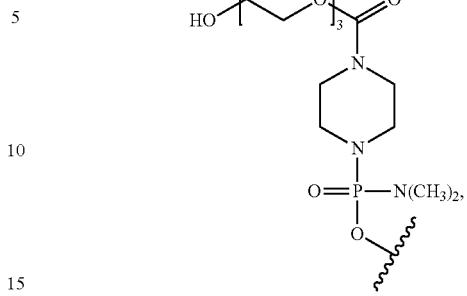

and R² is G.

In some embodiments, the CPP is of a sequence selected from SEQ ID NOS: 17 to 32.

In some embodiments, G is of the formula:

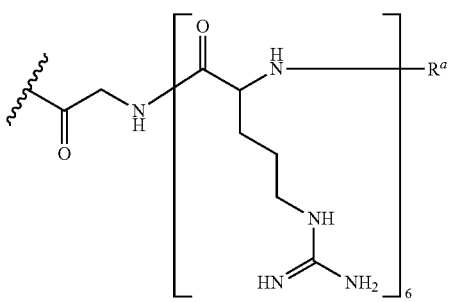

wherein $R^a$ is selected from H, acetyl, benzoyl, and stearoyl.

In certain embodiments, the CPP is of the formula:

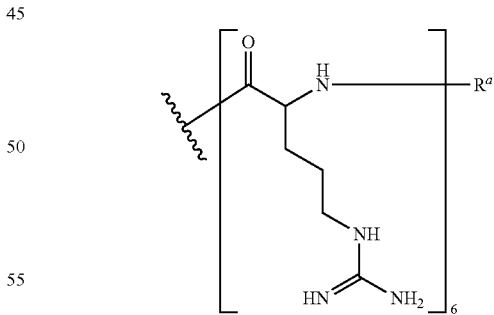

wherein $R^a$ is selected from H, acetyl, benzoyl, and stearoyl.

In various embodiments, each Y is O, and R² is selected from H or G. In some embodiments, R² is G, wherein the CPP is of a sequence selected from SEQ ID NOS: 17 to 32 described below.

In other embodiments, the modified antisense oligomer is a compound of formula (IV):

(IV)

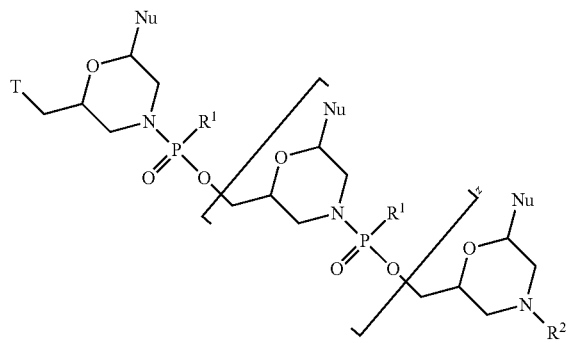

or a pharmaceutically acceptable salt thereof, where:
  each Nu is a nucleobase which taken together forms a targeting sequence;
  Z is an integer from 6 to 38;
  T is selected from a moiety of the formula:

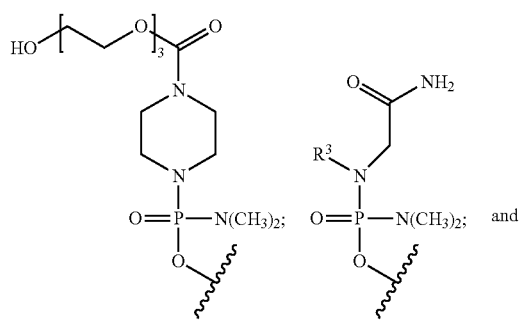

-continued

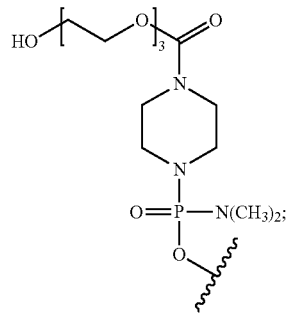

wherein $R^3$ is selected from H and $C_1$-$C_6$ alkyl;
each instance of $R^1$ is independently —N($R^4$)$_2$, wherein each $R^4$ is independently selected from H and $C_1$-$C_6$ alkyl; and
$R^2$ is selected from H, acyl, trityl, 4-methoxytrityl, and $C_1$-$C_6$ alkyl.

In various embodiments, $R^2$ is selected from H or acyl. In some embodiments, $R^2$ is H.

In certain embodiments, T is of the formula:

and $R^2$ is hydrogen.

In other embodiments, the modified antisense oligomer is a compound of formula (IVa):

(IVa)

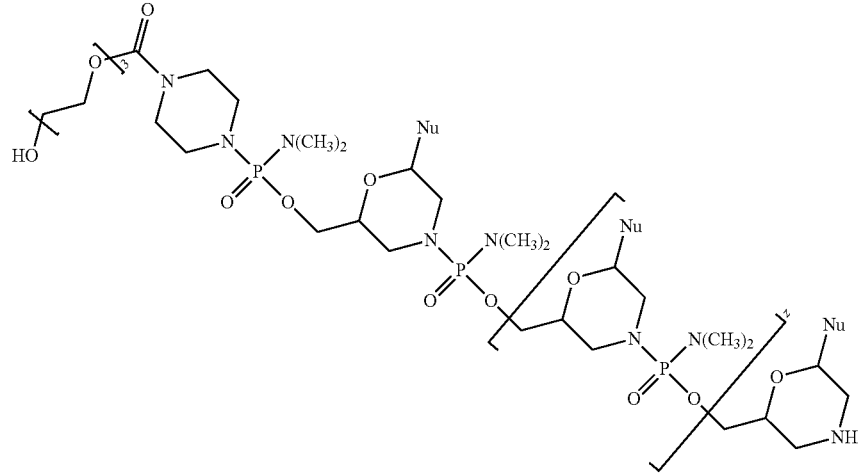

or a pharmaceutically acceptable salt thereof, where:
each Nu is a nucleobase which taken together forms a targeting sequence;
Z is an integer from 6 to 38.

In other embodiments, the modified antisense oligomer is a compound of formula (V):

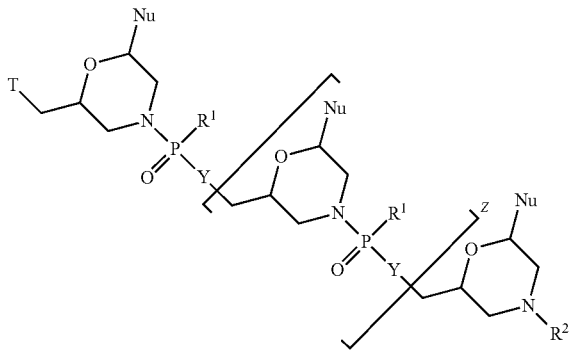

(V)

or a pharmaceutically acceptable salt thereof, wherein:
each Nu is a nucleobase which taken together forms a targeting sequence;
Z is an integer from 6 to 38;
each Y is independently selected from O and —NR$^4$, wherein each R$^4$ is independently selected from H, C$_1$-C$_6$ alkyl, aralkyl, —C(=NH)NH$_2$, —C(O)(CH$_2$)$_{11}$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and C$_1$-C$_6$ alkyl and n is an integer from 1 to 5;
T is selected from OH and a moiety of the formula:

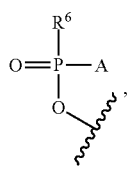

wherein:
A is selected from —OH, —N(R$^7$)$_2$R$^8$, and R$^1$ wherein:
each R$^7$ is independently selected from H and C$_1$-C$_6$ alkyl, and
R$^8$ is selected from an electron pair and H, and
R$^6$ is selected from OH, —N(R$^9$)CH$_2$C(O)NH$_2$, and a moiety of the formula:

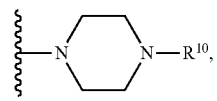

wherein:
R$^9$ is selected from H and C$_1$-C$_6$ alkyl; and
R$^{10}$ is selected from G, —C(O)—R$^{11}$OH, acyl, trityl, 4-methoxytrityl, —C(=NH)NH$_2$, —C(O)(CH$_2$)$_m$NR$^{12}$C(=NH)NH$_2$, and —C(O)(CH$_2$)$_2$NHC(O)(CH$_2$)$_5$NR$^{12}$C(=NH)NH$_2$, wherein:
m is an integer from 1 to 5,
R$^{11}$ is of the formula —(O-alkyl)$_y$- wherein y is an integer from 3 to 10 and each of the y alkyl groups is independently selected from C$_2$-C$_6$ alkyl; and
R$^{12}$ is selected from H and C$_1$-C$_6$ alkyl;
each instance of R$^1$ is independently selected from:
—N(R$^{13}$)$_2$R$^{14}$ wherein each R$^{13}$ is independently selected from H and C$_1$-C$_6$ alkyl, and R$^{14}$ is selected from an electron pair and H;
a moiety of formula (II):

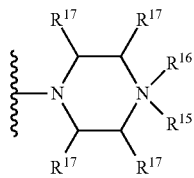

(II)

wherein:
R$^{15}$ is selected from H, G, C$_1$-C$_6$ alkyl, —C(=NH)NH$_2$, —C(O)(CH$_2$)$_q$NR$^{18}$C(=NH)NH$_2$, and —C(O)(CH$_2$)$_2$NHC(O)(CH$_2$)$_5$NR$^{18}$C(=NH)NH$_2$, wherein:
R$^{18}$ is selected from H and C$_1$-C$_6$ alkyl; and
q is an integer from 1 to 5,
R$^{16}$ is selected from an electron pair and H; and
each R$^{17}$ is independently selected from H and methyl; and
a moiety of formula (III):

(III)

wherein:
R$^{19}$ is selected from H, C$_1$-C$_6$ alkyl, —C(=NH)NH$_2$, —C(O)(CH$_2$)$_r$NR$^{22}$C(=NH)NH$_2$, —C(O)CH(NH$_2$)(CH$_2$)$_3$NHC(=NH)NH$_2$, —C(O)(CH$_2$)$_2$NHC(O)(CH$_2$)$_5$NR$^{22}$C(=NH)NH$_2$, —C(O)CH(NH$_2$)(CH$_2$)$_4$NH$_2$, and G
wherein:
R$^{22}$ is selected from H and C$_1$-C$_6$ alkyl; and
r is an integer from 1 to 5,
R$^{20}$ is selected from H and C$_1$-C$_6$ alkyl; and
R$^{21}$ is selected from an electron pair and H; and
R$^2$ is selected from G, H, acyl, trityl, 4-methoxytrityl, and C$_1$-C$_6$ alkyl,
wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

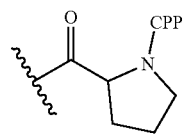

wherein the CPP is attached to the linker moiety by an amide bond at the CPP carboxy terminus, with the proviso that up to one instance of G is present, and wherein at least one of the following conditions is present:

c) at least one are R¹ is of formula (II) or of formula (III), or d) R² is G or T is:

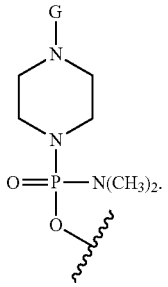

In certain embodiments, at least one R¹ is selected from:

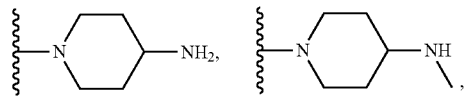

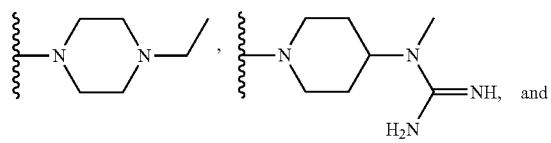

In some embodiments, at least one R¹ is:

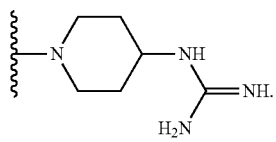

In some embodiments, each Y is O, each R¹ is independently selected from

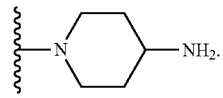

and —N(CH₃)₂; T is:

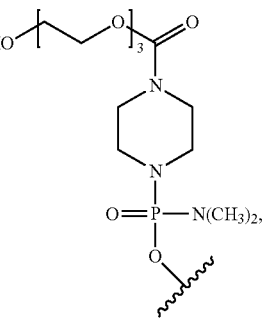

and R² is H, wherein at least one R¹ is

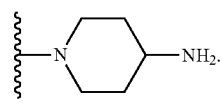

In various embodiments, at least one R¹ is:

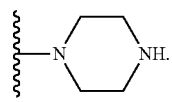

In certain embodiments, each Y is O, each R¹ is independently selected from

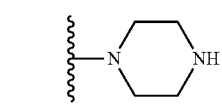

and —N(CH₃)₂; T is:

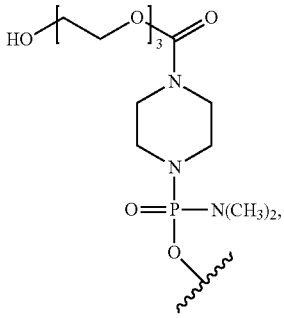

and R² is H, wherein at least one R¹ is

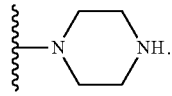

In some embodiments, at least on R¹ is:

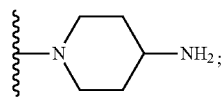

and
at least one other R¹ is:

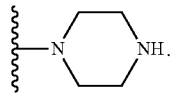

In certain embodiments, at least one R¹ is:

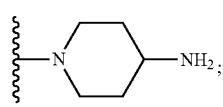

T is:

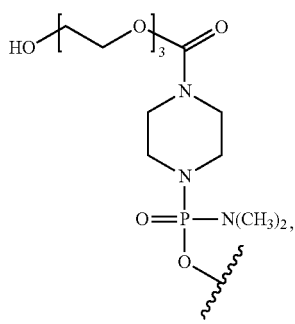

and R² is H or acyl.
In some embodiments, at least one R¹ is:

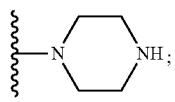 [SMILES: *N1CCNCC1]

T is:

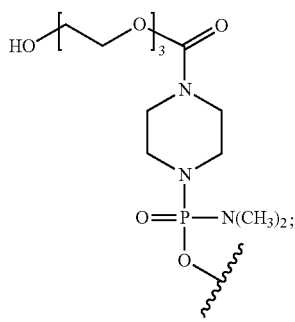

and R² is H or acyl.

In certain embodiments, at least one R¹ is:

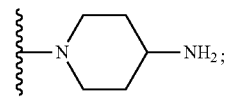

at least one other R¹ is:

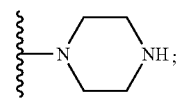

T is:

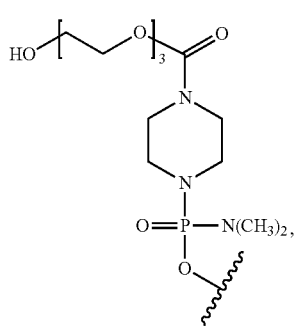

and R² is H or acyl.
In some embodiments, T is of the formula:

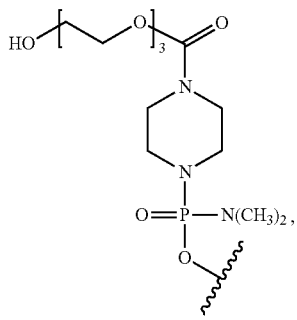

each Y is O, and R² is H.
In various embodiments, T is of the formula:

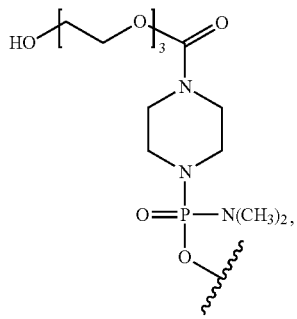

and R² is G.

In some embodiments, T is of the formula:

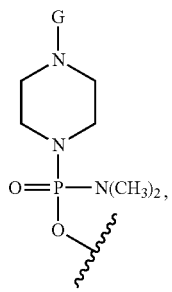

and R² is H or acyl.

In various embodiments, R² is selected from H or acyl, T is of the formula:

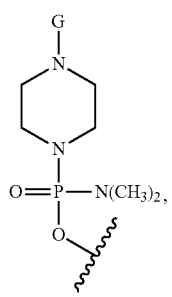

each Y is O and each R¹ is —N(CH$_3$)$_2$.

In certain embodiments, T is of the formula:

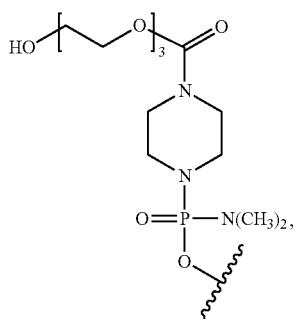

each Y is O, each R¹ is —N(CH$_3$)$_2$, and R² is G.

In some embodiments, at least one R¹ is:

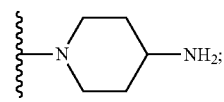

T is:

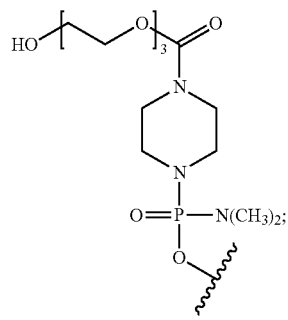

and R² is G.

In some embodiments, at least one R¹ is:

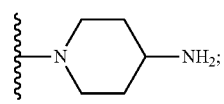

T is of the formula:

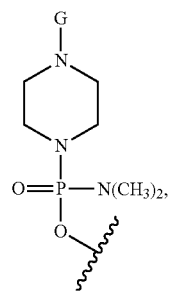

and R² is H or acyl.

In various embodiments, the CPP is of a sequence selected from SEQ ID NOS: 17 to 32.

In some embodiments, G is of the formula:

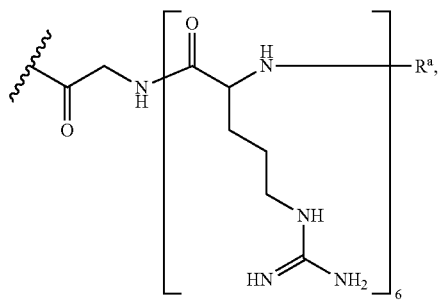

wherein R$^a$ is selected from H, acetyl, benzoyl, and stearoyl.

In certain embodiments, the CPP is of the formula:

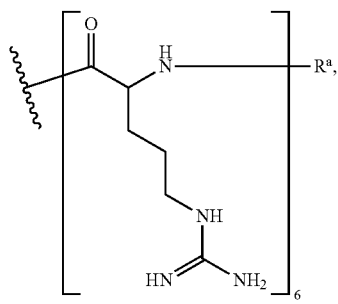

wherein $R^a$ is selected from H, acetyl, benzoyl, and stearoyl.

In various embodiments, each Y is O, and $R^2$ is selected from H or G. In some embodiments, $R^2$ is G wherein the CPP is of a sequence selected from SEQ ID NOS: 17 to 32. In certain embodiments, $R^2$ is H.

In some embodiments, the modified antisense oligomer is a compound of formula (Va):

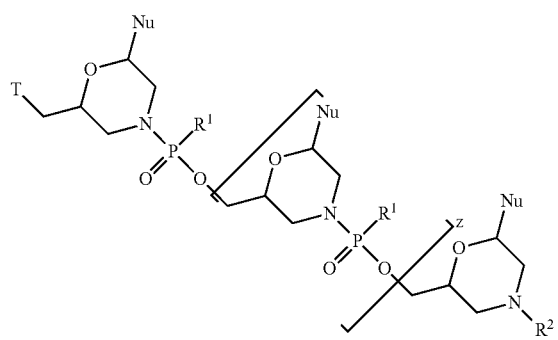

(Va)

or a pharmaceutically acceptable salt thereof, where:

each Nu is a nucleobase which taken together forms a targeting sequence;

Z is an integer from 6 to 38;

T is a moiety selected from:

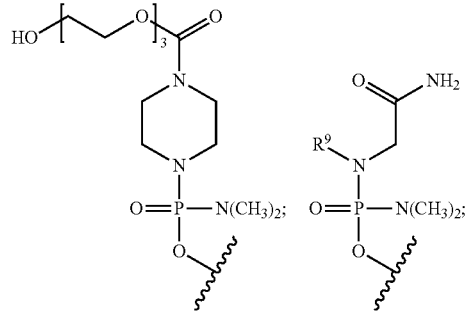

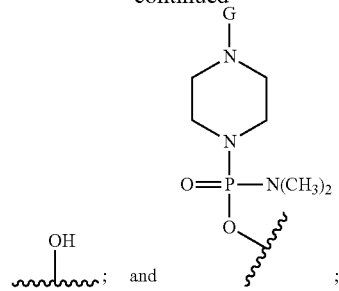

each $R^1$ is independently selected from:

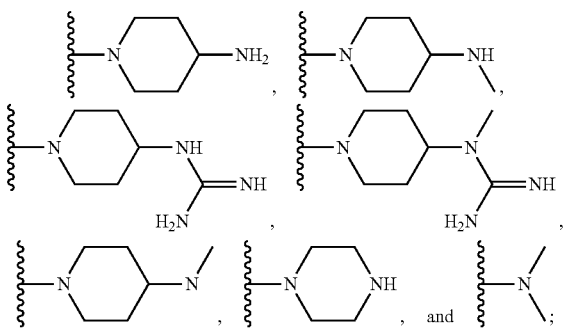

and $R^2$ is selected from G, H, acyl, trityl, 4-methoxytrityl, and $C_1$-$C_6$ alkyl, wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

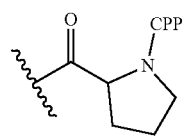

wherein the CPP is attached to the linker moiety by an amide bond at the CPP carboxy terminus;

wherein at least one of the following conditions is present:

e) at least one are $R^1$ is:

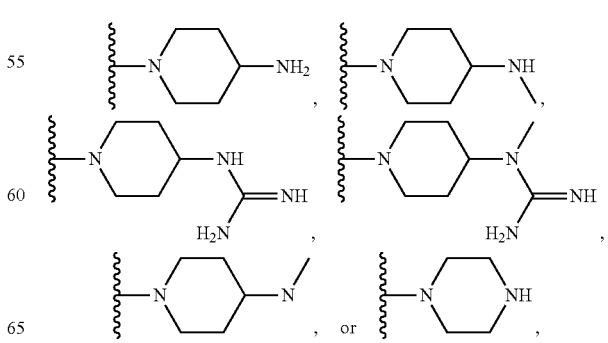

or f) $R^2$ is G or T is:

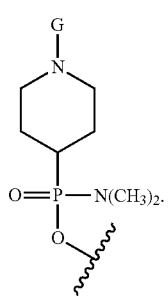

In certain embodiments, at least one $R^1$ is selected from:

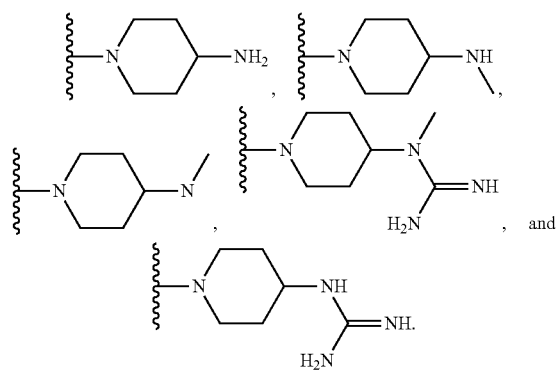

In some embodiments, at least one $R^1$ is:

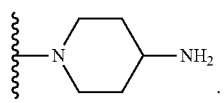

In some embodiments, each $R^1$ is independently selected from

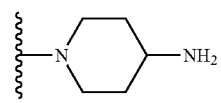

and —N(CH$_3$)$_2$; T is:

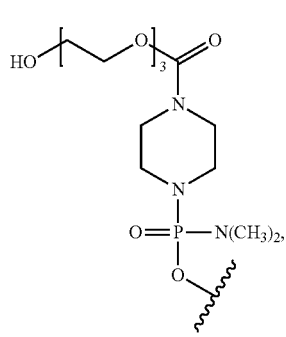

and $R^2$ is H, wherein at least one $R^1$ is

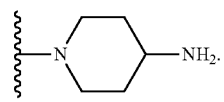

In various embodiments, at least one $R^1$ is:

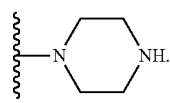

In certain embodiments, each $R^1$ is independently selected from

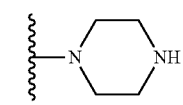

and —N(CH$_3$)$_2$; T is:

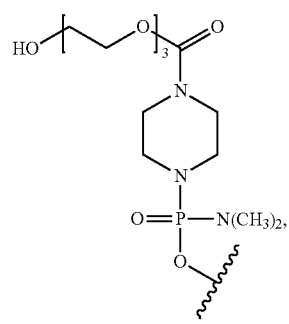

and $R^2$ is H, wherein at least one $R^1$ is

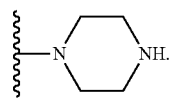

In some embodiments, at least on $R^1$ is:

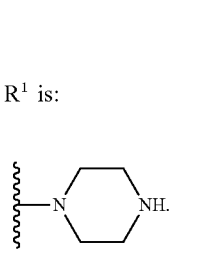

and at least one other $R^1$ is:

In certain embodiments, at least one $R^1$ is:

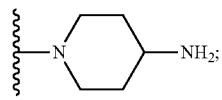

T is:

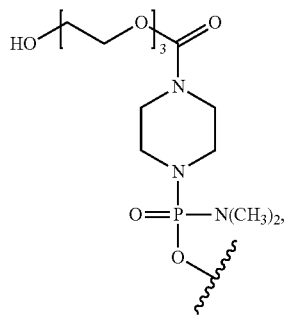

and $R^2$ is H or acyl.

In certain embodiments, each $R^1$ is independently selected from:

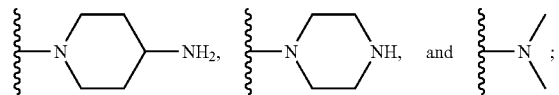

In various embodiments, at least one of the following conditions is present:
a) at least one are $R^1$ is:

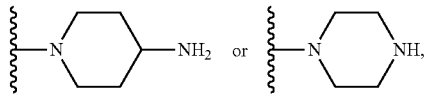

or
b) $R^2$ is G or T is:

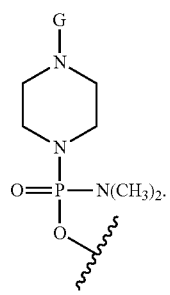

In some embodiments, at least one $R^1$ is:

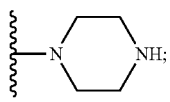

T is:

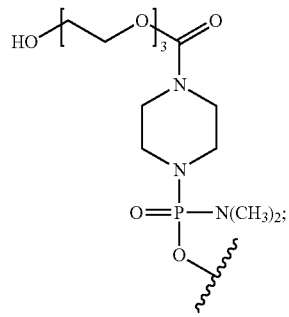

and $R^2$ is H or acyl.

In various embodiments, $R^2$ is selected from H or acyl, T is of the formula:

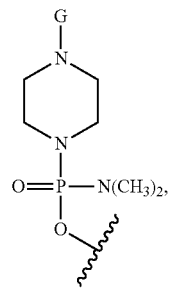

each $R^1$ is —$N(CH_3)_2$.

In certain embodiments, at least one $R^1$ is:

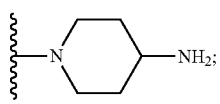

at least one other $R^1$ is:

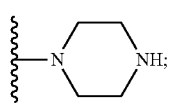

T is:

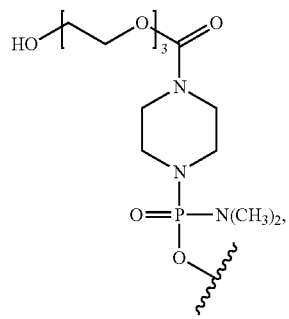

and $R^2$ is H or acyl.

In various embodiments, T is of the formula:

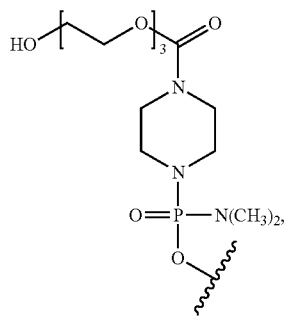

and R² is G.

In certain embodiments, T is of the formula:

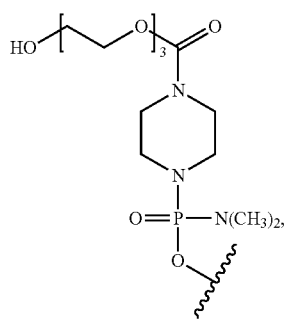

each is —N(CH₃)₂, and R² is G.

In some embodiments, T is of the formula:

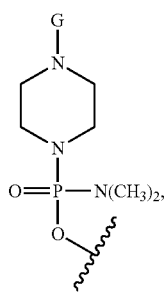

and R² is H or acyl.

In some embodiments, at least one R¹ is:

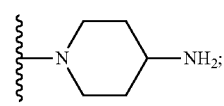

T is:

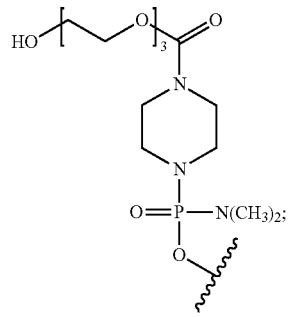

and R² is G.

In some embodiments, at least one R¹ is:

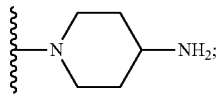

T is of the formula:

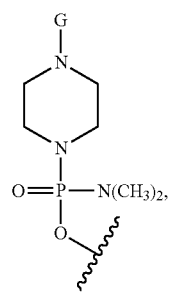

and R² is H or acyl.

In various embodiments, the CPP is of a sequence selected from SEQ ID NOS: 17 to 32.

In some embodiments, G is of the formula:

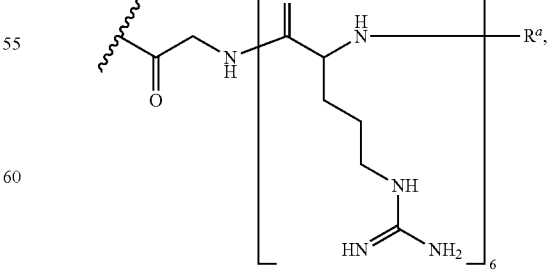

wherein $R^a$ is selected from H, acetyl, benzoyl, and stearoyl.

In certain embodiments, the CPP is of the formula:

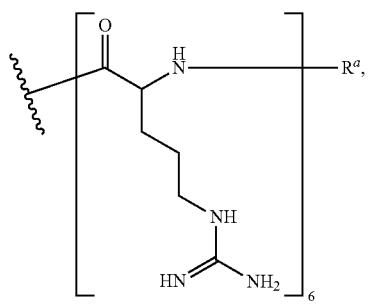

wherein $R^a$ is selected from H, acetyl, benzoyl, and stearoyl.

In some embodiments, the modified antisense oligomer is a compound of formula (Vb):

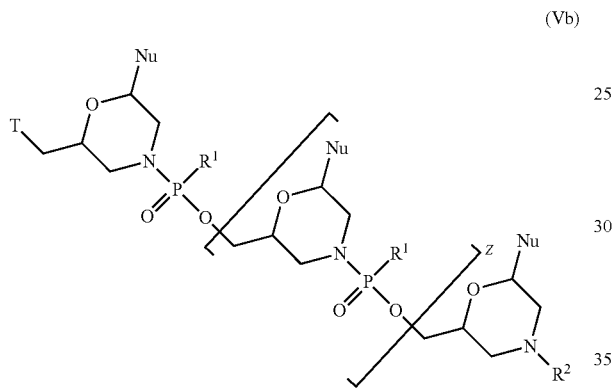

(Vb)

or a pharmaceutically acceptable salt thereof, where:
each Nu is a nucleobase which taken together forms a targeting sequence;
Z is an integer from 6 to 38;
T is a moiety selected from:

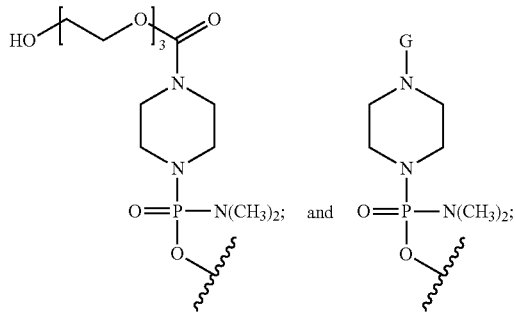

each $R^1$ is independently selected from:

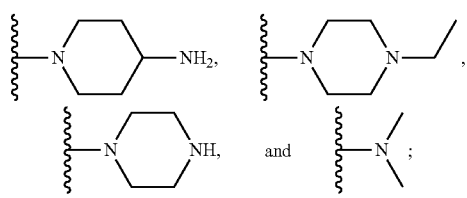

and
$R^2$ is selected from G, H, and acyl,
wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

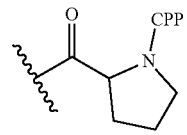

wherein the CPP is attached to the linker moiety by an amide bond at the CPP carboxy terminus; and
wherein at least one of the following conditions is present:
c) at least one are $R^1$ is.

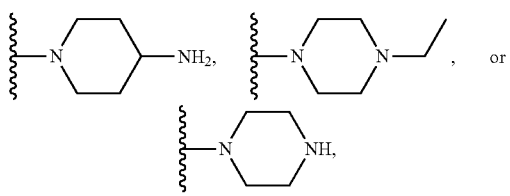

or
d) $R^2$ is G or T is:

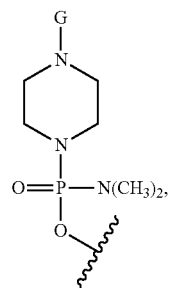

In certain embodiments, each $R^1$ is independently selected from:

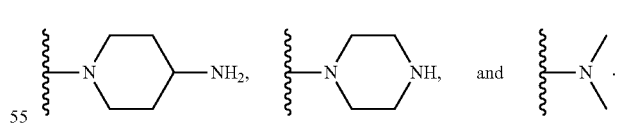

In various embodiments, at least one of the following conditions is present:
a) at least one are $R^1$ is:

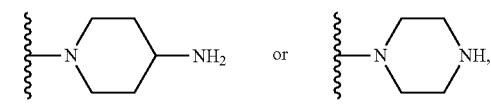 [SMILES: *N1CCC(N)CC1 ; "or" ; *N1CCNCC1]

or b) $R^2$ is G or T is:

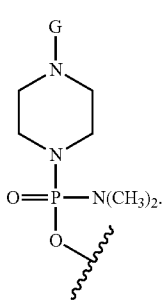

In some embodiments, at least one $R^1$ is:

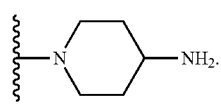

In some embodiments, each $R^1$ is independently selected from

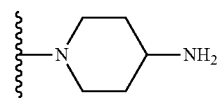

and —N(CH$_3$)$_2$; T is:

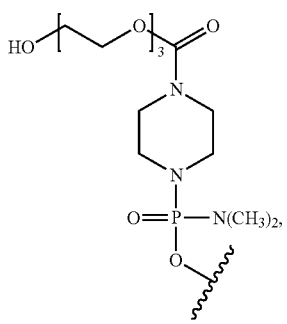

and $R^2$ is H, wherein at least one $R^1$ is

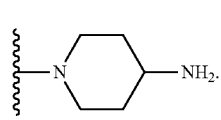

In certain embodiments, each $R^1$ is independently selected from

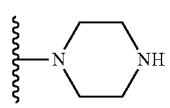 [SMILES: *N1CCNCC1]

and —N(CH$_3$)$_2$; T is:

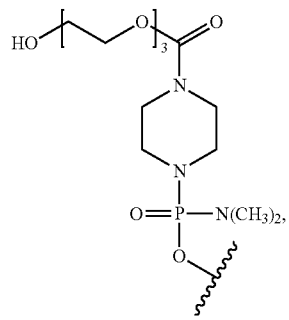

and $R^2$ is H, wherein at least one $R^1$ is

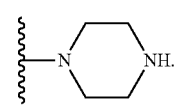

In various embodiments, at least one $R^1$ is:

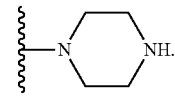

In some embodiments, at least on $R^1$ is:

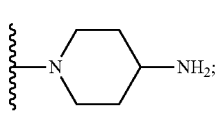 [SMILES: *N1CCC(N)CC1]

and at least one other $R^1$ is:

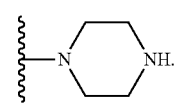

In certain embodiments, at least one $R^1$ is:

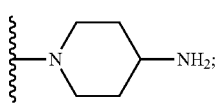

T is:
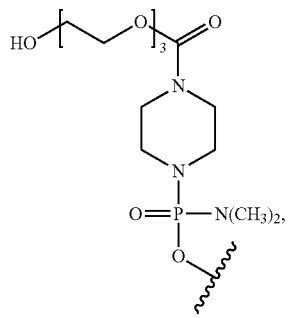
and R² is H or acyl.
In some embodiments, at least one R¹ is:
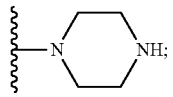 [SMILES: *N1CCNCC1]
T is:
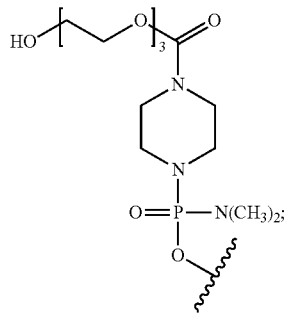
and R² is H or acyl.
In certain embodiments, at least one R¹ is:
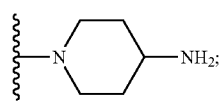
at least one other R¹ is:
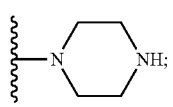
T is:
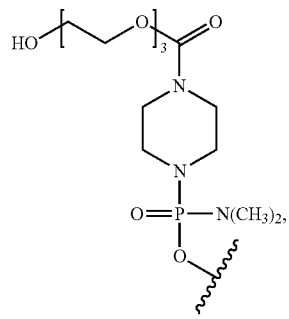
and R² is H or acyl.
In various embodiments, T is of the formula:
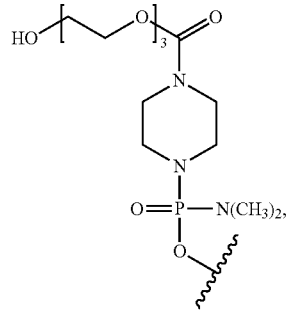
and R² is G.
In some embodiments, T is of the formula:
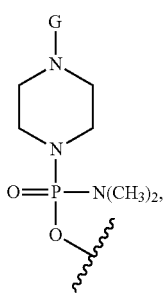
and R² is H or acyl.
In some embodiments, at least one R¹ is:
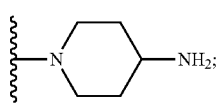

T is:

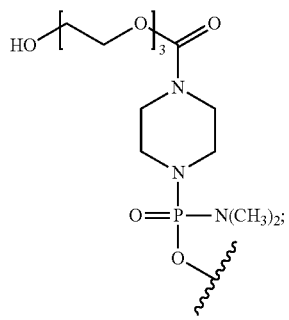

and R² is G.

In certain embodiments, T is of the formula:

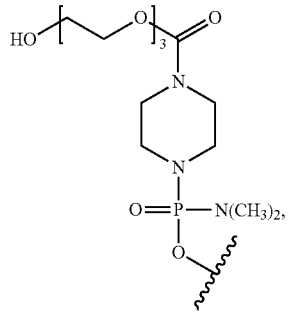

each R¹ is —N(CH₃)₂, and R² is G.

In various embodiments, R² is selected from H or acyl, T is of the formula:

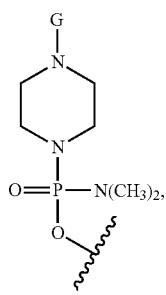

and each R¹ is —N(CH₃)₂.

In some embodiments, at least one R¹ is:

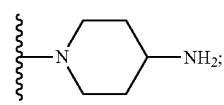

T is of the formula:

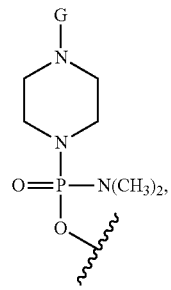

and R² is H or acyl.

In some embodiments, G is of the formula:

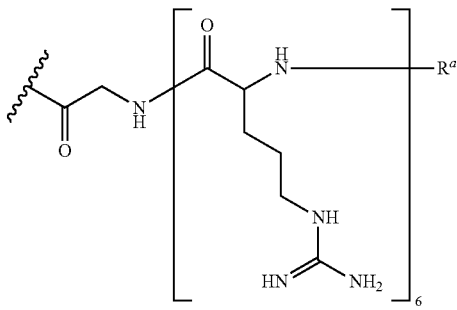

wherein $R^a$ is selected from H, acetyl, benzoyl, and stearoyl.

In certain embodiments, the CPP is of the formula:

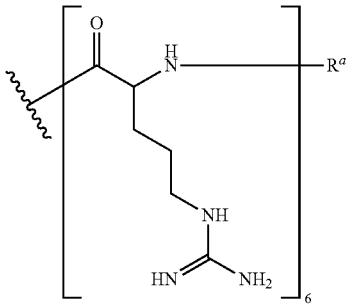

wherein $R^a$ is selected from H, acetyl, benzoyl, and stearoyl.

In some embodiments, T is of the formula:

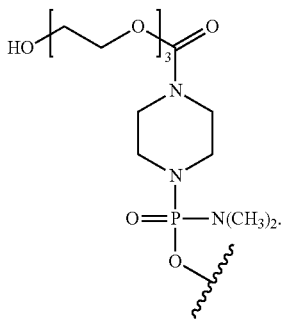

In certain embodiments, the modified antisense oligomer of the disclosure is a compound of formula (VI):

(VI)

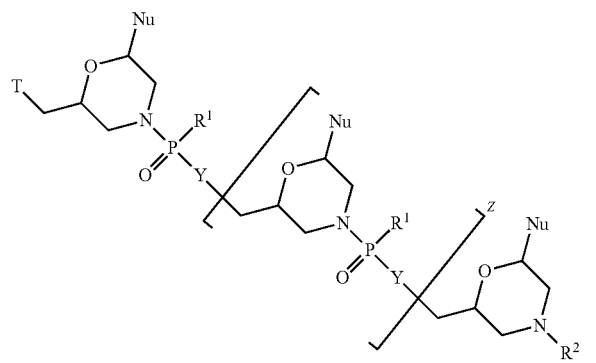

or a pharmaceutically acceptable salt thereof, where:

each Nu is a nucleobase which taken together form a targeting sequence;

Z is an integer from 6 to 38;

each Y is independently selected from O and —NR$^4$, wherein each R$^4$ is independently selected from H, C$_1$-C$_6$ alkyl, aralkyl, —C(=NH)NH$_2$, —C(O)(CH$_2$)$_{11}$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and C$_1$-C$_6$ alkyl and n is an integer from 1 to 5;

T is selected from a moiety of the formula:

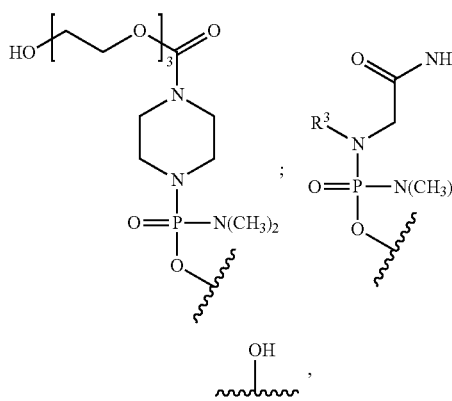

wherein R$^3$ is selected from H and C$_1$-C$_6$ alkyl;

each R$^1$ is independently selected from:

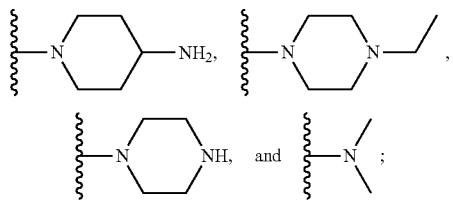

and

R$^2$ is selected from H, acyl, trityl, 4-methoxytrityl, and C$_1$-C$_6$ alkyl, wherein at least one R$^1$ is

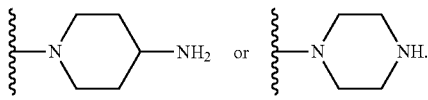

In some embodiments, each Y is O and at least one R$^1$ is:

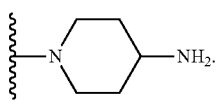

In various embodiments, each Y is O and at least one R$^1$ is:

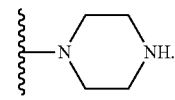

In some embodiments, each Y is O, at least on R$^1$ is:

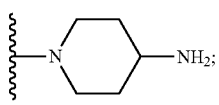

and
at least one other R$^1$ is:

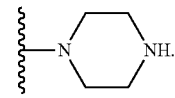

In certain embodiments, each Y is O, at least one R$^1$ is:

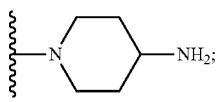

T is:

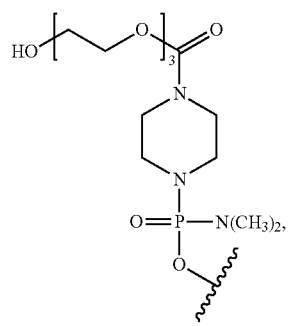

and R$^2$ is H or acyl.-

In various embodiments, each Y is O, each $R^1$ is independently selected from

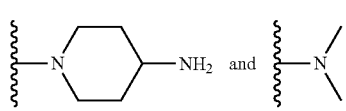

wherein at least one $R^1$ is

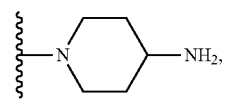 [SMILES: *N1CCC(N)CC1]

T is:

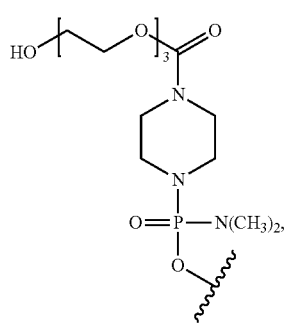

and $R^2$ is H or acyl.

In some embodiments, each Y is O, at least one $R^1$ is:

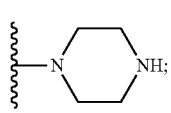 [SMILES: *N1CCNCC1]

T is:

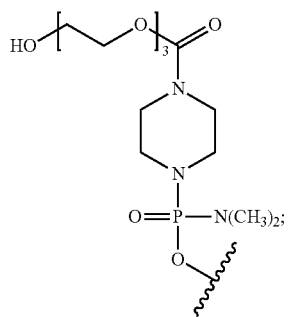

and $R^2$ is H or acyl.

In various embodiments, each Y is O, each R is independently selected from

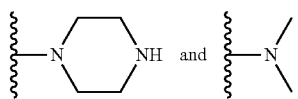

wherein at least one $R^1$ is

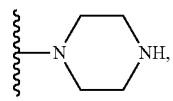

T is:

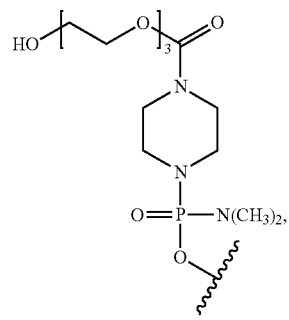

and $R^2$ is H or acyl.

In certain embodiments, each Y is O, at least one $R^1$ is:

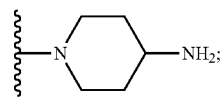

at least one other $R^1$ is:

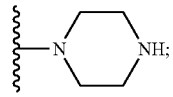

T is:

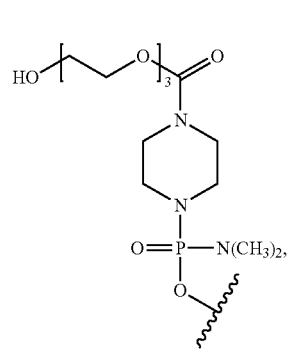

and $R^2$ is H or acyl.

In certain embodiments, the modified antisense oligomer of the disclosure is a compound of formula (VIa):

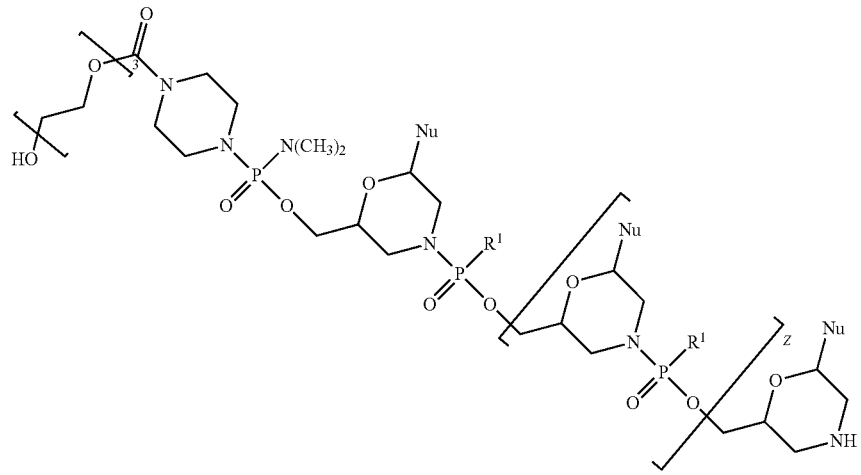

(VIa)

or a pharmaceutically acceptable salt thereof, where:
each Nu is a nucleobase which taken together form a targeting sequence;
Z is an integer from 6 to 38;
each $R^1$ is independently selected from:

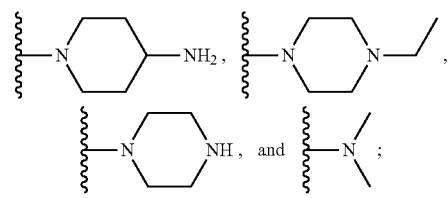

and
$R^2$ is selected from H, acyl, trityl, 4-methoxytrityl, and $C_1$-$C_6$ alkyl,
wherein at least one $R^1$ is

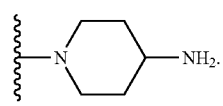

In some embodiments, at least one $R^1$ is:

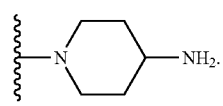

In various embodiments, each $R^1$ is independently selected from

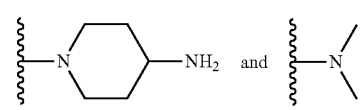

wherein at least one $R^1$ is

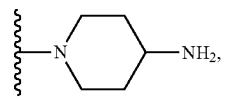

and T is:

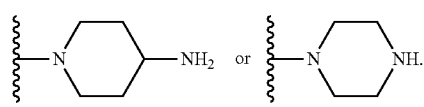

In various embodiments, at least one $R^1$ is:

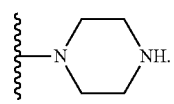

In various embodiments, each $R^1$ is independently selected from

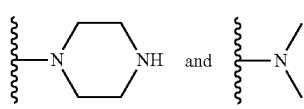

wherein at least one $R^1$ is

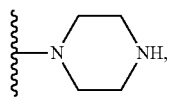

and T is:

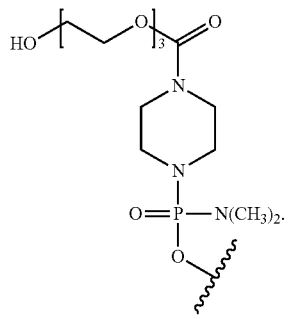

In some embodiments, at least on $R^1$ is:

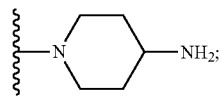

and at least one other $R^1$ is:

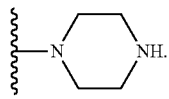

In some embodiments, the modified antisense oligomer is a compound of formula (VII):

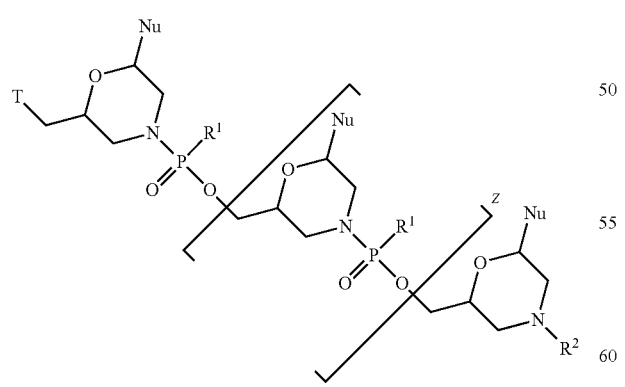

(VII)

or a pharmaceutically acceptable salt thereof, where:

each Nu is a nucleobase which taken together form a targeting sequence;

Z is an integer from 6 to 38;

T is selected from a moiety of the formula:

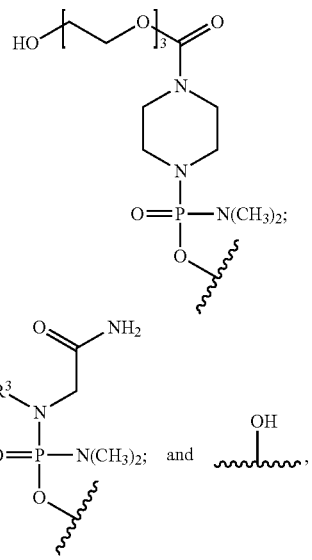

each $R^1$ is independently selected from:

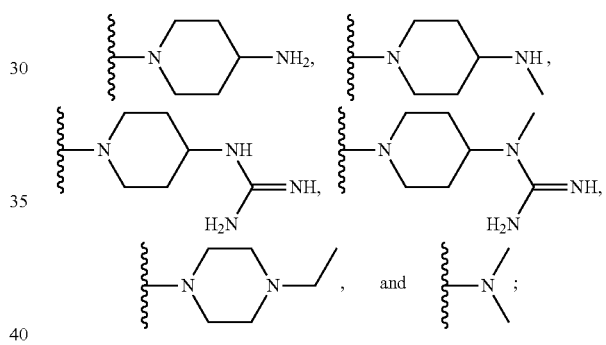

$R^2$ is selected from H, acyl, trityl, 4-methoxytrityl, and $C_1$-$C_6$ alkyl, wherein at least one $R^1$ is:

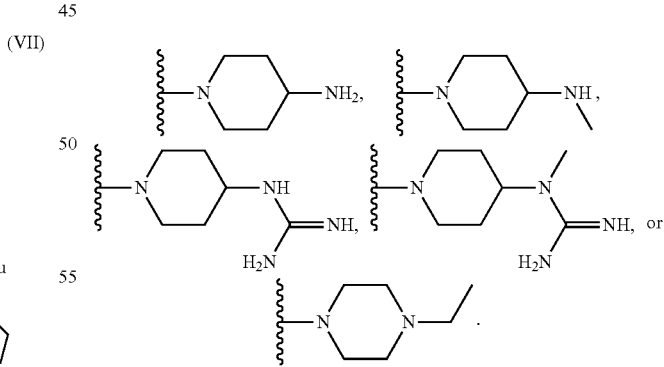

In some embodiments, at least one $R^1$ is:

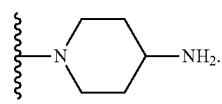 [SMILES: *N1CCC(N)CC1]

In certain embodiments, at least one $R^1$ is:

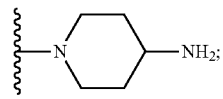 [SMILES: *N1CCC(N)CC1]

and T is:

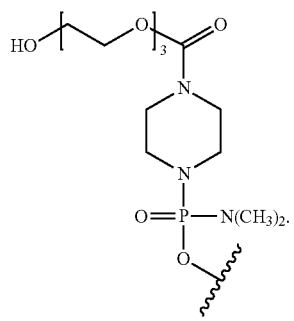

and T is:

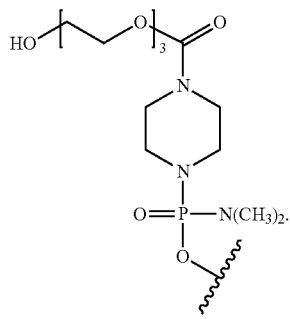

In some embodiments, the modified antisense oligomer is a compound of formula (VIIa):

(VIIa)

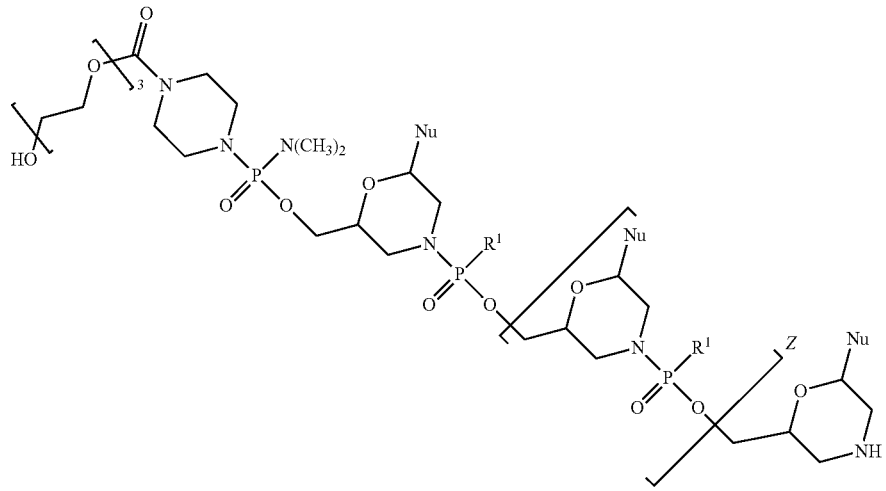

In various embodiments, each $R^1$ is independently selected from

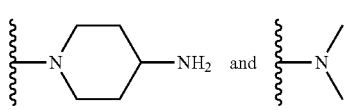

wherein at least one $R^1$ is

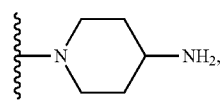

or a pharmaceutically acceptable salt thereof, where:

each Nu is a nucleobase which taken together form a targeting sequence;

Z is an integer from 6 to 38; and each $R^1$ is independently selected from:

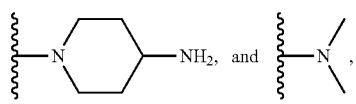

wherein at least one R¹ is:

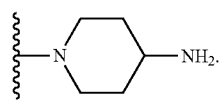

In various embodiments, each Y is O, and R² is selected from H or G. In some embodiments, R² is G, wherein the CPP is a sequence selected from SEQ ID NOS: 17 to 32. In certain embodiments, R² is H.

In some embodiments, the modified antisense oligomer is a compound of formula (VIII):

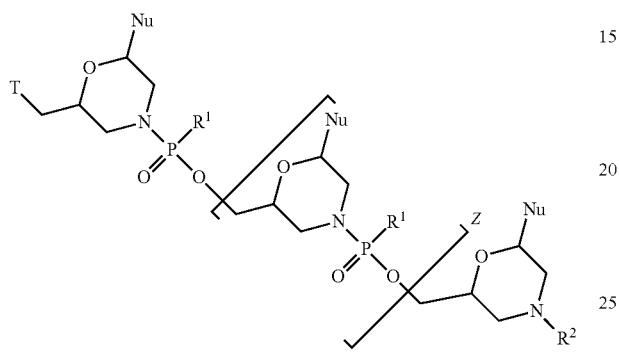

(VIII)

or a pharmaceutically acceptable salt thereof, where:
each Nu is a nucleobase which taken together form a targeting sequence;
Z is an integer from 6 to 38;
T is selected from a moiety of the formula:

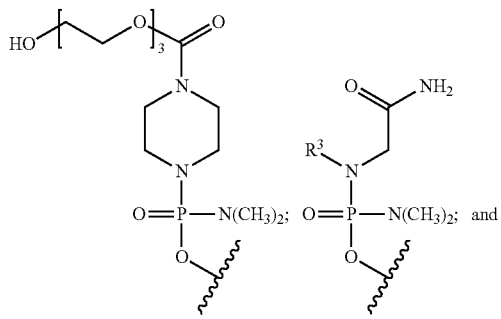

-continued

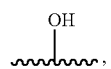

each R¹ is independently selected from:

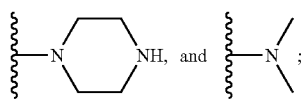

R² is selected from H, acyl, trityl, 4-methoxytrityl, and $C_1$-$C_6$ alkyl,
wherein at least one R¹ is:

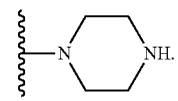

In certain embodiments, T is:

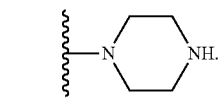

In some embodiments, the modified antisense oligomer is a compound of formula (VIIIa):

(VIIIa)

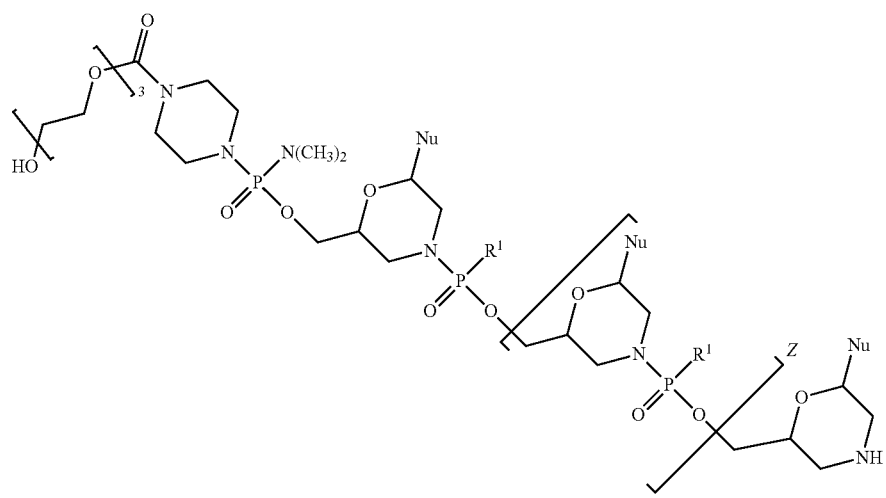

or a pharmaceutically acceptable salt thereof, where:

each Nu is a nucleobase which taken together form a targeting sequence;

Z is an integer from 6 to 38; and each IV is independently selected from:

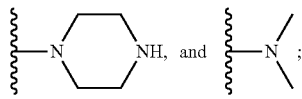

wherein at least one R¹ is:

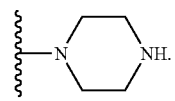

In certain embodiments, the modified antisense oligomer is a compound of formula (IX):

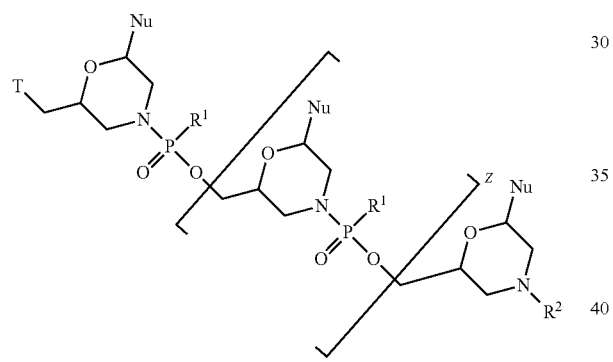

or a pharmaceutically acceptable salt thereof, where:

each Nu is a nucleobase which taken together forms a targeting sequence;

Z is an integer from 6 to 38;

T is a moiety selected from:

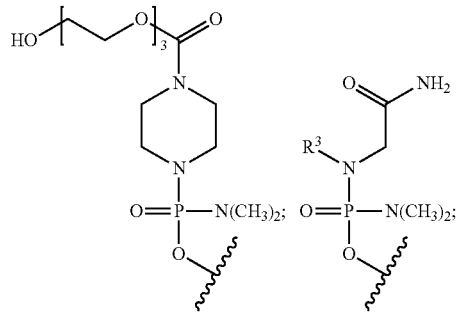

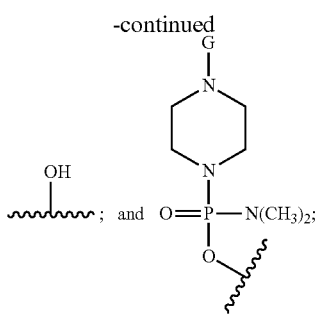

wherein $R^3$ is selected from H and $C_1$-$C_6$ alkyl;

each instance of $R^1$ is independently —N($R^4$)$_2$ wherein each $R^4$ is independently selected from H and $C_1$-$C_6$ alkyl; and $R^2$ is selected from G, H, acyl, trityl, 4-methoxytrityl, and $C_1$-$C_6$ alkyl, wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

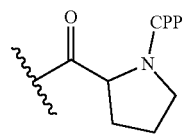

wherein the CPP is attached to the linker moiety by an amide bond at the CPP carboxy terminus; and wherein $R^2$ is G or T is:

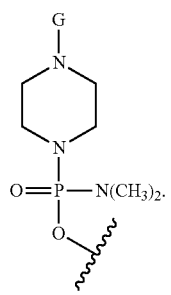

In various embodiments, T is of the formula:

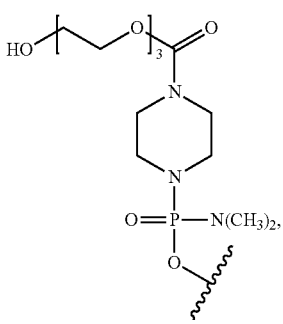

and $R^2$ is G.

In some embodiments, T is of the formula:

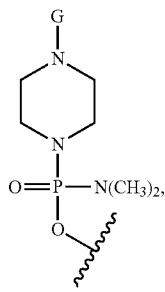

and R² is H or acyl.

In some embodiments, the CPP is of a sequence selected from SEQ ID NOS: 17 to 32.

In some embodiments, G is of the formula:

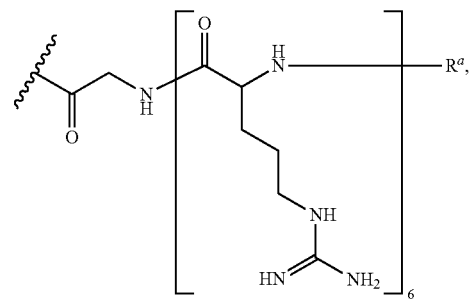

wherein $R^a$ is selected from H, acetyl, benzoyl, and stearoyl.

In certain embodiments, the CPP is of the formula:

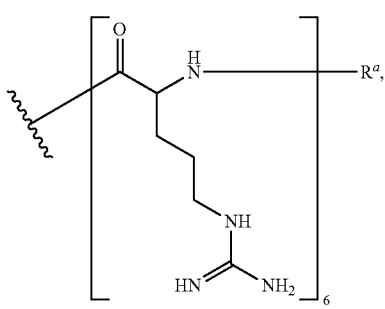

wherein $R^a$ is selected from H, acetyl, benzoyl, and stearoyl.

In some embodiments, each $R^1$ is $-N(CH_3)_2$.

In certain embodiments, the modified antisense oligomer is a compound of formula (IXa):

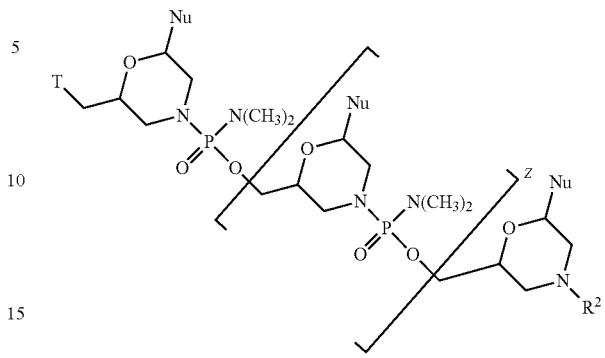

(IXa)

or a pharmaceutically acceptable salt thereof, where:

each Nu is a nucleobase which taken together forms a targeting sequence;

Z is an integer from 6 to 38;

T is a moiety selected from:

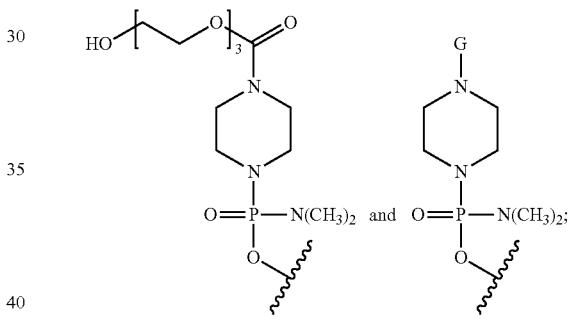

and

R² is selected from G, H, and acyl, wherein G is a cell penetrating peptide ("CPP") and linker moiety selected from $-C(O)(CH_2)_5NH-CPP$, $-C(O)(CH_2)_2NH-CPP$, $-C(O)(CH_2)_2NHC(O)(CH_2)_5NH-CPP$, and $-C(O)CH_2NH-CPP$, or G is of the formula:

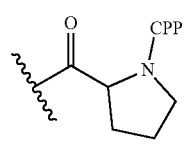

wherein the CPP is attached to the linker moiety by an amide bond at the CPP carboxy terminus; and wherein $R^2$ is G or T is:

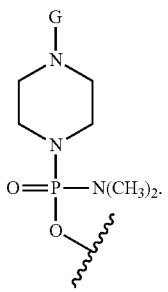

In various embodiments, T is of the formula:

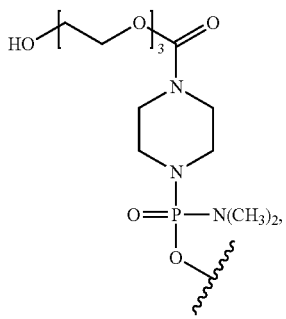

and $R^2$ is G.

In some embodiments, T is of the formula:

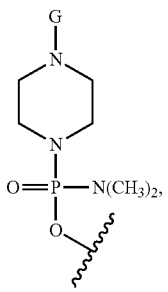

and $R^2$ is H or acyl.

In some embodiments, the CPP is of a sequence selected from SEQ ID NOS: 17 to 32.

In some embodiments, G is of the formula:

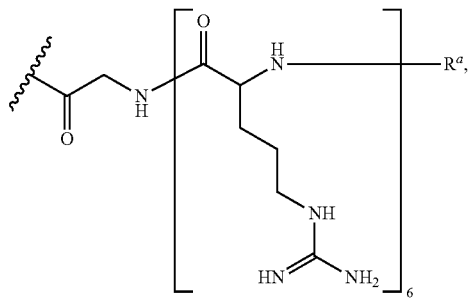

wherein $R^a$ is selected from H, acetyl, benzoyl, and stearoyl.

In certain embodiments, the CPP is of the formula:

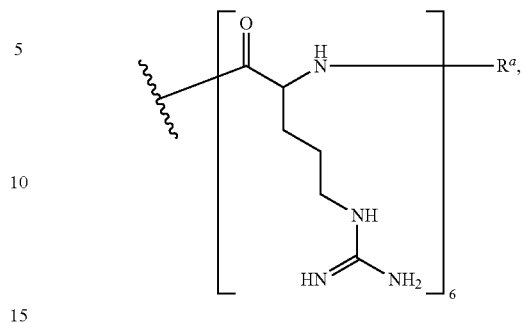

wherein $R^a$ is selected from H, acetyl, benzoyl, and stearoyl.

In certain embodiments, the modified antisense oligomer is a compound of formula (X):

(X)

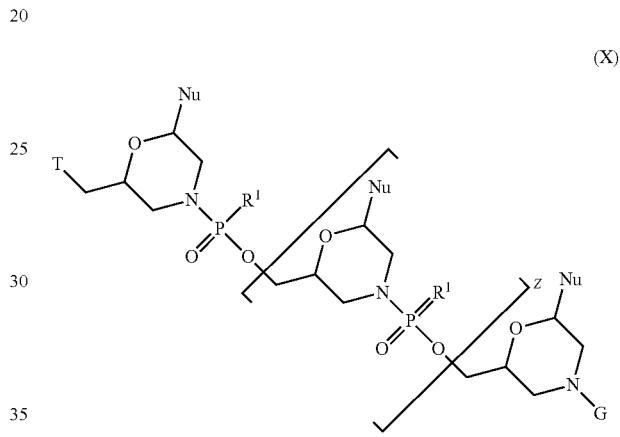

or a pharmaceutically acceptable salt thereof, where:

each Nu is a nucleobase which taken together forms a targeting sequence;

Z is an integer from 6 to 38;

T is a moiety selected from:

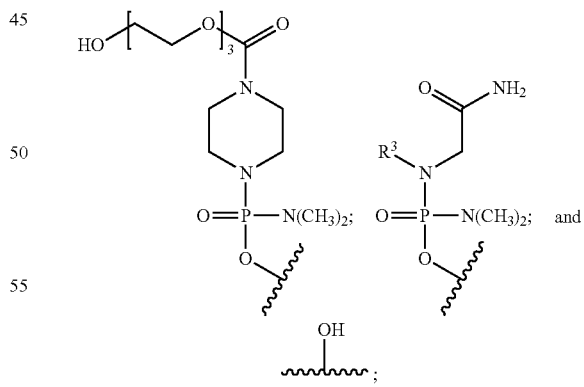

wherein $R^3$ is selected from H and $C_1$-$C_6$ alkyl; and
each instance of $R^1$ is independently —N(R^4)_2 wherein each $R^4$ is independently selected from H and $C_1$-$C_6$ alkyl, wherein G is a cell penetrating peptide ("CPP") and linker moiety selected from —C(O)(CH_2)_5NH—CPP, —C(O)(CH_2)_2NH—CPP, —C(O)(CH_2)_2NHC(O)(CH_2)_5NH—CPP, and —C(O)CH_2NH—CPP, or G is of the formula:

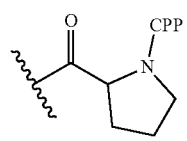

wherein the CPP is attached to the linker moiety by an amide bond at the CPP carboxy terminus.

In various embodiments, T is of the formula:

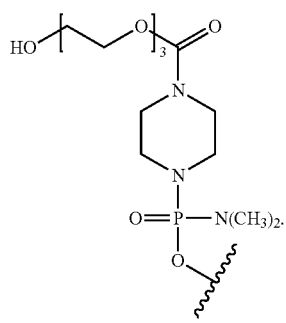

In some embodiments, the CPP is of a sequence selected from SEQ ID NOS: 17 to 32.

In some embodiments, G is of the formula:

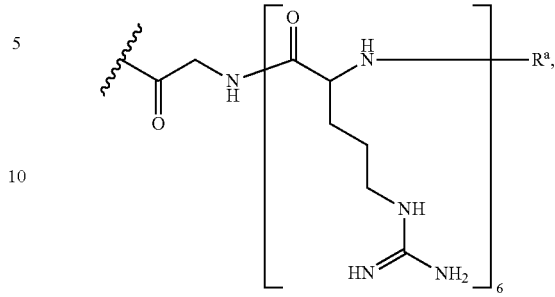

wherein $R^a$ is selected from H, acetyl, benzoyl, and stearoyl. In certain embodiments, the CPP is of the formula:

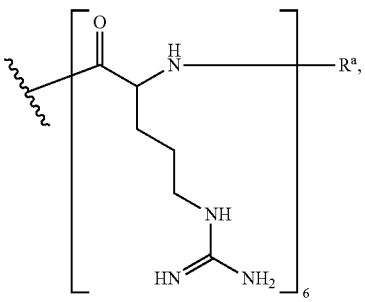

wherein $R^a$ is selected from H, acetyl, benzoyl, and stearoyl.

In some embodiments, each $R^1$ is —$N(CH_3)_2$.

In certain embodiments, the modified antisense oligomer is a compound of formula (Xa):

(Xa)

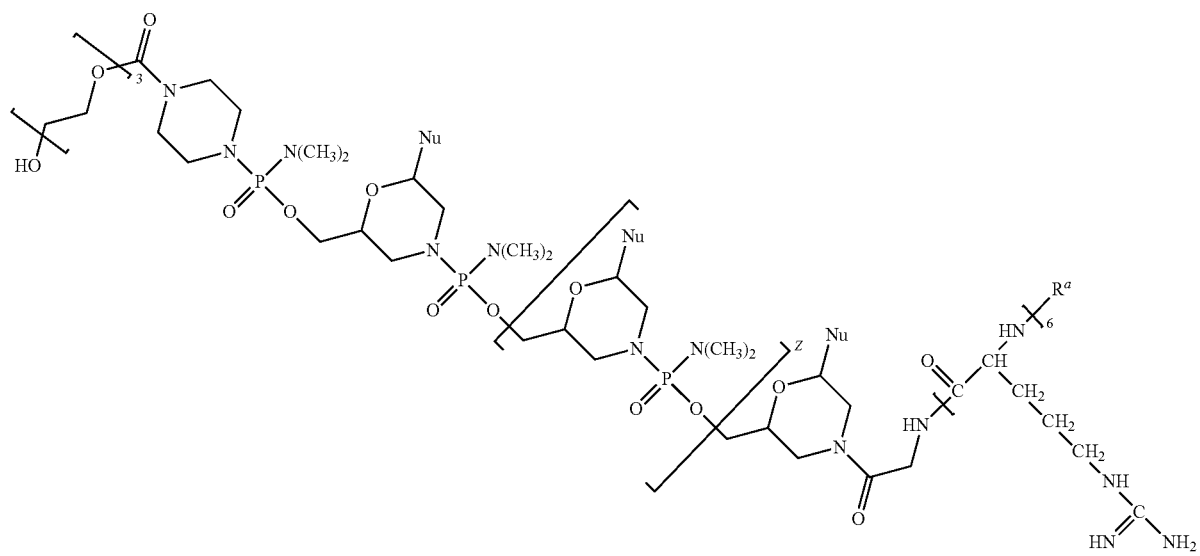

or a pharmaceutically acceptable salt thereof, where:

each Nu is a nucleobase which taken together form a targeting sequence;

Z is an integer from 6 to 38; and $R^a$ is selected from H, acetyl, benzoyl, and stearoyl.

In some embodiments, $R^a$ is acyl.

In certain embodiments, the modified antisense oligomer is a compound of formula (XI):

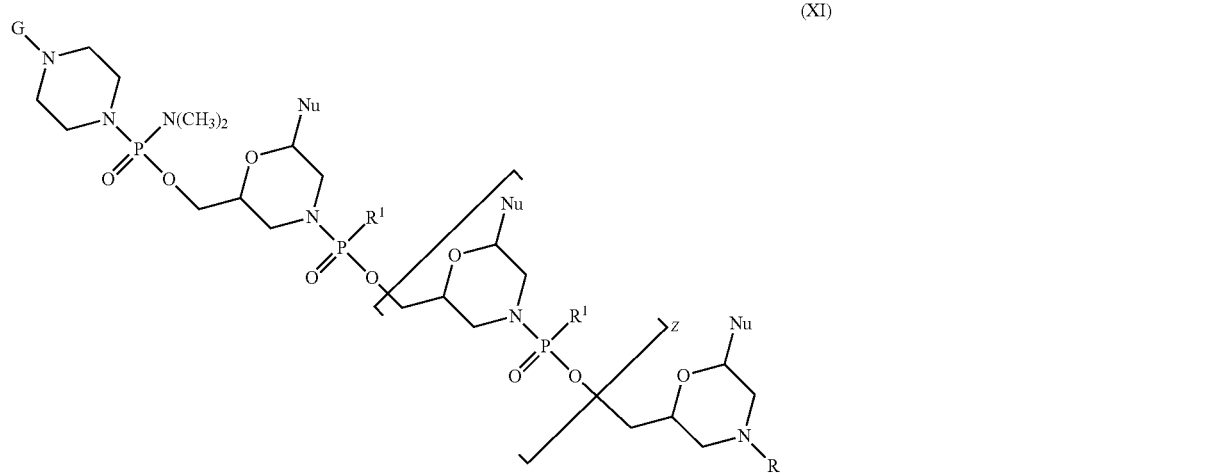

(XI)

or a pharmaceutically acceptable salt thereof, where:

each Nu is a nucleobase which taken together forms a targeting sequence; Z is an integer from 6 to 38;

each instance of $R^1$ is independently —N(R²)₂ wherein each $R^2$ is independently selected from H and $C_1$-$C_6$ alkyl; and R is selected from H or acyl, wherein G is a cell penetrating peptide ("CPP") and linker moiety selected from —C(O)(CH₂)₅NH—CPP, —C(O)(CH₂)₂NH—CPP, —C(O)(CH₂)₂NHC(O)(CH₂)₅NH—CPP, and —C(O)CH₂NH—CPP, or G is of the formula:

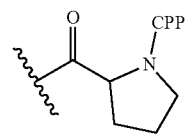

wherein the CPP is attached to the linker moiety by an amide bond at the CPP carboxy terminus.

In some embodiments, the CPP is of a sequence selected from SEQ ID NOS: 17 to 32.

In some embodiments, G is of the formula:

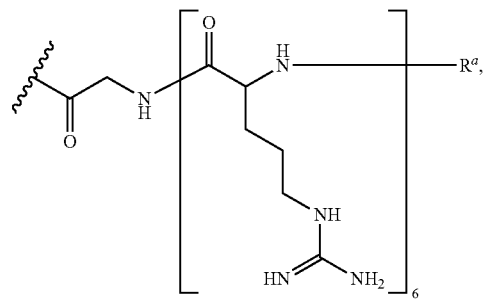

wherein $R^a$ is selected from H, acetyl, benzoyl, and stearoyl.
In certain embodiments, the CPP is of the formula:

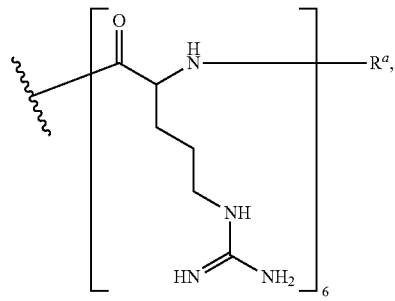

wherein $R^a$ is selected from H, acetyl, benzoyl, and stearoyl.

In some embodiments, each R' is —N(CH₃)₂.

In certain embodiments, the modified antisense oligomer is a compound of formula (XIa):

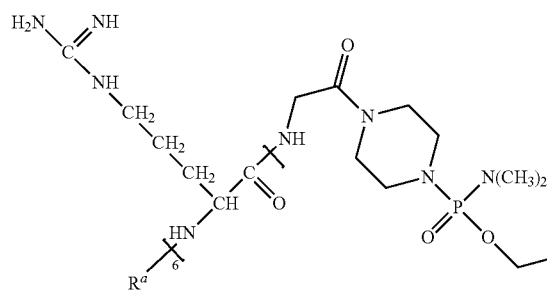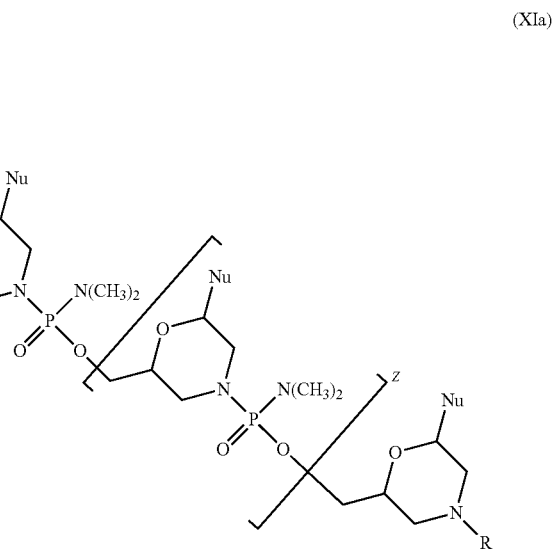

(XIa)

or a pharmaceutically acceptable salt thereof, where:

each Nu is a nucleobase which taken together form a targeting sequence;

Z is an integer from 6 to 38;

R is selected from H or acyl; and $R^a$ is selected from H, acetyl, benzoyl, and stearoyl.

In some embodiments, $R^a$ is acyl. In certain embodiments, R is H.

In some embodiments, the targeting sequence of formulas (I), (IV), (IVa), (V), (Va), (VI), (VIa), (VII), (VIIa), (VIII), (VIIIa), (IX), (IXa), (X), (Xa), (XI), and (XIa) is selected from:

a) SEQ ID NO: 7 (XYAYXXXYAXAAXGYXGG) wherein Z is 16;

b) SEQ ID NO: 8 (AXXYAYXXXYAXAAXGYXGG) wherein Z is 18; and c) SEQ ID NO: 6 (GXAAGAXXYAYXXXYAX-AAXGYXGG) wherein Z is 23;

wherein each X is independently selected from uracil (U) or thymine (T), and wherein each Y is independently selected from cytosine (C) or 5-Methylcytosine (5mC). In some embodiments, each X of SEQ ID NOS: 6 to 8 is thymine (T), and each Y of SEQ ID NOS: 6 to 8 is cytosine (C).

In various embodiments, at least one X of the targeting sequence is T. In various embodiments, each X of the targeting sequence is T.

In various embodiments, at least one X of the targeting sequence is U. In various embodiments, each X of the targeting sequence is U.

In various embodiments, at least one Y of the targeting sequence is 5mC. In various embodiments, each Y of the targeting sequence is 5mC.

In various embodiments, at least one Y of the targeting sequence is C. In various embodiments, each Y of the targeting sequence is C.

In various embodiments, at least one X of SEQ ID NOS: 4 to 16 is T. In various embodiments, each X of SEQ ID NOS: 4 to 16 is T.

In various embodiments, at least one X of the targeting sequence is U. In various embodiments, each X of SEQ ID NOS: 4 to 16 is U.

In various embodiments, at least one Y of SEQ ID NOS: 4 to 16 is 5mC. In various embodiments, each Y of SEQ ID NOS: 4 to 16 is 5mC.

In various embodiments, at least one Y of SEQ ID NOS: 4 to 16 is C. In various embodiments, each Y of SEQ ID NOS: 4 to 16 is C.

In some embodiments, each Z of the modified antisense oligomers of the disclosure, including compounds of formulas (I), (IV), (IVa), (V), (Va), (VI), (VIa), (VII), (VIIa), (VIII), (VIIIa), (IX), (IXa), (X), (Xa), (XI), and (XIa), is an integer from 6 to 28.

In some embodiments, each Z of the modified antisense oligomers of the disclosure, including compounds of formulas (I), (IV), (IVa), (V), (Va), (VI), (VIa), (VII), (VIIa), (VIII), (VIIIa), (IX), (IXa), (X), (Xa), (XI), and (XIa), is an integer from 8 to 28.

In some embodiments, each Z of the modified antisense oligomers of the disclosure, including compounds of formulas (I), (IV), (IVa), (V), (Va), (VI), (VIa), (VII), (VIIa), (VIII), (VIIIa), (IX), (IXa), (X), (Xa), (XI), and (XIa), is an integer from 14 to 28.

In some embodiments, each Z of the modified antisense oligomers of the disclosure, including compounds of formulas (I), (IV), (IVa), (V), (Va), (VI), (VIa), (VII), (VIIa), (VIII), (VIIIa), (IX), (IXa), (X), (Xa), (XI), and (XIa), is an integer from 16 to 28.

In some embodiments, each Z of the modified antisense oligomers of the disclosure, including compounds of formulas (I), (IV), (IVa), (V), (Va), (VI), (VIa), (VII), (VIIa), (VIII), (VIIIa), (IX), (IXa), (X), (Xa), (XI), and (XIa), is an integer from 6 to 26.

In some embodiments, each Z of the modified antisense oligomers of the disclosure, including compounds of formulas (I), (IV), (IVa), (V), (Va), (VI), (VIa), (VII), (VIIa), (VIII), (VIIIa), (IX), (IXa), (X), (Xa), (XI), and (XIa), is an integer from 8 to 26.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 14 to 26.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 16 to 26.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 6 to 23.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 8 to 23.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 14 to 23.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 16 to 23.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 6 to 16.

In some embodiments, each Z of the modified antisense oligomers of the disclosure, including compounds of formulas (I), (IV), (IVa), (V), (Va), (Vb), (VI), (VIa), (VII), (Vila), (VIII), (VIIIa), (IX), (IXa), (X), (Xa), (XI), and (XIa), is 6.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 8 to 16.

In some embodiments, each Z of the modified antisense oligomers of the disclosure, including compounds of formulas (I), (IV), (IVa), (V), (Va), (Vb), (VI), (VIa), (VII), (Vila), (VIII), (VIIIa), (IX), (IXa), (X), (Xa), (XI), and (XIa), is 8.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 6 to 10.

In some embodiments, each Z of the modified antisense oligomers of the disclosure, including compounds of formulas (I), (IV), (IVa), (V), (Va), (Vb), (VI), (VIa), (VII), (Vila), (VIII), (VIIIa), (IX), (IXa), (X), (Xa), (XI), and (XIa), is 10.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 16 to 18.

In some embodiments, each Z of the modified antisense oligomers of the disclosure, including compounds of formulas (I), (IV), (IVa), (V), (Va), (Vb), (VI), (VIa), (VII), (Vila), (VIII), (VIIIa), (IX), (IXa), (X), (Xa), (XI), and (XIa), is 16.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 18 to 20.

In some embodiments, each Z of the modified antisense oligomers of the disclosure, including compounds of formulas (I), (IV), (IVa), (V), (Va), (Vb), (VI), (VIa), (VII), (Vila), (VIII), (VIIIa), (IX), (IXa), (X), (Xa), (XI), and (XIa), is 18.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is an integer from 23 to 25.

In some embodiments, each Z of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is 23.

In some embodiments, each Nu of the modified antisense oligomers of the disclosure, including compounds of formulas (I), (IV), (IVa), (V), (Va), (Vb), (VI), (VIa), (VII), (VIIa), (VIII), (VIIIa), (IX), (IXa), (X), (Xa), (XI), and (XIa), is independently selected from adenine, guanine, thymine, uracil, cytosine, hypoxanthine (inosine), 2,6-diaminopurine, 5-methyl cytosine, C5-propynyl-modified pyrimidines, and 10-(9-(aminoethoxy)phenoxazinyl).

In various embodiments including, for example, the compounds of formulas (I), (IV), (IVa), (V), (Vb), (Va), (VI), (VIa), (VII), (VIIa), (VIII), (VIIIa), (IX), (IXa), (X), (Xa), (XI), and (XIa), the targeting sequence is complementary to a target region within SMN2 pre-mRNA. In some embodiments, the targeting sequence is complementary to 8 or more contiguous nucleotides in a target region within intron 6 or intron 7 (e.g., SEQ ID NOS: 4 to 16 or 33 to 45) of SMN2 pre-mRNA.

In various embodiments, the targeting sequence of formulas (I), (IV), (IVa), (V), (Va), (VI), (Via), (VII), (VIIa), (VIII), (VIIIa), (IX), (IXa), (X), (Xa), (XI), and (XIa) comprises one of SEQ ID NOS: 4 to 16 or 33 to 45, is selected from one of SEQ ID NOS: 4 to 16 or 33 to 45, is a fragment of at least 8 contiguous nucleotides of a sequence selected from at least one of SEQ ID NOS: 4 to 16 or 33 to 45, or is a variant having at least 90% sequence identity to a sequence selected from at least one of SEQ ID NOS: 4 to 16 or 33 to 45, wherein for SEQ ID NOS: 4 to 16 each X is independently selected from uracil (U) or thymine (T), and wherein each Y is independently selected from cytosine (C) or 5-Methylcytosine (5mC). In some embodiments, each X of SEQ ID NOS: 4 to 16 is thymine (T), and each Y of SEQ ID NOS: 4 to 16 is cytosine (C).

In some embodiments, the targeting sequence of the modified antisense oligomers of the disclosure, including compounds of formulas (I), (IV), (IVa), (V), (Vb), (Va), (VI), (VIa), (VII), (VIIa), (VIII), (VIIIa), (IX), (IXa), (X), (Xa), (XI), and (XIa), comprises a sequence selected from SEQ ID NOS: 4 to 16, is selected from SEQ ID NOS: 4 to 16, is a fragment of at least 8 contiguous nucleotides of a sequence selected from SEQ ID NOS: 4 to 16, or is a variant having at least 90% sequence identity to a sequence selected from SEQ ID NOS: 4 to 16, wherein each X is independently selected from uracil (U) or thymine (T), and wherein each Y is independently selected from cytosine (C) or 5-Methylcytosine (5mC).

In some embodiments, the targeting sequence of the modified antisense oligomers of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a sequence selected from SEQ ID NOS: 6, 7, and 8, is selected from SEQ ID NOS: 6, 7, and 8, is a fragment of at least 8 contiguous nucleotides of a sequence selected from SEQ ID NOS: 6, 7, and 8, or is a variant having at least 90% sequence identity to a sequence selected from SEQ ID NOS: 6, 7, and 8, wherein each X is independently selected from uracil (U) or thymine (T), and wherein each Y is independently selected from cytosine (C) or 5-Methylcytosine (5mC).

In various embodiments, the targeting sequence of formulas (I), (IV), (IVa), (V), (Va), (VI), (Via), (VII), (VIIa), (VIII), (VIIIa), (IX), (IXa), (X), (Xa), (XI), and (XIa) comprises one of SEQ ID NOS: 33 to 45, is selected from one of SEQ ID NOS: 33 to 45, is a fragment of at least 8 contiguous nucleotides of a sequence selected from at least one of SEQ ID NOS: 33 to 45, or is a variant having at least 90% sequence identity to a sequence selected from at least one of SEQ ID NOS: 33 to 45.

In some embodiments, the targeting sequence of the modified antisense oligomers of the disclosure, including compounds of formula (I), (IV), (IVa), (V), (Va), (Vb), (VI), (Via), (VII), (VIIa), (VIII), (VIIIa), (IX), (IXa), (X), (Xa), (XI), and (XIa), comprises a sequence selected from SEQ ID NOS: 35, 36, and 37, is selected from SEQ ID NOS: 35, 36, and 37, is a fragment of at least 8 contiguous nucleotides of a sequence selected from SEQ ID NOS: 35, 36, and 37, or is a variant having at least 90% sequence identity to a sequence selected from SEQ ID NOS: 35, 36, and 37.

In some embodiments, the targeting sequence of formulas (I), (IV), (IVa), (V), (Va), (VI), (VIa), (VII), (VIIa), (VIII), (VIIIa), (IX), (IXa), (X), (Xa), (XI), and (XIa) is selected from:

a) SEQ ID NO: 35 (TCACTTTCATAATGCTGG) wherein Z is 16;

b) SEQ ID NO: 36 (ATTCACTTTCATAATGCTGG) wherein Z is 18; and c) SEQ ID NO: 37 (GTAAGATTCACTTTCAT-AATGCTGG) wherein Z is 23.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence selected from SEQ ID NOS: 7, 10, 14, and 15.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence selected from SEQ ID NOS: 8 and 12.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence selected from SEQ ID NOS: 13 and 16.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence selected from SEQ ID NOS: 6, 7, and 8.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence that is SEQ ID NO 6.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence that is SEQ ID NO 7.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence that is SEQ ID NO 8.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence selected from SEQ ID NOS: 35, 36, and 37.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence that is SEQ ID NO 35.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence that is SEQ ID NO 36.

In some embodiments, the modified antisense oligomer of the disclosure, including compounds of formula (I), (IV), (IVa), (V), (Va), (Vb), (VI), (VIa), (VII), (VIIa), (VIII), (VIIIa), (IX), (IXa), (X), (Xa), (XI), and (XIa), comprises a targeting sequence that is SEQ ID NO 37.

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-1 | PMO-APN | 33 | GCT GGC AG$_8$ | TEG | H |
| PMO-APN-2 | PMO-APN | 33 | GCT GGC AG$_8$ | TEG | H |
| PMO-APN-3 | PMO-APN | 33 | GCT GGC AG$_8$ | TEG | H |
| PMO-APN-4 | PMO-APN | 33 | GCT GGC AG$_8$ | TEG | H |
| PMO-APN-5 | PMO-APN | 33 | GCT GGC AG$_8$ | TEG | H |
| PMO-APN-6 | PMO-APN | 33 | GCT GGC AG$_8$ | TEG | H |
| PMO-APN-7 | PMO-APN | 33 | GCT GGC AG$_8$ | TEG | H |
| PMO-APN-8 | PMO-APN | 33 | GCT GGC AG$_8$ | TEG | H |

| Compound Name | Modification | Targeting SEQ ID NO | Targeting Sequences | 5' end | 3' end |
|---|---|---|---|---|---|
| PMO-APN-9 | PMO-APN | 37 | GTA AGA TTC ACT TTC ATA ATG CTG G$_{25}$ | TEG | H |
| PMO-APN-10 | PMO-APN | 37 | GTA AGA TTC ACT TTC ATA ATG CTG G$_{25}$ | H | H |
| PMO-APN-11 | PMO-APN | 37 | GTA AGA TTC ACT TTC ATA ATG CTG G$_{25}$ | TEG | H |
| PMO-APN-12 | PMO-APN | 35 | TCA CTT TCA TAA TGC TGG$_{18}$ | TEG | H |
| PMO-APN-13 | PMO-APN | 35 | TCA CTT TCA TAA TGC TGG$_{18}$ | TEG | H |
| PMO-APN-14 | PMO-APN | 35 | TCA CTT TCA TAA TGC TGG$_{18}$ | TEG | H |
| PMO-APN-15 | PMO-APN | 35 | TCA CTT TCA TAA TGC TGG$_{18}$ | TEG | H |
| PMO-APN-16 | PMO-APN | 35 | TCA CTT TCA TAA TGC T GG$_{18}$ | TEG | H |
| PMO-APN-17 | PMO-APN | 36 | ATT CAC TTT CAT AAT GCT GG$_{20}$ | TEG | H |
| PMO-APN-18 | PMO-APN | 38 | AAA AGT CTG CTG GTC TGC C$_{19}$ | TEG | H |
| PMO-APN-19 | PMO-APN | 38 | AAA AGT CTG CTG GTC TGC C$_{19}$ | TEG | H |
| PMO-APN-20 | PMO-APN | 38 | AAA AGT CTG CTG GTC TGC C$_{19}$ | TEG | H |
| PMO-APN-21 | PMO-APN | 38 | AAA AGT CTG CTG GTC TGC C$_{19}$ | TEG | H |
| PMO-APN-22 | PMO-APN | 38 | AAA AGT CT G CTG GTC TGC C$_{19}$ | TEG | H |
| PMO-APN-23 | PMO-APN | 38 | AAA AGT CTG CTG GTC TGC C$_{19}$ | TEG | H |
| PMO-APN-24 | PMO-APN | 38 | AAA AGT CTG CTG GTC TGC C$_{19}$ | TEG | H |
| PMO-APN-25 | PMO-APN | 38 | AAA AGT CTG CTG GTC TGC C$_{19}$ | TEG | H |
| PMO-APN-26 | PMO-APN | 38 | AAA AGT CTG CTG GTC TGC C$_{19}$ | TEG | H |
| PMO-APN-27 | PMO-APN | 38 | AAA AGT CTG CTG GTC TGC C$_{19}$ | TEG | H |
| PMO-APN-28 | PMO-APN | 39 | ATA GAT ATA GAT AGC TAT AT$_{20}$ | TEG | H |
| PMO-APN-29 | PMO-APN | 40 | AAT AGT TTT GGC ATC AAA ATT CT$_{23}$ | TEG | H |
| PMO-APN-30 | PMO-APN | 41 | GAT ATA AAA TGG CAT CAT ATC CTA A$_{25}$ | TEG | H |
| PMO-APN-31 | PMO-APN | 42 | ATT AAC CTT TTA TCT AAT AGT TTT GG$_{26}$ | TEG | H |
| PMO-APN-32 | PMO-APN | 43 | ACA ACT TTG GGA GGC GGA GG$_{20}$ | TEG | H |
| PMO-APN-33 | PMO-APN | 44 | GTA GGG ATG TAG ATT AAC CT$_{20}$ | TEG | H |
| PMO-APN-34 | PMO-APN | 45 | CTA TAT ATA GAT AGT TAT TCA ACA AA$_{26}$ | TEG | H |
| PMO-Plus-1 | PMO-Plus | 33 | GCT GGC AG$_8$ | | TEG | H |
| PMO-Plus-2 | PMO-Plus | 33 | GCT GGC AG$_8$ | TEG | H |
| PMO-Plus-3 | PMO-Plus | 37 | GTA AGA TTC ACT TTC ATA ATG CTG G$_{25}$ | TEG | H |
| PMO-Plus-4 | PMO-Plus | 35 | TCA CTT TCA TAA TGC TGG$_{18}$ | TEG | H |
| PMO-Plus-5 | PMO-Plus | 35 | TCA CTT TCA TAA TGC TGG$_{18}$ | TEG | H |
| PMO-Plus-6 | PMO-Plus | 35 | TCA CTT TCA TAA TGC TGG$_{18}$ | TEG | H |
| PMO-Plus-7 | PMO-Plus | 35 | TCA CTT TCA TAA TGC TGG$_{18}$ | TEG | H |
| PMO-Plus-8 | PMO-Plus | 35 | TCA CTT TCA TAA TGC TGG$_{18}$ | TEG | H |
| PMO-Plus-9 | PMO-Plus | 36 | ATT CAC TTT CAT AAT GCT GG$_{20}$ | TEG | H |
| PMO-Plus-10 | PMO-Plus | 39 | ATA GAT ATA GAT AGC TAT AT$_{20}$ | TEG | H |
| PMO-Plus-11 | PMO-Plus | 40 | AATAGT TTT GGC ATC AAA ATT CT$_{23}$ | TEG | H |
| PMO-Plus-12 | PMO-Plus | 41 | GAT ATA AAA TGG CAT CAT ATC CTA A$_{25}$ | TEG | H |

-continued

| Compound Name | Modification | Targeting SEQ ID NO | Targeting Sequences | 5' end | 3' end |
|---|---|---|---|---|---|
| PMO-Plus-13 | PMO-Plus | 42 | ATT AAC CTT TTA TCT AAT AGT TTT GG$_{26}$ | TEG | H |
| PMO-Plus-14 | PMO-Plus | 43 | ACA ACT TTG GGA GGC GGA GG$_{20}$ | TEG | H |
| PMO-Plus-15 | PMO-Plus | 44 | GTA GGG ATG TAG ATT AAC CT$_{20}$ | TEG | H |
| PMO-Plus-16 | PMO-Plus | 45 | CTA TAT ATA GAT AGT TAT TCA ACA AA$_{26}$ | TEG | H |
| PMO-R$_6$Gly-1 | PMO-R$_6$Gly- | 33 | GCT GGC AG$_8$ | TEG | Ac-R$_6$Gly-(SEQ ID NO: 53) |
| PMO-R$_6$Gly-2 | PMO-R$_6$Gly | 37 | GTA AGA TTC ACT TTC ATA ATG CTG G$_{25}$ | TEG | Ac-R$_6$Gly-(SEQ ID NO: 53) |
| PMO-R$_6$Gly-3 | PMO-R$_6$Gly | 35 | TCA CTT TCA TAA TGC TGG$_{18}$ | TEG | Ac-R$_6$Gly-(SEQ ID NO: 53) |
| PMO-R$_6$Gly-4 | PMO-R$_6$Gly | 36 | ATT CAC TTT CAT AAT GCT GG$_{20}$ | TEG | Ac-R$_6$Gly-(SEQ ID NO: 53) |
| PMO-R$_6$Gly-5 | PMO-R$_6$Gly | 39 | ATA GAT ATA GAT AGC TAT AT$_{20}$ | TEG | Ac-R$_6$Gly-(SEQ ID NO: 53) |
| PMO-R$_6$Gly-6 | PMO-R$_6$Gly | 40 | AAT AGT TTT GGC ATC AAA ATT CT$_{23}$ | TEG | Ac-R$_6$Gly-(SEQ ID NO: 53) |
| PMO-R$_6$Gly-7 | PMO-R$_6$Gly | 41 | GAT ATA AAA TGG CAT CAT ATC CTA A$_{25}$ | TEG | Ac-R$_6$Gly-(SEQ ID NO: 53) |
| PMO-R$_6$Gly-8 | PMO-R$_6$Gly | 42 | ATT AAC CTT TTA TCT AAT AGT TTT GG$_{26}$ | TEG | Ac-R$_6$Gly-(SEQ ID NO: 53) |
| PMO-R$_6$Gly-9 | PMO-R$_6$Gly | 43 | ACA ACT TTG GGA GGC GGA GG$_{20}$ | TEG | Ac-R$_6$Gly-(SEQ ID NO: 53) |
| PMO-R$_6$Gly-10 | PMO-R$_6$Gly | 44 | GTA GGG ATG TAG ATT AAC CT$_{20}$ | TEG | Ac-R$_6$Gly-(SEQ ID NO: 53) |
| PMO-R$_6$Gly-11 | PMO-R$_6$Gly | 45 | CTA TAT ATA GAT AGT TAT TCA ACA AA$_{26}$ | TEG | Ac-R$_6$Gly-(SEQ ID NO: 53) |
| PMO-ETpipT-1 | PMO-ETpipT | 36 | ATT CAC TTT CAT AAT GCT GG$_{20}$ | TEG | H |
| PMO-ETpipT-2 | PMO-ETpipT | 45 | CTA TAT ATA GAT AGT TAT TCA ACA AA$_{26}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-9 | PMO-APN | 37 | GTA AGA TTC ACT TTC ATA ATG CTG G$_{25}$ | TEG | H |
| PMO-APN-10 | PMO-APN | 37 | GTA AGA TTC ACT TTC ATA ATG CTG G$_{25}$ | H | H |
| PMO-APN-11 | PMO-APN | 37 | GTA AGA TTC ACT TTC ATA ATG CTG G$_{25}$ | TEG | H |
| PMO-APN-12 | PMO-APN | 35 | TCA CTT TCA TAA TGC TGG$_{18}$ | TEG | H |
| PMO-APN-13 | PMO-APN | 35 | TCA CTT TCA TAA TGC TGG$_{18}$ | TEG | H |
| PMO-APN-14 | PMO-APN | 35 | TCA CTT TCA TAA TGC TGG$_{18}$ | TEG | H |
| PMO-APN-15 | PMO-APN | 35 | TCA CTT TCA TAA TGC TGG$_{18}$ | TEG | H |
| PMO-APN-16 | PMO-APN | 35 | TCA CTT TCA TAA TGC TGG$_{18}$ | TEG | H |
| PMO-APN-17 | PMO-APN | 36 | ATT CAC TTT CAT AAT GCT GG$_{20}$ | TEG | H |
| PMO-APN-18 | PMO-APN | 38 | AAA AGT CTG CTG GTC TGC C$_{19}$ | TEG | H |

-continued

| Compound Name | Modification | Targeting SEQ ID NO | Targeting Sequences | 5' end | 3' end |
|---|---|---|---|---|---|
| PMO-APN-19 | PMO-APN | 38 | AAA AGT CTG CTG GTC TGC C$_{19}$ | TEG | H |
| PMO-APN-20 | PMO-APN | 38 | AAA AGT CTG CTG GTC TGC C$_{19}$ | TEG | H |
| PMO-APN-21 | PMO-APN | 38 | AAA AGT CTG CTG GTC TGC C$_{19}$ | TEG | H |
| PMO-APN-22 | PMO-APN | 38 | AAA AGT CTG CTG GTC TGC C$_{19}$ | TEG | H |
| PMO-APN-23 | PMO-APN | 38 | AAA AGT CTG CTG GTC TGC C$_{19}$ | TEG | H |
| PMO-APN-24 | PMO-APN | 38 | AAA AGT CTG CTG GTC TGC C$_{19}$ | TEG | H |
| PMO-APN-25 | PMO-APN | 38 | AAA AGT CTG CTG GTC TGC C$_{19}$ | TEG | H |
| PMO-APN-26 | PMO-APN | 38 | AAA AGT CTG CTG GTC TGC C$_{19}$ | TEG | H |
| PMO-APN-27 | PMO-APN | 38 | AAA AGT CTG CTG GTC TGC C$_{19}$ | TEG | H |
| PMO-APN-28 | PMO-APN | 39 | ATA GAT ATA GAT AGC TAT AT$_{20}$ | TEG | H |
| PMO-APN-29 | PMO-APN | 40 | AAT AGT TTT GGC ATC AAA ATT CT$_{23}$ | TEG | H |
| PMO-APN-30 | PMO-APN | 41 | GAT ATA AAA TGG CAT CAT ATC CTA A$_{25}$ | TEG | H |
| PMO-APN-31 | PMO-APN | 42 | ATT AAC CTT TTA TCT AAT AGT TTT GG$_{26}$ | TEG | H |
| PMO-APN-32 | PMO-APN | 43 | ACA ACT TTG GGA GGC GGA GG$_{20}$ | TEG | H |
| PMO-APN-33 | PMO-APN | 44 | GTA GGG ATG TAG ATT AAC CT$_{20}$ | TEG | H |
| PMO-APN-34 | PMO-APN | 45 | CTA TAT ATA GAT AGT TAT TCA ACA AA$_{26}$ | TEG | H |
| PMO-Plus-3 | PMO-Plus | 37 | GTA AGA TTC ACT TTC ATA ATG CTG G$_{25}$ | TEG | H |
| PMO-Plus-4 | PMO-Plus | 35 | TCA CTT TCA TAA TGC TGG$_{18}$ | TEG | H |
| PMO-Plus-5 | PMO-Plus | 35 | TCA CTT TCA TAA TGC TGG$_{18}$ | TEG | H |
| PMO-Plus-6 | PMO-Plus | 35 | TCA CTT TCA TAA TGC TGG$_{18}$ | TEG | H |
| PMO-Plus-7 | PMO-Plus | 35 | TCA CTT TCA TAA TGC TGG$_{18}$ | TEG | H |
| PMO-Plus-8 | PMO-Plus | 35 | TCA CTT TCA TAA TGC TGG$_{18}$ | TEG | H |
| PMO-Plus-9 | PMO-Plus | 36 | ATT CAC TTT CAT AAT GCT GG$_{20}$ | TEG | H |
| PMO-Plus-10 | PMO-Plus | 39 | ATA GAT ATA GAT AGC TAT AT$_{20}$ | TEG | H |
| PMO-Plus-11 | PMO-Plus | 40 | AAT AGT TTT GGC ATC AAA ATT CT$_{23}$ | TEG | H |
| PMO-Plus-12 | PMO-Plus | 41 | GAT ATA AAA TGG CAT CAT ATC CTA A$_{25}$ | TEG | H |
| PMO-Plus-13 | PMO-Plus | 42 | ATT AAC CTT TTA TCT AAT AGT TTT GG$_{26}$ | TEG | H |
| PMO-Plus-14 | PMO-Plus | 43 | ACA ACT TTG GGA GGC GGA GG$_{20}$ | TEG | H |
| PMO-Plus-15 | PMO-Plus | 44 | GTA GGG ATG TAG ATT AAC CT$_{20}$ | TEG | H |
| PMO-Plus-16 | PMO-Plus | 45 | CTA TAT ATA GAT AGT TAT TCA ACA AA$_{26}$ | TEG | H |
| PMO-R$_6$Gly-2 | PMO-R$_6$Gly | 37 | GTA AGA TTC ACT TTC ATA ATG CTG G$_{25}$ | TEG | Ac-R$_6$Gly- (SEQ ID NO: 53) |
| PMO-R$_6$Gly-3 | PMO-R$_6$Gly | 35 | TCA CTT TCA TAA TGC TGG$_{18}$ | TEG | Ac-R$_6$Gly- (SEQ ID NO: 53) |
| PMO-R$_6$Gly-4 | PMO-R$_6$Gly | 36 | ATT CAC TTT CAT AAT GCT GG$_{20}$ | TEG | Ac-R$_6$Gly- (SEQ ID NO: 53) |
| PMO-R$_6$Gly-5 | PMO-R$_6$Gly | 39 | ATA GAT ATA GAT AGC TAT AT$_{20}$ | TEG | Ac-R$_6$Gly- (SEQ ID NO: 53) |
| PMO-R$_6$Gly-6 | PMO-R$_6$Gly | 40 | AAT AGT TTT GGC ATC AAA ATT CT$_{23}$ | TEG | Ac-R$_6$Gly- (SEQ ID NO: 53) |

-continued

| Compound Name | Modification | Targeting SEQ ID NO | Targeting Sequences | 5' end | 3' end |
|---|---|---|---|---|---|
| PMO-$R_6$Gly-7 | PMO-$R_6$Gly | 41 | GAT ATA AAA TGG CAT CAT ATC CTA A$_{25}$ | TEG | Ac-$R_6$Gly-(SEQ ID NO: 53) |
| PMO-$R_6$Gly-8 | PMO-$R_6$Gly | 42 | ATT AAC CTT TTA TCT AAT AGT TTT GG$_{26}$ | TEG | Ac-$R_6$Gly-(SEQ ID NO: 53) |
| PMO-$R_6$Gly-9 | PMO-$R_6$Gly | 43 | ACA ACT TTG GGA GGC GGA GG$_{20}$ | TEG | Ac-$R_6$Gly-(SEQ ID NO: 53) |
| PMO-$R_6$Gly-10 | PMO-$R_6$Gly | 44 | GTA GGG ATG TAG ATT AAC CT$_{20}$ | TEG | Ac-$R_6$Gly-(SEQ ID NO: 53) |
| PMO-$R_6$Gly-11 | PMO-$R_6$Gly | 45 | CTA TAT ATA GAT AGT TAT TCA ACA AA$_{26}$ | TEG | Ac-$R_6$Gly-(SEQ ID NO: 53) |
| PMO-ETpipT-1 | PMO-ETpipT | 36 | ATT CAC TTT CAT AAT GCT GG$_{20}$ | TEG | H |
| PMO-ETpipT-2 | PMO-ETpipT | 45 | CTA TAT ATA GAT AGT TAT TCA ACA AA$_{26}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-1 | PMO-APN | 33 | GCT GGC AG$_8$ | TEG | H |
| PMO-APN-2 | PMO-APN | 33 | GCT GGC AG$_8$ | TEG | H |
| PMO-APN-3 | PMO-APN | 33 | GCT GGC AG$_8$ | TEG | H |
| PMO-APN-4 | PMO-APN | 33 | GCT GGC AG$_8$ | TEG | H |
| PMO-APN-5 | PMO-APN | 33 | GCT GGC AG$_8$ | TEG | H |
| PMO-APN-6 | PMO-APN | 33 | GCT GGC AG$_8$ | TEG | H |
| PMO-APN-7 | PMO-APN | 33 | GCT GGC AG$_8$ | TEG | H |
| PMO-APN-8 | PMO-APN | 33 | GCT GGC AG$_8$ | TEG | H |
| PMO-Plus-1 | PMO-Plus | 33 | GCT GGC AG$_8$ | TEG | H |
| PMO-Plus-2 | PMO-Plus | 33 | GCT GGC AG$_8$ | TEG | H |
| PMO-$R_6$Gly-1 | PMO-$R_6$Gly | 33 | GCT GGC AG$_8$ | TEG | Ac-$R_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-12 | PMO-APN | 35 | TCA CTT TCA TAA TGC TGG$_{18}$ | TEG | H |
| PMO-APN-13 | PMO-APN | 35 | TCA CTT TCA TAA TGC TGG$_{18}$ | TEG | H |
| PMO-APN-14 | PMO-APN | 35 | TCA CTT TCA TAA TGC TGG$_{18}$ | TEG | H |
| PMO-APN-15 | PMO-APN | 35 | TCA CTT TCA TAA TGC TGG$_{18}$ | TEG | H |
| PMO-APN-16 | PMO-APN | 35 | TCA CTT TCA TAA TGC TGG$_{18}$ | TEG | H |
| PMO-Plus-4 | PMO-Plus | 35 | TCA CTT TCA TAA TGC TGG$_{18}$ | TEG | H |

| Compound Name | Modification | Targeting SEQ ID NO | Targeting Sequences | 5' end | 3' end |
|---|---|---|---|---|---|
| PMO-Plus-5 | PMO-Plus | 35 | TCA CTT TCA TAA TGC TGG$_{18}$ | TEG | H |
| PMO-Plus-6 | PMO-Plus | 35 | TCA CTT TCA TAA TGC TGG$_{18}$ | TEG | H |
| PMO-Plus-7 | PMO-Plus | 35 | TCA CTT TCA TAA TGC TGG$_{18}$ | TEG | H |
| PMO-Plus-8 | PMO-Plus | 35 | TCA CTT TCA TAA TGC TGG$_{18}$ | TEG | H |
| PMO-R$_6$Gly-3 | PMO-R$_6$Gly | 35 | TCA CTT TCA TAA TGC TGG$_{18}$ | TEG | Ac-R$_6$Gly- (SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-18 | PMO-APN | 38 | AAA AGT CTG CTG GTC TGC C$_{19}$ | TEG | H |
| PMO-APN-19 | PMO-APN | 38 | AAA AGT CTG CTG GTC TGC C$_{19}$ | TEG | H |
| PMO-APN-20 | PMO-APN | 38 | AAA AGT CTG CTG GTC TGC C$_{19}$ | TEG | H |
| PMO-APN-21 | PMO-APN | 38 | AAA AGT CTG CTG GTC TGC C$_{19}$ | TEG | H |
| PMO-APN-22 | PMO-APN | 38 | AAA AGT CTG CTG GTC TGC C$_{19}$ | TEG | H |
| PMO-APN-23 | PMO-APN | 38 | AAA AGT CTG CTG GTC TGC C$_{19}$ | TEG | H |
| PMO-APN-24 | PMO-APN | 38 | AAA AGT CTG CTG GTC TGC C$_{19}$ | TEG | H |
| PMO-APN-25 | PMO-APN | 38 | AAA AGT CTG CTG GTC TGC C$_{19}$ | TEG | H |
| PMO-APN-26 | PMO-APN | 38 | AAA AGT CTG CTG GTC TGC C$_{19}$ | TEG | H |
| PMO-APN-27 | PMO-APN | 38 | AAA AGT CTG CTG GTC TGC C$_{19}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-17 | PMO-APN | 36 | ATT CAC TTT CAT AAT GCT GG$_{20}$ | TEG | H |
| PMO-APN-28 | PMO-APN | 39 | ATA GAT ATA GAT AGC TAT AT$_{20}$ | TEG | H |
| PMO-Plus-9 | PMO-Plus | 36 | ATT CAC TTT CAT AAT GCT GG$_{20}$ | TEG | H |
| PMO-Plus-10 | PMO-Plus | 39 | ATA GAT ATA GAT AGC TAT AT$_{20}$ | TEG | H |
| PMO-Plus-14 | PMO-Plus | 43 | ACA ACT TTG GGA GGC GGA GG$_{20}$ | TEG | H |
| PMO-Plus-15 | PMO-Plus | 44 | GTA GGG ATG TAG ATT AAC CT$_{20}$ | TEG | H |
| PMO-R$_6$Gly-4 | PMO-R$_6$Gly | 36 | ATT CAC TTT CAT AAT GCT GG$_{20}$ | TEG | Ac-R$_6$Gly- (SEQ ID NO: 53) |
| PMO-R$_6$Gly-5 | PMO-R$_6$Gly | 39 | ATA GAT ATA GAT AGC TAT AT$_{20}$ | TEG | Ac-R$_6$Gly- (SEQ ID NO: 53) |

-continued

| Compound Name | Modification | Targeting SEQ ID NO | Targeting Sequences | 5' end 3' end |
|---|---|---|---|---|
| PMO-R$_6$Gly-9 | PMO-R$_6$Gly | 43 | ACA ACT TTG GGA GGC GGA GG$_{20}$ | TEG Ac-R$_6$Gly-(SEQ ID NO: 53) |
| PMO-R$_6$Gly-10 | PMO-R$_6$Gly | 44 | GTA GGG ATG TAG ATT AAC CT$_{20}$ | TEG Ac-R$_6$Gly-(SEQ ID NO: 53) |
| PMO-ETpipT-1 | PMO-ETpipT | 36 | A<u>TT</u> CAC <u>TTT</u> CA<u>T</u> AA<u>T</u> GC<u>T</u> GG$_{20}$ | TEG H |

In some embodiments, the modified antisense oligomer of the disclosure is selected from the following compounds:

| Compound Name | Modification | Targeting SEQ ID NO | Targeting Sequences | 5' end 3' end |
|---|---|---|---|---|
| PMO-2 | PMO | 37 | GTA AGA TTC ACT TTC ATA ATG CTG G$_{25}$ | TEG H |
| PMO-3 | | 35 | TCA CTT TCA TAA TGC TGG$_{18}$ | TEG H |
| PMO-4 | | 36 | ATT CAC TTT CAT AAT GCT GG$_{20}$ | TEG H |
| PMO-APN-11 | PMO-APN | 37 | G<u>TA</u> AGA <u>TT</u>C AC<u>T</u> TTC A<u>T</u>A A<u>T</u>G C<u>T</u>G G$_{25}$ | TEG H |
| PMO-APN-16 | | 35 | <u>T</u>CA C<u>TT</u> TCA <u>T</u>AA <u>T</u>GC <u>T</u>GG$_{18}$ | TEG H |
| PMO-APN-17 | | 36 | A<u>TT</u> CAC <u>TTT</u> CA<u>T</u> AA<u>T</u> GC<u>T</u> GG$_{20}$ | TEG H |
| PMO-Plus-3 | PMO-Plus | 37 | G<u>TA</u> AGA <u>TT</u>C AC<u>T</u> TTC A<u>T</u>A A<u>T</u>G C<u>T</u>G G$_{25}$ | TEG H |
| PMO-Plus-8 | | 35 | <u>T</u>CA C<u>TT</u> TCA <u>T</u>AA <u>T</u>GC <u>T</u>GG$_{18}$ | TEG H |
| PMO-Plus-9 | | 36 | A<u>TT</u> CAC <u>TTT</u> CA<u>T</u> AA<u>T</u> GC<u>T</u> GG$_{20}$ | TEG H |
| PMO-R$_6$Gly-2 | PMO-R$_6$Gly | 37 | GTA AGA TTC ACT TTC ATA ATG CTG G$_{25}$ | TEG Ac-R$_6$Gly-(SEQ ID NO: 53) |
| PMO-R$_6$Gly-3 | | 35 | TCA CTT TCA TAA TGC TGG$_{18}$ | TEG Ac-R$_6$Gly-(SEQ ID NO: 53) |
| PMO-R$_6$Gly-4 | | 36 | ATT CAC TTT CAT AAT GCT GG$_{20}$ | TEG Ac-R$_6$Gly-(SEQ ID NO: 53) |
| PMO-APN-11 | PMO-APN | 37 | G<u>TA</u> AGA <u>TT</u>C AC<u>T</u> TTC A<u>T</u>A A<u>T</u>G C<u>T</u>G G$_{25}$ | TEG H |
| PMO-APN-16 | | 35 | <u>T</u>CA C<u>TT</u> TCA <u>T</u>AA <u>T</u>GC <u>T</u>GG$_{18}$ | TEG H |
| PMO-APN-17 | | 36 | A<u>TT</u> CAC <u>TTT</u> CA<u>T</u> AA<u>T</u> GC<u>T</u> GG$_{20}$ | TEG H |
| PMO-Plus-3 | PMO-Plus | 37 | G<u>TA</u> AGA <u>TT</u>C AC<u>T</u> TTC A<u>T</u>A A<u>T</u>G C<u>T</u>G G$_{25}$ | TEG H |
| PMO-Plus-8 | | 35 | <u>T</u>CA C<u>TT</u> TCA <u>T</u>AA <u>T</u>GC <u>T</u>GG$_{18}$ | TEG H |
| PMO-Plus-9 | | 36 | A<u>TT</u> CAC <u>TTT</u> CA<u>T</u> AA<u>T</u> GC<u>T</u> GG$_{20}$ | TEG H |
| PMO-R$_6$Gly-2 | PMO-R$_6$Gly | 37 | GTA AGA TTC ACT TTC ATA ATG CTG G$_{25}$ | TEG Ac-R$_6$Gly-(SEQ ID NO: 53) |
| PMO-R$_6$Gly-3 | | 35 | TCA CTT TCA TAA TGC TGG$_{18}$ | TEG Ac-R$_6$Gly-(SEQ ID NO: 53) |

| Compound Name | Modification | Targeting SEQ ID NO | Targeting Sequences | 5' end | 3' end |
|---|---|---|---|---|---|
| PMO-R$_6$Gly-4 | | 36 | ATT CAC TTT CAT AAT GCT GG$_{20}$ | TEG | Ac-R$_6$Gly- (SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-29 | PMO-APN | 40 | AAT AGT TTT GGC ATC AAA ATT CT$_{23}$ | TEG | H |
| PMO-Plus-11 | PMO-Plus | 40 | AAT AGT TTT GGC ATC AAA ATT CT$_{23}$ | TEG | H |
| PMO-R$_6$Gly-6 | PMO-R$_6$Gly | 40 | AAT AGT TTT GGC ATC AAA ATT CT$_{23}$ | TEG | Ac-R$_6$Gly- (SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-9 | PMO-APN | 37 | GTA AGA TTC ACT TTC ATA ATG CTG G$_{25}$ | TEG | H |
| PMO-APN-10 | PMO-APN | 37 | GTA AGA TTC ACT TTC ATA ATG CTG G$_{25}$ | H | H |
| PMO-APN-11 | PMO-APN | 37 | GTA AGA TTC ACT TTC ATA ATG CTG G$_{25}$ | TEG | H |
| PMO-APN-30 | PMO-APN | 41 | GAT ATA AAA TGG CAT CAT ATC CTA A$_{25}$ | TEG | H |
| PMO-Plus-3 | PMO-Plus | 37 | GTA AGA TTC ACT TTC ATA ATG CTG G$_{25}$ | TEG | H |
| PMO-Plus-12 | PMO-Plus | 41 | GAT ATA AAA TGG CAT CAT ATC CTA A$_{25}$ | TEG | H |
| PMO-R$_6$Gly-2 | PMO-R$_6$Gly | 37 | GTA AGA TTC ACT TTC ATA ATG CTG G$_{25}$ | TEG | Ac-R$_6$Gly- (SEQ ID NO: 53) |
| PMO-R$_6$Gly-7 | PMO-R$_6$Gly | 41 | GAT ATA AAA TGG CAT CAT ATC CTA A$_{25}$ | TEG | Ac-R$_6$Gly- (SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-31 | PMO-APN | 42 | ATT AAC CTT TTA TCT AAT AGT TTT GG$_{26}$ | TEG | H |
| PMO-APN-34 | PMO-APN | 45 | CTA TAT ATA GAT AGT TAT TCA ACA AA$_{26}$ | TEG | H |
| PMO-Plus-13 | PMO-Plus | 42 | ATT AAC CTT TTA TCT AAT AGT TTT GG$_{26}$ | TEG | H |
| PMO-Plus-16 | PMO-Plus | 45 | CTA TAT ATA GAT AGT TAT TCA ACA AA$_{26}$ | TEG | H |
| PMO-R$_6$Gly-8 | PMO-R$_6$Gly | 42 | ATT AAC CTT TTA TCT AAT AGT TTT GG$_{26}$ | TEG | Ac-R$_6$Gly- (SEQ ID NO: 53) |
| PMO-R$_6$Gly-11 | PMO-R$_6$Gly | 45 | CTA TAT ATA GAT AGT TAT TCA ACA AA$_{26}$ | TEG | Ac-R$_6$Gly- (SEQ ID NO: 53) |

-continued

| Compound Name | Modification | Targeting SEQ ID NO | Targeting Sequences | 5' end | 3' end |
|---|---|---|---|---|---|
| 2'-OMe-11 | 2'-OMe | 51 | CUA UAU AUA GAU AGU UAU UCA ACA AA$_{26}$ | H | H |
| PMO-ETpipT-2 | PMO-ETpipT | 45 | CTA TAT ATA GAT AGT TAT TCA ACA AA$_{26}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-17 | PMO-APN | 36 | ATT CAC TTT CAT AAT GCT GG$_{20}$ | TEG | H |
| PMO-Plus-9 | PMO-Plus | 36 | ATT CAC TTT CAT AAT GCT GG$_{20}$ | TEG | H |
| PMO-R$_6$Gly-4 | PMO-R$_6$Gly | 36 | ATT CAC TTT CAT AAT GCT GG$_{20}$ | TEG Ac-R$_6$Gly- (SEQ ID NO: 53) | |
| PMO-ETpipT-1 | PMO-ETpipT | 36 | ATT CAC TTT CAT AAT GCT GG$_{20}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-28 | PMO-APN | 39 | ATA GAT ATA GAT AGC TAT AT$_{20}$ | TEG | H |
| PMO-Plus-10 | PMO-Plus | 39 | ATA GAT ATA GAT AGC TAT AT$_{20}$ | TEG | H |
| PMO-R$_6$Gly-5 | PMO-R$_6$Gly | 39 | ATA GAT ATA GAT AGC TAT AT$_{20}$ | TEG Ac-R$_6$Gly- (SEQ ID NO: 53) | |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-Plus-14 | PMO-Plus | 43 | ACA ACT TTG GGA GGC GGA GG$_{20}$ | TEG | H |
| PMO-R$_6$Gly-9 | PMO-R$_6$Gly | 43 | ACA ACT TTG GGA GGC GGA GG$_{20}$ | TEG Ac-R$_6$Gly- (SEQ ID NO: 53) | |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-9 | PMO-APN | 37 | GTA AGA TTC ACT TTC ATA ATG CTG G$_{25}$ | TEG | H |
| PMO-APN-10 | PMO-APN | 37 | GTA AGA TTC ACT TTC ATA ATG CTG G$_{25}$ | H | H |
| PMO-APN-11 | PMO-APN | 37 | GTA AGA TTC ACT TTC ATA ATG CTG G$_{25}$ | TEG | H |
| PMO-Plus-3 | PMO-Plus | 37 | GTA AGA TTC ACT TTC ATA ATG CTG G$_{25}$ | TEG | H |

| Compound Name | Modification | Targeting SEQ ID NO | Targeting Sequences | 5' end | 3' end |
|---|---|---|---|---|---|
| PMO-R$_6$Gly-2 | PMO-R$_6$Gly | 37 | GTA AGA TTC ACT TTC ATA ATG CTG G$_{25}$ | TEG | Ac-R$_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-30 | PMO-APN | 41 | GAT ATA AAA TGG CAT CAT ATC CTA A$_{25}$ | TEG | H |
| PMO-Plus-12 | PMO-Plus | 41 | GAT ATA AAA TGG CAT CAT ATC CTA A$_{25}$ | TEG | H |
| PMO-R$_6$Gly-7 | PMO-R$_6$Gly | 41 | GAT ATA AAA TGG CAT CAT ATC CTA A$_{25}$ | TEG | Ac-R$_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-31 | PMO-APN | 42 | ATT AAC CTT TTA TCT AAT AGT TTT GG$_{26}$ | TEG | H |
| PMO-Plus-13 | PMO-Plus | 42 | ATT AAC CTT TTA TCT AAT AGT TTT GG$_{26}$ | TEG | H |
| PMO-R$_6$Gly-8 | PMO-R$_6$Gly | 42 | ATT AAC CTT TTA TCT AAT AGT TTT GG$_{26}$ | TEG | Ac-R$_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-34 | PMO-APN | 45 | CTA TAT ATA GAT AGT TAT TCA ACA AA$_{26}$ | TEG | H |
| PMO-Plus-16 | PMO-Plus | 45 | CTA TAT ATA GAT AGT TAT TCA ACA AA$_{26}$ | TEG | H |
| PMO-R$_6$Gly-11 | PMO-R$_6$Gly | 45 | CTA TAT ATA GAT AGT TAT TCA ACA AA$_{26}$ | TEG | Ac-R$_6$Gly-(SEQ ID NO: 53) |
| 2'-OMe-11 | 2'-OMe | 51 | CUA UAU AUA GAU AGU UAU UCA ACA AA$_{26}$ | H | H |
| PMO-ETpipT-2 | PMO-ETpipT | 45 | CTA TAT ATA GAT AGT TAT TCA ACA AA$_{26}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-16 | PMO-APN | 35 | TCA CTT TCA TAA TGC TGG$_{18}$ | TEG | H |
| PMO-Plus-8 | PMO-Plus | 35 | TCA CTT TCA TAA TGC TGG$_{18}$ | TEG | H |

-continued

| Compound Name | Modification | Targeting SEQ ID NO | Targeting Sequences | 5' end | 3' end |
|---|---|---|---|---|---|
| PMO-R$_6$Gly-3 | PMO-R$_6$Gly | 35 | TCA CTT TCA TAA TGC TGG$_{18}$ | TEG | Ac-R$_6$Gly- (SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-1 | PMO-APN | 33 | GCT GGC AG$_8$ | TEG | H |
| PMO-APN-2 | PMO-APN | 33 | GCT GGC AG$_8$ | TEG | H |
| PMO-APN-3 | PMO-APN | 33 | GCT GGC AG$_8$ | TEG | H |
| PMO-APN-4 | PMO-APN | 33 | GCT GGC AG$_8$ | TEG | H |
| PMO-APN-5 | PMO-APN | 33 | GCT GGC AG$_8$ | TEG | H |
| PMO-APN-6 | PMO-APN | 33 | GCT GGC AG$_8$ | TEG | H |
| PMO-APN-7 | PMO-APN | 33 | GCT GGC AG$_8$ | TEG | H |
| PMO-APN-8 | PMO-APN | 33 | GCT GGC AG$_8$ | TEG | H |
| PMO-APN-9 | PMO-APN | 37 | GTA AGA TTC ACT TTC ATA ATG CTG G$_{25}$ | TEG | H |
| PMO-APN-10 | PMO-APN | 37 | GTA AGA TTC ACT TTC ATA ATG CTG G$_{25}$ | H | H |
| PMO-APN-11 | PMO-APN | 37 | GTA AGA TTC ACT TTC ATA ATG CTG G$_{25}$ | TEG | H |
| PMO-APN-12 | PMO-APN | 35 | TCA CTT TCA TAA TGC TGG$_{38}$ | TEG | H |
| PMO-APN-13 | PMO-APN | 35 | TCA CTT TCA TAA TGC TGG$_{38}$ | TEG | H |
| PMO-APN-14 | PMO-APN | 35 | TCA CTT TCA TAA TGC TGG$_{38}$ | TEG | H |
| PMO-APN-15 | PMO-APN | 35 | TCA CTT TCA TAA TGC TGG$_{38}$ | TEG | H |
| PMO-APN-16 | PMO-APN | 35 | TCA CTT TCA TAA TGC TGG$_{38}$ | TEG | H |
| PMO-APN-17 | PMO-APN | 36 | ATT CAC TTT CAT AAT GCT GG$_{20}$ | TEG | H |
| PMO-APN-18 | PMO-APN | 38 | AAA AGT CTG CTG GTC TGC C$_{19}$ | TEG | H |
| PMO-APN-19 | PMO-APN | 38 | AAA AGT CTG CTG GTC TGC C$_{19}$ | TEG | H |
| PMO-APN-20 | PMO-APN | 38 | AAA AGT CTG CTG GTC TGC C$_{19}$ | TEG | H |
| PMO-APN-21 | PMO-APN | 38 | AAA AGT CTG CTG GTC TGC C$_{19}$ | TEG | H |
| PMO-APN-22 | PMO-APN | 38 | AAA AGT CTG CTG GTC TGC C$_{19}$ | TEG | H |
| PMO-APN-23 | PMO-APN | 38 | AAA AGT CTG CTG GTC TGC C$_{19}$ | TEG | H |
| PMO-APN-24 | PMO-APN | 38 | AAA AGT CTG CTG GTC TGC C$_{19}$ | TEG | H |
| PMO-APN-25 | PMO-APN | 38 | AAA AGT CTG CTG GTC TGC C$_{19}$ | TEG | H |
| PMO-APN-26 | PMO-APN | 38 | AAA AGT CTG CTG GTC TGC C$_{19}$ | TEG | H |
| PMO-APN-27 | PMO-APN | 38 | AAA AGT CTG CTG GTC TGC C$_{19}$ | TEG | H |
| PMO-APN-28 | PMO-APN | 39 | ATA GAT ATA GAT AGC TAT AT$_{20}$ | TEG | H |
| PMO-APN-29 | PMO-APN | 40 | AAT AGT TTT GGC ATC AAA ATT CT$_{23}$ | TEG | H |
| PMO-APN-30 | PMO-APN | 41 | GAT ATA AAA TGG CAT CAT ATC CTA A$_{25}$ | TEG | H |

-continued

| Compound Name | Modification | Targeting SEQ ID NO | Targeting Sequences | 5' end 3' end |
|---|---|---|---|---|
| PMO-APN-31 | PMO-APN | 42 | ATT AAC CTT TTA TCT AAT AGT TTT GG$_{26}$ | TEG H |
| PMO-APN-32 | PMO-APN | 43 | ACA ACT TTG GGA GGC GGA GG$_{20}$ | TEG H |
| PMO-APN-33 | PMO-APN | 44 | GTA GGG ATG TAG ATT AAC CT$_{20}$ | TEG H |
| PMO-APN-34 | PMO-APN | 45 | CTA TAT ATA GAT AGT TAT TCA ACA AA$_{26}$ | TEG H |
| PMO-Plus-1 | PMO-Plus | 33 | GCT GGC AG$_{8}$ | TEG H |
| PMO-Plus-2 | PMO-Plus | 33 | GCT GGC AG$_{8}$ | TEG H |
| PMO-Plus-3 | PMO-Plus | 37 | GTA AGA TTC ACT TTC ATA ATG CTG G$_{25}$ | TEG H |
| PMO-Plus-4 | PMO-Plus | 35 | TCA CTT TCA TAA TGC TGG$_{38}$ | TEG H |
| PMO-Plus-5 | PMO-Plus | 35 | TCA CTT TCA TAA TGC TGG$_{38}$ | TEG H |
| PMO-Plus-6 | PMO-Plus | 35 | TCA CTT TCA TAA TGC TGG$_{38}$ | TEG H |
| PMO-Plus-7 | PMO-Plus | 35 | TCA CTT TCA TAA TGC TGG$_{38}$ | TEG H |
| PMO-Plus-8 | PMO-Plus | 35 | TCA CTT TCA TAA TGC TGG$_{38}$ | TEG H |
| PMO-Plus-9 | PMO-Plus | 36 | ATT CAC TTT CAT AAT GCT GG$_{20}$ | TEG H |
| PMO-Plus-10 | PMO-Plus | 39 | ATA GAT ATA GAT AGC TAT AT$_{20}$ | TEG H |
| PMO-Plus-11 | PMO-Plus | 40 | AAT AGT TTT GGC ATC AAA ATT CT$_{23}$ | TEG H |
| PMO-Plus-12 | PMO-Plus | 41 | GAT ATA AAA TGG CAT CAT ATC CTA A$_{25}$ | TEG H |
| PMO-Plus-13 | PMO-Plus | 42 | ATT AAC CTT TTA TCT AAT AGT TTT GG$_{26}$ | TEG H |
| PMO-Plus-14 | PMO-Plus | 43 | ACA ACT TTG GGT GGC GGA GG$_{20}$ | TEG H |
| PMO-Plus-15 | PMO-Plus | 44 | GTA GGG ATG TAG ATT AAC CT$_{20}$ | TEG H |
| PMO-Plus-16 | PMO-Plus | 45 | CTA TAT ATA GAT AGT TAT TCA ACA AA$_{26}$ | TEG H |
| PMO-R$_6$Gly-1 | PMO-R$_6$Gly | 33 | GCT GGC AG$_{8}$ | TEG Ac-R$_6$Gly- (SEQ ID NO: 53) |
| PMO-R$_6$Gly-2 | PMO-R$_6$Gly | 37 | GTA AGA TTC ACT TTC ATA ATG CTG G$_{25}$ | TEG Ac-R$_6$Gly- (SEQ ID NO: 53) |
| PMO-R$_6$Gly-3 | PMO-R$_6$Gly | 35 | TCA CTT TCA TAA TGC TGG$_{38}$ | TEG Ac-R$_6$Gly- (SEQ ID NO: 53) |
| PMO-R$_6$Gly-4 | PMO-R$_6$Gly | 36 | ATT CAC TTT CAT AAT GCT GG$_{20}$ | TEG Ac-R$_6$Gly- (SEQ ID NO: 53) |
| PMO-R$_6$Gly-5 | PMO-R$_6$Gly | 39 | ATA GAT ATA GAT AGC TAT AT$_{20}$ | TEG Ac-R$_6$Gly-(SEQ ID NO: 53) |
| PMO-R$_6$Gly-6 | PMO-R$_6$Gly | 40 | AAT AGT TTT GGC ATC AAA ATT CT$_{23}$ | TEG Ac-R$_6$Gly- (SEQ ID NO: 53) |
| PMO-R$_6$Gly-7 | PMO-R$_6$Gly | 41 | GAT ATA AAA TGG CAT CAT ATC CTA A$_{25}$ | TEG Ac-R$_6$Gly- (SEQ ID NO: 53) |
| PMO-R$_6$Gly-8 | PMO-R$_6$Gly | 42 | ATT AAC CTT TTA TCT AAT AGT TTT GG$_{26}$ | TEG Ac-R$_6$Gly- (SEQ ID NO: 53) |
| PMO-R$_6$Gly-9 | PMO-R$_6$Gly | 43 | ACA ACT TTG GGA GGC GGA GG$_{20}$ | TEG Ac-R$_6$Gly- (SEQ ID NO: 53) |

-continued

| Compound Name | Modification | Targeting SEQ ID NO | Targeting Sequences | 5' end 3' end |
|---|---|---|---|---|
| PMO-R₆Gly-10 | PMO-R₆Gly | 44 | GTA GGG ATG TAG ATT AAC CT₂₀ | TEG Ac-R₆Gly-(SEQ ID NO: 53) |
| PMO-R₆Gly-11 | PMO-R₆Gly | 45 | CTA TAT ATA GAT AGT TAT TCA ACA AA₂₆ | TEG Ac-R₆Gly-(SEQ ID NO: 53) |
| PMO-ETpipT-1 | PMO-ETpipT | 36 | ATT CAC TTT CAT AAT GCT GG₂₀ | TEG H |
| PMO-ETpipT-2 | PMO-ETpipT | 45 | CTA TAT ATA GAT AGT TAT TCA ACA AA₂₆ | TEG H |

In some embodiments, the modified antisense oligomer of the disclosure is selected from the following compounds:

| Compound Name | Modification | Targeting SEQ ID NO | Targeting Sequences | 5' end 3' end |
|---|---|---|---|---|
| PMO-APN-9 | PMO-APN | 37 | GTA AGA TTC ACT TTC ATA ATG CTG G₂₅ | TEG H |
| PMO-APN-10 | PMO-APN | 37 | GTA AGA TTC ACT TTC ATA ATG CTG G₂₅ | H H |
| PMO-APN-11 | PMO-APN | 37 | GTA AGA TTC ACT TTC ATA ATG CTG G₂₅ | TEG H |
| PMO-APN-12 | PMO-APN | 35 | TCA CTT TCA TAA TGC TGG₁₈ | TEG H |
| PMO-APN-13 | PMO-APN | 35 | TCA CTT TCA TAA TGC TGG₁₈ | TEG H |
| PMO-APN-14 | PMO-APN | 35 | TCA CTT TCA TAA TGC TGG₁₈ | TEG H |
| PMO-APN-15 | PMO-APN | 35 | TCA CTT TCA TAA TGC TGG₁₈ | TEG H |
| PMO-APN-16 | PMO-APN | 35 | TCA CTT TCA TAA TGC TGG₃₈ | TEG H |
| PMO-APN-17 | PMO-APN | 36 | ATT CAC TTT CAT AAT GCT GG₂₀ | TEG H |
| PMO-APN-18 | PMO-APN | 38 | AAA AGT CTG CTG GTC TGC C₁₉ | TEG H |
| PMO-APN-19 | PMO-APN | 38 | AAA AGT CTG CTG GTC TGC C₁₉ | TEG H |
| PMO-APN-20 | PMO-APN | 38 | AAA AGT CTG CTG GTC TGC C₁₉ | TEG H |
| PMO-APN-21 | PMO-APN | 38 | AAA AGT CTG CTG GTC TGC C₁₉ | TEG H |
| PMO-APN-22 | PMO-APN | 38 | AAA AGT CTG CTG GTC TGC C₁₉ | TEG H |
| PMO-APN-23 | PMO-APN | 38 | AAA AGT CTG CTG GTC TGC C₁₉ | TEG H |
| PMO-APN-24 | PMO-APN | 38 | AAA AGT CTG CTG GTC TGC C₁₉ | TEG H |
| PMO-APN-25 | PMO-APN | 38 | AAA AGT CTG CTG GTC TGC C₁₉ | TEG H |
| PMO-APN-26 | PMO-APN | 38 | AAA AGT CTG CTG GTC TGC C₁₉ | TEG H |
| PMO-APN-27 | PMO-APN | 38 | AAA AGT CTG CTG GTC TGC C₁₉ | TEG H |
| PMO-APN-28 | PMO-APN | 39 | ATA GAT ATA GAT AGC TAT AT₂₀ | TEG H |
| PMO-APN-29 | PMO-APN | 40 | AAT AGT TTT GGC ATC AAA ATT CT₂₃ | TEG H |
| PMO-APN-30 | PMO-APN | 41 | GAT ATA AAA TGG CAT CAT ATC CTA A₂₅ | TEG H |
| PMO-APN-31 | PMO-APN | 42 | ATT AAC CTT TTA TCT AAT AGT TTT GG₂₆ | TEG H |
| PMO-APN-32 | PMO-APN | 43 | ACA ACT TTG GGA GGC GGA GG₂₀ | TEG H |
| PMO-APN-33 | PMO-APN | 44 | GTA GGG ATG TAG ATT AAC CT₂₀ | TEG H |
| PMO-APN-34 | PMO-APN | 45 | CTA TAT ATA GAT AGT TAT TCA ACA AA₂₆ | TEG H |
| PMO-Plus-3 | PMO-Plus | 37 | GTA AGA TTC ACT TTC ATA ATG CTG G₂₅ | TEG H |

-continued

| Compound Name | Modification | Targeting SEQ ID NO | Targeting Sequences | 5' end | 3' end |
|---|---|---|---|---|---|
| PMO-Plus-4 | PMO-Plus | 35 | <u>T</u>CA CTT TCA TAA TGC TGG$_{38}$ | TEG | H |
| PMO-Plus-5 | PMO-Plus | 35 | <u>T</u>CA C<u>T</u>T TCA TAA TGC TGG$_{38}$ | TEG | H |
| PMO-Plus-6 | PMO-Plus | 35 | <u>T</u>CA C<u>TT</u> TCA <u>T</u>AA TGC TGG$_{38}$ | TEG | H |
| PMO-Plus-7 | PMO-Plus | 35 | <u>T</u>CA C<u>TT</u> TCA <u>T</u>AA <u>T</u>GC TGG$_{38}$ | TEG | H |
| PMO-Plus-8 | PMO-Plus | 35 | <u>T</u>CA C<u>TT</u> TCA <u>T</u>AA <u>T</u>GC <u>T</u>GG$_{38}$ | TEG | H |
| PMO-Plus-9 | PMO-Plus | 36 | A<u>T</u>T CAC <u>T</u>TT CA<u>T</u> AA<u>T</u> GC<u>T</u> GG$_{20}$ | TEG | H |
| PMO-Plus-10 | PMO-Plus | 39 | A<u>T</u>A GA<u>T</u> A<u>T</u>A GA<u>T</u> AGC <u>T</u>A<u>T</u> A<u>T</u>$_{20}$ | TEG | H |
| PMO-Plus-11 | PMO-Plus | 40 | AA<u>T</u> AG<u>T</u> <u>TTT</u> GGC A<u>T</u>C AAA ATT CT$_{23}$ | TEG | H |
| PMO-Plus-12 | PMO-Plus | 41 | GA<u>T</u> ATA A<u>AA</u> TGG CAT CA<u>T</u> ATC C<u>T</u>A A$_{25}$ | TEG | H |
| PMO-Plus-13 | PMO-Plus | 42 | AT<u>T</u> AAC C<u>T</u>T TTA <u>T</u>CT AAT AGT <u>T</u>TT GG$_{26}$ | TEG | H |
| PMO-Plus-14 | PMO-Plus | 43 | AC<u>AA</u>C<u>T</u> TTG GG<u>A</u>GGC GG<u>A</u> GG$_{20}$ | TEG | H |
| PMO-Plus-15 | PMO-Plus | 44 | G<u>T</u>A GGG <u>A</u>TG <u>T</u>AG A<u>TT</u> A<u>A</u>C C<u>T</u>$_{20}$ | TEG | H |
| PMO-Plus-16 | PMO-Plus | 45 | C<u>T</u>A TA<u>T</u> ATA GA<u>T</u> AGT <u>T</u>AT <u>T</u>CA ACA AA$_{26}$ | TEG | H |
| PMO-R$_6$Gly-2 | PMO-R$_6$Gly | 37 | GTA AGA TTC ACT TTC ATA ATG CTG G$_{25}$ | TEG | Ac-R$_6$Gly-<br>(SEQ ID NO: 53) |
| PMO-R$_6$Gly-3 | PMO-R$_6$Gly | 35 | TCA CTT TCA TAA TGC TGG$_{18}$ | TEG | Ac-R$_6$Gly-<br>(SEQ ID NO: 53) |
| PMO-R$_6$Gly-4 | PMO-R$_6$Gly | 36 | ATT CAC TTT CAT AAT GCT GG$_{20}$ | TEG | Ac-R$_6$Gly-<br>(SEQ ID NO: 53) |
| PMO-R$_6$Gly-5 | PMO-R$_6$Gly | 39 | ATA GAT ATA GAT AGC TAT AT$_{20}$ | TEG | Ac-R$_6$Gly-<br>(SEQ ID NO: 53) |
| PMO-R$_6$Gly-6 | PMO-R$_6$Gly | 40 | AAT AGT TTT GGC ATC AAA ATT CT$_{23}$ | TEG | Ac-R$_6$Gly-<br>(SEQ ID NO: 53) |
| PMO-R$_6$Gly-7 | PMO-R$_6$Gly | 41 | GAT ATA AAA TGG CAT CAT ATC CTA A$_{25}$ | TEG | Ac-R$_6$Gly-<br>(SEQ ID NO: 53) |
| PMO-R$_6$Gly-8 | PMO-R$_6$Gly | 42 | ATT AAC CTT TTA TCT AAT AGT TTT GG$_{26}$ | TEG | Ac-R$_6$Gly-<br>(SEQ ID NO: 53) |
| PMO-R$_6$Gly-9 | PMO-R$_6$Gly | 43 | ACA ACT TTG GGA GGC GGA GG$_{20}$ | TEG | Ac-R$_6$Gly-<br>(SEQ ID NO: 53) |
| PMO-R$_6$Gly-10 | PMO-R$_6$Gly | 44 | GTA GGG ATG TAG ATT AAC CT$_{20}$ | TEG | Ac-R$_6$Gly-<br>(SEQ ID NO: 53) |
| PMO-R$_6$Gly-11 | PMO-R$_6$Gly | 45 | CTA TAT ATA GAT AGT TAT TCA ACA AA$_{26}$ | TEG | Ac-R$_6$Gly-<br>(SEQ ID NO: 53) |
| PMO-ETpipT-1 | PMO-ETpipT | 36 | A<u>T</u>T CAC <u>T</u>TT CA<u>T</u> AA<u>T</u> GC<u>T</u> GG$_{20}$ | TEG | H |
| PMO-ETpipT-2 | PMO-ETpipT | 45 | C<u>T</u>A TA<u>T</u> ATA GA<u>T</u> AGT <u>T</u>AT <u>T</u>CA ACA AA$_{26}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-1 | PMO-APN | 33 | GCT GGC AG$_8$ | TEG | H |
| PMO-APN-2 | PMO-APN | 33 | GCT GGC AG$_8$ | TEG | H |
| PMO-APN-3 | PMO-APN | 33 | GCT GGC AG$_8$ | TEG | H |
| PMO-APN-4 | PMO-APN | 33 | GCT GGC AG$_8$ | TEG | H |
| PMO-APN-5 | PMO-APN | 33 | GCT GGC AG$_8$ | TEG | H |
| PMO-APN-6 | PMO-APN | 33 | GCT GGC AG$_8$ | TEG | H |
| PMO-APN-7 | PMO-APN | 33 | GCT GGC AG$_8$ | TEG | H |
| PMO-APN-8 | PMO-APN | 33 | GCT GGC AG$_8$ | TEG | H |
| PMO-Plus-1 | PMO-Plus | 33 | GCT GGC AG$_8$ | TEG | H |
| PMO-Plus-2 | PMO-Plus | 33 | GCT GGC AG$_8$ | TEG | H |
| PMO-R$_6$Gly-1 | PMO-R$_6$Gly | 33 | GCT GGC AG$_8$ | TEG | Ac-R$_6$Gly- (SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-12 | PMO-APN | 35 | TCA CTT TCA TAA TGC TGG$_{18}$ | TEG | H |
| PMO-APN-13 | PMO-APN | 35 | TCA CTT TCA TAA TGC TGG$_{18}$ | TEG | H |
| PMO-APN-14 | PMO-APN | 35 | TCA CTT TCA TAA TGC TGG$_{18}$ | TEG | H |
| PMO-APN-15 | PMO-APN | 35 | TCA CTT TCA TAA TGC TGG$_{18}$ | TEG | H |
| PMO-APN-16 | PMO-APN | 35 | TCA CTT TCA TAA TGC TGG$_{18}$ | TEG | H |
| PMO-Plus-4 | PMO-Plus | 35 | TCA CTT TCA TAA TGC TGG$_{18}$ | TEG | H |
| PMO-Plus-5 | PMO-Plus | 35 | TCA CTT TCA TAA TGC TGG$_{18}$ | TEG | H |
| PMO-Plus-6 | PMO-Plus | 35 | TCA CTT TCA TAA TGC TGG$_{18}$ | TEG | H |
| PMO-Plus-7 | PMO-Plus | 35 | TCA CTT TCA TAA TGC TGG$_{18}$ | TEG | H |
| PMO-Plus-8 | PMO-Plus | 35 | TCA CTT TCA TAA TGC TGG$_{18}$ | TEG | H |
| PMO-R$_6$Gly-3 | PMO-R$_6$Gly | 35 | TCA CTT TCA TAA TGC TGG$_{18}$ | TEG | Ac-R$_6$Gly- (SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-18 | PMO-APN | 38 | AAA AGT CTG CTG GTC TGC C$_{19}$ | TEG | H |
| PMO-APN-19 | PMO-APN | 38 | AAA AGT CTG CTG GTC TGC C$_{19}$ | TEG | H |
| PMO-APN-20 | PMO-APN | 38 | AAA AGT CTG CTG GTC TGC C$_{19}$ | TEG | H |

-continued

| Compound Name | Modification | Targeting SEQ ID NO | Targeting Sequences | 5' end | 3' end |
|---|---|---|---|---|---|
| PMO-APN-21 | PMO-APN | 38 | AAA AGT CTG CTG GTC TGC C$_{19}$ | TEG | H |
| PMO-APN-22 | PMO-APN | 38 | AAA AGT CTG CTG GTC TGC C$_{19}$ | TEG | H |
| PMO-APN-23 | PMO-APN | 38 | AAA AGT CTG CTG GTC TGC C$_{19}$ | TEG | H |
| PMO-APN-24 | PMO-APN | 38 | AAA AGT CTG CTG GTC TGC C$_{19}$ | TEG | H |
| PMO-APN-25 | PMO-APN | 38 | AAA AGT CTG CTG GTC TGC C$_{19}$ | TEG | H |
| PMO-APN-26 | PMO-APN | 38 | AAA AGT CTG CTG GTC TGC C$_{19}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-17 | PMO-APN | 36 | ATT CAC TTT CAT AAT GCT GG$_{20}$ | TEG | H |
| PMO-APN-28 | PMO-APN | 39 | ATA GAT ATA GAT AGC TAT AT$_{20}$ | TEG | H |
| PMO-Plus-9 | PMO-Plus | 36 | ATT CAC TTT CAT AAT GCT GG$_{20}$ | TEG | H |
| PMO-Plus-10 | PMO-Plus | 39 | ATA GAT ATA GAT AGC TAT AT$_{20}$ | TEG | H |
| PMO-Plus-14 | PMO-Plus | 43 | ACA ACT TTG GGA GGC GGA GG$_{20}$ | TEG | H |
| PMO-Plus-15 | PMO-Plus | 44 | GTA GGG ATG TAG ATT AAC CT$_{20}$ | TEG | H |
| PMO-R$_6$Gly-4 | PMO-R$_6$Gly | 36 | ATT CAC TTT CAT AAT GCT GG$_{20}$ | TEG | Ac-R$_6$Gly- (SEQ ID NO: 53) |
| PMO-R$_6$Gly-5 | PMO-R$_6$Gly | 39 | ATA GAT ATA GAT AGC TAT AT$_{20}$ | TEG | Ac-R$_6$Gly- (SEQ ID NO: 53) |
| PMO-R$_6$Gly-9 | PMO-R$_6$Gly | 43 | ACA ACT TTG GGA GGC GGA GG$_{20}$ | TEG | Ac-R$_6$Gly- (SEQ ID NO: 53) |
| PMO-R$_6$Gly-10 | PMO-R$_6$Gly | 44 | GTA GGG ATG TAG ATT AAC CT$_{20}$ | TEG | Ac-R$_6$Gly- (SEQ ID NO: 53) |
| PMO-ETpipT-1 | PMO-ETpipT | 36 | ATT CAC TTT CAT AAT GCT GG$_{20}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-29 | PMO-APN | 40 | AAT AGT TTT GGC ATC AAA ATT CT$_{23}$ | TEG | H |
| PMO-Plus-11 | PMO-Plus | 40 | AAT AGT TTT GGC ATC AAA ATT CT$_{23}$ | TEG | H |
| PMO-R$_6$Gly-6 | PMO-R$_6$Gly | 40 | AAT AGT TTT GGC ATC AAA ATT CT$_{23}$ | TEG | Ac-R$_6$Gly- (SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-9 | PMO-APN | 37 | GTA AGA TTC ACT TTC ATA ATG CTG G$_{25}$ | TEG | H |
| PMO-APN-10 | PMO-APN | 37 | GTA AGA TTC ACT TTC ATA ATG CTG G$_{25}$ | H | H |
| PMO-APN-11 | PMO-APN | 37 | GTA AGA TTC ACT TTC ATA ATG CTG G$_{25}$ | TEG | H |
| PMO-APN-30 | PMO-APN | 41 | GAT ATA AAA TGG CAT CAT ATC CTA A$_{25}$ | TEG | H |
| PMO-Plus-3 | PMO-Plus | 37 | GTA AGA TTC ACT TTC ATA ATG CTG G$_{25}$ | TEG | H |
| PMO-Plus-12 | PMO-Plus | 41 | GAT ATA AAA TGG CAT CAT ATC CTA A$_{25}$ | TEG | H |
| PMO-R$_6$Gly-2 | PMO-R$_6$Gly | 37 | GTA AGA TTC ACT TTC ATA ATG CTG G$_{25}$ | TEG | Ac-R$_6$Gly-(SEQ ID NO: 53) |
| PMO-R$_6$Gly-7 | PMO-R$_6$Gly | 41 | GAT ATA AAA TGG CAT CAT ATC CTA A$_{25}$ | TEG | Ac-R$_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-31 | PMO-APN | 42 | ATT AAC CTT TTA TCT AAT AGT TTT GG$_{26}$ | TEG | H |
| PMO-APN-34 | PMO-APN | 45 | CTA TAT ATA GAT AGT TAT TCA ACA AA$_{26}$ | TEG | H |
| PMO-Plus-13 | PMO-Plus | 42 | ATT AAC CTT TTA TCT AAT AGT TTT GG$_{26}$ | TEG | H |
| PMO-Plus-16 | PMO-Plus | 45 | CTA TAT ATA GAT AGT TAT TCA ACA AA$_{26}$ | TEG | H |
| PMO-R$_6$Gly-8 | PMO-R$_6$Gly | 42 | ATT AAC CTT TTA TCT AAT AGT TTT GG$_{26}$ | TEG | Ac-R$_6$Gly-SEQ ID NO: 53) |
| PMO-R$_6$Gly-11 | PMO-R$_6$Gly | 45 | CTA TAT ATA GAT AGT TAT TCA ACA AA$_{26}$ | TEG | Ac-R$_6$Gly-(SEQ ID NO: 53) |
| 2'-OMe-11 | 2'-OMe | 51 | CUA UAU AUA GAU AGU UAU UCA ACA AA$_{26}$ | H | H |
| PMO-ETpipT-2 | PMO-ETpipT | 45 | CTA TAT ATA GAT AGT TAT TCA ACA AA$_{26}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-17 | PMO-APN | 36 | ATT CAC TTT CAT AAT GCT GG$_{20}$ | TEG | H |
| PMO-Plus-9 | PMO-Plus | 36 | ATT CAC TTT CAT AAT GCT GG$_{20}$ | TEG | H |
| PMO-R$_6$Gly-4 | PMO-R$_6$Gly | 36 | ATT CAC TTT CAT AAT GCT GG$_{20}$ | TEG | Ac-R$_6$Gly-(SEQ ID NO: 53) |
| PMO-ETpipT-1 | PMO-ETpipT | 36 | ATT CAC TTT CAT AAT GCT GG$_{20}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-17 | PMO-APN | 36 | ATT CAC TTT CAT AAT GCT GG$_{20}$ | TEG | H |
| PMO-Plus-9 | PMO-Plus | 36 | ATT CAC TTT CAT AAT GCT GG$_{20}$ | TEG | H |
| PMO-R$_6$Gly-4 | PMO-R$_6$Gly | 36 | ATT CAC TTT CAT AAT GCT GG$_{20}$ | TEG | Ac-R$_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-28 | PMO-APN | 39 | ATA GAT ATA GAT AGC TAT AT$_{20}$ | TEG | H |
| PMO-Plus-10 | PMO-Plus | 39 | ATA GAT ATA GAT AGC TAT AT$_{20}$ | TEG | H |
| PMO-R$_6$Gly-5 | PMO-R$_6$Gly | 39 | ATA GAT ATA GAT AGC TAT AT$_{20}$ | TEG | Ac-R$_6$Gly-(SEQ ID NO: 53) |

30

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-Plus-14 | PMO-Plus | 43 | ACA ACT TTG GGA GGC GGA GG$_{20}$ | TEG | H |
| PMO-R$_6$Gly-9 | PMO-R$_6$Gly | 43 | ACA ACT TTG GGA GGC GGA GG$_{20}$ | TEG | Ac-R$_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-9 | PMO-APN | 37 | GTA AGA TTC ACT TTC ATA ATG CTG G$_{25}$ | TEG | H |
| PMO-APN-10 | PMO-APN | 37 | GTA AGA TTC ACT TTC ATA ATG CTG G$_{25}$ | H | H |
| PMO-APN-11 | PMO-APN | 37 | GTA AGA TTC ACT TTC ATA ATG CTG G$_{25}$ | TEG | H |
| PMO-Plus-3 | PMO-Plus | 37 | GTA AGA TTC ACT TTC ATA ATG CTG G$_{25}$ | TEG | H |
| PMO-R$_6$Gly-2 | PMO-R$_6$Gly | 37 | GTA AGA TTC ACT TTC ATA ATG CTG G$_{25}$ | TEG | Ac-R$_6$Gly-(SEQ ID NO: 53) |

65

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-11 | PMO-APN | 37 | G<u>T</u>A AGA T<u>T</u>C AC<u>T</u> TTC A<u>T</u>A A<u>T</u>G CTG G$_{25}$ | TEG | H |
| PMO-Plus-3 | PMO-Plus | 37 | G<u>T</u>A AGA T<u>T</u>C AC<u>T</u> TTC A<u>T</u>A A<u>T</u>G CTG G$_{25}$ | TEG | H |
| PMO-R$_6$Gly-2 | PMO-R$_6$Gly | 37 | GTA AGA TTC ACT TTC ATA ATG CTG G$_{25}$ | TEG | Ac-R$_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-30 | PMO-APN | 41 | GA<u>T</u> ATA A<u>AA</u> TGG CAT CA<u>T</u> ATC C<u>T</u>A A$_{25}$ | TEG | H |
| PMO-Plus-12 | PMO-Plus | 41 | GA<u>T</u> ATA A<u>AA</u> TGG CAT CA<u>T</u> ATC C<u>T</u>A A$_{25}$ | TEG | H |
| PMO-R$_6$Gly-7 | PMO-R$_6$Gly | 41 | GAT ATA AAA TGG CAT CAT ATC CTA A$_{25}$ | TEG | Ac-R$_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-31 | PMO-APN | 42 | AT<u>T</u> AAC C<u>TT</u> TTA <u>T</u>CT AA<u>T</u> AGT <u>T</u>TT GG$_{26}$ | TEG | H |
| PMO-Plus-13 | PMO-Plus | 42 | AT<u>T</u> AAC C<u>TT</u> TTA <u>T</u>CT AA<u>T</u> AGT <u>T</u>TT GG$_{26}$ | TEG | H |
| PMO-R$_6$Gly-8 | PMO-R$_6$Gly | 42 | ATT AAC CTT TTA TCT AAT AGT TTT GG$_{26}$ | TEG | Ac-R$_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-34 | PMO-APN | 45 | C<u>T</u>A TA<u>T</u> ATA GA<u>T</u> AGT <u>T</u>AT <u>T</u>CA ACA AA$_{26}$ | TEG | H |
| PMO-Plus-16 | PMO-Plus | 45 | C<u>T</u>A TA<u>T</u> ATA GA<u>T</u> AGT <u>T</u>AT <u>T</u>CA ACA AA$_{26}$ | TEG | H |
| PMO-R$_6$Gly-11 | PMO-R$_6$Gly | 45 | CTA TAT ATA GAT AGT TAT TCA ACA AA$_{26}$ | TEG | Ac-R$_6$Gly-(SEQ ID NO: 53) |
| 2'-OMe-11 | 2'-OMe | 51 | <u>CUA UAU AUA GAU AGU UAU UCA ACA AA</u>$_{26}$ | H | H |
| PMO-ETpipT-2 | PMO-ETpipT | 45 | C<u>T</u>A TA<u>T</u> ATA GA<u>T</u> AGT TAT <u>T</u>CA ACA AA$_{26}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-16 | PMO-APN | 35 | TCA CTT TCA TAA TGC TGG$_{18}$ | TEG | H |
| PMO-Plus-8 | PMO-Plus | 35 | TCA CTT TCA TAA TGC TGG$_{18}$ | TEG | H |
| PMO-R$_6$Gly-3 | PMO-R$_6$Gly | 35 | TCA CTT TCA TAA TGC TGG$_{18}$ | TEG | Ac-R$_6$Gly-(SEQ ID NO: 53) |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-APN-11 | PMO-APN | 37 | GTA AGA TTC ACT TTC ATA ATG CTG G$_{25}$ | TEG | H |
| PMO-APN-16 | | 35 | TCA CTT TCA TAA TGC TGG$_{18}$ | TEG | H |
| PMO-APN-17 | | 36 | ATT CAC TTT CAT AAT GCT GG$_{20}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-Plus-3 | PMO-Plus | 37 | GTA AGA TTC ACT TTC ATA ATG CTG G$_{25}$ | TEG | H |
| PMO-Plus-8 | | 35 | TCA CTT TCA TAA TGC TGG$_{18}$ | TEG | H |
| PMO-Plus-9 | | 36 | ATT CAC TTT CAT AAT GCT GG$_{20}$ | TEG | H |

In some embodiments, the modified antisense oligomer of the disclosure is selected from the following compounds:

| Compound Name | Modification | Targeting SEQ ID NO | Targeting Sequences | 5' end | 3' end |
|---|---|---|---|---|---|
| PMO-R$_6$Gly-2 | PMO-R$_6$Gly | 37 | GTA AGA TTC ACT TTC ATA ATG CTG G$_{25}$ | TEG | Ac-R$_6$Gly-(SEQ ID NO: 53) |
| PMO-R$_6$Gly-3 | | 35 | TCA CTT TCA TAA TGC TGG$_{18}$ | TEG | Ac-R$_6$Gly-(SEQ ID NO: 53) |
| PMO-R$_6$Gly-4 | | 36 | ATT CAC TTT CAT AAT GCT GG$_{20}$ | TEG | Ac-R$_6$Gly-(SEQ ID NO: 53) |

For each of the compounds described in the tables of the preceeding pages, each X of the targeting sequence SEQ ID is thymine (T) and each Y of the targeting sequence SEQ ID is cystosine (C), each bolded and underline base indicates a subunit with an intersubunit linkage of the type indicated in the modification column between that subunit and the preceding subunit. If not bolded and underlined, the intersubunit linkages are dimethylamino phosphorodiamidate linkages.

The chemical structure of each of the compounds described in the tables above and throughout the disclosure would readily be understood by those of skill in the art based on the description provided throughout the disclosure. For example, it would be readily understood that PMO-2 has the following structure:

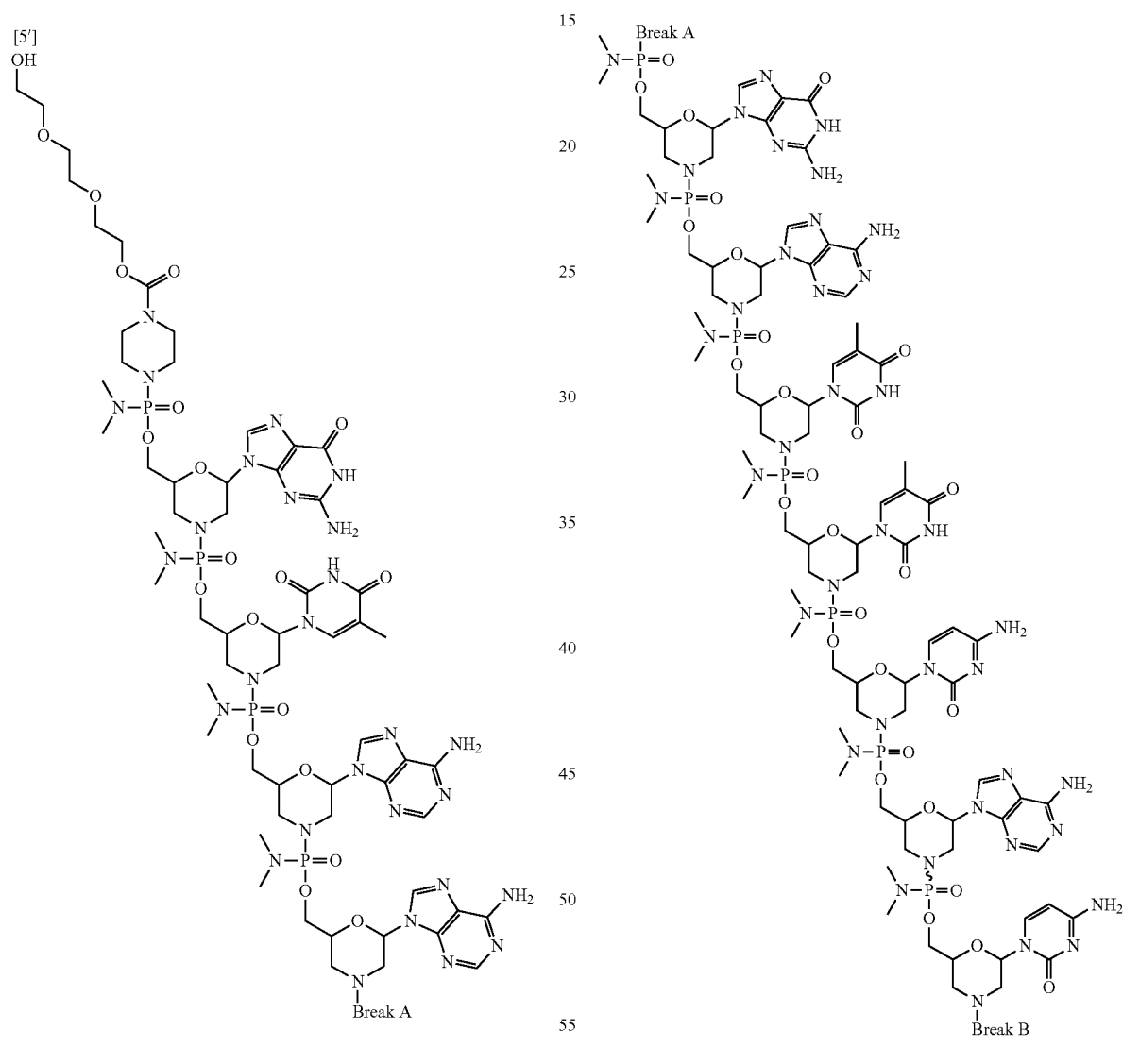

151
-continued
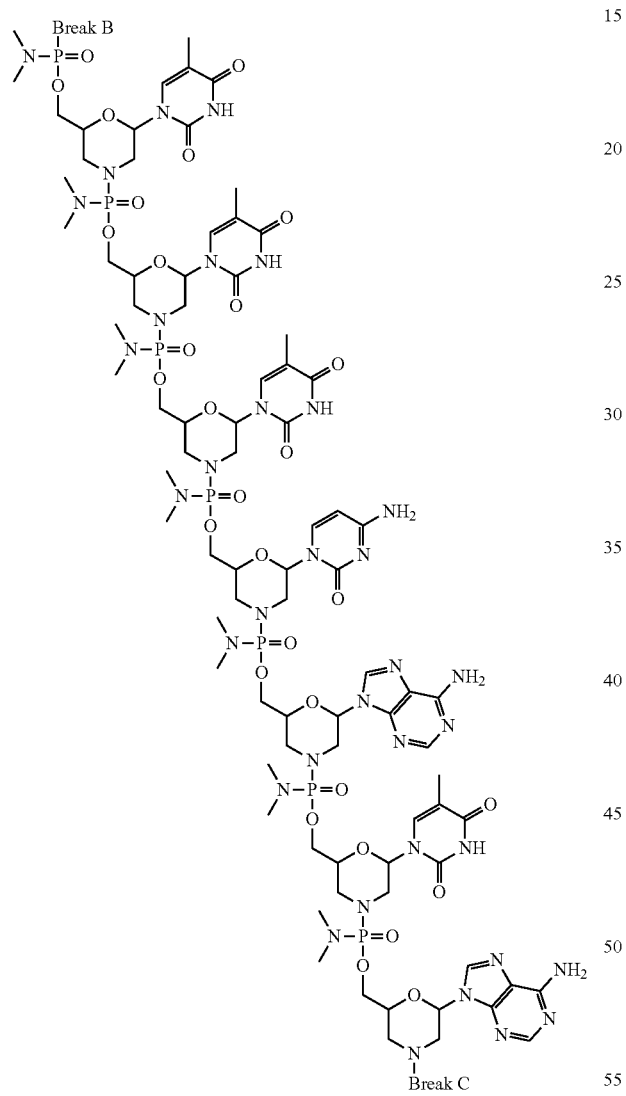
152
-continued
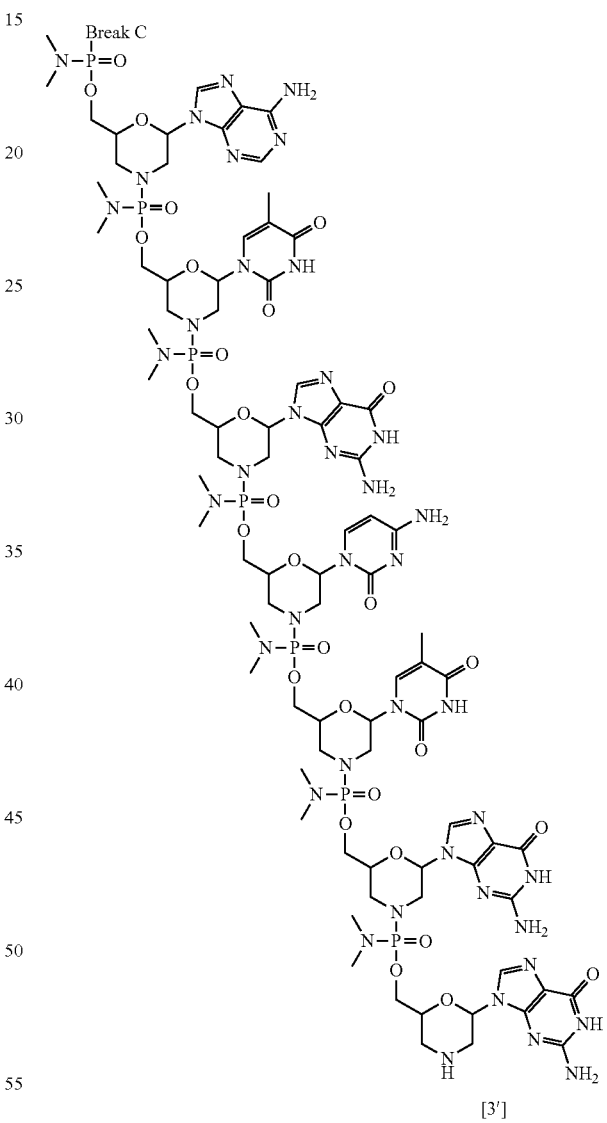
[3']

and that PMO-APN-11 has the following structure:
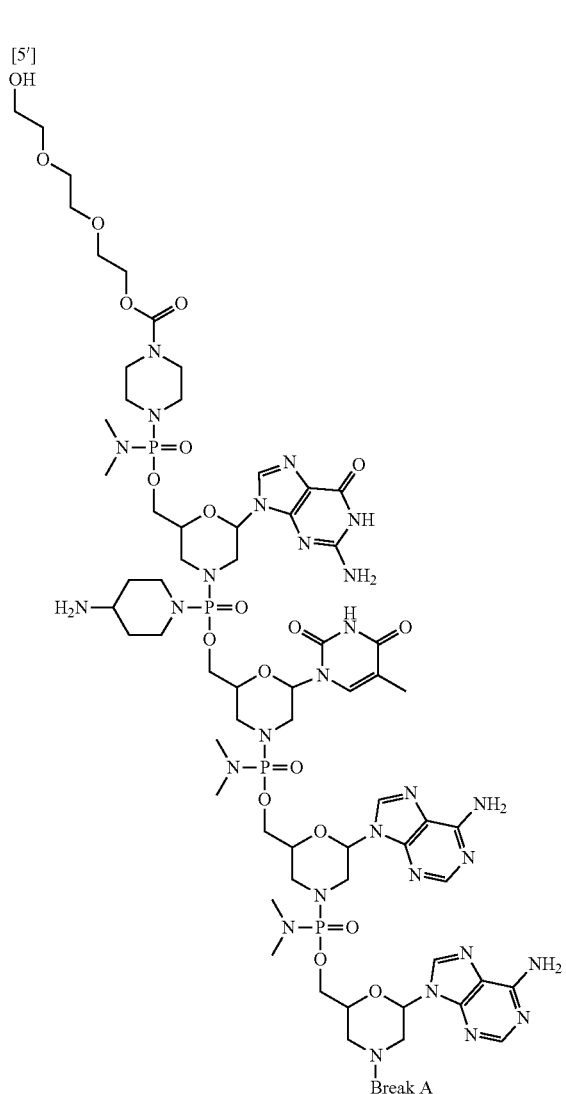
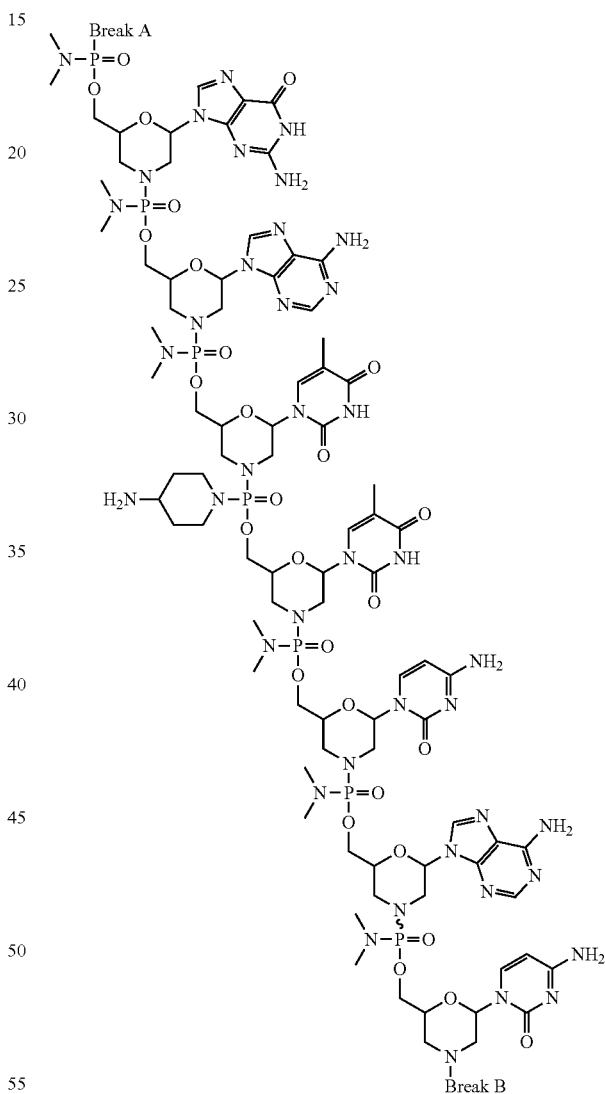

155
-continued
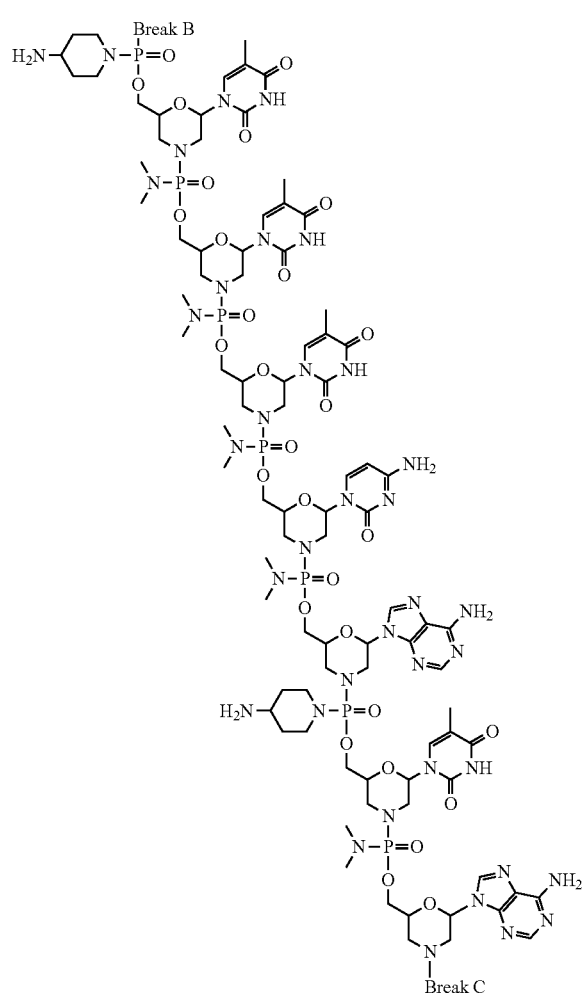
156
-continued
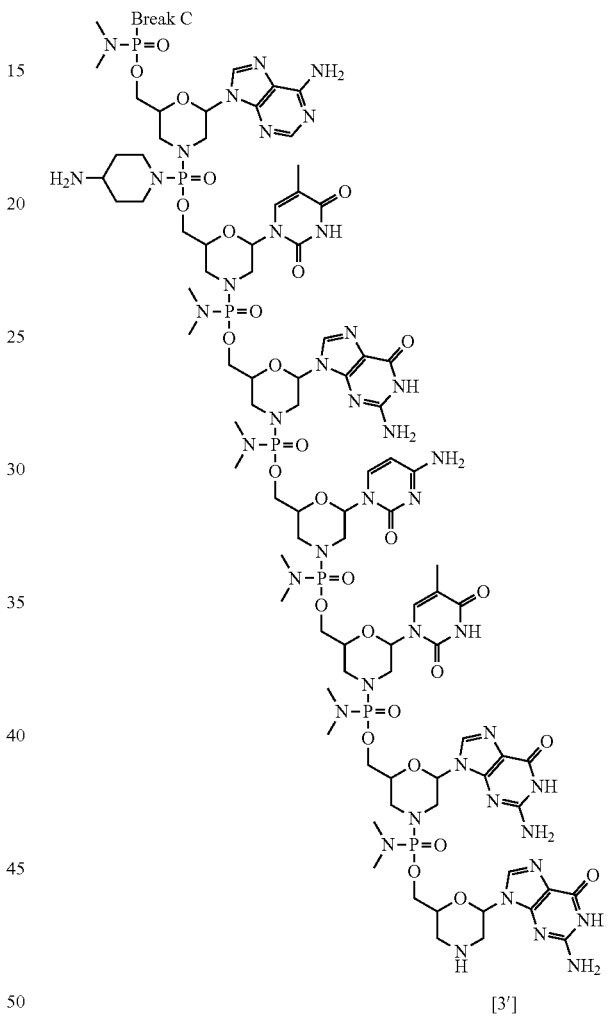

Similarly, it would be readily understood that PMO-Plus-3 has the following structure:
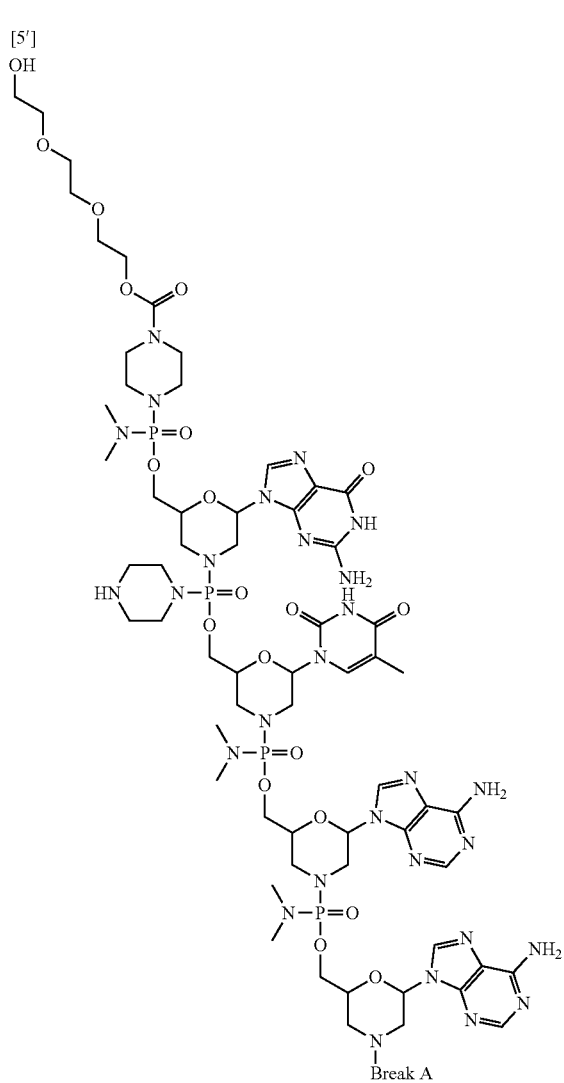
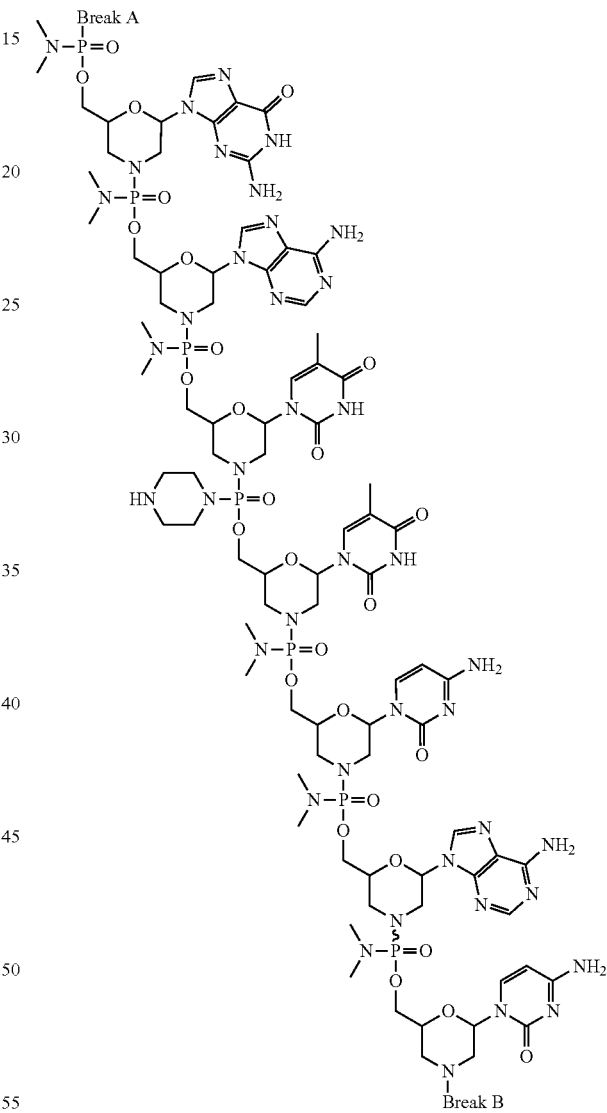

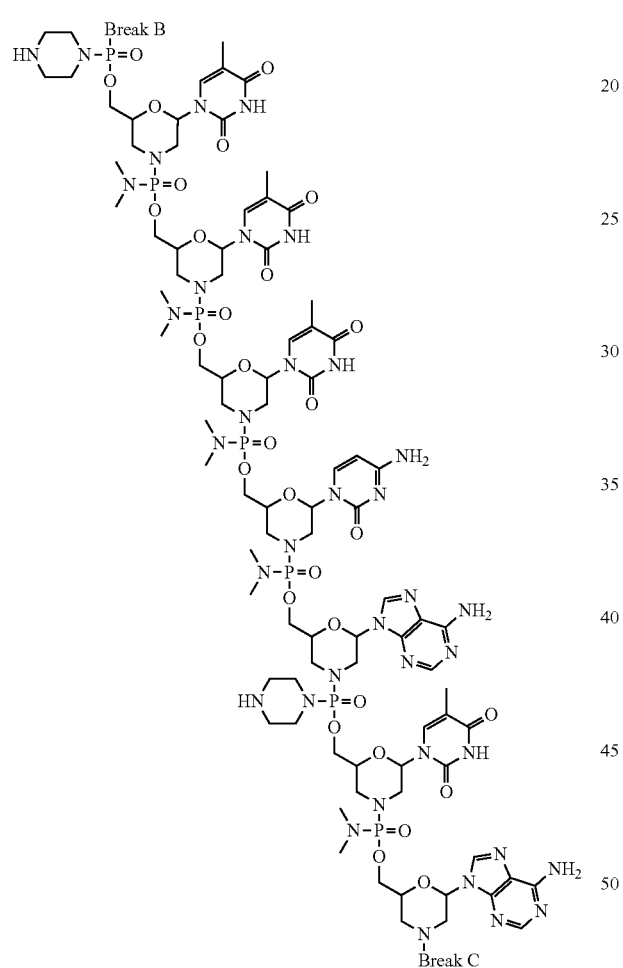
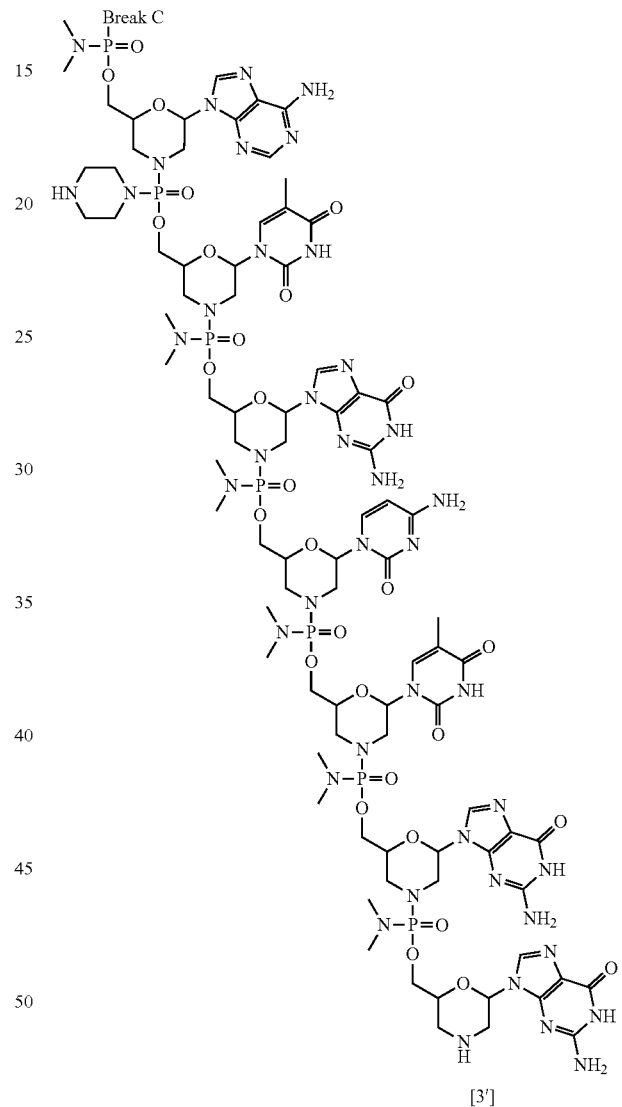

and that PMO-R₆Gly-2 has the following structure:
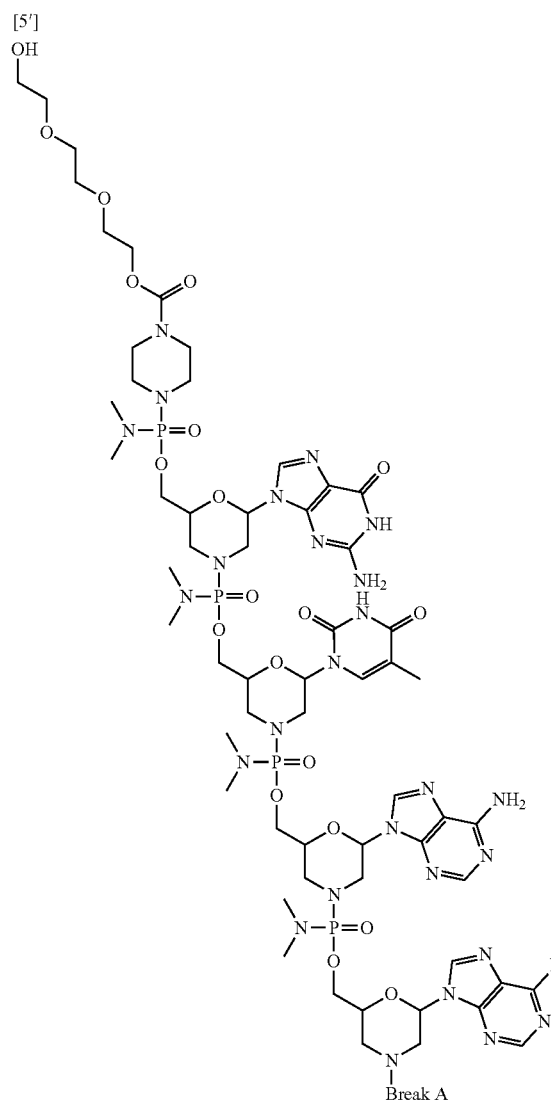
-continued
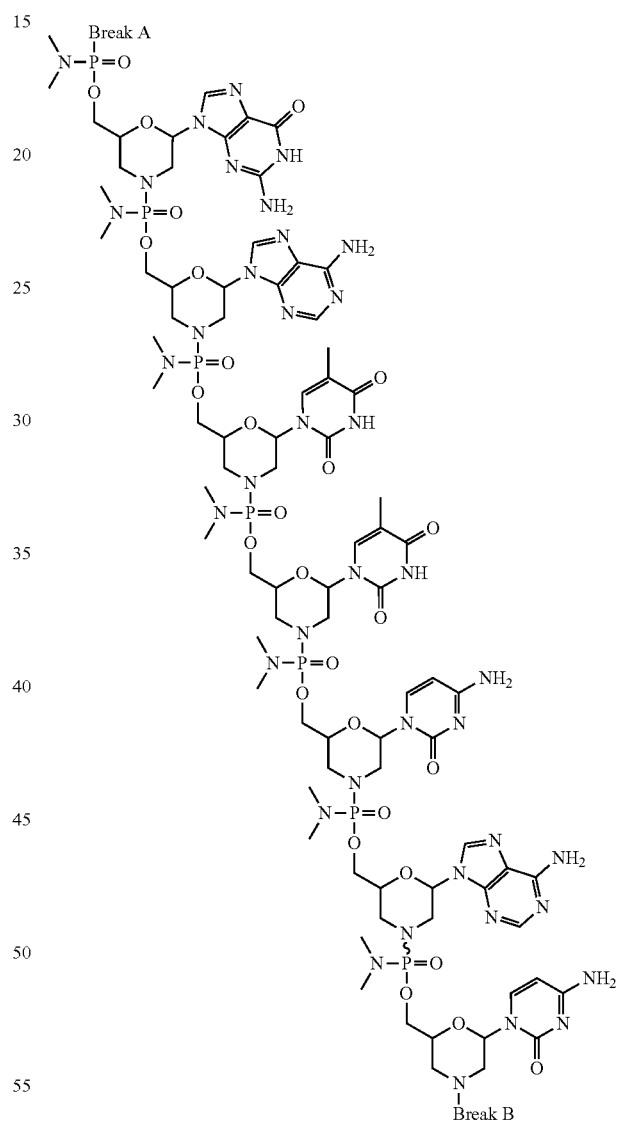

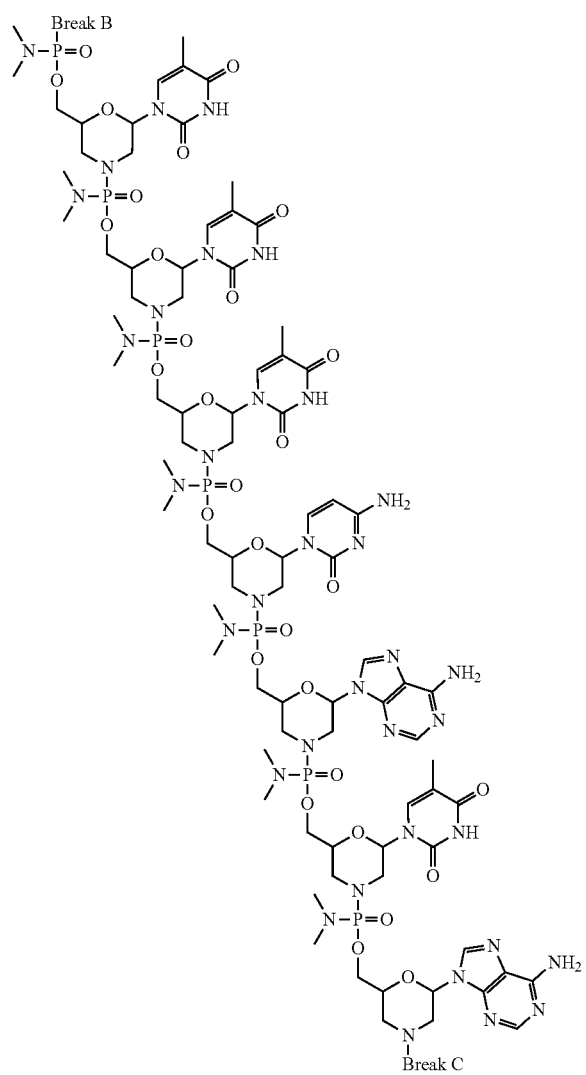

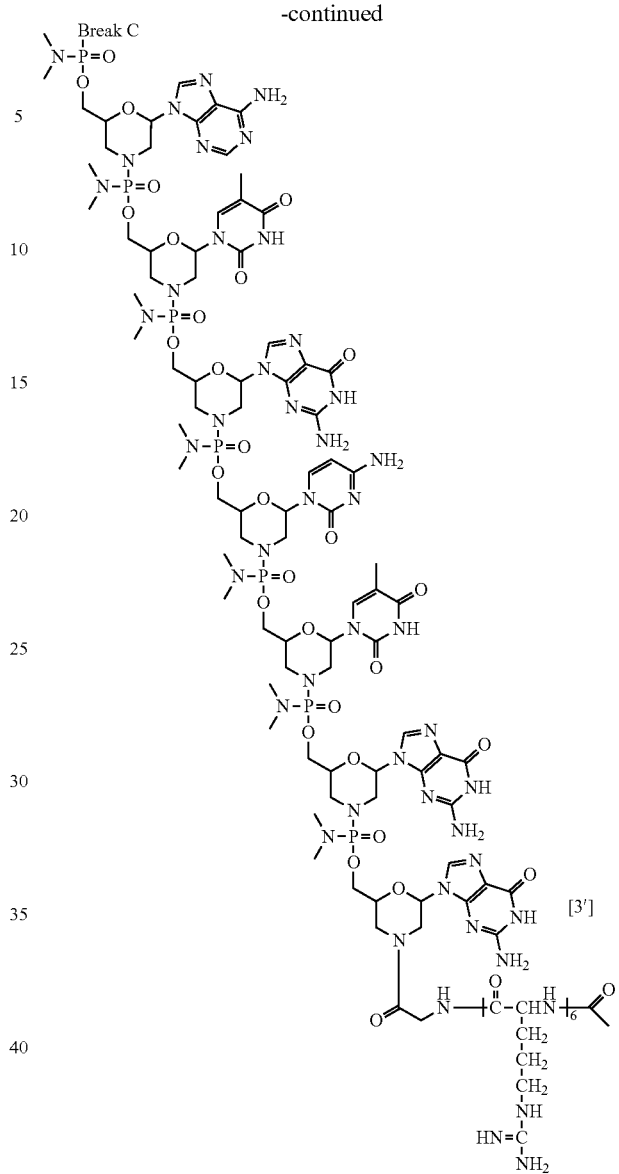

As already discussed, the structures of all other compounds of the tables would be similarly understood. For clarity, structures of the disclosure including, for example, the above structure of PMO-2, PMO-APN-11, PMO-Plus-3, and PMO-R$_6$Gly-2, are continuous from 5' to 3', and, for the convenience of depicting the entire structure in a compact form, various illustration breaks labeled "BREAK A" and "BREAK B," and "BREAKC" have been included. As would be understood by the skilled artisan, for example, each indication of "BREAK A" shows a continuation of the illustration of the structure at these points. The skilled artisan understands that the same is true for each instance of "BREAK B" and "BREAK C" in the structures above. None of the illustration breaks, however, are intended to indicate, nor would the skilled artisan understand them to mean, an actual discontinuation of the structure above.

Additional modified antisense oligomers/chemistries that can be used in accordance with the present disclosure include those described in the following patents and patent publications, which are hereby incorporated by reference in their entirety: PCT Publication Nos. WO 2007/002390; WO 2010/120820; and WO 2010/148249; U.S. Pat. No. 7,838, 657; and U.S. Patent Application No. 2011/0269820.

C. The Preparation of Morpholino Subunits and Phosphoramidate Internucleoside Linkers Morpholino monomer subunits, the modified internucleoside linkages, and oligomers comprising the same can be prepared as described, for example, in U.S. Pat. Nos. 5,185,444, and 7,943,762, which are hereby incorporated by reference in their entirety. The morpholino subunits can be prepared according to the following general Reaction Scheme I.

Reaction Scheme 1. Preparation, Protection, and Activation of Morpholino Subunit

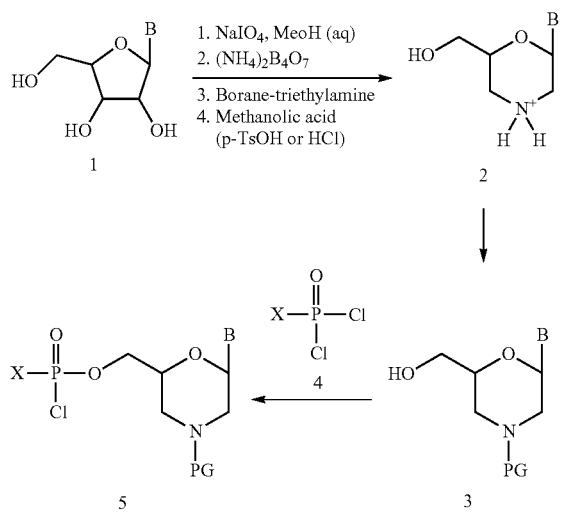

Referring to Reaction Scheme 1, where B represents a base pairing moiety and PG represents a protecting group, the morpholino subunits may be prepared from the corresponding ribonucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing moiety may be suitably protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in U.S. Pat. No. 8,076,476, which is hereby incorporated by reference in its entirety.

Reaction of compound 3 with the activated phosphorous compound 4, results in morpholino subunits having the desired linkage moiety compound 5. Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. Nos. 5,185,444, 7,943,762, and 8,779,128, which are hereby incorporated by reference in its entirety.

Compounds of structure 5 can be used in solid-phase automated oligomer synthesis for preparation of oligomers comprising the internucleoside linkages. Such methods are well known in the art. Briefly, a compound of structure 5 may be modified at the 5' end to contain a linker to a solid support. For example, compound 5 may be linked to a solid support by a linker comprising $L^{11}$ and $L^{15}$. Once supported, the protecting group (e.g., trityl) is removed and the free amine is reacted with an activated phosphorous moiety of a second compound of structure 5. This sequence is repeated until the desired length of oligo is obtained. The protecting group in the terminal 5' end may either be removed or left on if a 5'-modification is desired. The oligo can be removed from the solid support using any number of methods, for example treatment with DTT followed by ammonium hydroxide.

The preparation of modified morpholino subunits and morpholino-based oligomers are described in more detail in the Examples. The morpholino-based oligomers containing any number of modified linkages may be prepared using methods described herein, methods known in the art and/or described by reference herein. Also described in the examples are global modifications of morpholino-based oligomers prepared as previously described (see e.g., PCT Publication No. WO 2008/036127, which is hereby incorporated by reference in its entirety).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999), which is hereby incorporated by reference in its entirety. It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

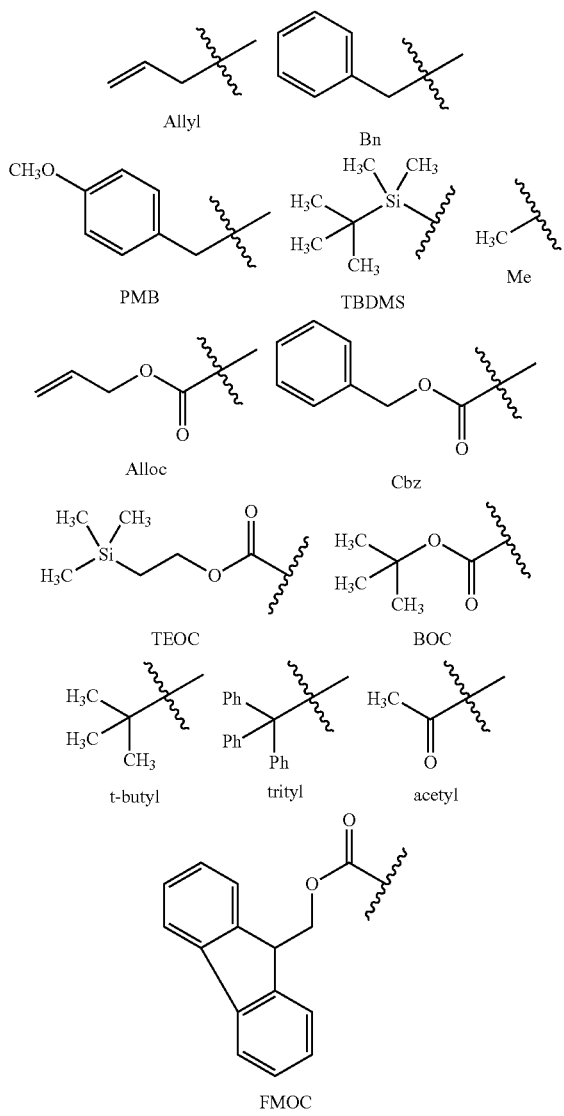

Unless otherwise noted, all chemicals were obtained from Sigma-Aldrich-Fluka (St. Louis, Mo.). Benzoyl adenosine, benzoyl cytidine, and phenylacetyl guanosine were obtained from Carbosynth Limited (Berkshire, UK).

Synthesis of PMO, PMOplus, PPMO, and PMO-X containing further linkage modifications as described herein was done using methods known in the art and described in pending U.S. patent application Ser. Nos. 12/271,036 and 12/271,040 and PCT Publication No. WO 2009/064471, which is hereby incorporated by reference in its entirety.

PMO with a 3' trityl modification are synthesized essentially as described in PCT Publication No. WO 2009/064471 with the exception that the detritylation step is omitted.

D. Cell-Penetrating Peptides

The modified antisense oligomer compounds of the disclosure may be conjugated to a peptide, also referred to herein as a cell penetrating peptide (CPP). In certain preferred embodiments, the peptide is an arginine-rich peptide transport moiety effective to enhance transport of the compound into cells. The transport moiety is preferably attached to a terminus of the oligomer. The peptides have the capability of inducing cell penetration within 30%, 40%, 50%, 60%, 70%, 80%, 90% or 100% of cells of a given cell culture population, including all integers in between, and allow macromolecular translocation within multiple tissues in vivo upon systemic administration. In one embodiment, the cell-penetrating peptide may be an arginine-rich peptide transporter. In another embodiment, the cell-penetrating peptide may be Penetratin or the Tat peptide. These peptides are well known in the art and are disclosed, for example, in US Publication No. 2010-0016215 A1, which is hereby incorporated by reference in its entirety. One approach to conjugation of peptides to modified antisense oligomers of the disclosure can be found in PCT publication WO2012/150960, which is hereby incorporated by reference in its entirety. Some embodiments of a peptide conjugated oligomer of the present disclosure utilize glycine as the linker between the CPP and the modified antisense oligomer. For example, a peptide conjugated PMO of the disclosure consists of $R_6$-G-PMO.

The transport moieties as described above have been shown to greatly enhance cell entry of attached oligomers, relative to uptake of the oligomer in the absence of the attached transport moiety. Uptake is preferably enhanced at least ten fold, and more preferably twenty fold, relative to the unconjugated compound.

The use of arginine-rich peptide transporters (i.e., cell-penetrating peptides) are particularly useful in practicing the present disclosure. Certain peptide transporters have been shown to be highly effective at delivery of antisense compounds into primary cells including muscle cells (Marshall, Oda et al. 2007; Jearawiriyapaisarn, Moulton et al. 2008; Wu, Moulton et al. 2008, which are hereby incorporated by reference in their entirety). Furthermore, compared to other known peptide transporters such as Penetratin and the Tat peptide, the peptide transporters described herein, when conjugated to an antisense PMO, demonstrate an enhanced ability to alter splicing of several gene transcripts (Marshall, Oda et al. 2007, which is hereby incorporated by reference in its entirety).

Exemplary peptide transporters, excluding linkers are given below in Table 3.

TABLE 3

Exemplary peptide transporters

| NAME (DESIGNATION) | SEQUENCE | CPP SEQ ID NO[A] |
|---|---|---|
| rTAT | RRRQRRKKR | 17 |
| Tat | RKKRRQRRR | 18 |
| $R_9F_2$ | RRRRRRRRRFF | 19 |
| $R_5F_2R_4$ | RRRRRFFRRRR | 20 |
| $R_4$ | RRRR | 21 |

TABLE 3-continued

Exemplary peptide transporters

| NAME (DESIGNATION) | SEQUENCE | CPP SEQ ID NO[A] |
|---|---|---|
| $R_5$ | RRRRR | 22 |
| $R_6$ | RRRRRR | 23 |
| $R_7$ | RRRRRRR | 24 |
| $R_8$ | RRRRRRRR | 25 |
| $R_9$ | RRRRRRRRR | 26 |
| $(RX)_8$ | RAhxRAhxRAhxRAhxRAhxRAhxRAhxRAhx | 27 |
| $(RAhxR)_4$; (P007) | RAhxRRAhxRRAhxRRAhxR | 28 |
| $(RAhxR)_5$; (CP04057) | RAhxRRAhxRRAhxRRAhxRRAhxR | 29 |
| $(RAhxRRBR)_2$; (CP06062) | RAhxRBRRAhxRRBR | 30 |
| $(RAR)_4F_2$ | RARRARRARRARFF | 31 |
| $(RGR)_4F_2$ | RGRRGRRGRRGRFF | 32 |

[A] sequences assigned to CPP SEQ ID NOS do not include the linkage portion (e.g., C (cys), G (gly), P (pro), Ahx, B, AhxB where Ahx and B refer to 6-aminohexanoic acid and beta-alanine, respectively).

In various embodiments, G (as recited in formulas I, IV, V, Va, Vb, IX, IXa, X, and XI) is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

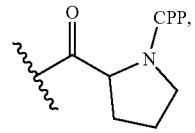

wherein the CPP is attached to the linker moiety by an amide bond at the CPP carboxy terminus. In some embodiments, the CPP is selected from SEQ ID NOS: 17 to 32.

In some embodiments, G (as recited in formulas I, IV, V, Va, Vb, IX, IXa, X, and XI) is of the formula:

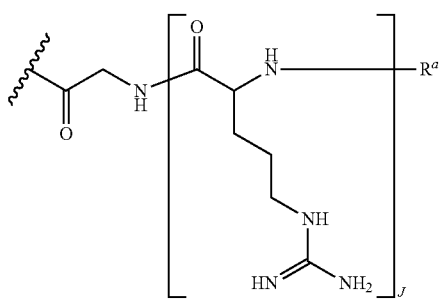

wherein IV is selected from H, acetyl, benzoyl, and stearoyl, and J is an integer from 4 to 9. In certain embodiments J is 6.

In some embodiments, G (as recited in formulas I, IV, V, Va, Vb, IX, IXa, X, and XI) is Ac—R$_6$Gly- (SEQ ID NO: 53), wherein G is of the formula:

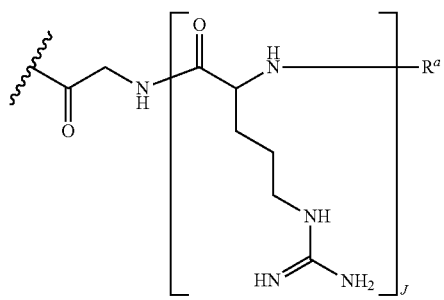

wherein $R^a$ is acetyl.

In various embodiments, the CPP (as recited in formulas I, IV, V, Va, Vb, IX, IXa, X, and XI) is of the formula:

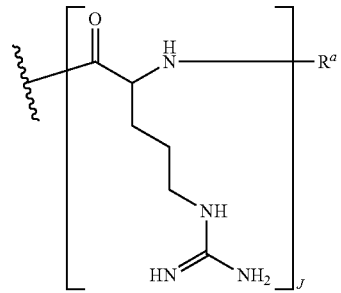

wherein IV is selected from H, acetyl, benzoyl, and stearoyl, and J is an integer from 4 to 9. In certain embodiments, the CPP is SEQ ID NO: 15. In various embodiments, J is 6. In some embodiments $R_a$ is selected from H and acetyl. For example, in some embodiments, $R_a$ is H. In certain embodiments, $R_a$ is acetyl.

IV. Formulations

The compounds of the disclosure may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, which are hereby incorporated by reference in their entirety.

The antisense compounds of the disclosure encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the disclosure, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligomers of the disclosure are prepared as SATE [(S-acetyl-2-thioethyl) phosphate] derivatives according to the methods disclosed in PCT Publication No. WO 1993/24510 to Gosselin et al., published Dec. 9, 1993 or in PCT Publication No. WO 1994/26764 and U.S. Pat. No. 5,770,713 to Imbach et al., which are hereby incorporated by reference in their entirety The term "pharmaceutically acceptable salts" refers to physiologically and pharmaceutically acceptable salts of the compounds of the disclosure: i.e., salts that retain the desired biological activity of the parent compound and do not impart undesired toxicological effects thereto. For oligomers, examples of pharmaceutically acceptable salts and their uses are further described in U.S. Pat. No. 6,287,860, which is hereby incorporated by reference in its entirety.

The present disclosure also includes pharmaceutical compositions and formulations which include the antisense compounds of the disclosure. The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligomers with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, gel capsules, liquid syrups, soft gels, suppositories, and enemas. The compositions of the present disclosure may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present disclosure include, but are not limited to, solutions, emulsions, foams and liposome-containing formulations. The pharmaceutical compositions and formulations of the present disclosure may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present disclosure. Emulsions and their uses are well known in the art and are further described in U.S. Pat. No. 6,287,860, which is hereby incorporated by reference in its entirety.

Formulations of the present disclosure include liposomal formulations. As used in the present disclosure, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic oligomers, such as a polyethylene glycol (PEG) moiety. Liposomes and their uses are further described in U.S. Pat. No. 6,287,860, which is hereby incorporated by reference in its entirety.

The pharmaceutical formulations and compositions of the present disclosure may also include surfactants. The use of surfactants in drug products, formulations and in emulsions is well known in the art. Surfactants and their uses are further described in U.S. Pat. No. 6,287,860, which is hereby incorporated by reference in its entirety.

In some embodiments, the present disclosure employs various penetration enhancers to effect the efficient delivery of nucleic acids, particularly oligomers. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is hereby incorporated by reference in its entirety.

One of skill in the art will recognize that formulations are routinely designed according to their intended use, i.e. route of administration.

Formulations for topical administration include those in which the oligomers of the disclosure are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g.

dioleoyltetramethylaminopropyl DOTAP and dioleoylphosphatidyl ethanolamine DOTMA).

For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860, which is hereby incorporated by reference in its entirety. Topical formulations are described in detail in U.S. patent application Ser. No. 09/315,298 filed on May 20, 1999 and Mourich et al., 2009, J. Invest. Dermatol., 129(8):1945-53, which are hereby incorporated by reference in their entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligomers of the disclosure are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860, which is hereby incorporated by reference in its entirety. In some embodiments, the present disclosure provides combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether. Oligomers of the disclosure may be delivered orally, in granular form including sprayed dried particles, or complexed to form micro or nanoparticles. Oligomer complexing agents and their uses are further described in U.S. Pat. No. 6,287,860, which is hereby incorporated by reference in its entirety. Oral formulations for oligomers and their preparation are described in detail in U.S. patent application Ser. No. 09/108,673 (filed Jul. 1, 1998), Ser. No. 09/315,298 (filed May 20, 1999) and Ser. No. 10/071,822 (filed Feb. 8, 2002), which are hereby incorporated by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

In another related embodiment, compositions of the disclosure may contain one or more antisense compounds, particularly oligomers, targeted to a first nucleic acid and one or more additional antisense compounds targeted to a second nucleic acid target. Alternatively, compositions of the disclosure may contain two or more antisense compounds targeted to different regions of the same nucleic acid target. Numerous examples of antisense compounds are known in the art. Two or more combined compounds may be used together or sequentially.

V. Methods of Use

Certain aspects relate to methods of increasing functional SMN protein using the modified antisense oligomers as described herein for therapeutic purposes (e.g., treating subjects with spinal muscular atrophy). In some aspects, the modified antisense oligomer comprises a nucleotide sequence of sufficient length and complementarity to specifically hybridize to a region within the pre-mRNA of the SMN2 gene, wherein binding of the modified antisense oligomer to the region increases the level of exon 7-containing SNM2 mRNA in a cell and/or tissue of the subject. The increase of exon 7-containing SMN2 mRNA in the subject may further translate to increased expression of functional SMN protein. Thus, the present disclosure relates to methods of increasing functional SMN protein by increasing exon 7-containing SMN2 mRNA using the modified antisense oligomers as described herein. In some embodiments, the present disclosure provides methods of treating an individual afflicted with or at risk for developing spinal muscular atrophy (SMA), comprising administering an effective amount of a modified antisense oligomer of the disclosure to the subject. Exemplary sequences tageted by the modified antisense oligomers as described herein are shown in Tables 1 and 2.

Also included are modified antisense oligomers for treating SMA or for use in the preparation of a medicament for the treatment of SMA, the treatment or the medicament comprising a modified antisense oligomer as described herein, e.g., where the modified antisense oligomer comprises 8 to 40 subunits, optionally having at least one subunit that is a nucleotide analog having (i) a modified internucleoside linkage, (ii) a modified sugar moiety, or (iii) a combination of the foregoing; and a targeting sequence complementary to 8 or more contiguous nucleotides in a target region within SMN2 pre-mRNA. In some embodiments, the target region comprises a region within intron 6, intron 7, or exon 7 of SMN2 gene and/or pre-mRNA SMN2 (SEQ ID NOS: 1-3). In further embodiments, the target region comprises a region within intron 7 (SEQ ID NO: 1). In some embodiments, the targeting sequence of the modified antisense oligomers (a) comprises a sequence selected from SEQ ID NOS: 4-16, (b) is selected from SEQ ID NOS: 4-16, (c) is a fragment of at least 8 contiguous nucleotides of a sequence selected from SEQ ID NOS: 4-16, or (d) is a variant having at least 90% sequence identity to a sequence selected from SEQ ID NOS: 4-16, where X is selected from uracil (U) or thymine (T), and C is selected from cytosine (C) or 5-methylcytosine (5mC).

In some embodiments, the methods of treating SMA or the medicaments for the treatment of SMA include modified antisense oligomers having a nucleotide analog subunit comprising a modified sugar moiety. The modified sugar moiety may be selected from a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' O-methoxyethyl subunit, a 2'-fluoro subunit, a 2'-O-[2-(N-methylcarbamoyl)ethyl] subunit, and a morpholino subunit.

These additional aspects and embodiments include modified antisense oligomers having a nucleotide analog subunit comprising a modified internucleoside linkage. In various embodiments, the modified internucleoside linkage is selected from a phosphorothioate internucleoside linkage, a phosphoramidate internucleoside linkage, a phosphorodiamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

These additional aspects and embodiments include modified antisense oligomers having a nucleotide analog subunit comprising at least one combination of a modified sugar moiety and a modified internucleoside linkage.

In some embodiments, the modified antisense oligomer is actively taken up by mammalian cells. In further embodiments, the modified antisense oligomer may be conjugated to a transport moiety (e.g., transport peptide or CPP) as described herein to facilitate such uptake.

Various aspects relate to methods of increasing the expression of exon 7-containing SMN mRNA transcript and/or functional SMN protein, using the modified antisense oligomers as described herein. In some instances, exon 7-containing SMN mRNA transcript and/or functional SMN protein is increased or enhanced by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject (for example, a subject having SMA), a control composition without the modified antisense oligomer, the absence of treatment, and/or an earlier time-point. Also included are methods of increasing the expression of functional SMN protein relative to the levels of a control, for example, a subject having SMA. As used herein, an "effective amount" or "therapeutic amount" refers to the dose(s) of the modified antisense oligomers that is capable to bind to the target region of SMN pre-mRNA transcript and to increase the expression of exon 7-containing SMN2 mRNA transcript and functional SMN protein in the range of the percentages disclosed with regard to the increase when administered to a subject, as compared to a control cell/subject.

Various aspects relate to methods of increasing expression of exon 7-containing SMN mRNA transcript and/or functional SMN protein in a cell, tissue, and/or subject, using the modified antisense oligomers as described herein. In some instances, exon 7-deleted SMN mRNA transcript or dysfunctional SMN protein is decreased or reduced by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject (for example, a subject having SMA), a control composition without the modified antisense oligomer, the absence of treatment, and/or an earlier time-point. Also included are methods of increasing the expression of exon 7-containing SMN mRNA transcript or decreasing the expression of dysfunctional SMN protein relative to the levels of a control, for example, a subject having SMA.

As used herein, a subject may have reduced expression and/or activity of SMN protein in one or more tissues (for example, relative to a healthy subject or an earlier point in time), including nervous system tissues such as spinal cord, brain, and pheripheral nervous system, heart, muscles, kidney and liver. In some embodiments, the subject has a decreased number of motor neurons in the spinal cord. The subject may have elevated circulating levels of biological markers associated with spinal muscular atrophy including creatine kinase. In some embodiments, the subject displays one or more symptoms related to SMA such as, but not limited to, muscle weakness, spinal curvature, and difficulties with breathing, sucking, swallowing, and sitting upright. In some embodiments, the subject does not present such symptoms yet, and the subject may be identified by currently available genetic testings, detecting the presence, mutation, and/or deletion of the SMN1 gene. In certain embodiments, the subject is a patient diagnosed as having SMA Type I, Type II, Type III, or Type IV.

Modified antisense oligomers herein may be administered to a subject to treat SMA. In some embodiments, the modified antisense oligomer is administered to a subject exhibiting one or more symptoms of SMA, in a suitable pharmaceutical carrier. As used herein, the term "treat" refers to an amelioration of SMA, or at least one discernible symptom related to SMA. In some embodiments, "treat" refers to an amelioration of at least one measurable physical and/or biological parameter that is not necessarily discernible by the subject. The subject may experience, for example, physical improvement of muscle strength and coordination, and the increased number of motor neurons in the spinal cord. Those parameters may be assessed by e.g., self-evalulation tests, physician's examinations, lab tests for physical and physiological measusrments, and biological tests of samples from the subject. In another embodiment, "treat" refers to slowing the progression or reversing the progression of SMA. As used herein, "prevent" or "inhibit" refers to delaying the onset or reducing the risk of developing SMA.

In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective administration and delivery of the modified antisense oligomer to the target nucleic acid is one aspect of treatment. Routes of modified antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. Vascular or extravascular circulation, the blood or lymph system, and the cerebrospinal fluid are some non-limiting sites where the RNA may be introduced. Direct CNS delivery may be employed, for instance, intracerebral ventricular (ICV) or intrathecal (IT) administration may be used as routes of administration.

In some embodiments, the modified antisense oligomer(s) as described herein are administered to the subject by ICV administration. For illustrative purposes only, an exemplary method to administer the modified antisense oligomer(s) through intracerebral ventricules is provided as following: a subject receives an intracranial catheter which is positioned in the lateral ventricle in the brain hemisphere. The non-dominant brain hemisphere is preferred for implanting the catheter. The catheter may be connected to a subcutaneously implanted infusion pump or an external pump containing a solution of the modified antisense oligomer(s). In certain embodiments, the modified antisense oligomer(s) as described herein are administered to the subject by IT administration. For example, a subject is place in a latheral position. The modified antisene oligomer(s) are loaded in a syringe with a spinal needle, and the needle is inserted at a lowder lumbar interspace, delivering the modified antisense oligomer(s) directly to the spinal cord. In some embodiments, a PMO, PMO-X, or PPMO forms of the modified antisense oligomer is administered by ICV or IT injection.

In particular embodiments, the modified antisense oligomer(s) are administered to the subject by intravenous (IV) or subcutaneous (SC), i.e., they are administered or delivered intravenously into a vein or subcutaneously into the fat layer between the skin and muscle. Non-limiting examples of intravenous injection sites include a vein of the arm, hand, leg, or foot. Non-limiting examples of subcutaneous injections sites include the abdomen, thigh, lower back or upper arm. In exemplary embodiments, a PMO, PMO-X, or PPMO forms of the modified antisense oligomer is administered by IV or SC. In other embodiments, the modified antisense oligomer(s) are administered to the subject by intramuscular (IM), e.g., they are administered or delivered intramuscularly into the deltoid muscle of the arm, the vastus lateralis muscle of the leg, the ventrogluteal muscles of the hips, the dorsogluteal muscles of the buttocks, the diaphragm and the intercostal muscles of the rib cage.

In certain embodiments, the modified antisense oligomers of the disclosure can be delivered by transdermal methods (e.g., via incorporation of the modified antisense oligomers into, e.g., emulsions, with such modified antisense oligomers optionally packaged into liposomes). Such transdermal and emulsion/liposome-mediated methods of delivery are described for delivery of modified antisense oligomers in the art, e.g., in U.S. Pat. No. 6,965,025, which are hereby incorporated by reference in their entirety.

The modified antisense oligomers described herein may also be delivered via an implantable device. Design of such a device is an art-recognized process, with, e.g., synthetic implant design described in, e.g., U.S. Pat. No. 6,969,400, which are hereby incorporated by reference in their entirety.

Modified antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, modified antisense oligomers may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49 (2000), which is hereby incorporated by reference in its entirety).

The modified antisense oligomers may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The modified antisense oligomers of the present disclosure may generally be utilized as the free acid or free base. Alternatively, the compounds of this disclosure may be used in the form of acid or base addition salts. Acid addition salts of the free amino compounds of the present disclosure may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure where hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the modified antisense oligomers of the disclosure. Further, in the case of a carboxylic acid (—COOH), esters may be employed, such as methyl esters, ethyl esters, and the like.

In some instances, liposomes may be employed to facilitate uptake of the modified antisense oligomer into cells (see, e.g., Williams, S. A., Leukemia 10(12):1980-1989, 1996; Lappalainen et al., Antiviral Res. 23:119, 1994; Uhlmann et al., modified antisense oligomers: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for modified antisense oligomer administration, for example, as described in PCT Publication No. WO 1993/01286. Alternatively, the oligomers may be administered in microspheres or microparticles. (See, e.g., Wu, G. Y. and Wu, C. H., J. Biol. Chem. 262:4429-4432, 30 1987). Alternatively, the use of gas-filled microbubbles complexed with the modified antisense oligomers can enhance delivery to target tissues, as described in U.S. Pat. No. 6,245,747. Sustained release compositions may also be used. These may include semipermeable polymeric matrices in the form of shaped articles such as films or microcapsules. Each such reference is hereby incorporated by reference in their entirety.

In some embodiments, the antisense compound is administered in an amount and manner effective to result in a peak blood concentration of at least 200-400 nM modified antisense oligomer. Typically, one or more doses of modified antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The modified antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the modified antisense oligomers of the disclosure may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered modified antisense oligomer may be determined from biological samples (tissue, blood, urine etc.) taken from a subject prior to, during and subsequent to administration of the modified antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mRNA which comprises SMN protein exon 7 in relation to a reference exon 7-deleted SMN protein mRNA as determined by standard techniques such as RT-PCR, northern blotting, ELISA or western blotting. In some embodiments, treatment is monitored by symptomatic assessments. Those assessments include, but not limited to, self-evaluation, physician's examinations, motor function tests (e.g., Modified Hammersmith Functional Motor Scale [MHFMS] and Children's Hospital of Philadelphia Infant Test of Neuromuscular Disorders [CHOP INTEND]) including measurements of muscle size, muscle tone, tenderness, strength, reflex, involuntary muscle movements, electromyography, nerve conduction velocity test, and cardiovascular function tests including electrocardiogram (EKG or EGG).

VI. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on EC50s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, where the oligomer is administered in maintenance doses, ranging from 1-1000 mg oligomer per 70 kg of body weight for oral administration, or 0.5 mg to 1000 mg oligomer per 70 kg of body weight for i.v. administration, once or more daily, to once every 20 years.

While the present disclosure has been described with specificity in accordance with certain of its embodiments, the following examples serve only to illustrate the disclosure and are not intended to limit the same. Each of the references, patents, patent applications, GenBank accession numbers, and the like recited in the present application are hereby incorporated by reference in its entirety.

VII. EXAMPLES

The following Examples may be used for illustrative purposes and should not be deemed to narrow the scope of the invention.

Modified antisense oligomers of the disclosure were designed to bind to a target region within SMN2 pre-mRNA transcript and prepared using the following protocol:

Procedure a for the Preparation of Active Subunits:

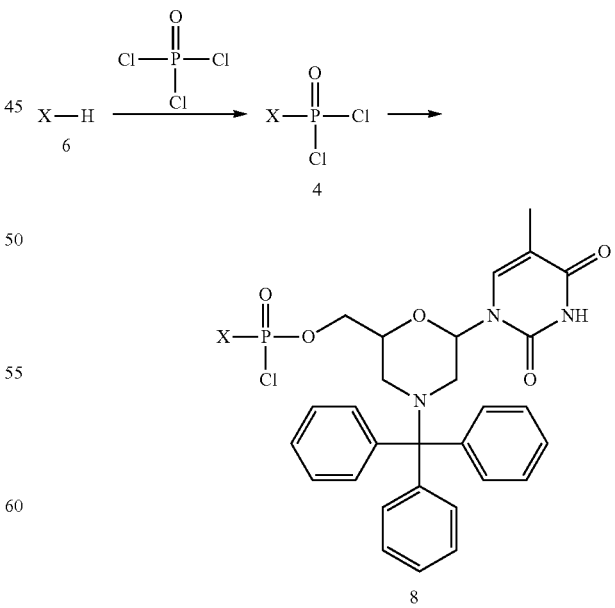

To a stirred solution of 6 (1 eq) in dichloromethane was added POCl$_3$ (1.1 eq), followed by diisopropylethylamine (3 eq) at 0° C., cooled by an ice-bath. After 15 minutes, the ice-bath was removed and the solution was allowed to warm to room temperature for one hour. Upon reaction completion, the reaction solution was diluted with dichloromethane, washed with 10% aqueous citric acid three times. After drying over MgSO₄, the organic layer was passed through a plug of silica gel and concentrated in vacuo. The resulting phosphoroamidodichloride (4) was used directly for the next step without further purification.

To a solution of the phosphoroamidodichloride (4) (1 eq), 2,6-lutidine (1 eq) in dichloromethane was added Mo(Tr)T (7) (0.5 eq)/dichloromethane solution, followed by N-methylimidazole (0.2 eq). The reaction stirred at room temperature overnight. Upon reaction completion, the reaction solution was diluted with dichloromethane, and washed with 10% aqueous citric acid three times. After drying over MgSO₄, the organic layer was filtered, then concentrated. The product (8) was purified by silica gel chromatography (eluting with a gradient of ethyl acetate/hexanes), and then stored at −20° C. The structure was confirmed by LCMS analysis.

Procedure B for the Preparation of Activated Subunits:

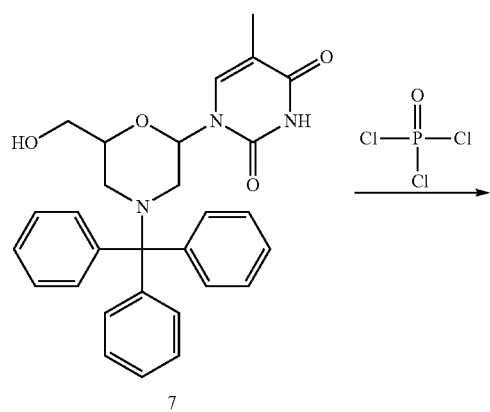

7

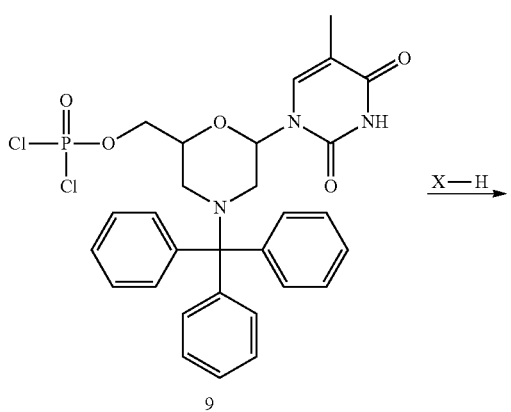

9

-continued

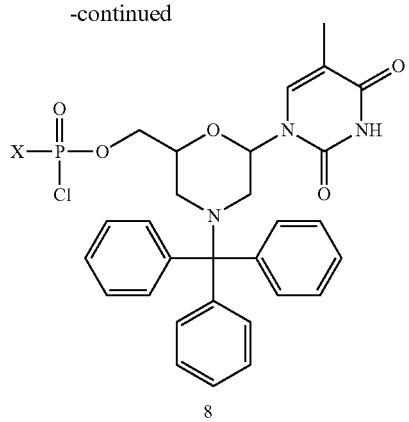

8

To a solution of POCl₃ (1.1 eq) in dichloromethane was added 2,6-lutidine (2 eq), followed by dropwise addition of Mo(Tr)T (7) (1 eq)/dichloromethane solution at 0° C. After 1 hour, the reaction solution was diluted with dichloromethane, and quickly washed three times with 10% aqueous citric acid. The desired phosphodichloridate (9) was obtained after drying over MgSO₄ and evaporation of solvent.

To a solution of the phosphodichloridate (1 eq) in dichloromethane was added amine (1 eq)/dichloromethane dropwise to the solution at 0° C. After 15 minutes, the reaction mixture was allowed to warm to room temperature for about an hour. Upon reaction completion, the product (8) as a white solid was collected by precipitation with the addition of hexanes, followed by filtration. The product was stored at −20° C. after drying under vacuum. The structure was confirmed by LCMS analysis.

Example 1: ((2S,6R)-6-(5-methyl-2,4-dioxo-3,4-dihydropyrimidin-1(2H)-yl)-4-tritylmorpholin-2-yl)methyl phosphorodichloridate

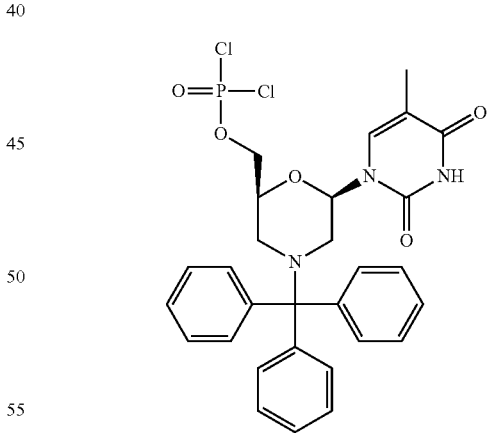

To a cooled (ice/water bath) DCM solution (20 mL) of phosphorus oxychloride (2.12 mL, 22.7 mmol) was added dropwise 2,6-lutidine (4.82 mL, 41.4 mmol) then a DCM solution (20 mL) Mo(Tr)T (2) (10.0 g, 20.7 mmol) was added dropwise over 15 min (int. temp. 0-10° C.) then bath was removed a stirring continued at ambient temperature for 20 min. The reaction was washed with citric acid solution (40 mL×3, 10% w/v aq), dried (MgSO₄), filtered and concentrated to a white foam (9.79 g) then used directly for the following procedure.

Example 2: (6-(5-methyl-2,4-dioxo-3,4-dihydropyrimidin-1(2H)-yl)-4-tritylmorpholin-2-yl)methyl (4-(dimethylamino)piperidin-1-yl)phosphonochloridate

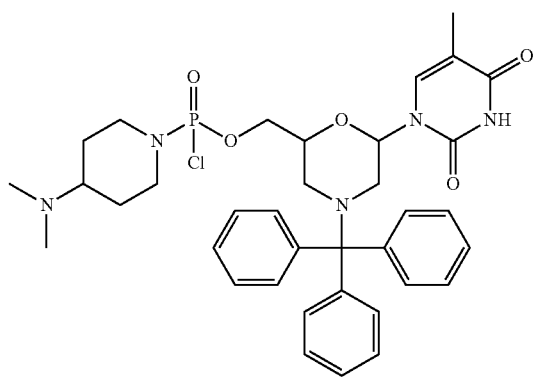 [SMILES: Cc1cn(C2CN(C(c3ccccc3)(c3ccccc3)c3ccccc3)CC(COP(=O)(Cl)N3CCC(N(C)C)CC3)O2)c(=O)[nH]c1=O]

To a cooled (ice/water bath) DCM solution (5 mL) of the dichlorophosphate from example 1 (5.00 g, 5.00 mmol) was added a DCM solution (5 mL) of the piperidine (0.61 g, 4.76 mmol) dropwise then the bath was removed and stirring continued at ambient temperature for 30 min. The reaction was loaded directly onto a column. Chromatography with [SiO$_2$ column (40 g), DCM/EtOH eluant (gradient 1:0 to 1:1)] afforded the title compound (2.5 g) as a white foam. ESI/MS calcd. for 1-(4-nitrophenyl)piperazine derivative $C_{46}H_{55}N_8O_7P$ 862.4, found m/z=863.6 (M+1).

Example 3: 1-(1-(chloro((6-(5-methyl-2,4-dioxo-3,4-dihydropyrimidin-1(2H)-yl)-4-tritylmorpholin-2-yl)methoxy)phosphoryl)piperidin-4-yl)-1-methylpyrrolidin-1-ium chloride

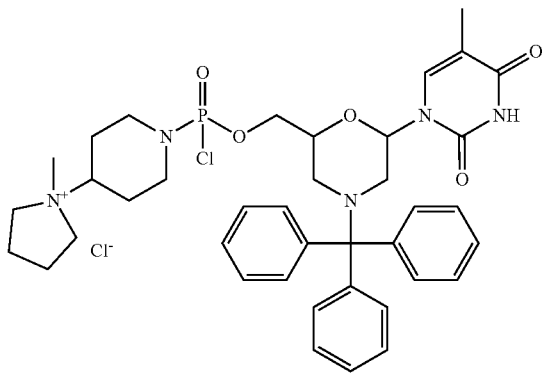 [SMILES: Cc1cn(C2CN(C(c3ccccc3)(c3ccccc3)c3ccccc3)CC(COP(=O)(Cl)N3CCC([N+]4(C)CCCC4)CC3)O2)c(=O)[nH]c1=O ; [Cl-]]

The title compound was synthesized in a manner analogous to that described in Example 2 to afford the title compound (0.6 g) as a white solid. ESI/MS calcd. for 1-(4-nitrophenyl)piperazine derivative $C_{49}H_{60}N_8O_7P$ 903.4, found m/z=903.7 (M+).

Example 4: ((2S,6R)-6-(5-methyl-2,4-dioxo-3,4-dihydropyrimidin-1(2H)-yl)-4-tritylmorpholin-2-yl)methyl (4-methylpiperazin-1-yl)phosphonochloridate

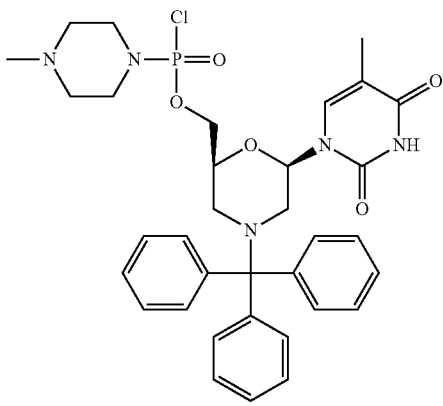 [SMILES: Cc1cn([C@H]2CN(C(c3ccccc3)(c3ccccc3)c3ccccc3)C[C@@H](COP(=O)(Cl)N3CCN(C)CC3)O2)c(=O)[nH]c1=O]

To a cooled (ice/water bath) DCM solution (10 mL) of phosphorus oxychloride (1.02 mL, 11.0 mmol) was added dropwise 2,6-lutidine (3.49 mL, 29.9 mmol) then a DCM solution (10 mL) of methyl piperazine (1.00 g, 10.0 mmol) was added dropwise and stirring continued for 1 h. A DCM solution (10 mL) of Mo(Tr)T (2) (4.82, 10.0 mmol) and NMI (79 µL, 1.0 mmol) was added and stirred 4 h then loaded directly onto a column.

Chromatography with [SiO$_2$ column (80 g), DCM/Acetone with 2% TEA eluant (gradient 1:0 to 0:1)] afforded the title compound (0.8 g) as a white foam. ESI/MS calcd. for 1-(4-nitrophenyl)piperazine derivative $C_{43}H_{48}N_7O_8P$ 834.4, found m/z=835.5 (M+1).

Example 5: ((2S,6R)-6-(5-methyl-2,4-dioxo-3,4-dihydropyrimidin-1(2H)-yl)-4-tritylmorpholin-2-yl)methyl (4-ethylpiperazin-1-yl)phosphonochloridate

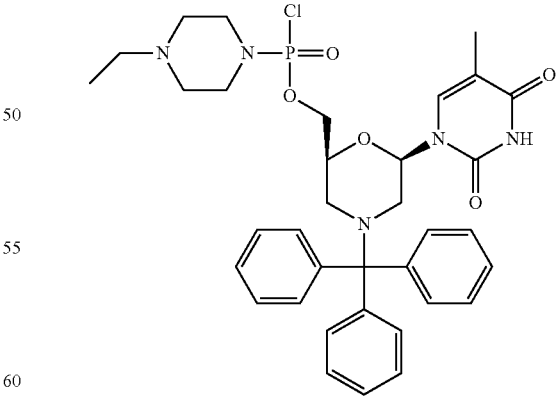

The title compound was synthesized in a manner analogous to that described in Example 4 to afford the title compound (11.5 g) as a white foam. ESI/MS calcd. for 1-(4-nitrophenyl)piperazine derivative $C_{45}H_{53}N_8O_7P$ 848.4, found m/z=849.7 (M+1).

Example 6: ((2S,6R)-6-(6-benzamido-9H-purin-9-yl)-4-tritylmorpholin-2-yl)methyl (4-ethylpiperazin-1-yl)phosphonochloridate

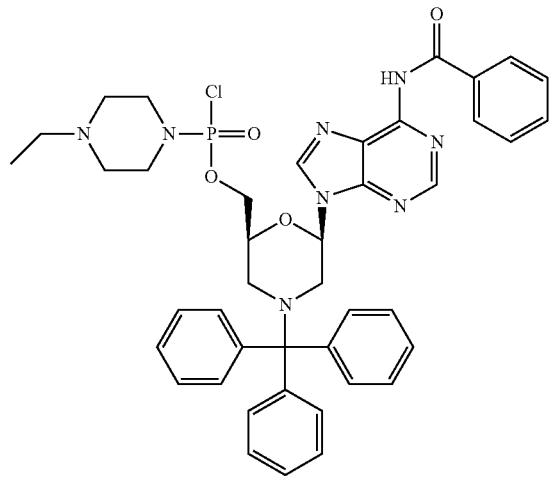 [SMILES: CCN1CCN(P(=O)(Cl)OC[C@@H]2CN(C(c3ccccc3)(c3ccccc3)c3ccccc3)C[C@H](n3cnc4c(NC(=O)c5ccccc5)ncnc43)O2)CC1]

The title compound was synthesized in a manner analogous to that described in Example 4 to afford the title compound (4.5 g) as a white foam. ESI/MS calcd. for 1-(4-nitrophenyl)piperazine derivative $C_{52}H_{56}N_{11}O_6P$ 961.4, found m/z=962.8 (M+1).

Example 7: ((2S,6R)-6-(5-methyl-2,4-dioxo-3,4-dihydropyrimidin-1(2H)-yl)-4-tritylmorpholin-2-yl)methyl (4-isopropylpiperazin-1-yl)phosphonochloridate

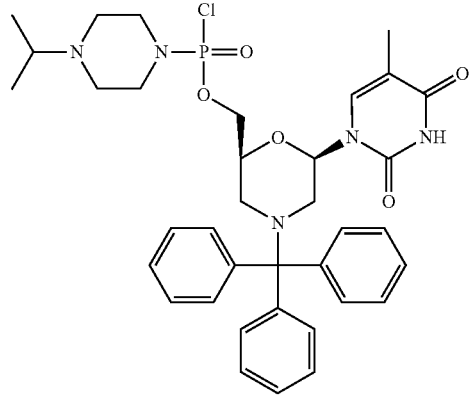 [SMILES: Cc1cn([C@H]2CN(C(c3ccccc3)(c3ccccc3)c3ccccc3)C[C@@H](COP(=O)(Cl)N3CCN(C(C)C)CC3)O2)c(=O)[nH]c1=O]

The title compound was synthesized in a manner analogous to that described in Example 4 to afford the title compound (3.5 g) as a white foam. ESI/MS calcd. for 1-(4-nitrophenyl)piperazine derivative $C_{46}H_{55}N_8O_7P$ 862.4, found m/z=863.7 (M+1).

Example 8: ((2S,6R)-6-(5-methyl-2,4-dioxo-3,4-dihydropyrimidin-1(2H)-yl)-4-tritylmorpholin-2-yl)methyl methyl(2-(2,2,2-trifluoroacetamido)ethyl)phosphoramidochloridate

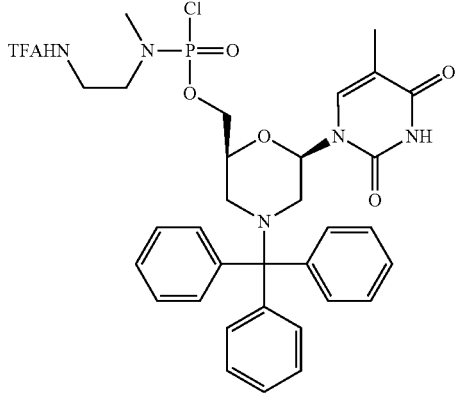

1The title compound was synthesized in a manner analogous to that described in Example 4 to afford the title compound (1.0 g) as a white foam. ESI/MS calcd. for 1-(4-nitrophenyl)piperazine derivative $C_{44}H_{48}F_3N_8O_8P$ 904.3, found m/z=903.7 (M-1).

Example 9: ((2S,6R)-6-(5-methyl-2,4-dioxo-3,4-dihydropyrimidin-1(2H)-yl)-4-tritylmorpholin-2-yl)methyl methyl(2-(2,2,2-trifluoro-N-methylacetamido)ethyl)phosphoramidochloridate

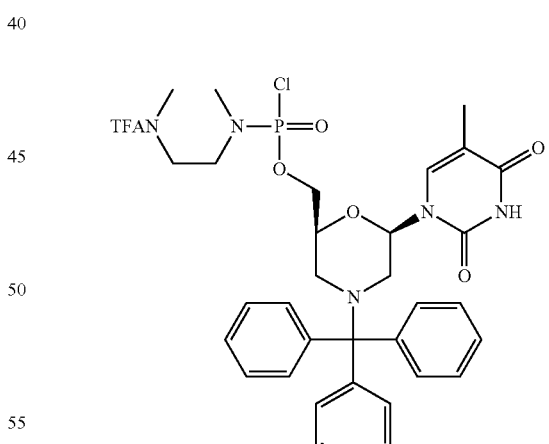

The title compound was synthesized in a manner analogous to that described in Example 4 to afford the title compound (1.8 g) as a white foam. ESI/MS calcd. for 1-(4-nitrophenyl)piperazine derivative $C_{45}H_{50}F_3N_8O_8P$ 918.3, found m/z=1836.6 (2M+).

Example 10: ((2S,6R)-6-(5-methyl-2,4-dioxo-3,4-dihydropyrimidin-1(2H)-yl)-4-tritylmorpholin-2-yl)methyl (4-(2,2,2-trifluoroacetamido)piperidin-1-yl)phosphonochloridate

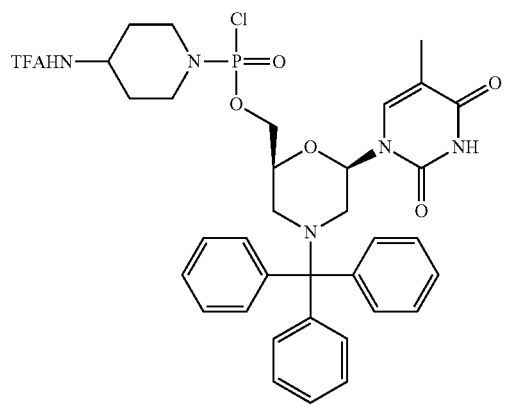

To a cooled solution (ice/water bath) of phosphorus oxychloride (17.7 mL, 190 mmol) in DCM (190 mL) was added dropwise 2,6-lutidine (101 mL, 864 mmol) then Mo(Tr)T (2) (83.5 g, 173 mmol) portionwise over 15 min (int. temp. 0-10° C.) and stirred. After 30 min, the 4-aminopiperidine monotrifluoroacetamide (48.9 g, ~190 mmol) was added dropwise over 15 min (int. temp. 0-8° C.) and stirred. After 1 h, DIPEA (50 mL) was added dropwise (int. temp. 0-10° C.) and stirred 1 h. The reaction was washed with citric acid solution (500 mL×3, 10% w/v aq), dried (MgSO$_4$), filtered and concentrated to a viscous oil which was loaded directly onto a column. Chromatography with [SiO$_2$ column (330 g), hexanes/EtOAc eluant (gradient 1:0 to 0:1)] afforded the title compound (91.3 g, 70% yield) as a white foam. ESI/MS calcd. for 1-(4-nitrophenyl)piperazine derivative C$_{43}$H$_{48}$N$_7$O$_8$P 930.9, found m/z=954.4 (M+Na).

Examples 11 through 14 were prepared via procedure A described above.

Example 11: (6-(5-methyl-2,4-dioxo-3,4-dihydropyrimidin-1(2H)-yl)-4-tritylmorpholin-2-yl)methyl (4-(1-(2,2,2-trifluoroacetyl)piperidin-4-yl)piperazin-1-yl)phosphonochloridate

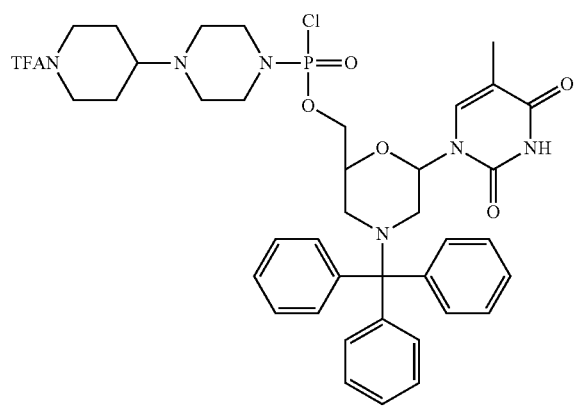

Example 12: (6-(5-methyl-2,4-dioxo-3,4-dihydropyrimidin-1(2H)-yl)-4-tritylmorpholin-2-yl)methyl (4-morpholinopiperidin-1-yl)phosphonochloridate

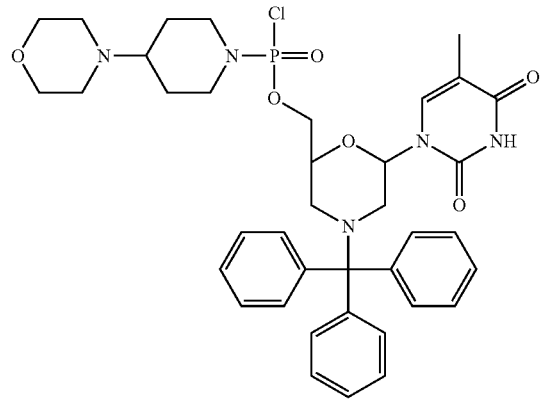 [SMILES: Cc1cn(C2CN(C(c3ccccc3)(c3ccccc3)c3ccccc3)CC(COP(=O)(Cl)N3CCC(N4CCOCC4)CC3)O2)c(=O)[nH]c1=O]

Example 13: (6-(5-methyl-2,4-dioxo-3,4-dihydropyrimidin-1(2H)-yl)-4-tritylmorpholin-2-yl)methyl bis(3-(2,2,2-trifluoroacetamido)propyl)phosphoramidochloridate

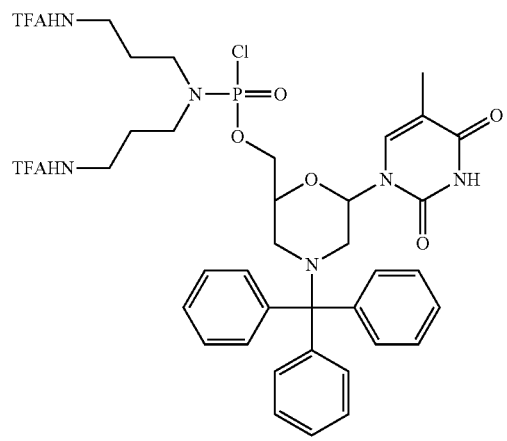

Example 14: (6-(5-methyl-2,4-dioxo-3,4-dihydropyrimidin-1(2H)-yl)-4-tritylmorpholin-2-yl)methyl [1,4'-bipiperidin]-1'-ylphosphonochloridate

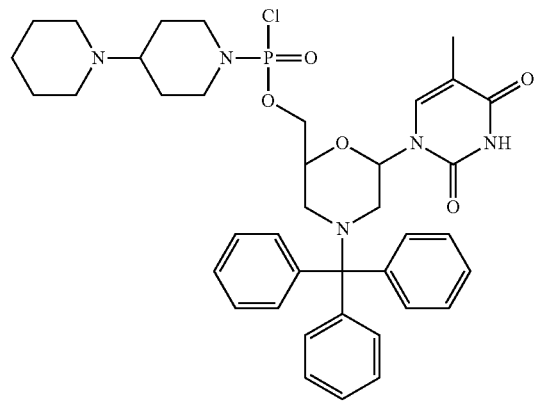 [SMILES: Cc1cn(C2CN(C(c3ccccc3)(c3ccccc3)c3ccccc3)CC(COP(=O)(Cl)N3CCC(N4CCCCC4)CC3)O2)c(=O)[nH]c1=O]

Examples 15 through 20 below were prepared via procedure B described above.

Example 15: (6-(5-methyl-2,4-dioxo-3,4-dihydropyrimidin-1(2H)-yl)-4-tritylmorpholin-2-yl)methyl (4-(pyrimidin-2-yl)piperazin-1-yl)phosphonochloridate

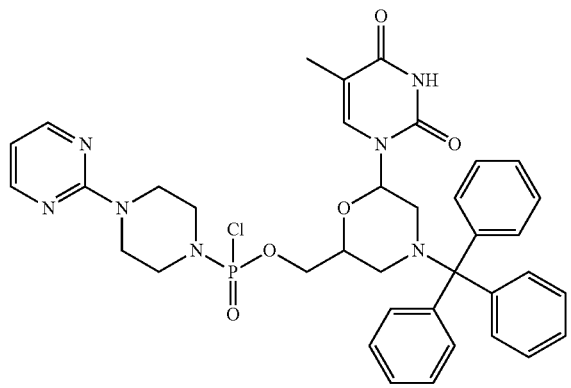 [SMILES: Cc1cn(C2CN(C(c3ccccc3)(c3ccccc3)c3ccccc3)CC(COP(=O)(Cl)N3CCN(c4ncccn4)CC3)O2)c(=O)[nH]c1=O]

Example 16: (6-(5-methyl-2,4-dioxo-3,4-dihydropyrimidin-1(2H)-yl)-4-tritylmorpholin-2-yl)methyl (4-(2-(dimethylamino)ethyl)piperazin-1-yl)phosphonochloridate

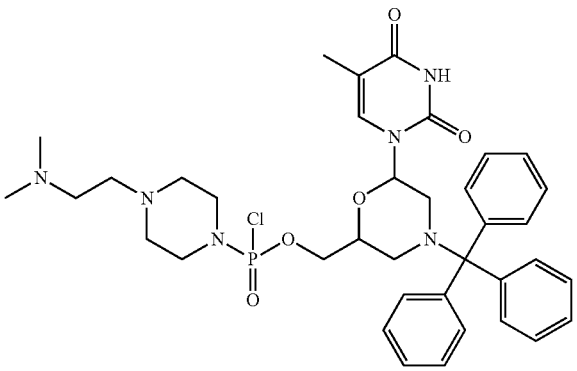 [SMILES: Cc1cn(C2CN(C(c3ccccc3)(c3ccccc3)c3ccccc3)CC(COP(=O)(Cl)N3CCN(CCN(C)C)CC3)O2)c(=O)[nH]c1=O]

Example 17: (6-(5-methyl-2,4-dioxo-3,4-dihydropyrimidin-1(2H)-yl)-4-tritylmorpholin-2-yl)methyl (4-phenylpiperazin-1-yl)phosphonochloridate

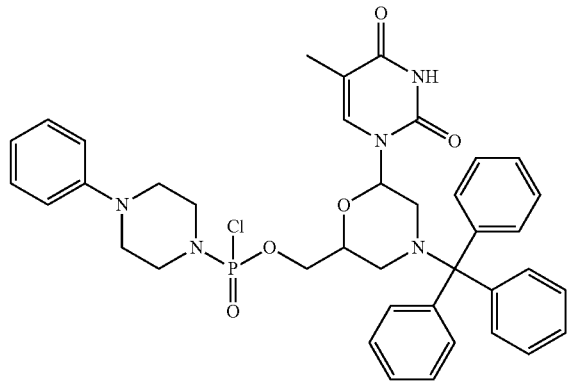 [SMILES: Cc1cn(C2CN(C(c3ccccc3)(c3ccccc3)c3ccccc3)CC(COP(=O)(Cl)N3CCN(c4ccccc4)CC3)O2)c(=O)[nH]c1=O]

Example 18: (6-(5-methyl-2,4-dioxo-3,4-dihydropyrimidin-1(2H)-yl)-4-tritylmorpholin-2-yl)methyl (4-(2,2,2-trifluoro-N-methylacetamido)piperidin-1-yl)phosphonochloridate

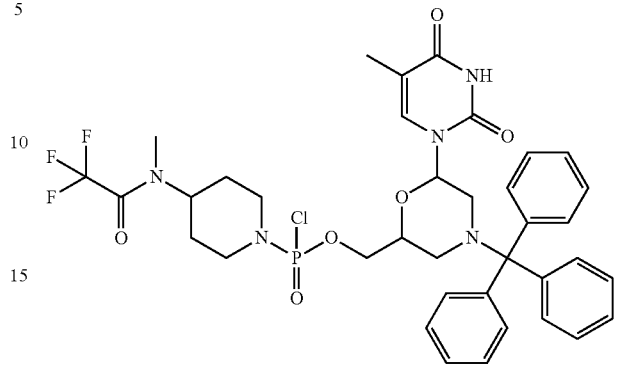

Example 19: (6-(5-methyl-2,4-dioxo-3,4-dihydropyrimidin-1(2H)-yl)-4-tritylmorpholin-2-yl)methyl methyl(3-(2,2,2-trifluoro-N-methylacetamido)propyl)phosphoramidochloridate

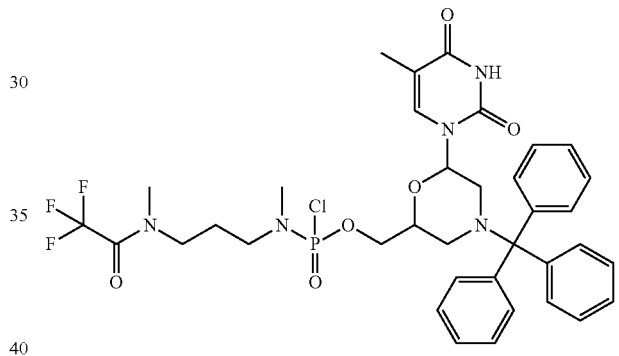

Example 20: ((2S,6R)-6-(6-benzamido-9H-purin-9-yl)-4-tritylmorpholin-2-yl)methyl (4-(2,2,2-trifluoroacetamido)piperidin-1-yl)phosphonochloridate

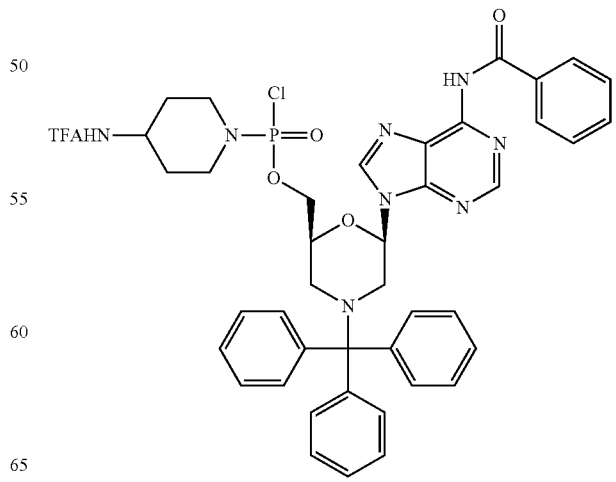

Example 21: (4-(pyrrolidin-1-yl)piperidin-1-yl)phosphonic dichloride hydrochloride To a cooled (ice/water bath) solution of phosphorus oxychloride (5.70 mL, 55.6 mmol) in DCM (30 mL) was added 2,6-lutidine (19.4 mL, 167 mmol) and a DCM solution (30 mL) of 4-(1-pyrrolidinyl)-piperidine (8.58 g, 55.6 mmol) and stirred for 1 hour. The suspension was filtered and solid washed with excess diethyl ether to afford the title pyrrolidine (17.7 g, 91% yield) as a white solid. ESI/MS calcd. for 1-(4-nitrophenyl)piperazine derivative $C_{19}H_{30}N_5O_4P$ 423.2, found m/z=422.2 (M-1).

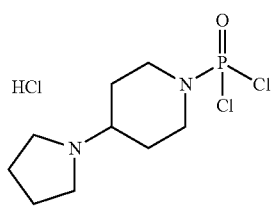 [SMILES: O=P(Cl)(Cl)N1CCC(N2CCCC2)CC1 ; Cl]

Example 22: ((2S,6R)-6-(5-methyl-2,4-dioxo-3,4-dihydropyrimidin-1(2H)-yl)-4-tritylmorpholin-2-yl)methyl (4-(pyrrolidin-1-yl)piperidin-1-yl)phosphonochloridate hydrochloride

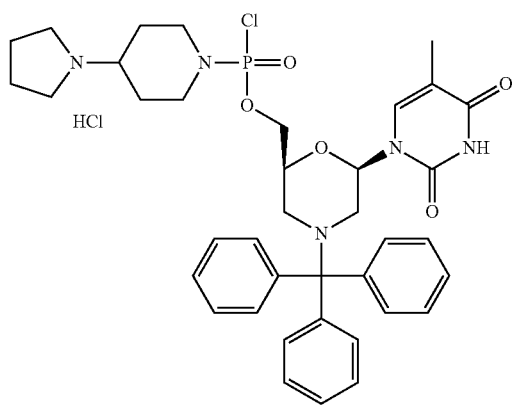 [SMILES: Cc1cn([C@H]2CN(C(c3ccccc3)(c3ccccc3)c3ccccc3)C[C@@H](COP(=O)(Cl)N3CCC(N4CCCC4)CC3)O2)c(=O)[nH]c1=O ; Cl]

To a stirred, cooled (ice/water bath) solution of the dichlorophosphoramidate from Example 21 (17.7 g, 50.6 mmol) in DCM (100 mL) was added a DCM solution (100 mL) of Mo(Tr)T (2) (24.5 g, 50.6 mmol), 2,6-Lutidine (17.7 mL, 152 mmol), and 1-methylimidazole (0.401 mL, 5.06 mmol) dropwise over 10 minutes. The bath was allowed to warm to ambient temperature as suspension was stirred. After 6 hours, the suspension was poured onto diethyl ether (1 L), stirred 15 minutes, filtered and solid washed with additional ether to afford a white solid (45.4 g). The crude product was purified by chromatography [SiO$_2$ column (120 gram), DCM/MeOH eluant (gradient 1:0 to 6:4)], and the combined fractions were poured onto diethyl ether (2.5 L), stirred 15 min, filtered, and the resulting solid washed with additional ether to afford the title compound (23.1 g, 60% yield) as a white solid. ESI/MS calcd. for 1-(4-nitrophenyl) piperazine derivative $C_{48}H_{57}N_8O_7P$ 888.4, found m/z=887.6 (M-1).

Example 23: Design and Manufacture of Modified Antisense Oligomers and Exemplary Modified Antisense Oligomers Preparation of trityl piperazine phenyl carbamate 35: To a cooled suspension of compound 11 in dichloromethane (6 mL/g 11) was added a solution of potassium carbonate (3.2 mL/g 11) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile.

Preparation of carbamate alcohol 36: Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane.

Preparation of Tail acid 37: To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO$_3$. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

Preparation of 38: To the solution of compound 37 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts.

Introduction of the activated "Tail" onto the anchor-loaded resin was performed in dimethyl imidazolidinone (DMI) by the procedure used for incorporation of the subunits during solid phase synthesis.

Preparation of the Solid Support for Synthesis of morpholino-based oligomers: This procedure was performed in a silanized, jacketed peptide vessel (ChemGlass, NJ, USA) with a coarse porosity (40-60 μm) glass frit, overhead stirrer, and 3-way Teflon stopcock to allow N2 to bubble up through the frit or a vacuum extraction.

The resin treatment/wash steps in the following procedure consist of two basic operations: resin fluidization or stirrer bed reactor and solvent/solution extraction. For resin fluidization, the stopcock was positioned to allow N2 flow up through the frit and the specified resin treatment/wash was added to the reactor and allowed to permeate and completely wet the resin. Mixing was then started and the resin slurry mixed for the specified time. For solvent/solution extraction, mixing and N2 flow were stopped and the vacuum pump was started and then the stopcock was positioned to allow evacuation of resin treatment/wash to waste. All resin treatment/wash volumes were 15 mL/g of resin unless noted otherwise.

To aminomethylpolystyrene resin (100-200 mesh; ~1.0 mmol/g load based on nitrogen substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was treated with a solution of disulfide anchor 34 in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 39 was dried under a N2 stream for 1-3 hr and then under vacuum to constant weight (±2%). Yield: 110-150% of the original resin weight.

Determination of the Loading of Aminomethylpolystyrene-disulfide resin: The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 µL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (µmol/g) using the appropriate volumes, dilutions, extinction coefficient (ε: 41 µmol-1 cm-1) and resin weight. The assay is performed in triplicate and an average loading calculated.

The resin loading procedure in this example will provide resin with a loading of approximately 500 µmol/g. A loading of 300-400 in µmol/g was obtained if the disulfide anchor incorporation step is performed for 24 hr at room temperature.

Tail loading: Using the same setup and volumes as for the preparation of aminomethylpolystyrene-disulfide resin, the Tail can be introduced into solid support. The anchor loaded resin was first deprotected under acidic condition and the resulting material neutralized before coupling. For the coupling step, a solution of 38 (0.2 M) in DMI containing 4-ethylmorpholine (NEM, 0.4 M) was used instead of the disulfide anchor solution. After 2 hr at 45° C., the resin 39 was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 40 was filtered and dried under high vacuum. The loading for resin 40 is defined to be the loading of the original aminomethylpolystyrene-disulfide resin 39 used in the Tail loading.

Solid Phase Synthesis: morpholino-based oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 µmol/g of resin is preferred. For larger oligomers, aminomethylpolystyrene-disulfide resin with loading of 300-400 µmol/g of resin is preferred. If a molecule with 5'-Tail is desired, resin that has been loaded with Tail is chosen with the same loading guidelines.

The following reagent solutions were prepared:
Detritylation Solution: 10% Cyanoacetic Acid (w/v) in 4:1 dichloromethane/acetonitrile; Neutralization Solution: 5% Diisopropylethylamine in 3:1 dichloromethane/isopropanol; Coupling Solution: 0.18 M (or 0.24 M for oligomers having grown longer than 20 subunits) activated morpholino subunit of the desired base and linkage type and 0.4 M N ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

TABLE 4

Synthesis Cycle for Modified Antisense Oligomers

| Step | Volume | Delivery | Hold time |
| --- | --- | --- | --- |
| Detritylation | 1.5 mL | Manifold | 15 sec. |
| Detritylation | 1.5 mL | Manifold | 15 sec. |
| Detritylation | 1.5 mL | Manifold | 15 sec. |
| Detritylation | 1.5 mL | Manifold | 15 sec. |
| Detritylation | 1.5 mL | Manifold | 15 sec. |
| Detritylation | 1.5 mL | Manifold | 15 sec. |
| Detritylation | 1.5 mL | Manifold | 15 sec. |
| DCM | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| DCM | 1.5 mL | Manifold | 30 sec. |
| Coupling | 350-500 uL | Syringe | 40 min. |
| DCM | 1.5 mL | Manifold | 30 sec. |
| Neutralization | 1.5 mL | Manifold | 30 sec. |
| Neutralization | 1.5 mL | Manifold | 30 sec. |
| DCM | 1.5 mL | Manifold | 30 sec. |
| DCM | 1.5 mL | Manifold | 30 sec. |
| DCM | 1.5 mL | Manifold | 30 sec. |

The sequences of the individual oligomers were programmed into the synthesizer so that each column receives the proper coupling solution (A,C,G,T,I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Cleavage from the resin and removal of bases and protecting groups: After methoxytritylation, the resin was washed 8 times with 2 mL 1-methyl-2-pyrrolidinone. One mL of a cleavage solution comprising 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 μL of cleavage solution. To the solution was added 4.0 mL conc. Aqueous ammonia (stored at −20° C.), the vial capped tightly (with Teflon lined screw cap), and the mixture swirled to mix the solution. The vial was placed in a 45° C. oven for 16-24 hr to effect cleavage of base and protecting groups.

Crude product purification: The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Demethoxytritylation of morpholino-based oligomers: The pooled fractions from the Macroprep purification were treated with 1 M H3PO4 to lower the pH to 2.5. After initial mixing, the samples sat at room temperature for 4 min, at which time they are neutralized to pH 10-11 with 2.8% ammonia/water. The products were purified by solid phase extraction (SPE).

SPE column packing and conditioning: Amberchrome CG-300M (Rohm and Haas; Philadelphia, Pa.) (3 mL) is packed into 20 mL fritted columns (BioRad Econo-Pac Chromatography Columns (732-1011)) and the resin rinsed with 3 mL of the following: 0.28% NH$_4$OH/80% acetonitrile; 0.5M NaOH/20% ethanol; water; 50 mM H3PO4/80% acetonitrile; water; 0.5 NaOH/20% ethanol; water; 0.28% NH$_4$OH.

SPE purification: The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia.

Product isolation: The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Analysis of morpholino-based oligomers by MALDI: MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydroxyacetophenone (THAP) or alpha-cyano-4-hydoxy-cinnamic acid (HCCA) as matrices.

Table 5 below provides non-limiting examples of modified antisense oligomers of the present disclosure that were synthesized. In these examples, each X of the targeting sequence SEQ ID is thymine (T) and each Y of the targeting sequence SEQ ID is cystosine (C). Additionally, each bolded and underline base indicates a subunit with an intersubunit linkage of the type indicated in the modification column between that subunit and the preceding subunit, otherwise, intersubunit linkages are dimethylamino phosphorodiamidate linkages.

TABLE 5

Exemplary Modified Antisense Oligomers

| Compound Name | Modification | Targeting SEQ ID NO | Targeting Sequences | 5' end 3' end |
|---|---|---|---|---|
| PMO-1 | PMO | 33 | GCT GGC AG$_8$ | TEG H |
| PMO-2 | | 37 | GTA AGA TTC ACT TTC ATA ATG CTG G$_{25}$ | TEG H |
| PMO-3 | | 35 | TCA CTT TCA TAA TGC TGG$_{18}$ | TEG H |
| PMO-4 | | 36 | ATT CAC TTT CAT AAT GCT GG$_{20}$ | TEG H |
| PMO-5 | | 38 | AAA AGT CTG CTG GTC TGC C$_{19}$ | TEG H |
| PMO-6 | | 39 | ATA GAT ATA GAT AGC TAT AT$_{20}$ | TEG H |
| PMO-7 | | 40 | AAT AGT TTT GGC ATC AAA ATT CT$_{23}$ | TEG H |
| PMO-8 | | 41 | GAT ATA AAA TGG CAT CAT ATC CTA A$_{25}$ | TEG H |
| PMO-9 | | 42 | ATT AAC CTT TTA TCT AAT AGT TTT GG$_{26}$ | TEG H |
| PMO-10 | | 43 | ACA ACT TTG GGA GGC GGA GG$_{20}$ | TEG H |
| PMO-11 | | 44 | GTA GGG ATG TAG ATT AAC CT$_{20}$ | TEG H |
| PMO-12 | | 45 | CTA TAT ATA GAT AGT TAT TCA ACA AA$_{26}$ | TEG H |
| PMO-APN-1 | PMO-APN | 33 | GCT GGC AG$_8$ | TEG H |
| PMO-APN-2 | | 33 | GCT GGC AG$_8$ | TEG H |
| PMO-APN-3 | | 33 | GCT GGC AG$_8$ | TEG H |
| PMO-APN-4 | | 33 | GCT GGC AG$_8$ | TEG H |
| PMO-APN-5 | | 33 | GCT GGC AG$_8$ | TEG H |
| PMO-APN-6 | | 33 | GCT GGC AG$_8$ | TEG H |

TABLE 5-continued

Exemplary Modified Antisense Oligomers

| Compound Name | Modification | Targeting SEQ ID NO | Targeting Sequences | 5' end | 3' end |
|---|---|---|---|---|---|
| PMO-APN-7 | | 33 | GCT GGC AG$_8$ | TEG | H |
| PMO-APN-8 | | 33 | GCT GGC AG$_8$ | TEG | H |
| PMO-APN-9 | | 37 | GTA AGA TTC ACT TTC ATA ATG CTG G$_{25}$ | TEG | H |
| PMO-APN-10 | | 37 | GTA AGA TTC ACT TTC ATA ATG CTG G$_{25}$ | H | H |
| PMO-APN-11 | | 37 | GTA AGA TTC ACT TTC ATA ATG CTG G$_{25}$ | TEG | H |
| PMO-APN-12 | | 35 | TCA CTT TCA TAA TGC TGG$_{18}$ | TEG | H |
| PMO-APN-13 | | 35 | TCA CTT TCA TAA TGC TGG$_{18}$ | TEG | H |
| PMO-APN-14 | | 35 | TCA CTT TCA TAA TGC TGG$_{18}$ | TEG | H |
| PMO-APN-15 | | 35 | TCA CTT TCA TAA TGC TGG$_{18}$ | TEG | H |
| PMO-APN-16 | | 35 | TCA CTT TCA TAA TGC TGG$_{18}$ | TEG | H |
| PMO-APN-17 | | 36 | ATT CAC TTT CAT AAT GCT GG$_{20}$ | TEG | H |
| PMO-APN-18 | | 38 | AAA AGT CTG CTG GTC TGC C$_{19}$ | TEG | H |
| PMO-APN-19 | | 38 | AAA AGT CTG CTG GTC TGC C$_{19}$ | TEG | H |
| PMO-APN-20 | | 38 | AAA AGT CTG CTG GTC TGC C$_{19}$ | TEG | H |
| PMO-APN-21 | | 38 | AAA AGT CTG CTG GTC TGC C$_{19}$ | TEG | H |
| PMO-APN-22 | | 38 | AAA AGT CTG CTG GTC TGC C$_{19}$ | TEG | H |
| PMO-APN-23 | | 38 | AAA AGT CTG CTG GTC TGC C$_{19}$ | TEG | H |
| PMO-APN-24 | | 38 | AAA AGT CTG CTG GTC TGC C$_{19}$ | TEG | H |
| PMO-APN-25 | | 38 | AAA AGT CTG CTG GTC TGC C$_{19}$ | TEG | H |
| PMO-APN-26 | | 38 | AAA AGT CTG CTG GTC TGC C$_{19}$ | TEG | H |
| PMO-APN-27 | | 38 | AAA AGT CTG CTG GTC TGC C$_{19}$ | TEG | H |
| PMO-APN-28 | | 39 | ATA GAT ATA GAT AGC TAT AT$_{20}$ | TEG | H |
| PMO-APN-29 | | 40 | AAT AGT TTT GGC ATC AAA ATT CT$_{23}$ | TEG | H |
| PMO-APN-30 | | 41 | GAT ATA AAA TGG CAT CAT ATC CTA A$_{25}$ | TEG | H |
| PMO-APN-31 | | 42 | ATT AAC CTT TTA TCT AAT AGT TTT GG$_{26}$ | TEG | H |
| PMO-APN-32 | | 43 | ACA ACT TTG GGA GGC GGA GG$_{20}$ | TEG | H |
| PMO-APN-33 | | 44 | GTA GGG ATG TAG ATT AAC CT$_{20}$ | TEG | H |
| PMO-APN-34 | | 45 | CTA TAT ATA GAT AGT TAT TCA ACA AA$_{26}$ | TEG | H |
| PMO-Plus-1 | PMO-Plus | 33 | GCT GGC AG$_8$ | TEG | H |
| PMO-Plus-2 | | 33 | GCT GGC AG$_8$ | TEG | H |
| PMO-Plus-3 | | 37 | GTA AGA TTC ACT TTC ATA ATG CTG G$_{25}$ | TEG | H |
| PMO-Plus-4 | | 35 | TCA CTT TCA TAA TGC TGG$_{18}$ | TEG | H |
| PMO-Plus-5 | | 35 | TCA CTT TCA TAA TGC TGG$_{18}$ | TEG | H |
| PMO-Plus-6 | | 35 | TCA CTT TCA TAA TGC TGG$_{18}$ | TEG | H |
| PMO-Plus-7 | | 35 | TCA CTT TCA TAA TGC TGG$_{18}$ | TEG | H |
| PMO-Plus-8 | | 35 | TCA CTT TCA TAA TGC TGG$_{18}$ | TEG | H |
| PMO-Plus-9 | | 36 | ATT CAC TTT CAT AAT GCT GG$_{20}$ | TEG | H |
| PMO-Plus-10 | | 39 | ATA GAT ATA GAT AGC TAT AT$_{20}$ | TEG | H |
| PMO-Plus-11 | | 40 | AAT AGT TTT GGC ATC AAA ATT CT$_{23}$ | TEG | H |
| PMO-Plus-12 | | 41 | GAT ATA AAA TGG CAT CAT ATC CTA A$_{25}$ | TEG | H |
| PMO-Plus-13 | | 42 | ATT AAC CTT TTA TCT AAT AGT TTT GG$_{26}$ | TEG | H |
| PMO-Plus-14 | | 43 | ACAACT TTG GGA GGC GGA GG$_{20}$ | TEG | H |
| PMO-Plus-15 | | 44 | GTA GGG ATG TAG ATT AAC CT$_{20}$ | TEG | H |
| PMO-Plus-16 | | 45 | CTA TAT ATA GAT AGT TAT TCA ACA AA$_{26}$ | TEG | H |
| PMO-R$_6$Gly-1 | PMO-R$_6$Gly | 33 | GCT GGC AG$_8$ | TEG | Ac-R$_6$Gly-(SEQ ID NO: 53) |
| PMO-R$_6$Gly-2 | | 37 | GTA AGA TTC ACT TTC ATA ATG CTG G$_{25}$ | TEG | Ac-R$_6$Gly-(SEQ ID NO: 53) |
| PMO-R$_6$Gly-3 | | 35 | TCA CTT TCA TAA TGC TGG$_{18}$ | TEG | Ac-R$_6$Gly-(SEQ ID NO: 53) |
| PMO-R$_6$Gly-4 | | 36 | ATT CAC TTT CAT AAT GCT GG$_{20}$ | TEG | Ac-R$_6$Gly-(SEQ ID NO: 53) |

TABLE 5-continued

Exemplary Modified Antisense Oligomers

| Compound Name | Modification | Targeting SEQ ID NO | Targeting Sequences | 5' end 3' end |
|---|---|---|---|---|
| PMO-R$_6$Gly-5 | | 39 | ATA GAT ATA GAT AGC TAT AT$_{20}$ | TEG Ac-R$_6$Gly- (SEQ ID NO: 53) |
| PMO-R$_6$Gly-6 | | 40 | AAT AGT TTT GGC ATC AAA ATT CT$_{23}$ | TEG Ac-R$_6$Gly- (SEQ ID NO: 53) |
| PMO-R$_6$Gly-7 | | 41 | GAT ATA AAA TGG CAT CAT ATC CTA A$_{25}$ | TEG Ac-R$_6$Gly- (SEQ ID NO: 53) |
| PMO-R$_6$Gly-8 | | 42 | ATT AAC CTT TTA TCT AAT AGT TTT GG$_{26}$ | TEG Ac-R$_6$Gly- (SEQ ID NO: 53) |
| PMO-R$_6$Gly-9 | | 43 | ACA ACT TTG GGA GGC GGA GG$_{20}$ | TEG Ac-R$_6$Gly- (SEQ ID NO: 53) |
| PMO-R$_6$Gly-10 | | 44 | GTA GGG ATG TAG ATT AAC CT$_{20}$ | TEG Ac-R$_6$Gly- (SEQ ID NO: 53) |
| PMO-R$_6$Gly-11 | | 45 | CTA TAT ATA GAT AGT TAT TCA ACA AA$_{26}$ | TEG Ac-R$_6$Gly- (SEQ ID NO: 53) |
| 2'-OMe-1 | 2'-OMe | 46 | AUG CUG GCA G$_{10}$ | H  H |
| 2'-OMe-2 | | 47 | UCA CUU UCA UAA UGC UGG$_{18}$ | H  H |
| 2'-OMe-3 | | 48 | AUU CAC UUU CAU AAU GCU GG$_{20}$ | H  H |
| 2'-OMe-4 | | 49 | AAA AGU CUG CUG GUC UGC C$_{19}$ | H  H |
| 2'-OMe-5 | | 39 | AUA GAU AUA GAU AGC UAU AU$_{20}$ | H  H |
| 2'-OMe-6 | | 50 | AAU AGU UUU GGC AUC AAA AUU CU$_{23}$ | H  H |
| 2'-OMe-7 | | 41 | GAU AUA AAA UGG CAU CAU AUC CUA A$_{25}$ | H  H |
| 2'-OMe-8 | | 42 | AUU AAC CUU UUA UCU AAU AGU UUU GG$_{26}$ | H  H |
| 2'-OMe-9 | | 43 | ACA ACU UUG GGA GGC GGA GG$_{20}$ | H  H |
| 2'-OMe-10 | | 44 | GUA GGG AUG UAG AUU AAC CU$_{20}$ | H  H |
| 2'-OMe-11 | | 51 | CUA UAU AUA GAU AGU UAU UCA ACA AA$_{26}$ | H  H |
| PMO-ETpipT-1 | PMO-ETpipT[1] | 36 | ATT CAC TTT CAT AAT GCT GG$_{20}$ | TEG H |
| PMO-ETpipT-2 | | 45 | CTA TAT ATA GAT AGT TAT TCA ACA AA$_{26}$ | TEG H |

*"Ac" indicates an CH$_3$C(=O)- moiety conjugated to the peptide amino terminus

Example 24

In Vitro Exon-7 Inclusion Rate of PMO-Based Oligomers

Exemplary methods to measure in vitro exon-7 inclusion rates are described herein. PMO-based oligomers were tested to determine whether the antisense oligomers would enhance SMN2 exon-7 inclusion. Each of the antisense oligomers shown in Table 1 was introduced into cells using the nucleofection protocol described below. Exon-7 inclusion rates were calculated using the reverse transcriptase PCR protocol and visualization techniques provided below. In order to verify that the expression of exon-7 containing SMN2 protein was induced by the antisense oligomers, western blot analysis was performed following the protocol described below.

Nucleofection of PMO-Based Oligomers to SMA Cells

PMO-based oligomers were prepared as 1-2 mM stock solutions in nuclease-free water (not treated with DEPC) from which appropriate dilutions were made for nucleofection. Patient-derived fibroblasts from an individual with SMA (Coriell, GM03813) were cultured in Eagle's Minimum Essential Medium with 10% fetal bovine serum. Cells were passaged 3-5 days before an experiment, and were approximately 80% confluent at the time of nucleofection. Fibroblasts were trypsinized, counted, and centrifuged at 90 rcf for 10 minutes. 1-5×10$^5$ cells per well were resuspended in P3 nucleofection solution (Lonza). PMO-based oligomer solution and cells were then added to each well of a Nucleocuvette 16-well strip, and pulsed with program CA-137. Cells were incubated at room temperature for 10 minutes, transferred to a 24-well plate in duplicate, and placed in 37° C. cell incubator. After 24 hours of incubation, total RNA was isolated from treated cells with GE Illustra RNAspin 96 RNA isolation kit (GE Healthcare) by following the manufacturer's recommended protocol. Isolated RNA samples were stored at −80° C. prior to analysis.

Reverse Transcriptase PCR

In order to amplify the SMN2 allele, reverse transcriptase PCR was performed using SuperScript III One-Step RT-PCR system (Invitrogen). 400 ng of RNA isolated from nucleofected cells was reverse transcribed and amplified with following gene-specific primers: Forward primer 5'-ACTTTCCCCAATCTGTGAAGT-3' (SEQ ID NO: 52) and Reverse primer 5'-CATTTAGTGCTGCTCTATGCC-3' (SEQ ID NO: 54). The PCR conditions for reverse transcription and amplification were set up as following: Reverse Transcription at 55° C. for 20 min; RT Inactivation at 94° C. for 2 min; Denaturation at 94° C. for 2 min; Annealing at 59° C. for 45 sec; Extension at 68° C. for 1 min; Denaturation/Annealing/Extension repeated for 45 cycles. If exon-7 is properly included, the amplicon size should be 494 bp. The amplicon size for exon-7 exclusion should be 434 bp. The cDNA samples were stored at −20° C. for further analysis.

Visualization of Amplicons

In order to calculate exon-7 inclusion rate, the cDNA samples were visualized, and molar concentration of the amplicons in the samples were measured. The cDNA samples were prepared and loaded into LabChip (Perkin Elmer) according to the manufacturer's protocol. Briefly, the cDNA samples were thawed and mixed with a DNA dye provided by the manufacturer. Once the samples were loaded into LabChip, the prepared LabChip was inserted into LabChip GX instrument (Caliper). LabChip GX calculates the molar concentration of each amplicon based on the intensity of the bands corresponding to the amplicons.

Western Blot Analysis

PMO oligomers were nucleofected to SMA patient derived fibroblasts as described above. After 24 hr of nucleofection, cells were lysed with RIPA lysis buffer (Thermo Scientific). Each lysate was spun down at 14,000×g for 10 min. Cell debris pellets were discarded after centrifugation and only supernatants were collected for further analysis. 20 ug of each protein sample was loaded on a TGX stain free gel (Bio-rad), and separated by protein electrophoresis. The gel was transferred to PVDF transfer membrane (Bio-rad) and SMN protein was detected with anti-SMN antibody (BD Transduction Laboratories). If the SMN protein contains a portion encoded by exon-7, the size of the protein is 38 kDa. Actin was measured as a loading control by blotting with anti-actin antibody (Abcam).

Figure 3:
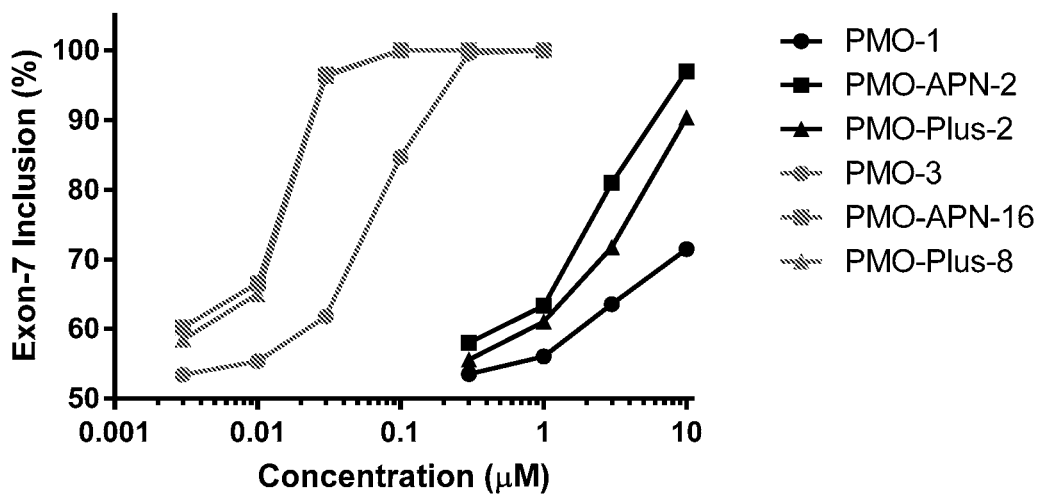
FIG. 3 depicts in vitro exon-7 inclusion rates of phosphorodiamidate morpholino-based oligomers (PMO-based oligomers) targeting overlapping regions in intron-7. Multiple doses from 0.003 µM to 10 µM, represented on x-axis, were tested in GM03813, SMA patient derived fibroblasts. Exon-7 inclusion rates, represented on y-axis, were calculated from the intensities of exon-7 included and excluded amplicons.

In Vitro Exon-7 Inclusion Rate of PMO-Based Oligomers Targeting Overlapping Regions PMO-based oligomers targeting overlapping regions in intron-7 were tested in order to measure the efficiency of the compounds to induce in vitro exon-7 inclusion. Varying amounts of PMO, PMO-APN, and PMO-Plus 8-mer oligomers targeting −7/−14 region of intron-7 (compounds PMO-1, PMO-APN-2, and PMO-Plus-2) and PMO, PMO-APN, and PMO-Plus 18-mer oligomers targeting −10/−27 region of intron-7 (compounds PMO-3, PMO-APN-16, and PMO-Plus-8) were nucleofected to SMA patient derived fibroblasts (GM03813). In vitro exon-7 inclusion rates were calculated for each PMO-based oligomer as described above. As summarized in FIG. 3 and Table 6, the compounds targeting the −10/−27 region were 100-fold more potent as compared to those targeting the −7/−14 region. PMO-APN and PMO-Plus modifications further enhanced the potency to induce exon-7 inclusion compared to PMO modification in both target regions.

TABLE 6

In vitro Exon-7 Inclusion Rate of PMO-based Oligomers

| Compound Name | Targeting SEQ ID NO | Exon-7 Inclusion Rate (%) | | | | | | | |
|---|---|---|---|---|---|---|---|---|---|
| | | 0.003 µM | 0.01 µM | 0.03 µM | 0.1 µM | 0.3 µM | 1.0 µM | 3.0 µM | 10.0 µM |
| PMO-1 | 4 | — | — | — | — | 53.57 | 56.06 | 63.61 | 71.47 |
| PMO-3 | 7 | 53.45 | 55.40 | 61.80 | 84.69 | 99.57 | 100 | — | — |
| PMO-APN-2 | 4 | — | — | — | — | 58.04 | 63.37 | 80.95 | 96.99 |
| PMO-APN-16 | 7 | 60.23 | 66.59 | 96.56 | 100 | 100 | 100 | — | — |
| PMO-Plus-2 | 4 | — | — | — | — | 55.63 | 61.08 | 71.76 | 90.33 |
| PMO-Plus-8 | 7 | 58.49 | 65.04 | 96.26 | 100 | 100 | 100 | — | — |

Figure 4:
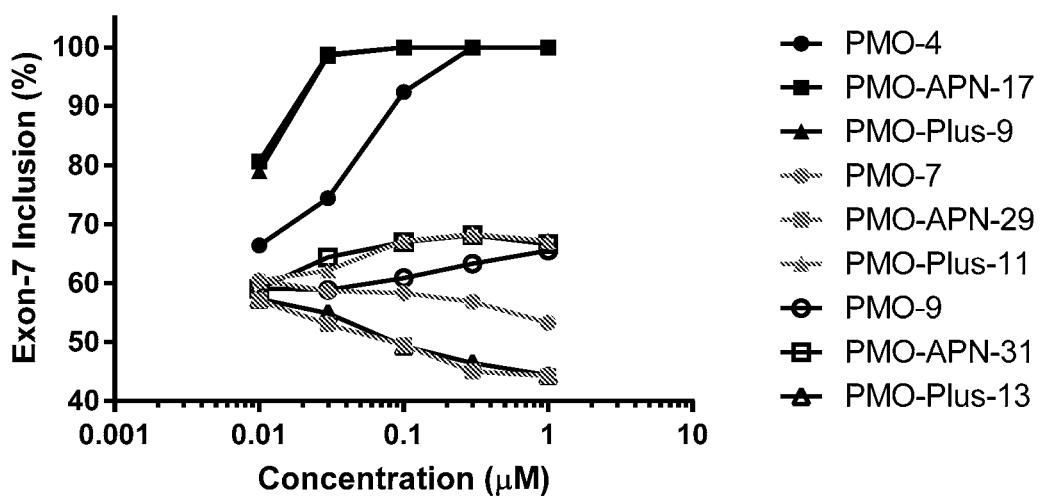
FIG. 4 shows in vitro exon-7 inclusion rates of PMO-based oligomers targeting intron-7. Multiple doses from 0.01 µM to 1 µM, represented on x-axis, were tested in GM03813 fibroblasts. Exon-7 inclusion rates, represented on y-axis, were calculated from the intensities of exon-7 included and excluded amplicons.

In Vitro Exon-7 Inclusion Rate of PMO-Based Oligomers Targeting Different Regions PMO-based oligomers targeting regions in intron-7 were tested and the efficiency of the compounds to induce in vitro exon-7 inclusion was calculated as described above. Various amounts of PMO, PMO-APN, and PMO-Plus oligomers targeting −10/−29 region of intron-7 (compounds PMO-4, PMO-APN-17, and PMO-Plus-9) were nucleofected to GM03813 fibroblasts. In parallel, varying amounts of PMO, PMO-APN, and PMO-PLUS oligomers targeting the −137/−159 region or the −149/−174 region of intron-7 (compounds PMO-7, PMO-9, PMO-APN-29, PMO-APN-31, and PMO-Plus-11, and PMO-Plus-13) were nucleofected as well. In vitro exon-7 inclusion rates were calculated for each PMO-based oligomer as described above. As shown in FIG. 4 and Table 7, the oligomers targeting the −10/−27 region were far more potent compared to the other compounds. While PMO-APN and PMO-Plus modifications further enhanced the potency of the compounds targeting the −10/−29 region of intron-7, the enhancing effects of those chemical modifications were far less with compounds targeting the −149/−174 region of intron-7. Surprisingly, those chemical modifications caused an increase in exon-7 skipping (exon-7 exclusion instead of exon-7 inclusion) with oligomers targeting the −137/−159 region of intron-7 rather than exon-7 inclusion.

TABLE 7

In vitro Exon-7 Inclusion Rate of PMO-based Oligomers
Exon-7 Inclusion Rate (%)

| Compound Name | Targeting SEQ ID NO | 0.01 μM | 0.03 μM | 0.1 μM | 0.3 μM | 1.0 μM |
|---|---|---|---|---|---|---|
| PMO-4 | 8 | 66.40 | 74.44 | 92.43 | 100 | 100 |
| PMO-7 | 11 | 60.51 | 58.73 | 58.32 | 56.85 | 53.29 |
| PMO-9 | 13 | 59.14 | 58.87 | 60.89 | 63.31 | 65.55 |
| PMO-APN-17 | 8 | 80.65 | 98.82 | 100 | 100 | 100 |
| PMO-APN-29 | 11 | 57.10 | 53.02 | 49.50 | 45.02 | 44.32 |
| PMO-APN-31 | 13 | 59.10 | 64.38 | 67 | 68.14 | 66.63 |

TABLE 7-continued

In vitro Exon-7 Inclusion Rate of PMO-based Oligomers
Exon-7 Inclusion Rate (%)

| Compound Name | Targeting SEQ ID NO | 0.01 μM | 0.03 μM | 0.1 μM | 0.3 μM | 1.0 μM |
|---|---|---|---|---|---|---|
| PMO-Plus-9 | 8 | 78.98 | 98.56 | 100 | 100 | 100 |
| PMO-Plus-11 | 11 | 60.43 | 62.16 | 67.15 | 68.28 | 67.17 |
| PMO-Plus-13 | 13 | 57.34 | 54.91 | 49.35 | 46.47 | 44.41 |

In Vitro Exon-7 Inclusion Rate of PMO-Based Oligomers with Different Lengths

Figure 5A:
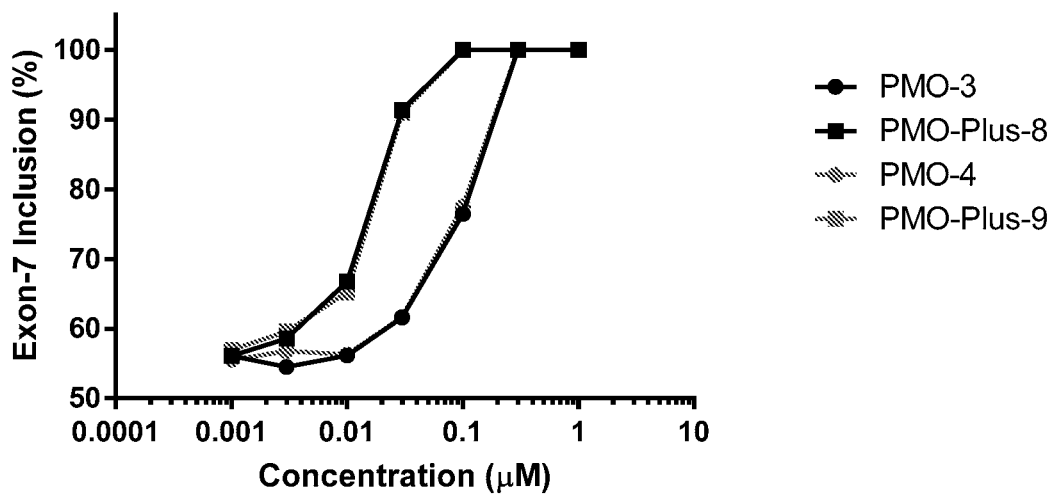
FIGS. 5A and 5B depict in vitro exon-7 inclusion rates of PMO-based oligomers with different lengths. The data of 18-mers and 20-mers are shown in FIG. 5A while the data of 18-mers and 25-mers are shown in FIG. 5B. Multiple doses from 0.001 µM to 1 µM were tested in GM03813 fibroblasts and are represented on the x-axis. Exon-7 inclusion rates, represented on y-axis, were calculated from the intensities of exon-7 included and excluded amplicons.
Figure 5B:
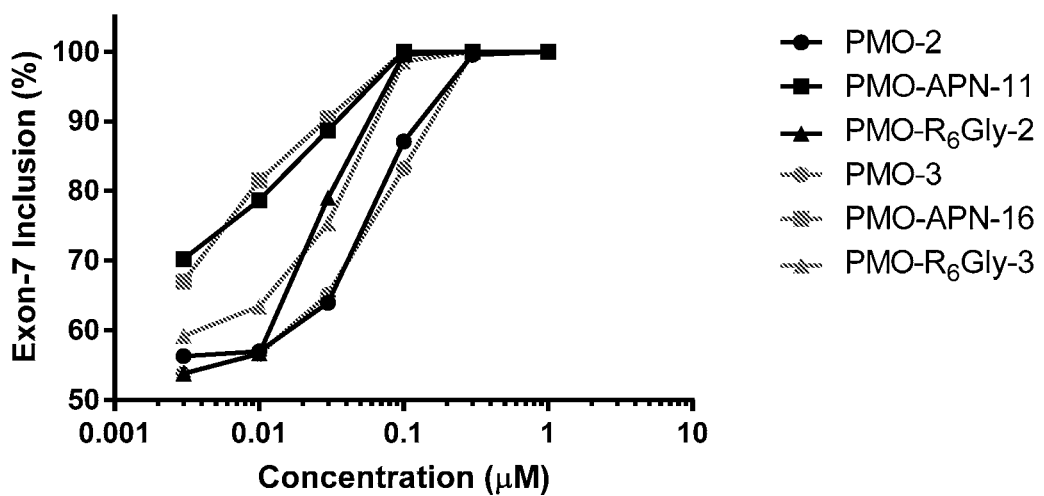

PMO-based oligomers with varying lengths were tested to measure the efficiency of the compounds to induce in vitro exon-7 inclusion. Various amounts of PMO, PMO-APN, PMO-Plus, and PMO-$R_6$Gly oligomers with different lengths (compounds PMO-2-4, PMO-APN-11, PMO-APN-16, PMO-Plus-8, PMO-Plus-9, PMO-$R_6$Gly-2, and PMO-$R_6$Gly-3) were nucleofected to GM03813 fibroblasts. In vitro exon-7 inclusion rates were calculated for each PMO-based oligomer as described above. FIG. 5A and Table 8 summarize exon-7 inclusion rates upon nucleofection of the modified 18-mers and 20-mers. Within the dose range tested, modified 18-mers and 20-mers showed similar potency to induce in vitro exon-7 inclusion. Likewise, as shown in FIG. 5B and Table 9, similar potency to induce in vitro exon-7 inclusion was observed with modified 18-mers and 25-mers. As before, the compounds having PMO-APN, PMO-Plus, and PMO-$R_6$Gly modifications outperformed the PMO compound.

TABLE 8

In vitro Exon-7 Inclusion Rate of PMO-based Oligomers
Exon-7 Inclusion Rate (%)

| Compound Name | Targeting SEQ ID NO | 0.001 μM | 0.003 μM | 0.01 μM | 0.03 μM | 0.1 μM | 0.3 μM | 1.0 μM |
|---|---|---|---|---|---|---|---|---|
| PMO-3 | 7 | 56.10 | 54.50 | 56.15 | 61.62 | 76.49 | 100 | 100 |
| PMO-4 | 8 | 55.54 | 56.81 | 56.29 | 61.65 | 77.51 | 100 | 100 |
| PMO-Plus-8 | 7 | 56.12 | 58.58 | 66.73 | 91.43 | 100 | 100 | 100 |
| PMO-Plus-9 | 8 | 56.97 | 59.61 | 65.24 | 91.06 | 100 | 100 | 100 |

TABLE 9

In vitro Exon-7 Inclusion Rate of PMO-based Oligomers
Exon-7 Inclusion Rate (%)

| Compound Name | Targeting SEQ ID NO | 0.003 μM | 0.01 μM | 0.03 μM | 0.1 μM | 0.3 μM | 1.0 μM |
|---|---|---|---|---|---|---|---|
| PMO-2 | 6 | 56.30 | 56.97 | 63.97 | 87.08 | 99.50 | 100 |
| PMO-3 | 7 | 53.81 | 56.62 | 65.13 | 83.21 | 100 | 100 |
| PMO-APN-11 | 6 | 70.23 | 78.65 | 88.70 | 100 | 100 | 100 |
| PMO-APN-16 | 7 | 67.00 | 81.52 | 90.38 | 100 | 100 | 100 |
| PMO-$R_6$Gly-2 | 6 | 53.77 | 56.67 | 79 | 99.59 | 100 | 100 |
| PMO-$R_6$Gly-3 | 7 | 59.21 | 63.46 | 75.31 | 98.54 | 100 | 100 |

Figure 6:
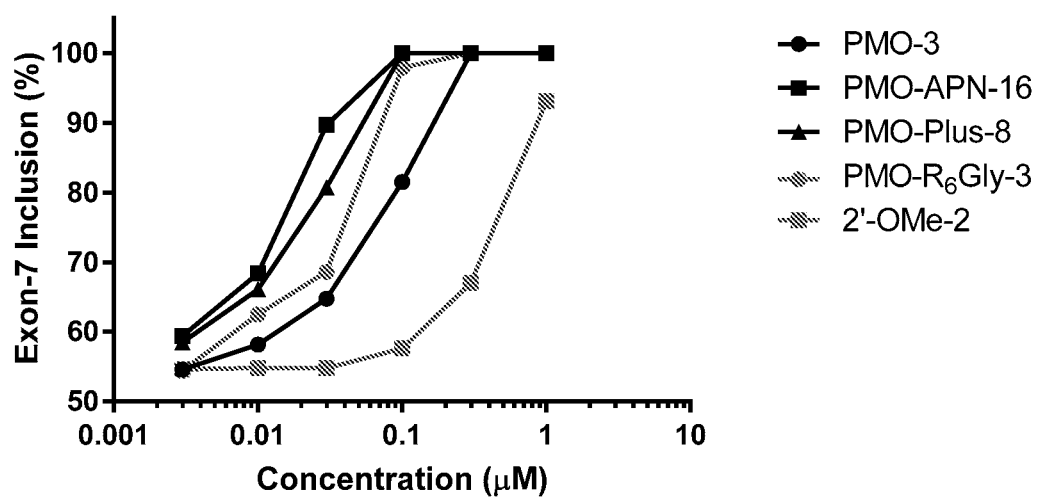
FIG. 6 shows in vitro exon-7 inclusion rates of PMO-based oligomers with different chemical modifications. 2'-OMe modified antisense oligomer targeting the same region was tested as well. Multiple doses from 0.003 µM to 1 µM, represented on x-axis, were tested in GM03813 fibroblasts. Exon-7 inclusion rates, represented on y-axis, were calculated from the intensities of exon-7 included and excluded amplicons.

In Vitro Exon-7 Inclusion Rate of PMO-Based Oligomers with Different Modifications PMO-based oligomers modified with PMO, PMO-APN, PMO-Plus, and PMO-$R_6$Gly were tested in order to analyze the effects of chemical modification on in vitro exon-7 inclusion. 2'-OMe modified oligomer was tested in parallel with PMO-based oligomers. By following the protocol described above, varying amounts of PMO, PMO-APN, PMO-Plus, PMO-$R_6$Gly, and 2'-OMe oligomers (comopunds PMO-3, PMO-APN-16, PMO-Plus-8, PMO-$R_6$Gly-3, and 2'-OMe-2) were nucleofected to GM03813fibroblasts. In vitro exon-7 inclusion rates were calculated for each compound as described above. As shown in FIG. 6 and Table 10, compounds modified with PMO-APN, PMO-PLUS, or PMO-$R_6$Gly exhibited significantly improved potency to induce exon-7 inclusion compared to compounds modified with PMO. Moreover, all of compounds modified with PMO or next generation PMOs showed greatly improved potency, far exceeding potency of 2'-OMe oligomer.

TABLE 10

In vitro Exon-7 Inclusion Rate of PMO-based Oligomers

| Compound Name | Targeting SEQ ID NO | Exon-7 Inclusion Rate (%) | | | | | |
|---|---|---|---|---|---|---|---|
| | | 0.003 μM | 0.01 μM | 0.03 μM | 0.1 μM | 0.3 μM | 1.0 μM |
| PMO-3 | 7 | 54.60 | 58.19 | 64.78 | 81.51 | 100 | 100 |
| PMO-APN-16 | 7 | 59.40 | 68.40 | 89.65 | 100 | 100 | 100 |
| PMO-Plus-8 | 7 | 58.50 | 66.10 | 80.74 | 100 | 100 | 100 |
| PMO-$R_6$Gly-3 | 7 | 54.44 | 62.53 | 68.62 | 97.71 | 100 | 100 |
| 2'-OMe-2 | 7 | 54.64 | 54.85 | 54.78 | 57.65 | 67.04 | 93.07 |

Figure 7A:
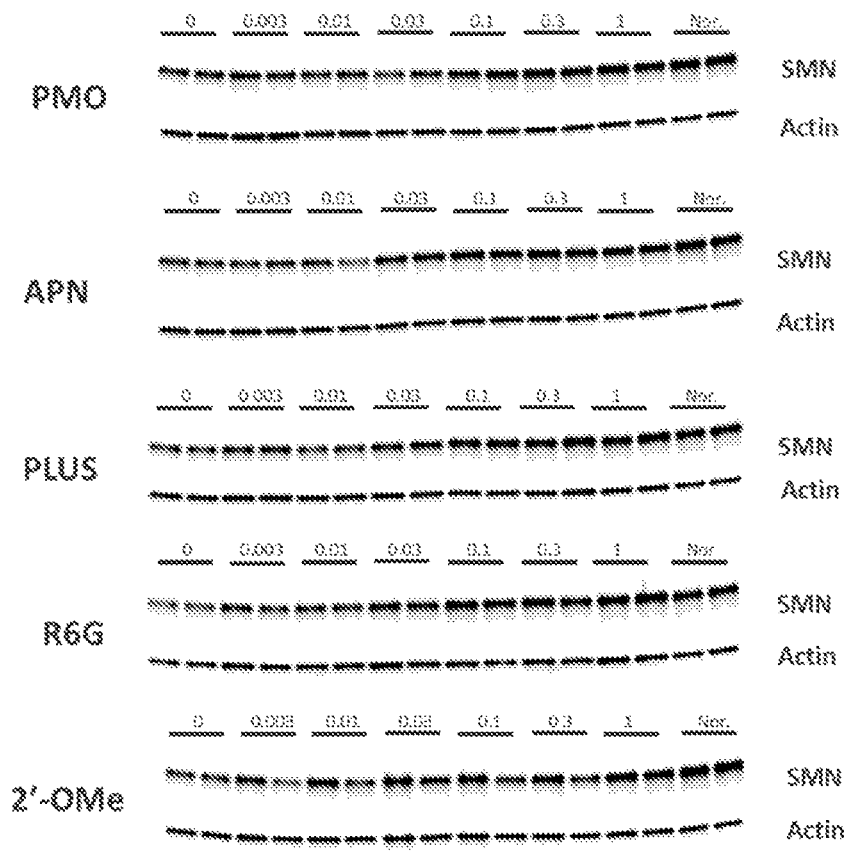
FIG. 7A shows the western-blot analysis of exon 7-containing SMN proteins as induced by PMO-based oligomers with different chemical modifications. 2'-OMe modified antisense oligomers targeting the same region as PMO-based oligomers were tested in parallel. SMN2 proteins were blotted with anti-SMN antibodies. Actin was detected with anti-Actin antibodies as a loading control.
Figure 7B:
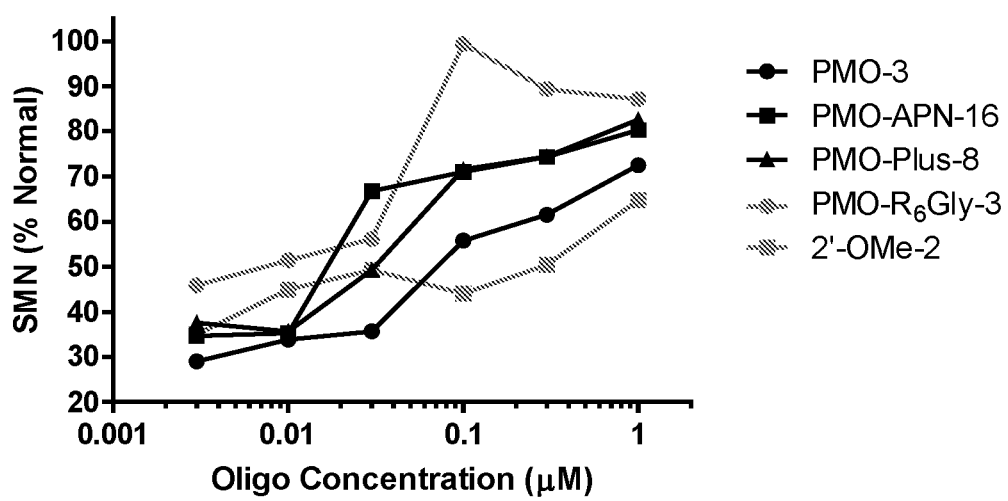
FIG. 7B represents the average quantified intensity of the bands corresponding to SMN proteins per each experimental group as shown in FIG. 7A.

When exon-7 inclusion is induced, the expression level of SMN2 protein including exon-7 encoded portion should be also increased accordingly. In order to confirm that PMO-based oligomers indeed induced exon-7 inclusion in vitro, western blot analysis was performed as described above (FIGS. 7A and 7B). As low as at 0.1 μM of concentration, PMO, PMO-APN, PMO-Plus, and PMO-$R_6$Gly compounds were able to induce the expression of SMN2 protein including exon-7 encoded portion in SMA patient derived fibroblasts, comparable to the level of SMN1 expression in normal fibroblasts.

Example 25

In Vivo Administration of PMO-Based Oligomers

Therapeutic efficacy and safety of PMO-based oligomers were tested in an appropriate animal model. Exemplary methods to analyze the efficacy of PMO-based oligomers in treating SMA are provided. Mice treated with PMO-based oligomers were monitored and tested for life-span, weight gain, grip strength and righting reflex by following protocols below. Other exemplary methods described herein are related to assessing histology, toxicity and immunogenic responses upon PMO-based oligomers administration in vivo. Table 11 summarizes PMO-based oligomers used in the following in vivo studies.

TABLE 11

PMO-based Oligomers for In Vivo Studies

| Compound Name | Modification | Targeting Sequence | Targeting SEQ ID NO | 5' end | 3' end |
|---|---|---|---|---|---|
| PMO-3 | PMO | TCA CTT TCA TAA TGC TGG$_{18}$ | 35 | TEG | H |
| PMO-APN-16 | PMO-APN | TCA CTT TCA TAA TGC TGG$_{18}$ | 35 | TEG | H |
| PMO-Plus-8 | PMO-Plus | TCA CTT TCA TAA TGC TGG$_{18}$ | 35 | TEG | H |
| PMO-$R_6$Gly-3 | PMO-$R_6$Gly | TCA CTT TCA TAA TGC TGG$_{18}$ | 35 | TEG | Ac-$R_6$Gly- (SEQ ID NO: 53) |

SMA Mouse Models

Various SMA mouse models are known in the art (see e.g., Schrank et al 1997; Hsieh-Li et al 2000; Monani et al 2000). Severity of SMA phenotype in mice depends on the number of copies of the SMN genes present in mice. For example, heterozygous mice lacking one copy of mSMN gene mimics Type III SMA in human. SMN-knockout mice are embryonic lethal. In order to create mice strain similar to Type I or Type II SMA in humans, human SMN2 can be introduced to the mice. The Taiwanese-SMA mouse model, for example, has four copies of the human SMN2 gene in SMN-null background (Smn−/−, hSMN2tg/tg). The Taiwanese mice display moderate to severe SMA phenotypes that are similar to Type I or Type II SMA in humans. An "sSMA" strain mouse (Smn−/−, hSMN2+/+) carries only two copies of the human SMN2 gene, resulting in a more severe phenotype than the Taiwanese mice. Another severe SMA mouse strain is the SMNΔ7 mice (Smn−/−, hSMN2+/+, SMNΔ7+/+). Average life span of SMNΔ7 mice is roughly 15-20 days. SMNΔ7 mice exhibit symptoms and neuropathology similar to Human Type I SMA patients.

Administration of PMO-Based Oligomers

PMO-based oligomers were delivered to SMNΔ7 mice via intracerebroventricular (ICV) injection as described previously (Passini et al. 2001). All PMO-based oligomers tested in vivo were dissolved in saline prior to the injection at a concentration of 5 µg/µl. A typical dosage to screen PMO-based oligomers in vivo was 20 ng, delivered by ICV injection at age P1 (the day after birth). Each mouse received an injection of 2 µl of PMO-based oligomers solution into each cerebral lateral ventricle, for a total of 4 µl per mouse. The dosage used in vivo can be multiplied and delivered at once or among multiple injections. Other exemplary delivery methods include subcutaneous injection, intramuscular injection, peripheral facial vein injection, ocular injection, intrathecal injection, and tail-vein injection. Any one of the delivery methods can be combined in order to administer PMO-based oligomers multiple times at different ages of the mice.

Based on the molecular mechanism of SMA development in humans, it is understood that early CNS treatment will likely yield robust effects. As ICV injection directly delivers PMO-based oligomers to the brain and spinal cord, and can be administered at an early age, ICV injection may be a preferred method to restore SMN levels within neurons. It is also possible that increasing SMN expression in the autonomic nervous system outside of the blood-brain barrier could alleviate the severity of SMA-related symptoms.

Analysis of SMA-Related Symptoms Upon Administration of PMO-Based Oligomers

SMNΔ7 mice treated with PMO-based oligomers were monitored for life-span and body weight, and tested for muscle strength and motor function. Because SMA mouse models display SMA-related symptoms that are similarly observed in Human SMA patients, various tests to measure SMA-related symptoms and phenotypes of mice are known in the art (Passini et al. 2011). The most notable phenotype of SMA mouse models is reduced life-span. A typical life-span of wild-type mice is roughly 2 years. However, depending on the severity of the SMA phenotype, the average median life-span of an SMA mouse model can vary between 5-25 days. Thus, monitoring the life-span of PMO-based oligomers treated mice compared to saline treated mice can be a good measurement to assess the efficacy of the oligomers in treating SMA. Other biometrics such as weight gain and behavioral biometrics including open field test and walking gait can be analyzed as well in order to assess well-being of treated mice. Body composition such as lean mass and fat mass measured by MRI can be analyzed as well throughout the study.

Other phenotypes of SMA mouse models include impaired neuromuscular function such as weakened muscle strength and motor function. In order to quantitatively measure neuromuscular function, mice treated with PMO-based oligomers were subjected to grip test, beginning at day 14. Forelimbs of each mouse were placed on a wire grid and the mouse was then gently dragged horizontally along the mesh. The peak amount of force that the mouse applies in order to grasp the mesh was measured in grams with a force transducer (Columbus Instruments). Fore and hind limb assessments can be performed concurrently or in separate trials. Beginning at day 4 after the initial injection, righting reflex was measured as well, following the protocols described previously (Passini et al. 2011). Briefly, the righting reflex was determined by measuring the time taken for a mouse to reposition itself onto all four paws after being placed in a supine position. The time taken to right itself inversely correlates with neuromuscular strength. Other tests such as use of a treadmill and wheel exercise can be used to measure general muscle strength improvements upon PMO-based oligomers administration. Physical examinations including measuring muscle size, tone, tenderness, frequency of involuntary movements, and cardiovascular functions are additionally conducted in order to analyze the whole-body effects of PMO-based oligomers in SMA mouse models.

Molecular and Cellular Analysis Upon Treatments with PMO-Based Oligomers

Molecular and cellular assays are conducted in order to analyze the physiological effects of PMO-based oligomers in vivo. After PMO-based oligomers are administered to mice, biopsy samples from tissues such as brain, spinal cord, and peripheral organs are collected regularly throughout the experiment. Treated mice are sacrificed at the end of the experiment and such tissues are weighed and collected for further analysis. Such assays are routinely used in the art and exemplary methods are described herein.

In order to verify that PMO-based oligomers indeed induce exon-7 inclusion in vivo, exon-7 inclusion rates in tissues such as brain, spinal cord and peripheral organs are measured. Total RNA is isolated and cDNA is generated by reverse transcription PCR as described above. Amplicons are visualized and exon-7 inclusion rate is calculated as described above. Biopsy samples are further processed to measure the amount of SMN2 protein including exon-7 encoded portion by western blot analysis by following the protocol described above.

The effects of PMO-based oligomers on spinal cord physiology are quantitatively analyzed. For example, the number of motor neurons present in spinal cord of treated SMA mice are counted, and compared with control mice. Methods to analyze motor neurons in the spinal cord are known in the art (Passini et al. 2011). Briefly, the samples of spinal cord isolated from the mice are fixed in paraformaldehyde and H&E (hematoxylin and eosin) stained. Multiple cross-sections are generated and stained with antibodies against specific markers for motor neurons such as choline acetyltransferase in order to visualize the neurons.

Heart and muscles are histologically analyzed as well by following methods known in the art (Avilia et al. 2007; Passini et al. 2010; Passini et al. 2011). For examples, heart and muscles including quadriceps and intercostal muscles are collected and fixed in paraformaldehyde and H&E stained. Based on cross-sections of tissues, the average thickness of muscle fibers in those tissues is measured. The architectures of neuromuscular junction of those tissues can be visualized with antibodies against specific markers such as neurofilament medium and acetylcholine receptor.

Administration of PMO-Based Oligomers to Non-Human Primates

Non-human primates such as cynomolgus monkeys are used to analyze the delivery feasibility of PMO-based oligomers. Various injection options such as intrathecal and ICV injections are known in the art (see e.g., Passini et al 2011; Smith et al 2006). Those methods are clinically feasible as both routes of administration are routinely used to deliver therapeutic agents in non-human primates and humans. For intrathecal injection, cynomolgus monkeys are anesthetized and implanted with intrathecal indwelling catheters. For ICV injections, stereotactic surgery to implant a cannula into the right (or left or both) cerebral lateral ventricle is performed for each monkey. The monkeys are allowed to recover from the implantation surgery for several days before receiving infusions of PMO-based oligomers. Various doses of PMO-based oligomers are infused over one or more days. 5-20 days after the initial infusion, all monkeys are sacrificed and tissues are collected for further analysis as described above.

Safety Analysis of PMO-Based Oligomers

Safety of PMO-based oligomers in vivo is assessed by various methods known in the art (see e.g., Hua et al. 2010). As chronic inflammation is associated with neurodegenerative diseases such as SMA, various biomarkers related to neuroinflammation are used to analyze the inflammatory response in tissues such as brain, spinal cord, heart and muscles upon administration of PMO-based oligomers. Exemplary biomarkers include allograft inflammatory factor-1, tumor necrosis factor-$\alpha$ and interleukin-1$\beta$. Immune cell infiltration can also be measured with specific immune cell markers such as CD4 and CD8. Reactive oxygen species in those tissues can be measured as well by following methods known in the art (Dikalov et al. 2007).

In addition to inflammation markers, other physiological parameters associated with toxicity can be measured in mice or non-human primates treated with PMO-based oligomers. The animals are challenged with a single dose or multiple doses of each compound, exceeding the maximal dose that elicts the desired biological response, i.e., 100% exon-7 inclusion rates in vivo. The animals treated with various doses of the compounds are monitored for any acute response. The local injection sites are monitored as well. Cardiovascular parameters such as blood pressure, and heart rate, and serum and urine biochemistry are measured in order to detect any potential acute or chronic effects of PMO-based oligomers. Genotoxicity is evaluated as well by following the protocols known in the art (see e.g., Sazani et al, 2010). Pharmacokinetics and pharmacodynamics of the compounds are also measured by sampling the serum of each treated animal in order to estimate the therapeutic dose by following the protocols known in the art (Heald et al, 2015).

Administration of PMO-Based Oligomers to SMN$\Delta$7 Mice

As an initial screening method, SMN$\Delta$7 mice were used for in vivo experiments. At age P1 (the day after birth), mice were treated with saline or 20 μg of PMO-based oligomers (compounds PMO-3, PMO-APN-16, PMO-Plus-8, and PMO-R$_6$Gly-3) by ICV injection as described above. All of the injections were performed with a 30.5-guage Hamilton Syring similarly to that described in Passini et al (2001). An age-matching group of wild-type mice was simultaneously monitored as a reference. At 63 days of age, any remaining mice were sacrificed for further molecular and cellular analysis as described above. Table 12 summarizes genotype, treatment, dose, and number of mice used for each experimental group.

TABLE 12

Experimental Design of in vivo PMO-based Oligomers Administration

| Genotype | Compound Name | Modification | Dose | N-value |
| --- | --- | --- | --- | --- |
| SMA | PMO-3 | PMO | 20 μg | 13 |
| SMA | PMO-APN-16 | PMO-APN | 20 μg | 13 |
| SMA | PMO-Plus-8 | PMO-Plus | 20 μg | 13 |
| SMA | PMO-R$_6$Gly-3 | PMO-R$_6$Gly | 20 μg | 13 |
| SMA | Saline | n/a | n/a | 13 |
| WT | Saline | n/a | n/a | 12 |

Survival of SMN$\Delta$7 Mice Treated with PMO-Based Oligomers

Figure 8A:
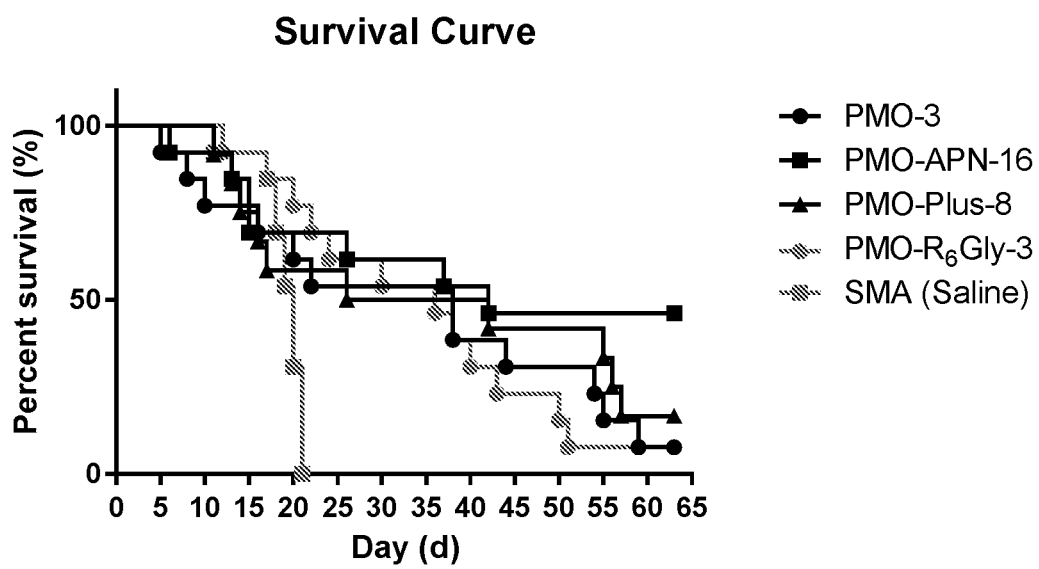
FIG. 8A depicts a survival curve of SMNΔ7 mice treated with either 20 µg of PMO, PMO-APN, PMO-Plus, or PMO-R$_6$Gly compounds or saline. Each mouse was treated at P1 (the day after the birth) with intraventricular (ICV) injection of saline or PMO-based oligomers. A percentage of any remaining mice compared to the initial number of mice per each experimental group is represented on y-axis.

As shown in FIG. 8A and Table 13, treatments with PMO-based oligomers significantly increased median life-span of SMN$\Delta$7 mice. P-value of each experimental group was calculated by log-rank Mantel-Cox test. While none of saline treated SMN$\Delta$7 mice survived beyond 21 days, all of the tested oligomers were able to extend median survival to 34-42 days. In addition, 8-46% of mice treated with the oligomers were still alive at 63 days of age. Moreover, mice treated with PMO oligomers displayed improved alertness and general well-being as they were well-groomed, ambulatory, and much active compared to saline treated SMN$\Delta$7 mice.

TABLE 13

Median Life-Span of SMN$\Delta$7 Mice Treated with PMO-based Oligomers

| Genotype | Compound Name | Median Life Span (d) | p-value |
| --- | --- | --- | --- |
| SMA | PMO-3 | 38 | 0.0199 |
| SMA | PMO-APN-16 | 42 | 0.0066 |
| SMA | PMO-Plus-8 | 34 | 0.052 |
| SMA | PMO-R$_6$Gly-3 | 38 | 0.0004 |
| SMA | Saline | 20 | n/a |

Body Weight of SMN$\Delta$7 Mice Treated with PMO-Based Oligomers

Figure 8B:
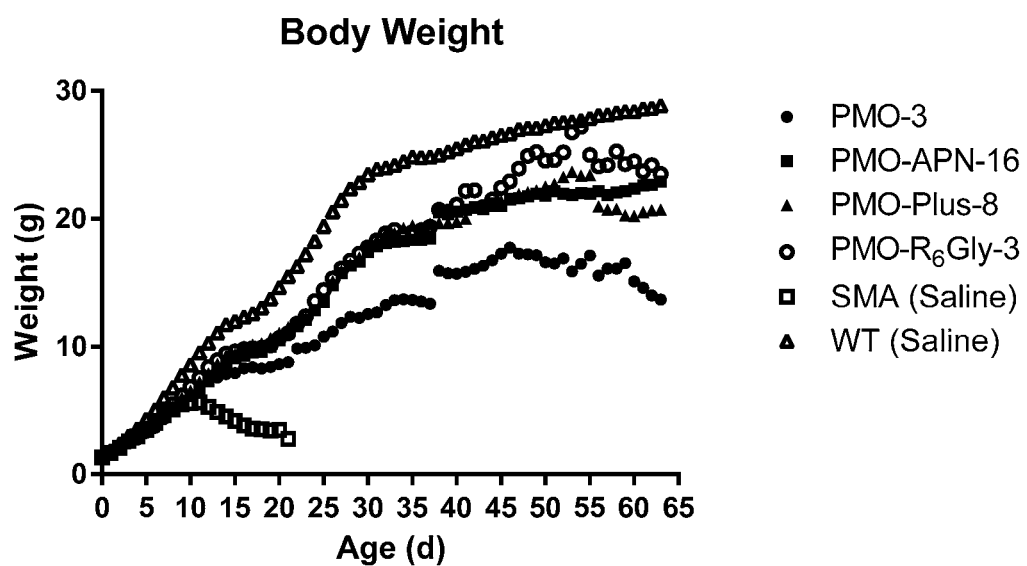
FIG. 8B shows weight gain of each experimental group throughout the experiment. A group of wild-type mice treated with saline was used as a reference.

During the experiment, body weight was recorded on daily basis (FIG. 8B). The average body weight at day 63 of each experimental group is summarized in Table 14. Mice treated with PMO-based oligomers significantly increased body weight throughout the experiment, comparable to the wild-type group. Surprisingly, mice treated with PMO-APN, PMO-Plus, or PMO-R$_6$Gly oligomers gained weight significantly more than PMO oligomers, demonstrating that those chemical modifications further enhanced the efficacy of the oligomers in treating SMA-related symptoms in vivo.

TABLE 14

Average Body Weight of SMNΔ7 Mice Treated with PMO-based Oligomers

| | Compound | | | | | |
|---|---|---|---|---|---|---|
| Day | PMO-3 | PMO-APN-16 | PMO-Plus-8 | PMO-R$_6$Gly-3 | SMA (Saline) | WT (Saline) |
| 14 | 7.9 g | 8.4 g | 9.3 g | 9.5 g | 4.3 g | 11.7 g |
| 21 | 8.8 g | 11.1 g | 11.5 g | 11.1 g | 2.8 g | 15.5 g |
| 28 | 12.3 g | 16.4 g | 16.5 g | 16.7 g | — | 22.4 g |
| 42 | 16.1 g | 21.0 g | 20.9 g | 22.2 g | — | 26.1 g |
| 63 | 13.7 g | 22.9 g | 20.7 g | 23.5 g | — | 28.9 g | throughout the extended survival period to the end of the study. This could not have been predicted from the in vitro screens described above.

TABLE 15

Righting Reflex of SMNΔ7 Mice Treated with PMO-based Oligomers

| | Compound | | | | | |
|---|---|---|---|---|---|---|
| Day | PMO-3 | PMO-APN-16 | PMO-Plus-8 | PMO-R$_6$Gly-3 | SMA (Saline) | WT (Saline) |
| 14 | 12.0 s | 6.3 s | 11.2 s | 6.58 s | 19.7 s | 1.0 s |
| 21 | 15.0 s | 1.1 s | 1.7 s | 1.80 s | 30.0 s | 1.0 s |
| 28 | 1.14 s | 1.0 s | 1.0 s | 1.0 s | — | 1.0 s |
| 42 | 1.2 s | 1.0 s | 1.0 s | 1.0 s | — | 1.0 s |
| 63 | 1.0 s | 1.0 s | 1.0 s | 1.0 s | — | 1.0 s |

TABLE 16

Grip Strength of SMNΔ7 Mice Treated with PMO-based Oligomers

| Genotype | Compound Name | Length | 14 (d) | 21 (d) | 28 (d) | 35 (d) | 42 (d) | 49 (d) | 56 (d) |
|---|---|---|---|---|---|---|---|---|---|
| SMA | PMO-3 | 18 | 36.3 | 73.3 | 82.7$^\&$ | 74.6$^\%$ | 86.5$^\%$ | 91.0$^\&$ | 83.4$^\&$ |
| SMA | PMO-APN-16 | 18 | 47.8$^\#$ | 77.6 | 113.1* | 100.3* | 111.9* | 124.3* | 127.3* |
| SMA | PMO-Plus-8 | 18 | 50.3$^\#$ | 81.7 | 103.3 | 92.5 | 117.1* | 118 | 115.8 |
| SMA | PMO-R$_6$Gly-3 | 18 | 53.2$^\#$ | 84.1 | 107.5 | 97.9 | 111.5* | 106.9 | NT |
| SMA | Saline | n/a | 24.1$^\#$ | — | — | — | — | — | — |
| WT | Saline | n/a | 59.5 | 86.7 | 115.7 | 111.3 | 125.4 | 125.4 | 124.4 |

Units for the above data is "Force (g)"
$^\#$p < 0.001 (compared to SMA mice treated with saline)
*p < 0.05 (compared to SMA mice treated with PMO-3).
$^\$$p < 0.05,
$^\&$p < 0.01 and
$^\%$p < 0.001 (compared to wild-type mice treated with saline).
NT: "Not Tested" (the remaining mouse was unable to perform the test due to forelimb necrosis)

Effects of PMO-based Oligomers on Muscle Strength and Motor Function

Figure 9A:
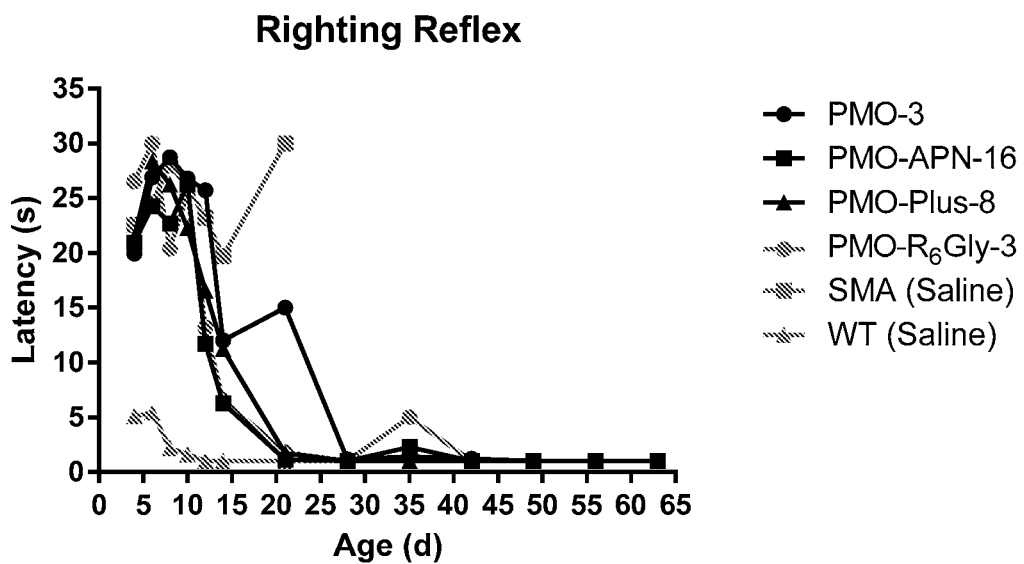
FIG. 9A depicts the righting reflexes of SMNΔ7 mice treated with either 20 µg of PMO-, PMO-APN, PMO-Plus, or PMO-R6Gly compounds or saline. A group of wild-type mice treated with saline was used as a reference. Each mouse was treated at P1 (the day after the birth) with intraventricular (ICV) injection and the righting reflex test was performed regularly from day 4. The time that a mouse took to right itself was measured, and the average time of each experimental group is represented in second (s) on y-axis.

In order to analyze the effect of PMO-based oligomers on muscle strength and motor function, righting reflex of mice treated with the oligonucleotides was measured regularly throughout the experiment by following the protocols described above. As shown in FIG. 9A and Table 15, mice treated PMO-based oligomers displayed significantly improved righting reflex, compared to saline treated SMNΔ7 mice. All of mice treated with the oligomers showed comparable reflex to the wild-type group after 28 days. Surprisingly and unexpectedly, mice treated with PMO-APN, PMO-Plus, or PMO-R$_6$Gly oligomers started to behave similarly to the wild-type at day 21, 7 days earlier than mice treated with PMO oligomers.

Figure 9B:
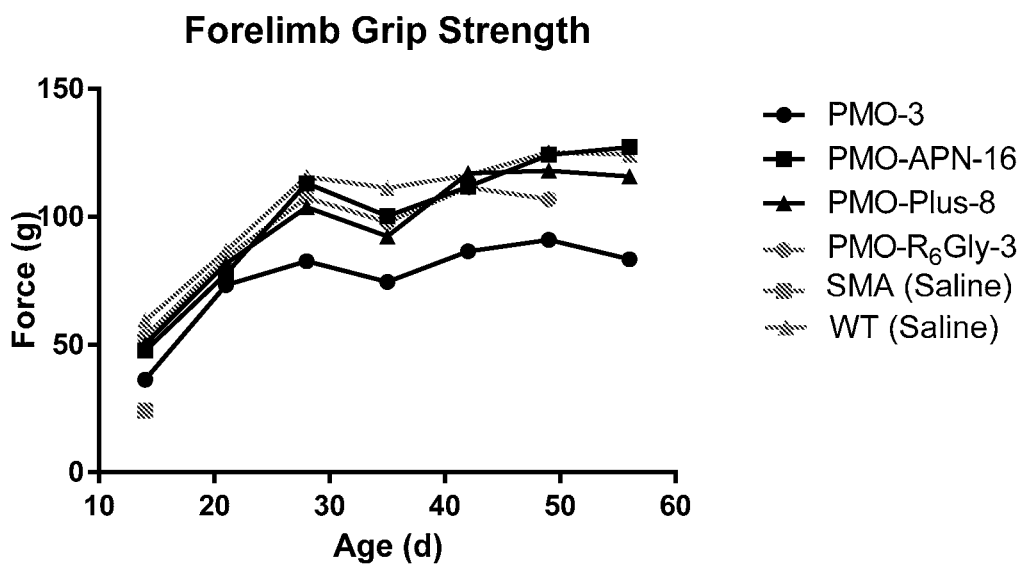
FIG. 9B shows grip test of each experimental group measured regularly throughout the experiment. The peak amount of force that a mouse applies in order to grasp a mesh was measured, and the average force of each group is represented in gram (g) on y-axis. The resulting data shows that a subset of PMO-based oligomers normalized the average force to that of the wild-type mice. Specifically, PMO-APN, PMO-Plus, and PMO-R$_6$Gly surprisingly normalized grip strength to wild type mice throughout the study period from day 14 and during the extended survival period.

Grip strength of mice treated with the oligomers was tested regularly as well by following the protocols described above and are shown in FIG. 9B and Table 16. Tables 15 and 16 summarize muscle strength and righting reflex of each experimental group measured at day 14, 21, 28, 42, and 56 or 63. All of the tested oligomers enhanced muscle strength of SMNΔ7 mice. Consistent with righting reflex, mice treated with PMO-APN, PMO-Plus, or PMO-R$_6$Gly oligomer were statistically undistinguishable from the wild-type group. Although PMO oligomer enhanced muscle strength of mice, PMO-APN, PMO-Plus, and PMO-R$_6$Gly modifications were significantly more effective than PMO modification and, surprisingly, normalized strength to that of the wild-type mice. Even more unexpected and surprising, grip strength of the PMO-APN, PMO-Plus, and PMO-R$_6$Gly treated mice normalized to wild type at about day 28 and remained statistically indistinguishable from wild type Effects of PMO-Based Oligomers on SMN Protein Expression In Vivo To confirm whether administration of PMO-based oligomers induces the expression of SMN protein in vivo, spinal cord samples from mice treated with PMO-based oligomers were collected at 63 days of age. As a positive control, age-matching wild-type mice were also sacrificed for spinal cord sample collection. Saline-treated SMNΔ7 mice were sacrificed at 12 days of ages and spinal cord samples from those mice were collected as a comparison. Protein extracts from the spinal cord samples were obtained by following the methods described in Example 24. The SMN protein expression level of each sample was detected by western blot analysis, also described in Example 24.

Figure 10A:
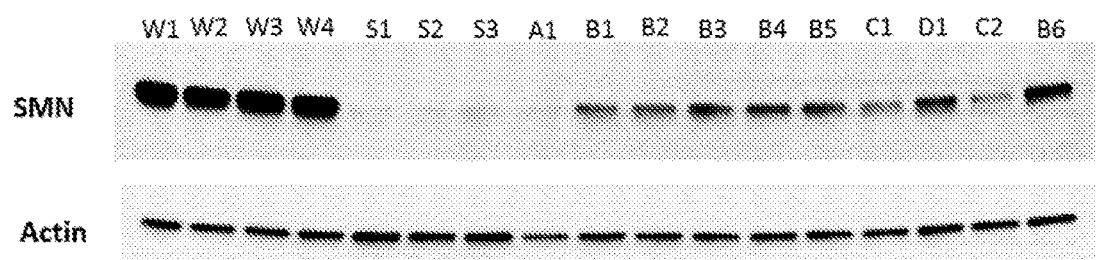
FIG. 10A shows the western-blot analysis of exon 7-containing SMN proteins in samples obtained from mice tested in FIG. 7A. SMN2 proteins were blotted with anti-SMN antibodies. Actin was detected with anti-Actin antibodies as a loading control. W1-W4 represent cervical spinal cord samples from four different saline-treated wild-type mice. S1-S3 represent cervical spinal cord samples from three different saline-treated SMNΔ7 mice. A1 represents a cervical spinal cord sample obtained from a SMNΔ7 mouse treated with PMO-3. B1-B6 represent cervical spinal cord samples from six different SMNΔ7 mice treated with PMO-APN-16. C1-C2 and D1 represent cervical spinal cord samples from SMNΔ7 mice treated with PMO-Plus-8 and PMO-R$_6$-Gly-3, respectively.
Figure 10B:
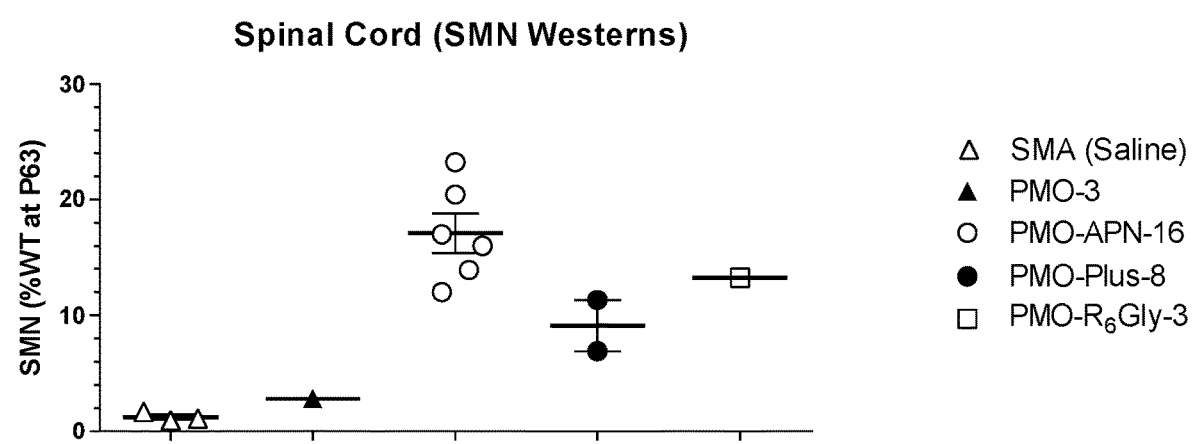
FIG. 10B represents the average quantified intensity of the bands corresponding to SMN proteins per each experimental group as shown in FIG. 10A.

As shown in FIG. 10A, spinal cord samples from mice treated with PMO-based oligomers showed significantly higher SMN protein expression levels. FIG. 10B shows the quantification of western blot analysis shown in FIG. 10A. Suprisingly, the SMN protein expression level in mice treated with PMO-APN-16 was about 25% of that in wild-type mice.

Example 26

In Vivo Effects of PMO-Based Oligomers with Different Lengths

The in vivo efficacy of a second set of PMO-based oligomers was tested in SMNΔ7 mice by following the methods described in Example 25. Briefly, at age P1 (the day after birth), mice were treated with saline or 20 μg of PMO-based oligomers (compound PMO-APN-16 of 18 nucleotides in length, and compounds PMO-2, PMO-APN-11, PMO-Plus-3, PMO-R$_6$Gly-2 of 25 nucleotides in length). An age-matching group of wild-type mice was simultaneously monitored as a reference. Table 17 summarizes genotype, treatment, dose, and number of mice used for each experimental group.

TABLE 17

Experimental Design of in vivo PMO-based Oligomers Administration

| Genotype | Compound Name | Length | Modification | Dose | N-value |
|---|---|---|---|---|---|
| SMA | PMO-APN-16 | 18 | PMO-APN | 20 µg | 13 |
| SMA | PMO-2 | 25 | PMO | 20 µg | 12 |
| SMA | PMO-APN-11 | 25 | PMO-APN | 20 µg | 12 |
| SMA | PMO-Plus-3 | 25 | PMO-Plus | 20 µg | 13 |
| SMA | PMO-R$_6$Gly-2 | 25 | PMO-R$_6$Gly | 20 µg | 13 |
| SMA | Saline | n/a | n/a | n/a | 12 |
| WT | Saline | n/a | n/a | n/a | 13 |

Survival of SMNΔ7 Mice Treated with PMO-Based Oligomers

Figure 11:
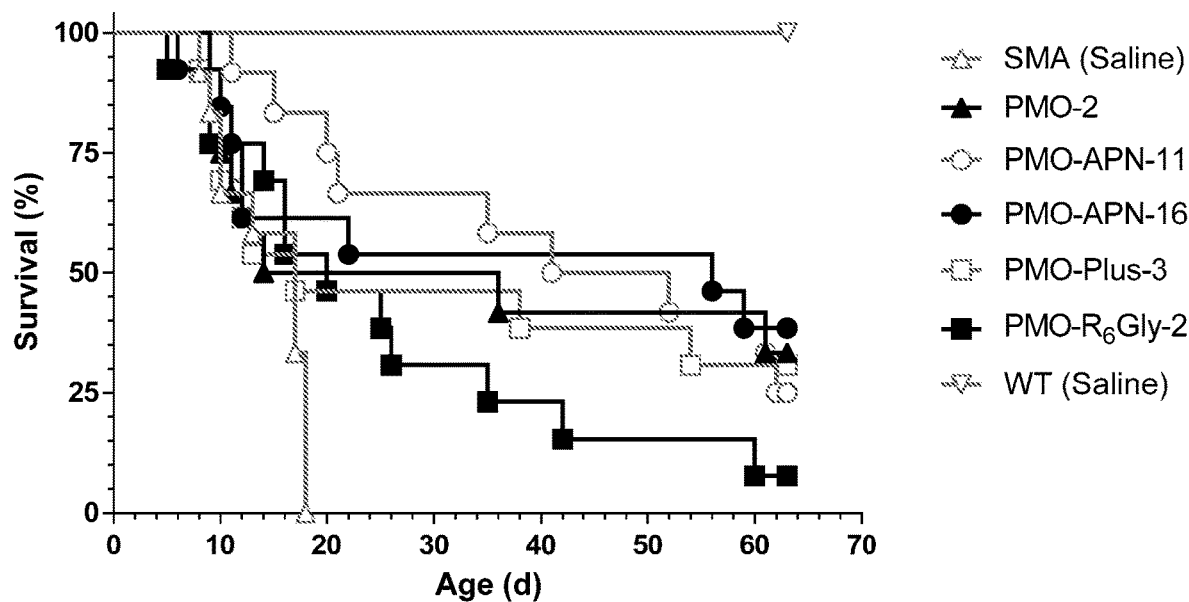
FIG. 11 depicts a survival curve of SMNΔ7 mice treated with either 20 μg of PMO, PMO-APN, PMO-Plus, or PMO-R$_6$Gly compounds with two different lengths or saline. A group of wild-type mice treated with saline was used as a reference. Each mouse was treated at P1 (the day after the birth) with intraventricular (ICV) injection of saline or PMO-based oligomers. The percentage of any remaining mice compared to the initial number of mice per each experimental group is represented on y-axis.

As shown in FIG. 11 and Table 18, treatments with PMO-based oligomers significantly increased the median life-span of SMNΔ7 mice. P-value of each experimental group was calculated by log-rank Mantel-Cox test. In particular, PMO-APN modified oligomers almost tripled the median survival of SMNΔ7 mice, as compared to saline-treated SMNΔ7 mice. SMNΔ7 mice treated with PMO-based oligomers were fit, well-groomed, ambulatory, and active, as compared to saline-treated SMNΔ7 mice.

TABLE 18

Median Life-Span of SMNΔ7 Mice Treated with PMO-based Oligomers

| Genotype | Compound Name | Length | Median Life Span (d) | p-value |
|---|---|---|---|---|
| SMA | PMO-APN-16 | 18 | 56 | 0.0155 |
| SMA | PMO-2 | 25 | 25 | 0.0842 |
| SMA | PMO-APN-11 | 25 | 47 | 0.0001 |
| SMA | PMO-Plus-3 | 25 | 17 | 0.1012 |
| SMA | PMO-R$_6$Gly-2 | 25 | 20 | 0.0479 |
| SMA | Saline | n/a | 17 | n/a |

Body Weight of SMNΔ7 Mice Treated with PMO-Based Oligomers

Figure 12:
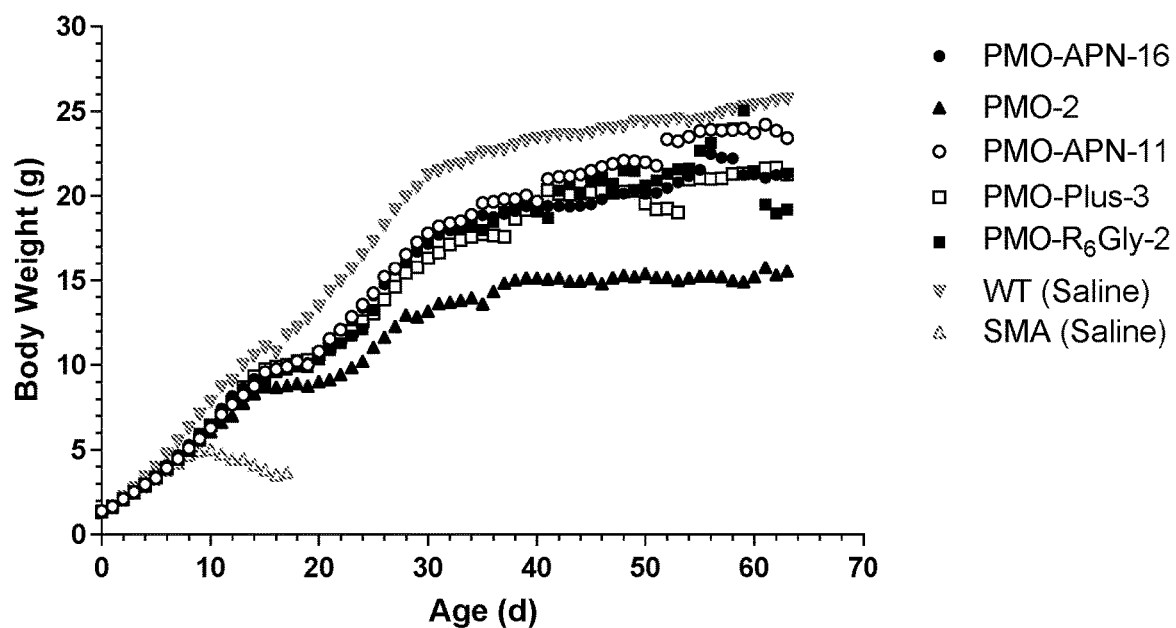
FIG. 12 shows weight gain of each experimental group throughout the experiment shown in FIG. 11. A group of wild-type mice treated with saline was used as a reference. Statistical analysis was done with linear regression.

Body weight of each treatment group was recorded on daily basis for 63 days post administration (FIG. 12). Body weight of each treatment group at 63 days of age is summarized in Table 19. Mice treated with PMO-based oligomers significantly increased body weight throughout the experiment, comparable to the wild-type group. Consistent with the body weight data discussed in Example 25, mice treated with PMO-APN, PMO-Plus, or PMO-R$_6$Gly oligomers gained weight significantly more than the corresponding PMO oligomer. These data again demonstrate that those chemical modifications further increase the in vivo efficacy of PMO-based oligomers.

TABLE 19

Body Weight of SMNΔ7 Mice Treated with PMO-based Oligomers

| | Compound | | | | | |
|---|---|---|---|---|---|---|
| Day | PMO-APN-16 | PMO-2 | PMO-APN-11 | PMO-Plus-3 | PMO-R$_6$Gly-2 | SMA (Saline) | WT (Saline) |
| 14 | 9.2 g | 8.3 g | 8.8 g | 9.0 g | 8.7 g | 4.1 g | 10.6 g |
| 21 | 11.1 g | 9.2 g | 11.6 g | 10.5 g | 10.9 g | — | 14.3 g |
| 28 | 16.3 g | 13.0 g | 16.6 g | 14.6 g | 16.2 g | — | 19.9 g |
| 42 | 19.4 g | 15.1 g | 21.2 g | 19.2 g | 20.4 g | — | 23.6 g |
| 63 | 21.3 g | 15.6 g | 23.4 g | 21.3 g | 19.2 g | — | 25.7 g |

Effects of PMO-Based Oligomers on Muscle Strength

Figure 13:
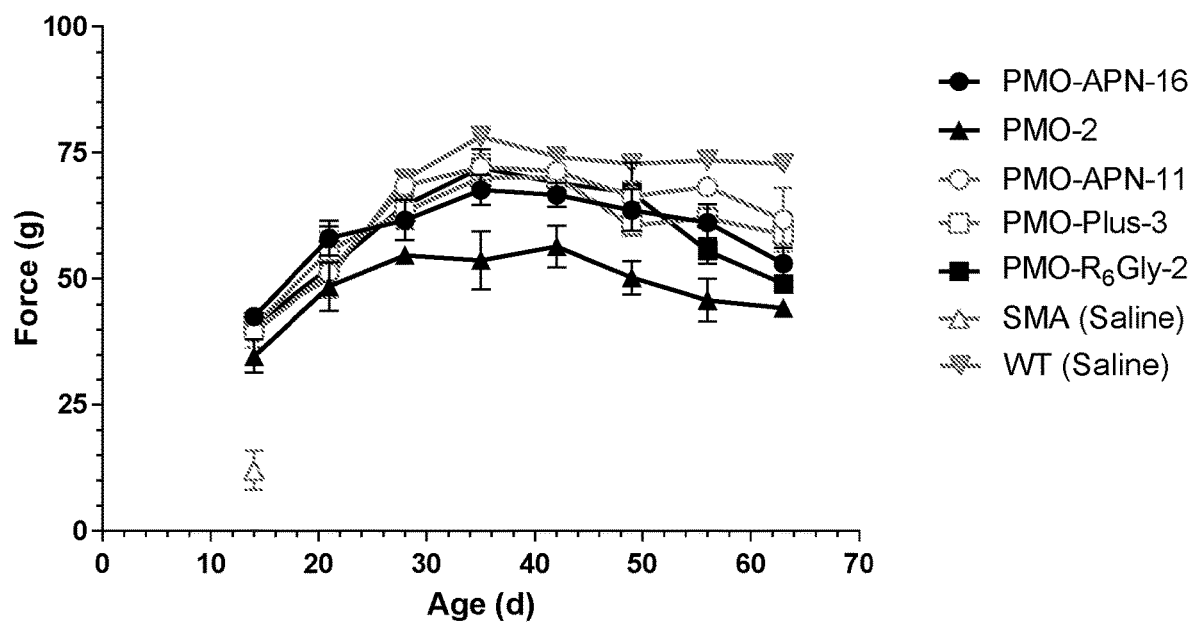
FIG. 13 shows grip test of each experimental group measured regularly throughout the experiment shown in FIG. 11. The peak amount of force that a mouse applies in order to grasp a mesh was measured, and the average force of each group is represented in gram (g) on y-axis.

Following the procedures described in Example 25, muscle strength of SMNΔ7 mice treated with PMO-based oligomers was monitored during the experiment. FIG. 13 and Table 20 summarize muscle strength of each experimental group measured at day 28, 35, 42, 49, 56, and 63. Statistics shown in Table 19 are calculated by One-way ANOVA Tukey's multiple comparison. Suprisingly, the average muscle strength of mice treated with PMO-based oligomers was comparable to the level of the wild-type mice group. Similar to the results shown in Example 25, PMO-APN, PMO-Plus, and PMO-R$_6$Gly modifications significantly enhanced the efficacy of the oligomers of 25 nucleotides in length, as compared to PMO modification.

TABLE 20

Muscle Strength of SMNΔ7 Mice Treated with PMO-based Oligomers

| Genotype | Compound Name | Length | 14 (d) | 21 (d) | 28 (d) | 35 (d) | 42 (d) | 49 (d) | 56 (d) | 63 (d) |
|---|---|---|---|---|---|---|---|---|---|---|
| SMA | PMO-APN-16 | 18 | 42.6[#] | 58.0 | 61.6 | 67.6* | 66.6 | 63.6 | 61.2*[$] | 53.0[%] |
| SMA | PMO-2 | 25 | 34.7[#] | 48.5 | 54.7[&] | 53.7[%] | 56.4[%] | 50.2[%] | 45.8[%] | 44.3[%] |
| SMA | PMO-APN-11 | 25 | 39.4[#] | 51.3 | 68.4* | 72.1* | 71.3* | 66.3* | 68.2* | 61.7* |
| SMA | PMO-Plus-3 | 25 | 40.7[#] | 55.5 | 63.3 | 70.0* | 70.0* | 60.6 | 62.0 | 58.8[&] |

TABLE 20-continued

Muscle Strength of SMNΔ7 Mice Treated with PMO-based Oligomers

| Genotype | Compound Name | Length | 14 (d) | 21 (d) | 28 (d) | 35 (d) | 42 (d) | 49 (d) | 56 (d) | 63 (d) |
|---|---|---|---|---|---|---|---|---|---|---|
| SMA | PMO-R$_6$Gly-2 | 25 | 40.9# | 52.0 | 64.5 | 72.0* | 69.0 | 67.0 | 55.5 | NT |
| SMA | Saline | n/a | 12.0 | — | — | — | — | — | — | — |

Units for the above data is "Force (g)"
$p < 0.001$ (compared to SMA mice treated with saline)
*$p < 0.05$ (compared to SMA mice treated with PMO-2).
$$p < 0.05$,
&$p < 0.01$ and
%$p < 0.001$ (compared to wild-type mice treated with saline).
NT: Not Tested (the remaining mouse was unable to perform the test due to forelimb necrosis).

Effects of PMO-Based Oligomers on SMN Protein Expression In Vivo

To confirm whether administration of PMO-based oligomers induces the expression of SMN protein in vivo, spinal cord samples from mice treated with PMO-based oligomers were collected at 63 days of age. As a positive control, age-matching wild-type mice were also sacrificed for spinal cord sample collection. Saline-treated SMNΔ7 mice were sacrificed at 12 days of ages and spinal cord samples from those mice were collected as a comparison. Protein extracts from the spinal cord samples were obtained by following the methods described in Example 24. The SMN protein expression level of each sample was detected by western blot analysis, also described in Example 24.

Figure 14A:
FIG. 14A shows the western-blot analysis of exon 7-containing SMN proteins in samples obtained from mice tested in FIG. 11. SMN2 proteins were blotted with anti-SMN antibodies. Actin was detected with anti-Actin antibodies as a loading control. WT1-WT3 represent cervical spinal cord samples from three different saline-treated wild-type mice. S1-S3 represent cervical spinal cord samples from three different saline-treated SMNΔ7 mice. B1-B5 represent cervical spinal cord samples obtained from five different SMNΔ7 mice treated with PMO-APN-16. C1-C4 represent cervical spinal cord samples obtained from four different SMNΔ7 mice treated with PMO-2. D1-D3 represent cervical spinal cord samples obtained from three different SMNΔ7 mice treated with PMO-APN-11. E1-E4 represent cervical spinal cord samples obtained from four different SMNΔ7 mice treated with PMO-Plus-3. Lastly, F1 represents a cervical spinal cord sample obtained from a SMNΔ7 mouse treated with PMO-R$_6$Gly-2.
Figure 14B:
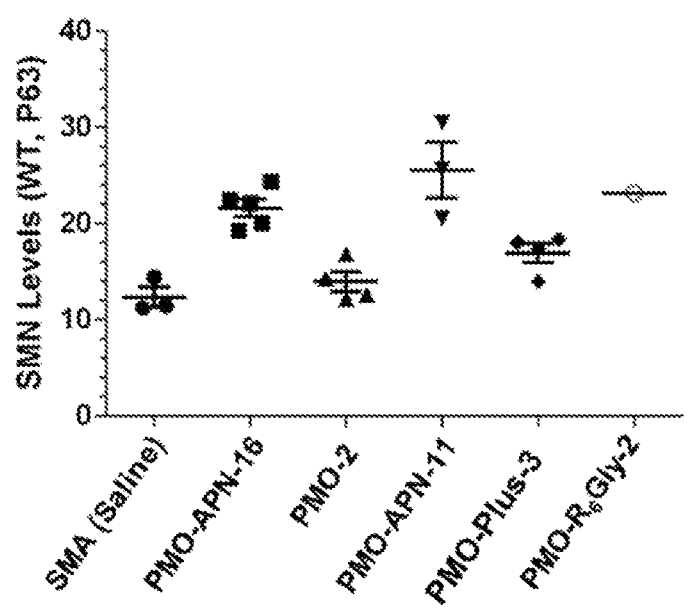
FIG. 14B represents the average quantified intensity of the bands corresponding to SMN proteins per each experimental group as shown in FIG. 14A.

As shown in FIGS. 14A and 14B, spinal cord samples from mice treated with PMO-based oligomers showed higher SMN protein expression levels.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:
1. A compound of formula (V):

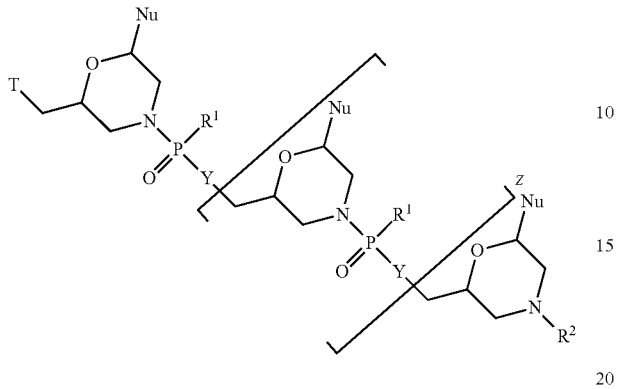

or a pharmaceutically acceptable salt thereof, wherein:
each Nu is a nucleobase which taken together forms a targeting sequence;
Z is an integer from 6 to 38;
each Y is independently selected from O and —$NR^4$, wherein each $R^4$ is independently selected from H, $C_1$-$C_6$ alkyl, aralkyl, —C(=NH)$NH_2$, —C(O)$(CH_2)_n$ $NR^5$C(=NH)$NH_2$, —C(O)$(CH_2)_2$NHC(O)$(CH_2)_5$$NR^5$C(=NH)$NH_2$, and G, wherein $R^5$ is selected from H and $C_1$-$C_6$ alkyl and n is an integer from 1 to 5;
T is selected from OH and a moiety of the formula:

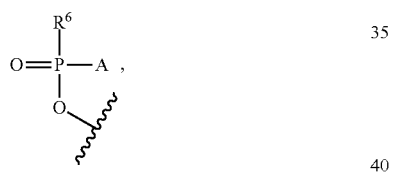

wherein:
A is selected from OH, —$N(R^7)_2R^8$, and $R^1$ wherein:
each $R^7$ is independently selected from H and $C_1$-$C_6$ alkyl, and
$R^8$ is selected from an electron pair and H, and
$R^6$ is selected from OH, —$N(R^9)CH_2C(O)NH_2$, and a moiety of the formula:

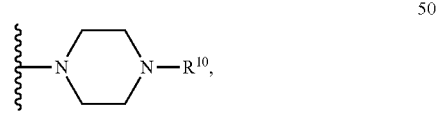

wherein:
$R^9$ is selected from H and $C_1$-$C_6$ alkyl; and
$R^{10}$ is selected from G, —C(O)—$R^{11}$OH, acyl, trityl, 4-methoxytrityl, —C(=NH)$NH_2$, —C(O)$(CH_2)_m$$NR^{12}$C(=NH)$NH_2$, and —C(O)$(CH_2)_2$NHC(O)$(CH_2)_5$$NR^{12}$C(=NH)$NH_2$, wherein:
m is an integer from 1 to 5,
$R^{11}$ is of the formula —(O-alkyl)$_y$,- wherein y is an integer from 3 to 10 and
each of the y alkyl groups is independently selected from $C_2$-$C_6$ alkyl; and
$R^{12}$ is selected from H and $C_1$-$C_6$ alkyl;

each instance of $R^1$ is independently selected from:
—$N(R^{13})_2R^{14}$ wherein each $R^{13}$ is independently selected from H and $C_1$-$C_6$ alkyl, and $R^{14}$ is selected from an electron pair and H;
a moiety of formula (II):

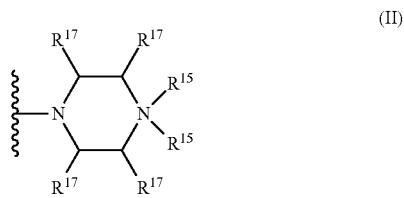

wherein:
$R^{15}$ is selected from H, G, $C_1$-$C_6$ alkyl, —C(=NH)$NH_2$, —C(O)$(CH_2)_q$$NR^{18}$C(=NH) $NH_2$, and —C(O)$(CH_2)_2$NHC(O)$(CH_2)_5$$NR^{18}$C (=NH)$NH_2$, wherein:
$R^{18}$ is selected from H and $C_1$-$C_6$ alkyl; and
q is an integer from 1 to 5,
$R^{16}$ is selected from an electron pair and H; and
each $R^{17}$ is independently selected from H and methyl; and
a moiety of formula (III):

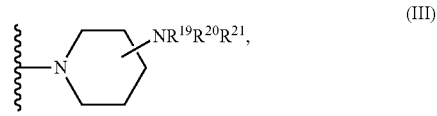

wherein:
$R^{19}$ is selected from H, $C_1$-$C_6$ alkyl, —C(=NH) $NH_2$, —C(O)$(CH_2)_r$$NR^{22}$C(=NH)$NH_2$, —C(O)CH($NH_2$)($CH_2$)$_3$NHC(=NH)$NH_2$, —C(O)$(CH_2)_2$NHC(O)$(CH_2)_5$$NR^{22}$C(=NH) $NH_2$, —C(O)CH($NH_2$)($CH_2$)$_4$$NH_2$, and G wherein:
$R^{22}$ is selected from H and $C_1$-$C_6$ alkyl; and
r is an integer from 1 to 5,
$R^{20}$ is selected from H and $C_1$-$C_6$ alkyl; and
$R^{21}$ is selected from an electron pair and H; and
$R^2$ is selected from G, H, acyl, trityl, 4-methoxytrityl, and $C_1$-$C_6$ alkyl,
wherein G is a cell penetrating peptide ("CPP") and linker moiety selected from —C(O)$(CH_2)_5$NH— CPP, —C(O)$(CH_2)_2$NH—CPP, —C(O)$(CH_2)_2$NHC (O)$(CH_2)_5$NH—CPP, and —C(O)$CH_2$NH—CPP, or G is of the formula:

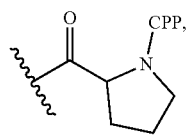

wherein the CPP is attached to the linker moiety by an amide bond at the CPP carboxy terminus, with the proviso that up to one instance of G is present,
wherein the targeting sequence comprises a sequence selected from SEQ ID NOS: 35 to 37, and wherein at least one of the following conditions is present:

a) at least one R¹ is of formula (II) or of formula (III), or
b) R² is G or T is:

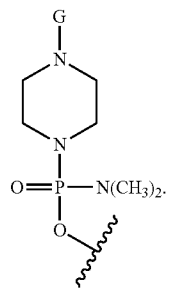

2. The compound of claim 1, wherein T is of the formula:

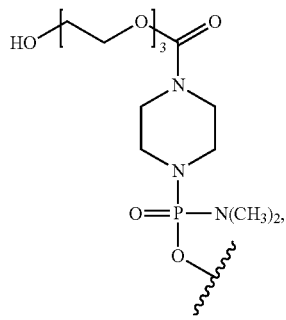

and R² is H.

3. The compound of claim 1, wherein each R¹ is independently selected from

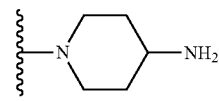 [SMILES: *N1CCC(N)CC1]

and —N(CH₃)₂, T is:

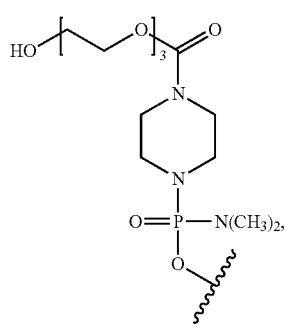

and R² is H, wherein at least one R¹ is

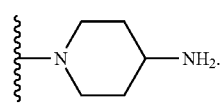

4. The compound of claim 1, each R¹ is independently selected from

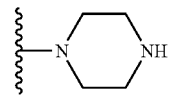

and —N(CH₃)₂, T is:

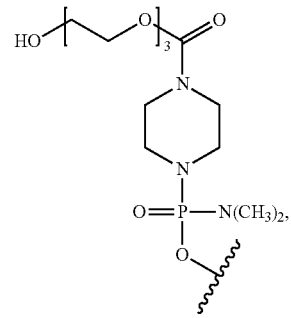

and R² is H, wherein at least one R¹ is

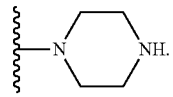

5. The compound of 1, wherein each R¹ is —N(CH₃)₂, R² is selected from H and acyl, and T is of the formula:

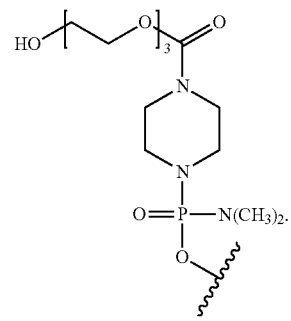

6. The compound of claim 1, wherein R² is G, T is of the formula:

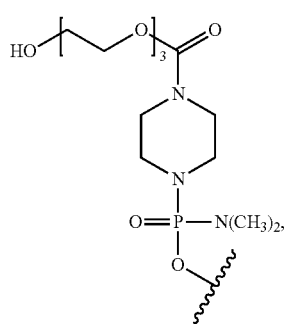

and each $R^1$ is —N(CH$_3$)$_2$.

7. The compound of claim 1, wherein $R^2$ is selected from H or acyl, T is of the formula:

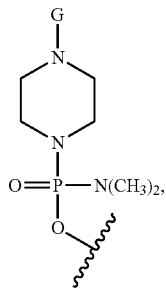

and each $R^1$ is —N(CH$_3$)$_2$.

8. The compound of claim 6, wherein G is —C(O)CH$_2$NH—CPP, wherein CPP comprises SEQ ID NO:23 and $R^a$, wherein $R^a$ is attached to SEQ ID NO:23 at the SEQ ID NO:23 N-terminus, and wherein $R^a$ is selected from H, acetyl, benzoyl, and stearoyl.

9. The compound of claim 1, wherein Z is an integer from 16 to 23.

10. A pharmaceutical composition, comprising a compound of formula (V):

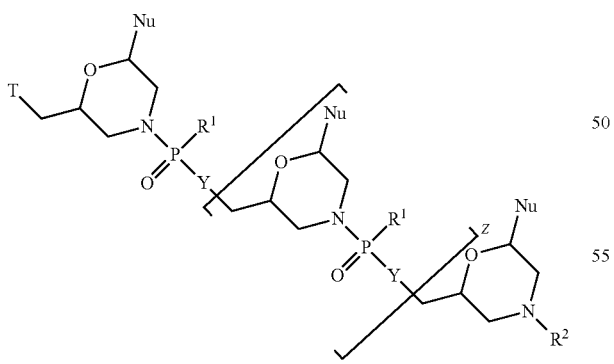

(V)

or a pharmaceutically acceptable salt thereof, wherein:
each Nu is a nucleobase which taken together forms a targeting sequence;
Z is an integer from 6 to 38;
each Y is independently selected from O and —NR$^4$, wherein each R$^4$ is independently selected from H, C$_1$-C$_6$ alkyl, aralkyl, —C(=NH)NH$_2$, —C(O)(CH$_2$)$_n$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and C$_1$-C$_6$ alkyl and n is an integer from 1 to 5;
T is selected from OH and a moiety of the formula:

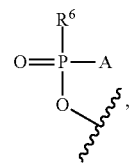

wherein:
A is selected from —OH, —N(R$^7$)$_2$R$^8$, and R$^1$ wherein:
each R$^7$ is independently selected from H and C$_1$-C$_6$ alkyl, and
R$^8$ is selected from an electron pair and H, and
R$^6$ is selected from OH, —N(R$^9$)CH$_2$C(O)NH$_2$, and a moiety of the formula:

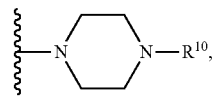

wherein:
R$^9$ is selected from H and C$_1$-C$_6$ alkyl; and
R$^{10}$ is selected from G, —C(O)—R$^{11}$OH, acyl, trityl, 4-methoxytrityl, —C(=NH)NH$_2$, —C(O)(CH$_2$)$_m$NR$^{12}$C(=NH)NH$_2$, and —C(O)(CH$_2$)$_2$NHC(O)(CH$_2$)$_5$NR$^{12}$C(=NH)NH$_2$, wherein:
m is an integer from 1 to 5,
R$^{11}$ is of the formula —(O-alkyl)$_y$- wherein y is an integer from 3 to 10 and
each of the y alkyl groups is independently selected from C$_2$-C$_6$ alkyl; and
R$^{12}$ is selected from H and C$_1$-C$_6$ alkyl;
each instance of R$^1$ is independently selected from:
—N(R$^{13}$)$_2$R$^{14}$ wherein each R$^{13}$ is independently selected from H and C$_1$-C$_6$ alkyl, and R$^{14}$ is selected from an electron pair and H;
a moiety of formula (II):

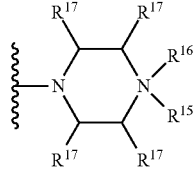

(II)

wherein:
R$^{15}$ is selected from H, G, C$_1$-C$_6$ alkyl, —C(=NH)NH$_2$, —C(O)(CH$_2$)$_q$NR$^{18}$C(=NH)NH$_2$, and —C(O)(CH$_2$)$_2$NHC(O)(CH$_2$)$_5$NR$^{18}$C(=NH)NH$_2$, wherein:
R$^{18}$ is selected from H and C$_1$-C$_6$ alkyl; and
q is an integer from 1 to 5,
R$^{16}$ is selected from an electron pair and H; and
each R$^{17}$ is independently selected from H and methyl; and a moiety of formula (III):

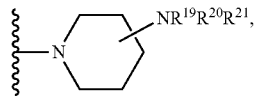

wherein:
R$^{19}$ is selected from H, C$_1$-C$_6$ alkyl, —C(=NH)NH$_2$, —C(O)(CH$_2$)$_r$NR$^{22}$C(=NH)NH$_2$, —C(O)CH(NH$_2$)(CH$_2$)$_3$NHC(=NH)NH$_2$, —C(O)(CH$_2$)$_2$NHC(O)(CH$_2$)$_5$NR$^{22}$C(=NH)NH$_2$, —C(O)CH(NH$_2$)(CH$_2$)$_4$NH$_2$, and G wherein:
R$^{22}$ is selected from H and C$_1$-C$_6$ alkyl; and
r is an integer from 1 to 5,
R$^{20}$ is selected from H and C$_1$-C$_6$ alkyl; and
R$^{21}$ is selected from an electron pair and H; and
R$^2$ is selected from G, H, acyl, trityl, 4-methoxytrityl, and C$_1$-C$_6$ alkyl,
wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

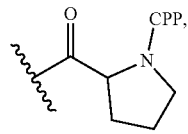

wherein the CPP is attached to the linker moiety by an amide bond at the CPP carboxy terminus, with the proviso that up to one instance of G is present,
wherein the targeting sequence comprises a sequence selected from SEQ ID NOS: 35 to 37, and wherein at least one of the following conditions is present:
c) at least one R$^1$ is of formula (II) or of formula (III), or
d) R$^2$ is G or T is:

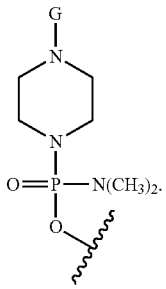

11. A method of treating spinal muscular atrophy in a subject in need thereof, comprising administering to the subject an effective amount of a compound of formula (V):

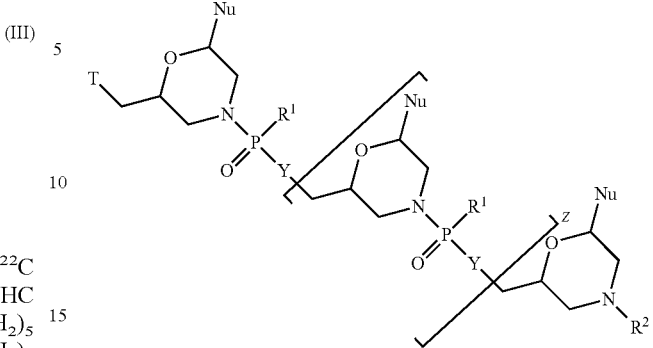

or a pharmaceutically acceptable salt thereof, wherein:
each Nu is a nucleobase which taken together forms a targeting sequence;
Z is an integer from 6 to 38;
each Y is independently selected from 0 and —NR$^4$, wherein each R$^4$ is independently selected from H, C1-C6 alkyl, aralkyl, —C(=NH)NH2, —C(O)(CH$_2$)$_n$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and C$_1$-C$_6$ alkyl and n is an integer from 1 to 5;
T is selected from OH and a moiety of the formula:

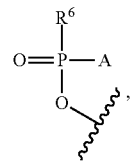

wherein:
A is selected from —OH, —N(R$^7$)$_2$R$^8$, and R$^1$ wherein:
each R$^7$ is independently selected from H and C$_1$-C$_6$ alkyl, and
R$^8$ is selected from an electron pair and H, and
R$^6$ is selected from OH, —N(R$^9$)CH$_2$C(O)NH$_2$, and a moiety of the formula:

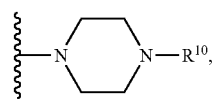

wherein:
R$^9$ is selected from H and C1-C6 alkyl; and
R$^{10}$ is selected from G, —C(O)—R$^{11}$OH, acyl, trityl, 4-methoxytrityl, —C(=NH)NH$_2$, —C(O)(CH$_2$)$_m$NR$^{12}$C(=NH)NH$_2$, and —C(O)(CH$_2$)$_2$NHC(O)(CH$_2$)$_5$NR$^{12}$C(=NH)NH$_2$, wherein:
m is an integer from 1 to 5,
R$^{11}$ is of the formula —(O-alkyl)$_y$- wherein y is an integer from 3 to 10 and
each of the y alkyl groups is independently selected from C2-C6 alkyl; and
R$^{12}$ is selected from H and C1-C6 alkyl;

each instance of $R^1$ is independently selected from:
—$N(R^{13})_2R^{14}$ wherein each $R^{13}$ is independently selected from H and $C_1$-$C_6$ alkyl, and $R^{14}$ is selected from an electron pair and H;

a moiety of formula (II):

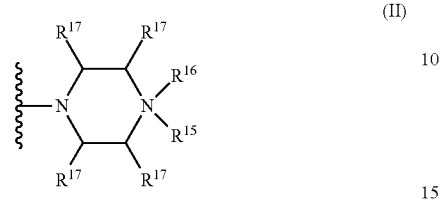

wherein:
$R^{15}$ is selected from H, G, $C_1$-$C_6$ alkyl, —C(=NH)NH$_2$, —C(O)(CH$_2$)$_q$NR$^{18}$C(=NH)NH$_2$, and —C(O)(CH$_2$)$_2$NHC(O)(CH$_2$)$_5$NR$^{18}$C(=NH)NH$_2$, wherein:
$R^{18}$ is selected from H and $C_1$-$C_6$ alkyl; and
q is an integer from 1 to 5,
$R^{16}$ is selected from an electron pair and H; and
each $R^{17}$ is independently selected from H and methyl; and a moiety of formula(III):

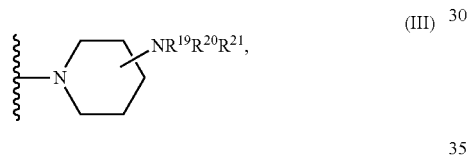

wherein:
$R^{19}$ is selected from H, C1-C6 alkyl, —C(=NH)NH$_2$, —C(O)(CH$_2$)$_r$NR$^{22}$C(=NH)NH$_2$, —C(O)CH(NH$_2$)(CH$_2$)$_3$NHC(=NH)NH$_2$, —C(O)(CH$_2$)$_2$NHC(O)(CH$_2$)$_5$NR$^{22}$C(=NH)NH$_2$, —C(O)CH(NH$_2$)(CH$_2$)$_4$NH$_2$, and G
wherein:

$R^{22}$ is selected from H and $C_1$-$C_6$ alkyl; and
r is an integer from 1 to 5,
$R^{20}$ is selected from H and $C_1$-$C_6$ alkyl; and
$R^{21}$ is selected from an electron pair and H; and
$R^2$ is selected from G, H, acyl, trityl, 4-methoxytrityl, and C1-C6 alkyl,
wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

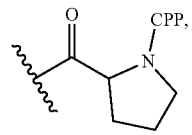

wherein the CPP is attached to the linker moiety by an amide bond at the CPP carboxy terminus, with the proviso that up to one instance of G is present,
wherein the targeting sequence comprises a sequence selected from SEQ ID NOS: 35 to 37, and wherein at least one of the following conditions is present:
a) at least one $R^1$ is of formula (II) or of formula (III), or
b) $R^2$ is G or T is:

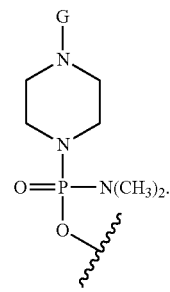

* * * * *